US008404834B2

(12) United States Patent
Hacket et al.

(10) Patent No.: US 8,404,834 B2
(45) Date of Patent: Mar. 26, 2013

(54) HYDROXYALKYL STARCH DERIVATIVES AND PROCESS FOR THEIR PREPARATION

(75) Inventors: Frank Hacket, Altenstadt (DE);
Thomas Hey, Bad Nauheim (DE);
Franziska Hauschild, Bad Nauheim (DE); Helmut Knoller, Friedberg (DE);
Martin Schimmel, Oberursel (DE);
Klaus Sommermeyer, Rossbach (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 12/747,981

(22) PCT Filed: Dec. 15, 2008

(86) PCT No.: PCT/EP2008/010660
§ 371 (c)(1),
(2), (4) Date: Jul. 12, 2010

(87) PCT Pub. No.: WO2009/077154
PCT Pub. Date: Jun. 25, 2009

(65) Prior Publication Data
US 2010/0305033 A1 Dec. 2, 2010

(30) Foreign Application Priority Data

Dec. 14, 2007 (EP) .................... 07024350

(51) Int. Cl.
*C08B 31/00* (2006.01)
*C08B 31/18* (2006.01)
*C08B 35/00* (2006.01)
(52) U.S. Cl. .............. 536/102; 536/104; 536/105
(58) Field of Classification Search .......... None
See application file for complete search history.

(56) References Cited

U.S. PATENT DOCUMENTS

| | | |
|---|---|---|
| 3,191,291 A | 6/1965 | Maier |
| 3,226,395 A | 12/1965 | Schimmelschmidt et al. |
| 3,873,614 A | 3/1975 | Lamberti et al. |
| 4,001,200 A | 1/1977 | Bonsen et al. |
| 4,064,118 A | 12/1977 | Wong |
| 4,125,492 A | 11/1978 | Cuatrecasas et al. |
| 4,179,337 A | 12/1979 | Davis et al. |
| 4,261,973 A | 4/1981 | Lee et al. |
| 4,412,989 A | 11/1983 | Iwashita et al. |
| 4,454,161 A | 6/1984 | Okada et al. |
| 4,667,016 A | 5/1987 | Lai et al. |
| 4,703,008 A | 10/1987 | Lin |
| 4,766,106 A | 8/1988 | Katre et al. |
| 4,847,325 A | 7/1989 | Shadle et al. |
| 4,900,780 A | 2/1990 | Cerny |
| 4,904,584 A | 2/1990 | Shaw |
| 4,925,677 A | 5/1990 | Feijen |
| 4,952,496 A | 8/1990 | Studier et al. |
| 5,068,321 A | 11/1991 | Buysch et al. |
| 5,079,337 A | 1/1992 | Leonard et al. |
| 5,110,909 A | 5/1992 | Dellacherie et al. |
| 5,214,132 A | 5/1993 | Kuga et al. |
| 5,217,998 A | 6/1993 | Hedlund et al. |
| 5,218,092 A | 6/1993 | Sasaki et al. |
| 5,218,108 A | 6/1993 | Sommermeyer et al. |
| 5,281,698 A | 1/1994 | Nitecki |
| 5,362,853 A | 11/1994 | Kuga et al. |
| 5,420,105 A | 5/1995 | Gustavson et al. |
| 5,470,843 A | 11/1995 | Stahl et al. |
| 5,484,903 A | 1/1996 | Szablikowski et al. |
| 5,543,332 A | 8/1996 | Lihme et al. |
| 5,581,476 A | 12/1996 | Osslund |
| 5,622,718 A | 4/1997 | Al-Shamkhani et al. |
| 5,723,589 A | 3/1998 | Miljkovic et al. |
| 5,736,533 A | 4/1998 | Simon et al. |
| 5,770,645 A | 6/1998 | Stamler et al. |
| 5,824,778 A | 10/1998 | Ishikawa et al. |
| 5,840,900 A | 11/1998 | Greenwald et al. |
| 5,876,980 A | 3/1999 | DeFrees et al. |
| 5,880,270 A | 3/1999 | Berninger et al. |
| 5,952,347 A | 9/1999 | Arison et al. |
| 5,981,507 A | 11/1999 | Josephson et al. |
| 5,990,237 A | 11/1999 | Bentley et al. |
| 6,011,008 A | 1/2000 | Domb et al. |
| 6,083,909 A | 7/2000 | Sommermeyer et al. |
| 6,172,208 B1 | 1/2001 | Cook |
| 6,261,800 B1 | 7/2001 | Nikolics et al. |
| 6,299,881 B1 | 10/2001 | Lees et al. |
| 6,340,746 B1 | 1/2002 | Roberts et al. |
| 6,375,846 B1 | 4/2002 | Jarrett et al. |

(Continued)

FOREIGN PATENT DOCUMENTS

| | | |
|---|---|---|
| CA | 2110543 | 6/1994 |
| CA | 2258947 | 1/1998 |

(Continued)

OTHER PUBLICATIONS

Abuchowski and Davis, Enzymes as drugs, Holcenberg and Rubberts, Publisher, pp. 367-383, John Wiley & Sons N.Y. (1981).
Alagon, T. P. King, "Activation of Plysaccharides with 2-Iminothiolane and Its Uses" Biochemistry, 1980, 19, 4341-4345.
Aly et al., Hemophilia A due to mutations that create new N-glycosylation sites 1992, Proc. Natl. Acad. Sci. USA: 4933.
Anderson et al., "Isolation and characterization of human factor VIII: Molecular forms in commercial factor VIII concentrate, cryoprecipitate, and plasma." 1986, Proc. Natl. Acad, Sci. 83: 2979.
Armitage, J. O.; Emerging applications of recombinant human granulocyte-macrophage colony-stimulating factor. Blood 1998, 92, pp. 4491-4508.

(Continued)

*Primary Examiner* — Marianne P Allen
(74) *Attorney, Agent, or Firm* — Occhiuti Rohlicek & Tsao LLP

(57) ABSTRACT

The invention relates to a method for the preparation of a hydroxyalkyl starch derivative which comprises reacting hydroxyalkyl starch (HAS) via the optionally oxidized reducing end of the HAS with the amino group M of a crosslinking compound which, apart from the amino group, comprises a specifically protected carbonyl group, namely an acetal group or a ketal group.

11 Claims, 33 Drawing Sheets

U.S. PATENT DOCUMENTS

| | | | |
|---|---|---|---|
| 6,395,266 B1 | 5/2002 | Martinez et al. |
| 6,417,347 B1 | 7/2002 | Herrmann et al. |
| 6,451,337 B1 | 9/2002 | Smith et al. |
| 6,500,930 B2 | 12/2002 | Adamson |
| 6,544,503 B1 | 4/2003 | Vanderhoff et al. |
| 6,555,660 B2 | 4/2003 | Nissen et al. |
| 6,586,398 B1 | 7/2003 | Kinstler et al. |
| 6,596,861 B1 | 7/2003 | Moreau |
| 6,624,142 B2 | 9/2003 | Greenwald et al. |
| 6,916,962 B2 | 7/2005 | Rosen et al. |
| 6,956,135 B2 | 10/2005 | Rosen et al. |
| 7,115,576 B2 | 10/2006 | Sommermeyer |
| 7,179,617 B2 | 2/2007 | DeFrees et al. |
| 7,258,661 B2 | 8/2007 | Davies et al. |
| 7,279,176 B1 | 10/2007 | West et al. |
| 7,541,328 B2 | 6/2009 | Hemberger et al. |
| 7,816,516 B2 | 10/2010 | Sommermeyer et al. |
| 2002/0065410 A1 | 5/2002 | Antrim |
| 2002/0151006 A1 | 10/2002 | Muir et al. |
| 2003/0194291 A1 | 10/2003 | Kramski |
| 2004/0043446 A1 | 3/2004 | DeFrees et al. |
| 2004/0180858 A1 | 9/2004 | Sommermeyer |
| 2005/0063943 A1 | 3/2005 | Sommermeyer et al. |
| 2005/0181985 A1 | 8/2005 | Hemberger et al. |
| 2005/0238723 A1 | 10/2005 | Zander et al. |
| 2006/0019877 A1 | 1/2006 | Conradt et al. |
| 2006/0052342 A1 | 3/2006 | Sommermeyer |
| 2006/0194940 A1 | 8/2006 | Kozlowski |
| 2006/0217293 A1 | 9/2006 | Orlando et al. |
| 2007/0134197 A1 | 6/2007 | Eichner et al. |
| 2009/0091549 A1 | 4/2009 | Matsumoto et al. |

FOREIGN PATENT DOCUMENTS

| | | |
|---|---|---|
| CA | A 2 233 725 | 9/1999 |
| CA | A 2 441 442 | 10/2002 |
| CA | A 2 478 478 | 9/2003 |
| CA | A 2 478 480 | 9/2003 |
| DE | 22 33 977 | 7/1972 |
| DE | 26 07 706 | 9/1976 |
| DE | 26 46 854 | 5/1977 |
| DE | 26 16 086 | 11/1977 |
| DE | 30 29 307 | 3/1982 |
| DE | 35 01 616 | 7/1986 |
| DE | 38 36 600 | 5/1990 |
| DE | 279 486 | 6/1990 |
| DE | 41 30 807 | 3/1993 |
| DE | 196 28 705 | 1/1998 |
| DE | 198 08 079 | 8/1999 |
| DE | 100 41 541 | 3/2002 |
| DE | 101 12 825 | 10/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 09 822 | 9/2003 |
| DE | 102 17 994 | 11/2003 |
| DE | 102 54 745 | 6/2004 |
| DE | 102 56 558 | 9/2004 |
| EP | 0 019 403 | 11/1980 |
| EP | 0 127 839 | 12/1984 |
| EP | 0 138 572 | 4/1985 |
| EP | 0 148 605 | 7/1985 |
| EP | 0 205 564 | 12/1986 |
| EP | 0 243 929 | 11/1987 |
| EP | 0 304 183 | 2/1989 |
| EP | 0 307 827 | 3/1989 |
| EP | 0 315 349 | 5/1989 |
| EP | 0 331 471 | 9/1989 |
| EP | 0 338 916 | 10/1989 |
| EP | 0 342 557 | 11/1989 |
| EP | 0 402 724 | 12/1990 |
| EP | 0 411 678 | 2/1991 |
| EP | 0 418 523 | 3/1991 |
| EP | 0 418 945 | 3/1991 |
| EP | 0 428 267 | 5/1991 |
| EP | 0 549 721 | 7/1993 |
| EP | 0 605 963 | 7/1994 |
| EP | 0 609 968 | 8/1994 |
| EP | 0 640 619 | 3/1995 |
| EP | 0 646 130 | 4/1995 |
| EP | 0 668 351 | 8/1995 |
| EP | 0 218 825 | 4/1997 |
| EP | 0 806 140 | 11/1997 |
| EP | 0 809 996 | 12/1997 |
| EP | 1 191 100 | 3/2002 |
| EP | 1 230 935 | 8/2002 |
| EP | 1 398 322 | 3/2004 |
| EP | 1 398 327 | 3/2004 |
| EP | 1 398 328 | 3/2004 |
| EP | 1 400 533 | 3/2004 |
| EP | 1 424 086 | 6/2004 |
| EP | 1 496 076 | 1/2005 |
| EP | 1 591 476 | 11/2005 |
| EP | 1 660 134 | 5/2006 |
| EP | 2 070 950 | 6/2009 |
| EP | 2143736 | 1/2010 |
| EP | 2154160 | 2/2010 |
| FR | 2 378 094 A | 8/1978 |
| GB | 1 419 080 A | 12/1975 |
| GB | 1 549 246 A | 7/1979 |
| IL | 166506 | 2/2010 |
| JP | 56-500495 | 4/1981 |
| JP | 10-287554 A | 10/1998 |
| JP | 2000-506119 | 5/2000 |
| JP | 2002-003398 | 1/2002 |
| JP | 2002-509898 | 4/2002 |
| JP | 20011294601 | 10/2011 |
| WO | WO 80/02374 | 11/1980 |
| WO | WO 90/07939 | 7/1990 |
| WO | 90/12874 | 11/1990 |
| WO | WO 90/15628 | 12/1990 |
| WO | WO 92/11037 | 7/1992 |
| WO | WO 93/23062 | 11/1993 |
| WO | WO 93/24476 | 12/1993 |
| WO | WO 94/01483 | 1/1994 |
| WO | WO 94/05332 | 3/1994 |
| WO | WO 94/07536 | 4/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |
| WO | WO 97/38727 | 10/1997 |
| WO | WO 97/42225 | 11/1997 |
| WO | WO 98/01158 | 1/1998 |
| WO | WO 98/05689 | 2/1998 |
| WO | WO 98/07713 | 2/1998 |
| WO | WO 98/08856 | 3/1998 |
| WO | WO 98/14215 | 4/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | WO 99/17783 | 4/1999 |
| WO | WO 99/42139 | 8/1999 |
| WO | WO 99/49897 | 10/1999 |
| WO | WO 00/18893 | 4/2000 |
| WO | WO 00/66633 | 11/2000 |
| WO | WO 00/78355 | 12/2000 |
| WO | WO 01/46291 | 6/2001 |
| WO | WO 01/70272 | 9/2001 |
| WO | WO 01/83522 | 11/2001 |
| WO | WO 01/93862 | 12/2001 |
| WO | WO 02/09766 | 2/2002 |
| WO | WO 02/20033 | 3/2002 |
| WO | WO 02/28841 | 4/2002 |
| WO | WO 02/40057 | 5/2002 |
| WO | WO 02/080979 | 10/2002 |

| | | |
|---|---|---|
| WO | WO 03/000738 | 1/2003 |
| WO | WO 03/031464 | 4/2003 |
| WO | WO 03/031581 | 4/2003 |
| WO | WO 03/049699 | 6/2003 |
| WO | WO 03/059246 | 7/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | WO 2004/022630 | 3/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/050710 | 6/2004 |
| WO | WO 2004/065425 | 8/2004 |
| WO | WO 2004/033651 | 11/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | WO 2005/072778 | 8/2005 |
| WO | WO 2005/074993 | 8/2005 |
| WO | WO 2005/083103 | 9/2005 |
| WO | WO 2005/092369 | 10/2005 |
| WO | WO 2005/092390 | 10/2005 |
| WO | WO 2005/092928 | 10/2005 |
| WO | WO 2005/112954 | 12/2005 |
| WO | WO 2006/108052 | 10/2006 |
| WO | WO 2007/053292 | 5/2007 |
| WO | WO 2010/042638 | 4/2010 |
| WO | WO 01/78682 | 10/2011 |

OTHER PUBLICATIONS

Ashwell G., "Carbohydrate Antigens: Coupling of Carbohydrates to Proteins by a Mixed Anhydride Reaction" Methods Enzymol. 1972, 28, 219-22).
Avigad G., Anal. "A Simple Spectrophotometric Determination of Formaldehyde and Other Aldehydes: Application to Periodate-Oxidized Glycol Systems" Biochem. 134 (1983) 449-504.
Axén R., Porath J., Ernback S., Chemical Coupling of Peptides and Proteins to Polysaccharides ba means of Cyanogen Halides, Nature, vol. 214, Jun. 24, 1967, pp. 1302-1304.
B. Kuberan et al., "Preparation and isolation of neoglycoconjugates using biotin-streptavidin complexes" Glycoconj. J. 1999, 16, 271-81.
Balazy et al., "S-Nitroglutathione, a Product of the Reaction between Peroxynitrite and Glutathione That Generates Nitric Oxide" 1998, The Journal of Biological Chemistry vol. 273 No. 48, pp. 32009-32015.
Baldwin, J.E. et al., "Synthesis of Polymer-Bound Hemoglobin Samples" Tetrahedron, vol. 27 (1981), pp. 1723-1726.
Balland et al., J. „Intracellular Distribution of ampicillin in murine macrophages infected with *Salmonella typhimurium* and treated with (3H)ampicillin-loaded nanoparticles Antimicrob. Chemother., vol. 37 (1996), 105-115.
Barbone, Aparicio, Anderson, Natarajan, Ritchie, 1994, Reticulocytes measurements as a bioassay for erythropoietin, J. Pharm. Biomed. Anal., 12(4), 515-22.
Barström M. et al., "New derivatives of reducing oligosaccharides and their use in enzymatic reactions: efficient synthesis of sialyl Lewis a and sialyl dimeric Lewis x glycoconjugates" Carbohydr. Res. 2000, 328, 525-31.
Bauer L. et al., „Synthesis of w-(Aminoowy)alkanethiols 1965, J. Org. Chem., 30, 949.
Bauer, L. and Suresh, K. S., J. "S-[w-(Aminooxy)alkyl]isothiuronium Salts, w,w'- Bis(aminooxy)alkanes and Related Compounds" Org. Chem. 1963, 28, p. 1604.
Bauer, Semin. "Role of Antithrombin III as a Regulator of in Vivo Coagulation" Hematol. 28:10, 1991.
Bendele et al, "Short Communication: Renal Tubular Vacuolation in Animals Treated with Polyethylene-Glycol-Conjugated Proteins" Toxicological Sciences 42, 152-157 (1998).
Benesch "Bis(pyridoxal) Polyphosphates as Specific Intramolecular Cross-Linking Agents for Hemoglobin" (Meth. Enzymol., vol. 231 (1994), 267-274).
Bepperling et al, "HES 130/0.4, a new HES specification: tissue storage after multiple infusions in rats" Crit. Care, vol. 3, Suppl. 1 (1999), p. 153.
Berg D.T. et. al. „Engineering the proteolytic specificity of activated protein C improves its pharmacological properties Proc. Natl. Acad. Sci. USA 100 (2003) pp. 4423-4428.
Berger, Greber, Mosbach, 1986, Galactosyltransferase-dependent sialylation of complex and endo-N-acetylglucosaminidase H-treated core N-glycans in vitro, FEBS Lett., 203(1), 64-8.
Bernardes et al., "The Direct Formation of Glycosyl Thiols from Reducing Sugars Allows One-Pot Protein Glycoconjugation" Angew. Chem. 118, 2006, 4111-4115.
Besheer Ahmed et al.: "Enzymatically catalysed HES conjugation using microbial transglutaminase: Proof of feasibility" , Journal of Pharmaceutical Sciences, Nov. 2009, 4420-4428.
Bhattacharyya et al. "Recombinant Factor VIII for Haemophilia, An Overview of Production Technologies" 2003, CRIPS 4/3: 2-8.
Bjork, "Antithrombin and related inhibitors of coagulation proteinases in Barett , Salvesen (eds.): Proteinase Inhibitors" vol. 17, Amsterdam , The Netherlands Elsevier Science Publishers (Biomedical Devision) 1986 p. 489.
Black, et al. "*N*-Bromoacetyl-glycopyranosylamines as affinity labels for a β-glucosidase and a cellulose" 1993, Carbohydr. Res., 250, 195.
Bobbit J.M., "Periodate Oxidation of Carbohydrates" Ad Carbohydr. Chem. 1956, 11, 1-41.
Boissel, Lee, Presnell, Cohen, Bunn, 1993, Erythropoietin structure-function relationships. Mutant proteins that test a model of tertiary structure, J Biol Chem., 268(21), 15983-93).
Boorsma et al. "Bioprocess Applications of Sindbis Virus-Based Temperature-Inducible Expression System" (2002) Biotechnol. Bioeng. 79(6): 602-609.
Boturyn D. et al., "Synthesis of Fluorescent Probes for the Detection of Abasic Sites in DNA" Tetrahedron 53 (1997) 5485-5492.
Bowen, Culligan, Beguin, Kendall, Villis, 1994, "Estimation of effective and total erythropoiesis in myelodysplasia using serum transferrin receptor and erythropoietin concentrations, with automated reticulocyte parameters" Leukemi, 8(1), 151-5.
Boyer et al, "Reaction in Biphasic Water/Organic Solvent System in the Presence of Surfactant: Inverse Phase Transfer Catalysis versus Interfacial Catalysis" Tetrahedron, 2000, 56, pp. 303-307.
Bunn & Jandl, J. "The Renal Handling of Hemoglobin" Exp. Med. 129, (1967) 925-934.
Burgess, A.W. et al. 1977, Stimulation by human placental conditioned medium of hemopoietic colony formation by human marrow cells, Blood 49 (1977), 573-583.
Bystricky S. et al., "Determination of the cross-linking effect of adipic acid dihydrazide on glycoconjugate preparation" Glycoconj. J. 1999, 16, 691-95.
C.Chu et al., "Further Studies on the Immunogenicity of *Haemophilus influenzac* Type b and Pneumococcal Type 6A Polysaccharide-Protein Conjugates" Infect. Immun. 1983, 40, 245-56.
Cabacungan J.C. et al. "Amine Boranes as Alternative Reducing Agents for Reductive Alkylation of Proteins" Anal. Biochem. 1982, 124, 272-78.
Carrell, R. W., et al. "Human α1-Antitrypsin: Carbohydrate Attachment and Sequence Homology" FEBS Letters 135 (1981) p. 301.
Carrell, Robin, et al. "Structural mobility of Antithrombin and its Modulation by Heparin" Thromb. Haemost. 78:516, 1997.
Carlsson J. et al., "Protein Thiolation and Reversible Protein-Protein Conjugation" Biochem J. 1978, 173, 723-37.
Carver, A., et al. "Expression of human α1 antitrypsin in transgenic sheep" Cytotechnology 9 (1992) p. 77.
Castillo et al., „Sensitive Substrates for Human Leukocyte and Porcine Pancreatic Elastase: A Study of the Merits of Various Chromophoric and Fluorogenic Leaving Groups in Assays for Serine Proteases Anal. Biochem. 1979, 99, 53-64.
Cebon, J.; Nicola, N.; Ward, M.; Gardner, I.; Dempsey, P.; Layton, J.; Dürhrsen, U.; Burgess, A.; Nice, E.; Morstyn, G. Granulocyte-macrophage colony stimulating factor from human lymphocytes. The effect of glycosylation on receptor binding and biological activity. J. Biol. Chem. 1990, 265, 4483-4491.

Cera C., et al: Water-Soluble Polysaccharide-Anthracycline Conjugates: Biological Activity, Anti-Cancer Drug Design, vol. 7, No. 2, Apr. 1992, pp. 143-151, XP000791063, ISSN: 0266:9536.

Cerami, Beyond erythropoiesis: novel applications for recombinant human erythropoietin, 2001, Semin Hematol., (3 Suppl 7):33-9 (Review).

Cerny et al.; A Hydroxyethyl Starch-Hemoglobin Polymer as a Blood Substitute, Clinical Hemorheology, vol. 2, No. 4, pp. 355-365 (1982).

Cervigni, S.E., Dumi, P., Mutter, M. (1996) Synthesis of Glycopeptides and Lipopeptides by Chemoselective Ligation. Angewandte Chemie International Edition in English, vol. 35, No. 11, p. 1230-1232.

Chamow S.M. et al., "Conjugation of Soluble CD4 without Loss of Biological Activity via a Novel Carbohydrate-directed Cross-linkig Reagent" J. Biol. Chem. 1992, 267, 15916-22.

Chang et al., "Blood Substitutes Based on Modified Hemoglobin Prepared by Encapsulation or Crosslinking: An Overview" Biomat. Art. Cells & Immob. Biotech., 20, (1992) 159-179.

Changon et al., „Murine renal cell carcinoma: evaluation of a dendritic-cell tumour vaccine'e.g. BJU Int., vol. 88 (2001), pp. 418-424.

Chaplin and Kennedy (eds.), 1986, Carbohydrate Analysis: a practical approach, IRL Press Practical approach series (ISBN 0-947946-44-3), p. 1-36; p. 37-53, p. 55-96.

Chaplin and Kennedy (eds.), 1996, Carbohydrate Analysis: a practical approach, expecially chapter 5 Montreuill, Glycoproteins, pp. 175-177; IRL Press Practical approach series (ISBN 0-947946-44-3).

Chaplin, M.F. (1982) A rapid and sensitive method for the analysis of carbohydrate components in glycoproteins using gas-liquid chromatography; Anal. Biochem. 123, 336-341.

Chapman et al., "Therapeutic antibody fragments with prolonged in vivo half-lives" Nature Biotech, vol. 17 (1999), pp. 780-783.

Chen, Hammond, Lang and Lebing, Purification of α1 Proteinase Inhibitor from Human Plasma Fraction IV-I by Ion Exchange Chromatography, VoxSanguinis 1998, 74, 232-241.

Choay, Ann. "Structural Studies on a Biologically Active Hexasaccharide Obtained from Heparin" NY Acad. Sci. 370:644, 1981.

Choay, J., et al. "Structure-Activity Relationship in Heparin: A Synthetic Pentasaccharide with High Affinity for Antithrombin III and Eliciting High Anti-Factor Xa Activity" Biochem. Biophys. Res. Commun. 116:492, 1983.

Chow et al., "In vitro induction of apoptosis of neoplastic cells in low-grade non-Hodgkin's lymphomas using combinations of established cytotoxic drugs with bendamustine" Haematologica, vol. 86 (2001), pp. 485-493.

Colman, A. Production of therapeutic proteins in the milk of transgenic livestock Biochem. Soc. Symp. 63 (1998) p. 141.

Conradt HS, Nimtz M, Dittmar KE, Lindenmaier W, Hoppe J, Hauser H, Expression of human interleukin-2 in recombinant baby hamster kidney, Ltk-, and Chinese hamster ovary cells. Structure of O-linked carbohydrate chains and their location within the polypeptide; J. Biol. Chem. 1989 264: 17368-17373.

Corey, E.J., et al., "A New Method for the Synthesis of 2-Pyridinethiol Carboxylic Esters" Tetrahedron Lett. (1979), 2875.

Cumber, et al. "Preparation of Antibody-Toxin Conjugates" 1985, Methods Enzymol., 112, 207.

De Koning M.C. et al; An approach to the synthesis of peptide-PNA-peptide conjugates via native ligation; Tetrahedron Letters; Elsevier; Amsterdam, NL, vol. 43, No. 45; Nov. 4, 2002; pp. 8173-8176; XP004387215; ISSN: 0040-4039.

Delgado et al. "The Uses and Properties of PEG-Linked Proteins" Critical Reviews in Therapeutic Drug Carrier Systems, vol. 9 (3, 4), (1992) pp. 249-304.

Delorme, Lorenzini, Giffin, Martin, Jacobsen, Boone, Elliott, 1992, Role of glycosylation on the secretion and biological activity of erythropoietin, Biochemistry, 31(41), 9871-6.

Denzlinger, C.; Tetzloff, W.; Gerhartz, H. H., Pokorny, R.; Sagebiel, S.; Haberl, C.; Wilmanns, W. Differential activation of the endogenous leukotriene biosynthesis by two different preparations of Granulocyte-Macrophage Colony-Stimulating Factor in healthy volunteers. Blood 1993, 81, pp. 2007-2013.

Dieterich et al, Hydroxyethyl Starch Antibodies in Humans: Incidence and Clinical Relevance, Anesth. Analg. 1998, 86:1123-1126.

Dittmar, Conradt, Hauser, Hofer, Lindenmaier, "Human Glycoproteins and Derived Variants from Recombineant Mammalian Cell Lines" 1989, Advances in Protein design; Bloecker, Collins, Schmidt, and Schomburg eds., GBF-Monographs, 12, 231-246, VCH Publishers, Weinheim, New York, Cambridge).

Donahue, R. E.; Wang, E. A.; Kaufman, R. J.; Foutch, L.; Leary, A. C.; Witek-Giannetti, J. S.; Metzeger, M.; Hewick, R. M.; Steinbrink, D. R.; Shaw, G.; Kamen, R.; Clark, S. C. Effects of N-linked carbohydrates on the in vivo properties of human GM-CkSF. Cold Spring Harbor Symp. Quant. Biol. 1986, 51, pp. 685-692.

Dorner AJ, Wasley LC, Kaufman RJ. Increased synthesis of secreted proteins induces expression of glucose-regulated proteins in butyrate-treated Chinese hamster ovary cells.J Biol Chem. 1989 Dec. 5; 264 (34):20602-7.

Dowling and Russel; "Pharmacokinetics of a long-acting oxytetracycline-polyethylene glycol formulation in horses" j. Vet. Pharmacol. Ther., vol. 23 (2000), 107-110.

Dreborg S. et al: "Immunotherapy with Monomethoxypolyethylene Glycol Modified Allergens", Critical Reviews in Therapeutic Drug Carrier Systems, Bd. 6, Nr. 4, 1990, Seiten 315-365, XP009022546, ISSN: 0743-4863.

Sadamoto R. et al; Control of Bacteria adhesion by cell-wall engineering; Journal of the American Chemical Society, Awashington DC, US, vol. 126, Mar. 31, 2004; pp. 3755-3761; XP008035406; ISSN: 002-7863.

Sadrzadeh et al; The Long-Acting Parenteral Iron Chelator, Hydroxyethyl Starch-Deferoxamine, Fails to Protect Against Alcohol-Induced Liver Injury in Rats; Journal of Pharmacology and Experimental Therapeutics, vol. 280, No. 2, pp. 1038-1042 (1997).

Sakai et al; Synthesis and Physicochemical Characterization of a Series of Hemoglobin-Based Oxygen Carriers: Objective Comparison between Cellular an Acellular Types; Bioconjugate Chemistry, vol. 11, No. 1, pp. 56-64 (2000).

Salo H. et al., "Aminooxy functionalized oligonucleotides: preparation, on-support derivatization, and postsynthetic attachment to polymer support" Bioconjugate Chemistry, vol. 10, No. 5, 1999, 815-823.

Sato et al., "Disposition of a Polymeric Prodrug of Mitomycin C, Mitomycin C-Dextran Conjugate, in the Perfused Rat Liver" J. Pharm. Sci., vol. 78 (1989), p. 11-16.

Sawaikar, D. D. et al; Products active on mosquitoes. Part VII, Synthesis and biological activity of longifolene derivatives Indian Journal of Chemistry, Section B: Organic Chemistry including Medicinal Chemistry, 34B(9), 832-5 Coden: IJSBDB, ISSN: 0376-4699, 1995, SP9043047.

Scaglione et al., "A New Model Examining Intracellular and Extracellular Activity of Amoxicillin, Azithromycin, and Clarithromycin in Infected Cells" Chemotherapie, vol. 39 (1993), 416-423.

Schaefer T et al.: „Two-Year Double-Blind Trial of a Monomethoxy Polyethylene Glycol MPEG Modified Grass Pollen Extract at Different Dose Levels, Annals of Allergy, Bd. 68, Nr. 4, 1992, Seiten 334-339, XP009022545, ISSN: 0003-4738.

Schlenke, Grabenhorst, Nimtz, Conradt, 1999, Construction and characterization of stably transfected BHK-21 cells with human-type sialylation characteristic, Cytotechnology, 30(1-3), 17-25.

Schlesinger "Alphaviruses—vectors for the expression of heterologous genes" (1993) Trends Biotechnol. 11(1):18-22.

Schneerson et al., "Preparation, characterization, and immunogenicity of *Haemophilus influenza* Type b polysachraride-protein conjugates", JEM, vol. 152, 1980, 2361-2376.

Schottelius M., Wester H.J., Reubi J.C., et al; Improvement of Pharmacokinetics of Ratioiodinated Tyr[3]-Octreotide by Conjugation with Carbohydrates, Bioconjugate Chem. 2002, 1021-1030.

Schröter, S., Derr, P., Conradt, H.S., Nimtz, M., Hale, G. & Kirchhoff, C. (1999) Male-specific modification of human CD52. J. Biol. Chem. 274, 29862-29873.

Seymour L et al, "A phase I study of BAY 38-3441 given as a short infusion daily for five days every 3 weeks. A National Cancer Institute of Canada Clinical Trials Group Study" European Journal of Cancer, Bd. 37, Apr. 1, 2001, Seite S73, XP004477499, ISSN: 0959-8049.

Shafer D.E. et al., "Activation of soluble polysaccharides with 1-cyno-4-dimethylaminopyridinium tetrafluoroborate (CDAP) for use in protein polysaccharide conjugate vaccines and immunological reagents. II. Selective crosslinking of proteins to CDAP-activated polysaccharides" Vaccine 2000, 18, 1273-81.

Shao J. and Tam J. P.: "Unprotected peptides as building blocks for the synthesis of peptide dendrimers with oxime, hydrazone and thiazolidine linkages" Journal of the American Chemical Society, vol. 117, No. 14, 1995, pp. 3893-3899, XP002172763.

Shah, R.G. et al. 1977, Characterization of colony-stimulating activity produced by human monocytes and phytohemagglutinin-stimulated lymphocytes, Blood 50 (1977), 811.

Shin, Y., et al., „Fmoc-Based Synthesis of Peptide-αThioesters: Application to the Total Chemical Synthesis of a Glycoprotein by Native Chemical Ligation J. Am. Chem. Soc. 121 (1999), 11684.

Shirafuji, N. et al.1989, A new bioassay for human granulocyte colony-stimulating factor (hG-CSF) using murine myeloblastic NFS-60 cells as targets and estimation of its levels in sera from normal healthy persons and patients with infectious and hematological disorders, Exp. Hematol. 1989, 17, 116-119.

Simmons G., et al; Potent inhibition of HIV-1 infectivity in macrophages and lymphocytes by a novel CCr5 antagonist; Science, American Association for the advancement of science, US, vol. 276, Apr. 11, 1997, pp. 276-279, XP002091209, ISSN: 0036-8075.

Skopp & Lane "Fingerprinting of proteins cleaved in solution by cyanogen bromide" (1988), Appl. Theor. Electrophor. 1, 61-64.

Skwarczynski, M. et al. : "Paclitaxel prodrugs: Toward smarter delivery of anticancer agents", Journal of Medicinal Chemistry, Dec. 2006, 7253-7269.

Snyder et al. „HbXL99α: A hemoglobin derivative that is cross-linked between the αsubunits is useful as a blood substitute (Proc. Natl. Acad. Sci. USA, 84, (1987), 7280-7284.

Somogyi, N.; "Somogyi Micro Copper Method" Method in Carbohydride Chemistry, vol. 1 (1962), p. 384-386.

Song et al., "Toxicity and Antitumor Activity of the Conjugate of Mitomycin C with Carboxymethyl-chitin" Arch. Pract. Pharm. vol. 53 (1993), p. 141-147.

Souza et al., Recombinant human granulocyte colony-stimulating factor: effects on normal and leukemic myeloid cells, Science 232 (1986) 61-65.

Soyez et al., "Biological evaluation of mitomycin C bound to a biodegradable polymeric carrier" J. Controlled Release, vol. 47 (1997), p. 71-80.

Spellman M.W., Basa L.J., Leonard C.K., Chakel J.A., O'Connor J.V., "Carbohydrate Structures of Human Tissue Plasminogen Activator Expressed in Chinese Hamster Ovary Cells" The Journal of Biological Chemistry 264 (1989) p. 14100.

Spivak and Hogans, "The In Vivo metabolism of Recombinant human Erythropoietin in the Rat" 1989, Blood 73, 90.

Staros J.V., "N-Hydroxysulfosuccinimide Active Esters: Bis(N-hydroxysulfosuccinimide) Esters of Two Dicarboxylic Acids Are Hydrophilic, Membrane-Impermeant, Protein Cross-Linkers" Biochemistry 1982, 21, 3950-55.

Stein et al. "Development and Characterization of Novel human multidrug Resistant Mammary Carcinoma Lines in vitro and in Vivo" Int. J. Cancer 72: 885-91 (1997).

Stetsenko, D.A. et al, Efficient conjugation of peptides to oligonucleotides by native ligation; Journal of Organic Chemistry; American Chemical Society; Easton, US, vol. 65, 2000; pp. 4900-4908; XP000992973; ISSN: 0022-3263.

Stewart R.J. et.al. "Identification of the Mechanism responsible for the Increased Fibrin specificity of TNK-Tissue Plasminogen Activator Relative to Tissue Plasminogen Activator" The Journal of Biological Chemistry 275 (2000) pp. 10112-10120.

Sunamoto J., Iwamoto K. "Protein-Coated and Plysaccharide-Coated Liposomes as Drug Carriers" CRC Critical Reciew in Therapeutic Drug Carrier Systems 1986, 2, 117-136.

Sytkowski, Lunn, Davis, Feldman, Siekman, 1998, Human erythropoietin dimers with markedly enhanced in vivo activity, Proc. Natl. Acad. Sci. USA, 95(3), 1184-8.

Sytkowski, Lunn, Risinger, and Davis, 1999, An Erythropoietin Fusion Protein Comprised of Identical Repeating Domains Exhibits Enhanced Biological Properites, J. Biol. Chem., 274, 24773-24778.

Takeuchi, Inoue, Strickland, Kubota, Wada, Shimizu, Hoshi, Kozutsumi, Takasaki, Kobata, 1989, Relationship between sugar chain structure and biological activity of recombinant human erythropoietin produced in Chinese hamster ovary cells, Proc. Natl. Acad. Sci. USA, 85(20), 7819-22.

Takeuchi, Kobata, Structures and functional roles of the sugar chains of human erythropoietins, Glycobiology, 1(4), 337-46 (Review) 1991.

Tam., J.P., et al., "Peptide synthesis using unprotected peptides through orthogonal coupling methods" Proc. Natl. Acad. Sci. USA 92 (1995) 12485.

Tanaka, H. et al. 1991, Pharmacokinetics of recombinant human granulocyte colony-stimulating factor conjugated to polyethylene glycol in rats, Cancer Research 51, 3710-3714,1991.

Tebbutt, Scott J. "Technology evaluation: Transgenic α-1-antitrypsin (AAT), PPL Therapeutics" Curr. Opin. Mol. Ther. 2 (2000) p. 199.

Thim, L. et al., "Amino Acid Sequence and Posttranslational Modifications of Human factor VIIa from Plasma and Transfected Baby Hamster Kidney Cells" Biochemistry 27:7785-7793(1988).

Thomas et al., "Measuring blood volume with fluorescent-labeled hydroxyethyl starch" Crit. Care Med. 2000 vol. 28, No. 3 (DS).

Thomas, E.W. "Carbohydrate Binding Sites" 1977, Methodes Enzymol., 46, 362.

Thorpe et al., "Blockade of the galactose-binding sites of ricin by its linkage antibody" 1984, Eur. J. Biochem., 140, 63.

Tomasik and Schilling, "Chemical Modification of Starch" Advances in carbonhydrate Chemistry and Biochemistry, vol. 59, 2004, 175-402.

Toole et al., "Molecular cloning of a cDNA encoding human antihaemophilic factor" 1984, Nature 312: 342.

Toyama et al; Surface Design of SPR-based immunosensor for the effective binding of antigen or antibody in the evanescent field using mixed polymer matrix Sensors and Actuators B, vol. 52, Issues 1-2, pp. 65-71 (1998).

Travis, J. et al. "Human Plasma Proteinase Inhibitors" Ann. Rev. Biochem. 52 (1983) p. 655.

Valasco de, Merkus, Anderton, Verheul, Lizzio, Van der Zee, van Eden, Hoffmann, Verhoef, Snippe, „Synthetic Peptides Representing T-Cell Epitopes Act as Carriers in Pneumococcal Polysaccharide Conjugate Vaccines 1995, Infect. Immun., 63, 961.

Van Patten SM, Hanson EH, Bernasconi R, Zhang K, Manavaln P, Cole ES, McPherson JM, Edmunds T, Oxidation of Methionine Residues in Antithrombin, J. Bio. Chemistry 274, 15 (1999) 10268-10276.

Vasey PA, Kaye SB, Morrison R, et al. (Jan. 1999) "Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee". *Clinical Cancer Research* 5 (1): 83-94.

Veronese et al.; "Surface Modification of Proteins" Applied Biochem. Biotech., vol. 11, 141-152 (1995).

Vilaseca L. et al; Protein conjugates of defined structure: Synthesis and use of a newcarrier molecule; Bioconjugate Chemistry, American Chemical Society, Washington US, vol. 4, No. 6, Nov. 1, 1993; pp. 515-520, XP000417288; ISSN: 1043-1802.

Wadhwa, M.; Hjelm Skog, A-L.; Bird, C.; Ragnhammar, P.; Lilljefors, M.; Gaines-Das, R.; Mellstedt, H.; Thorpe, R. Immunogenicity of Granulocyte-Macrophage Colony-Stimulating Factor (GM-CSF) products in patients undergoing combination therapy with GM-CSF. Clinical Cancer Research 1999, 5, pp. 1351-1361.

Waitzinger et al. "Pharmacokinetics and Tolerability of a New Hydroxyethyl Starch (HES) Specification [HES (130/0.4)] after Single-Dose Infusionof 6% or 10% Solutions in Healthy Volunteers" (Clin. Drug Invest. 1998; 16: 151-160).

Wang et al., "Delivery of Antisense Oligonucleotides Using HPMA Polymer: Synthesis of A Thiol Polymer and Its Conjugation to Water-Soluble Molecules" Bioconjugate Chem., 1998, 9: 749-757.

Watanabe, Y., et al., "A Facile Synthesis of Carboxylic Thiol Esters From Carboxylic Acids and Thiols" Chem. Lett. (1976) 741.

Webb R.R. 2nd et al; Synthesis of 1-(aminooxy)-4-'(3-nitro-2-pyridyl)dithio! Butane and 1-(aminooxy)-4-'(3-nitro-2- pyridyl)dithio! But-2-ene, novel heterobifunctional cross-linking regents; Bioconjugate Chemistry, vol. 1, No. 2, Mar. 1990, pp. 96-99, XP002223790, ISSN: 1043-1802.

Weidler et al., „Pharmacokinetic parameters as criteria for clinical use of hydroxyethyl starch preparations Arzneim.-Forschung/Drug Res., 41, (1991) 494-498 (English Summary).

Weisshaar G., Hiyama J., Renwick A.G.C., Nimtz M.; "NMR investigations of the N-linked oligosaccharides at individual glycosylation sites of human lutropin."; Eur. J. Biochem. 195:257-268(1991).

Whitesides et al., "Rates of Thiol-Disulfide Interchange Reactions between Mono-and Dithiols and Ellman's Reagent" 1977, J. Org. Chem., 42, 332.

Wilchek, M., Bayer, E.A., Labeling "Glycoconjugates with Hydrazide Reagents", 1987, Methods in Enzymology, 138, 429-442.

Wong S.Y.C. et al., "Analysis of carbohydrate-protein interactions with synthetic N-linkied neoglycoconjugate probes" Biochem. J. 1993, 296, 817-825.

Wong S.Y.C. et al., "Synthetic glycosylation of proteins using N-((β-saccharide) iodoacetamides: applications in site-specific glycosylation and solid-phase enzymic oligosaccharide synthesis" Biochem. J. 1994, 300, 843-850.

Wright, G., et al. "High Level Expression of Active Human Alpha-1-antitrypsin in the milk of transgenic sheep" Biotechnology (NY) 9 (1991) p. 830.

Xue and Wong; "Preparation of Conjugated Hemoglobins" Meth in Enzymol., 231, (1994), pp. 308-322.

Yalpani et al., Journal of Polymer Science: Polymer Chemistry Edition, vol. 23, 1395-1405 (1985), Selective Chemical Modifications of Dextran.

Yamaguchi, Akai, Kawanishi, Ueda, Masuda, Sasaki, 1991, Effects of site-directed removal of N-glycosylation sites in human erythropoietin on its production and biological properties, J. Biol. Chem., 266(30), 20434-9.

Yang W. et al.: "Functional Changes of Carboxymethyl Potato Starch by Conjugation with Amino Acids" Bioscience Biotechnology and Biochemistry, vol. 59, No. 12, 1995, pp. 2203-2206, XP008056456.

Yoshida T., "Glycamine Formation via Reductive Amination of Oligosaccharides with Benzylamine" Methods Enzymol. 1994, 247, 55-64.

Yoshitake S. et al., "Nucleotide Sequence of the Gene for Human Factor IX (Antihemophilic Factor B)" Biochemistry 24:3736-3750(1985).

Zalipsky S., "Functionalized Poly(eithylene glycol) for Preparation of Biologically Relevant Conjugates" Bioconjugate Chem. 1995, 6, 150-165.

Zara J.J. et al., "A Carbohydrate-Directed Heterobifunctional Cross-Linking Reagent for the Synthesis of Immunoconjugates" Anal. Biochem. 1991, 194, 156-62.

Zettlmissl et al., "Chacterization of Recombinant Human Antithrombin III Synthesized in Chinese Hamster Ovary Cells" 1989, J. Biol. Chem., 264, 21153-21159.

Zhang, L. et al, "Thiazolidine formation as a general and site-specific conjugation method . . . " Anal. Biochem. (1996) vol. 233, pp. 1996.

Zhou et al., 1998, Application of capillary electrophoresis, liquid chromatography, electrospray-mass spectrometry and matrix-assisted laserdesorption/ionization—time of flight—mass spectrometry to the characterization of recombinant human erythropoietin, Electrophoresis, 19(13), 2348-55.

Zou W. et al., "Allylmalonamide as a bivalent linker: Synthesis of biantennary GM3-saccharide-Keyhold limpet hemocyanin glycoconjugate and the immune response in mice" Glycoconj. J. 1999, 16, 507-15.

Zucali, Sulkowski, 1985, Purification of human urinary erythropoietin on controlled-pore glass and silicic acid, Exp. Hematol., 13(3), 833-7.

Veronese F. M., "Peptide and protein PEGylation—a review of problems and solutions" Biomaterials, Elsevier Science Publishers BV., Barking, GB, vol. 22, No. 5, Mar. 1, 2001, pp. 405-528, XP004227886, ISSN: 0142-9612.

McGraw-Hill's Access Science [online], "Oxime "[retrieved May 9, 2011]."Oxime" Retrieved from the internet <http://accessscience.com/content.aspx?searchStr=osime&id=480600>.

Dörwald, F. Z. (2005) Side Reactions in Organic Synthesis, A Guide to Successful Synthesis Design. Published by Wiley-VCH Verlag GmbH & Co. Preface p. IX-X.

Molecular Biosciences [online], "Heterobifunctional Crosslinkers" [retrieved on Jun. 6, 2011], retrieved from the internet http://web.archive.org/web/20011104182428/http://www.molbio.com/Heterobi.htm published Nov 2001.

Veronese, Francesco M., et al. "Immunological Propertiesof Uricase Conjugated to Neutral Soluble Polymers" Bioconjugate Chem., 2001, 12 (4), pp. 515-522 (Publication date (web): Jun. 9, 2001 (Article).

Jean G. Riess, "Oxygen Carriers (Blood Substitutes) Raison D'Etre, Chemistry and some Physiology" Chem. Rev., 2001, 101 (9), pp. 2797-2920, Publication date (web): Sep. 12, 2001 (Article).

Edmunds T, Van Patten SM, Pollock J, Hanson E, Bernasconi R, Higgins E, Manavalan P, Ziomek C, Meade H, McPherson J, Cole ES, Transgenically Produced Human Antithrombin: Structural and Functional Comparison to Human Plasma-Derived Antithrombin, Blood 91, 12 (1998) 4661-4671.

Blum, et al. Elektrophoresis, "Improved silver staining of plynt proteins, RNA and DANN polyacrylamide gels" vol. 8 (1997), p. 93-99.

Elliott, Lorenzini, Chang, Barzilay, Delorme, 1997, Mapping of the active site of recombinant human erythropoietin, Blood, 89(2), 493-502.

Etrych et al. "New HMPA copolymers containing doxorubicin bound via pH-sensitive linkage: synthesis and preliminary in vitro and in vivo biological properties", Journal of Controlled Release, Elsevier, vol. 73, No. 1 (2001), 89-102.

European Pharmacopoeia, 1996, Erythropoietin concentrated solution, Pharmaeuropa., 8, 371-377.

European Pharmacopeia 2001, 911-917.

European Pharmacopoeia (1996/2000); pp. 655-660.

European Pharmacopoeia; Erythropoietin Concentrated Solution, 4th Edition, 2002, pp. 1123-1128.

F.C. Hartman, "Cross-Linking of Bovine Pancreatic Ribonuclease a with Dimethyl Adipimidate" F. Wold, Biochemistry 1967, 6, 2439-48.

Fernandez-Santana V. et al., "Conjugation of 5-azido-3-oxapentyl glycosides with thiolated proteins through the use of thiophilic derivatives" Glycoconj. J. 1998, 15, 549-53.

Fibi et al., "Evidence for the Location of the Receptor-Binding Site of Human Erythropeietin at the Carboxyl Terminal Domain" 1991, Blood, 77, 1203 ff.

Fibi, Hermentin, Pauly, Lauffer, Zettlmeissl., 1995, N- and O-glycosylation muteins of recombinant human erythropoietin secreted from BHK-21 cells, Blood, 85(5), 1229-36.

Fissekis et al., "N-Pantoyl-(substituted)amines, Pantothenic Acid Analogues" 1960, Journal of Medicinal and Pharmaceutical Chemistry, 2, 47.

Forno Guillermina, Mariela Bollati Fogolin Mariela, Oggero Marcos, Kratje Ricardo, Etcheverrigaray Marina, Conradt Harald S., Nimtz Manfred (2004) N- and O-linked carbohydrates and glycosylation site occupancy in recombinant human granulocyte-macrophage colony-stimulating factor secreted by a Chinese hamster ovary cell line; European J. Biochem, 271(5) od. 273(5), 907-919.

Franzen, J. "Structural Studies on the Carbohydrate Portion of Human Antithrombin III" Biol. Chem. 255:5090, 1980.

Fujiki Y., Rathnam P., Saxena B.B.;"Studies on the disulfide bonds in human pituitary follicle-stimulating hormone."; Biochim. Biophys. Acta 624:428-435(1980).

Gaertner H.F. et al; Site-specific attachment of functionalized poly (ethylene glycol) to the amino terminus of prothein; Bioconjugate Chemistry, American Chemical, Society, Washington US; vol. 7, no. 1, Jan. 1996; pp. 38-44, XP 000646874, ISSN: 1043-1802.

Ganson, S.J. Kelly et al. "Control of hyperuricemia in subjects with refractory gout, and induction of antibody against poly(eithylene glycol) (PEG), in a phase I trial of subcutaneous PEGylated urate oxidase" Arthritis Research & Therapie 2006, 8:R12.

Gaucher S.P., Pedersen S.F., Leary J.A.; Stereospecific Synthesis and Characterization of Aminoglycoside Ligands from Diethylenetriamine, (1999), Journal of Organic Chemistry, v. 64, p. 402-4015.

Gelderblom et al. "Cremophore EL: the drawbacks and advantages of vehicle selection for drug formulation", European Journal of Cancer, vol. 31, Issue 13, pp. 1590-1598.

Gervais V. et al.,"NMR investigations of the role of the sugar moiety in glycosylated recombinant human granulocyte-colony-stimulating factor" Eur. J. Biochem. 1997, 247, 386-395.

Gerweck et al "Tumor PH controls in the in vivo efficacy of weeak acid and base chemotherapeutics" Mol Cancer Ther 2006;5(5):1275-9.

Gillis, Ferm, Ou, and Smith, "T Cell Growth Factor: Parameters of Production and a Quantitative Microassay for Activity" 1978, J.Immunol., 120, 2027-2032.

Gonzalez-Lio R., J. Thiem, "Chemoenzymatic synthesis of spacer-linked oligosaccharides for the preparation of neoglycoproteins" Carbohydr. Res. 1999, 317, 180-90.

Goronzy JJ, Gold KN, Weyand CM. T-Cell Derived Lymphokines as Regulators of Chronic Inflammation: Potential Targets for Immunomodulation? Am J Ther. Feb. 1996;3(2):109-114.

Gould et al., "The Development of Hemoglobin Solutions as Red Cell Stubstitutes: Hemoglobin Solutions" Transfus. Sci. 16, (1995) 5-17.

Grabenhorst E., Hoffmann A., Nimtz M., Zettlmeiβl G. and Conradt H. S. (1995), Construction of stable BHK-21 cells coexpressing human secretory glycoproteins and human Galβ1-4GlcNAc-Ra2,6-sialyltransferase: a2,6-linked NeuAc is preferably attached to the Galβ1-4GlcNAcβ1-2Manβ1-3-branch of biantennary oligosaccharides from secreted recombinant $-trace protein. Eur.J.Biochem., 232, 718-725.

Grabenhorst, Conradt, 1999, The cytoplasmic, transmembrane, and stem regions of glycosyltransferases specify their in vivo functional sublocalization and stability in the Golgi., J Biol Chem., 274(51), 36107-361116.

Grabenhorst, Hofer, Nimtz, Jager, Conradt, 1993, Biosynthesis and secretion of human interleukin 2 glycoprotein variants from baculovirus-infected Sf21 cells. Characterization of polypeptides and posttranslational modifications, Eur J Biochem., 215(1), 189-97.

Grabenhorst, Nimtz, Costa et al., 1998, In vivo specificity of human alpha 1,3/4-fucosyltransferases III-VII in the biosynthesis of Lewis(x) and sialyl Lewis(x) motifs on complex-type N-glycans—Coexpression studies from BHK-21 cells together with human beta-trace protein, J. Biol. Chem., 273(47), 30985-30994.

Grabenhorst, Schlenke, Pohl, Nimtz, Conradt, 1999, Genetic engineering of recombinant glycoproteins and the glycosylation pathway in mammalian host cells, Glycoconj J., 16(2), 81-97.

Gray G.R. , ,,The Direct Coupling of Oligosaccharides to Prteins and Derivatized Gels Arch. Biochem. Biophys. 1974, 163, 426-28 (Fig. 2.1a).

Greenfield et al., "Evaluation in Vitro of Adriamycin Immunoconjugates Synthesized Using an Acid-sensitive Hydrazone Linker" 1990, Cancer Research, 50, 6600.

Greenwald et al., "Drug Delivery Systems: Water Soluble Taxol 2'-Ply(ethylene glycol) Ester Prodrugs—Design and in vivo Effectiveness" J. Med. Chem., 1996, 39: 424-431.

Gribben, J.G.; Devereix, S.; Thomas, N. S. B.; Keim, M.; Jones, H. M.; Goldstone, A. H.; Linch, D. C. Development of antibodies to unprotected glycosylation sites on recombinant GM-CSF. Lancet 1990, 335, pp. 434-437.

Grieco, P., et al., "Aryl Selenocyanates and Aryl Thiocyanates: Reagents for the Preparation of Activated Esters" Tetrahedron Lett. 43 (1979) 1283.

Grimmecke H.D., H. Brade, Glycoconj. J. Studies on the reductive amination of 3-deoxy-D-*manno*-octulosonic acid (Kdo) 1998, 15, 555-62.

Guillaumie F. et al.: "Immobilization of Pectin Fragments on solid supports: novel coupling by thiazolidine formation" Bioconjugate Chemistry, vol. 13, 2002, pp. 285-294, XP002357091.

Guillermina Forno, Mariela Bollati Fogolin, Marcos Oggero, Ricardo Kratje, Marina Etcheverrigaray, Harald S. Conradt, Manfred Nimtz (2004) N- and O-linked carbohydrates and glycosylation site occupancy in recombinant human granulocyte-macrophage colony-stimulating factor secreted by a Chinese hamster ovary cell line; European J. Biochem, 273(5), 907919.

Habeeb, "Determination of Free Amino Groups in Prteins by Trinitrobenzenesulfonic Acid" Anal. Biochem., 1996, 14:328-336.

Hai et al. "Diaspirin Crosslinked Hemoglobin (CHLHb) Polymerization" (Art. Cells, Blood Subs. and Immob. Biotech, 22(3) (1994), 923-931.

Hamilton TC, et al. "Characterization of a Human Ovarian Carcinoma Cell Line (NIH: OVCAR-3)1 with Androgen and Estrogen Receptors" Cancer Res. 43: 5379-5389 (1983).

Hamma Tomoko et al; 4-(2-aminooxyethoxy)-2-(ethylureido)quinoline-oligonucleotide conjugates: synthesis, binding interactions, and derivatization with peptides; Bioconjugate Chemistry. Mar.-Apr. 2003, vol. 14, No. 2, Mar. 2003, pp. 320-330; XP002301933, ISSN 1043-1802.

Harada M et al, "Carrier and dose effects on the pharmacokinetics of T-0128, a camptothecin analogue-carboxymethyl dextran conjugate, in non-tumor- and tumor bearing rats" Journal of controlled release, Bd. 71, Nr. 1, 12. Mar. 12, 2001, Seiten 71-86, XP004229495, ISSN: 0168-3659, DOI:10.1016/S0168-3659(00)00321-7.

Harada M et al, "Determinants for the drug release from T-0128, camptothecin analogue-carboxymethyl dextran conjugate" Journal of controlled release, Bd. 69, Nr. 3, Dec. 3, 2000, Seiten 399-412, XP004221290, ISSN: 0168-3659, DOI:10.1016/S0168-3659(00)00321-7.

Harris et al., "Pegylation—A Novel Process for Modifying Pharmacokinetics" (2001) Clin. Pharmacokin. 40, 539-551.

Hashimoto et al, Kunststoffe, Kautschuk, Fasern, ,,Chemical Modification of the Reducing Chain End in Dextrans and Trimethylsilylation of Its Hydroxyl Groups vol. 9, 1992, S.1271-79.

Hattori et al., "Reduced Immunologenicity of β-Lactoglobulin by Conjugation with Carboxymethyl dextran" Bioconjug Chem Jan.-Feb. 2000, 11(1):84-93.

He et al. "A simplified system for generating recombinant adenoviruses" (1998) Proc. Natl. Acad. Sci. USA 95:2509-2514.

Heindel, Ned D. et al., "Hydrazide Pharmaceuticals as Conjugates to Polyaldehyde Dextran" 1990, Bioconjugate Chem. 1, 77-82.

Herman et al., Characterization, formulation, and stability of Neupogen® (Filgrastim), a recombinant human granulocyte-colony stimulating factor, in: Formulalion, characterization, and stability of protein drugs, Rodney Pearlman and Y. John Wang, eds., Plenum Press, New York, 1996, 303-328.

Hermentin P, Witzel R, Vliegenthart JF, Kamerling JP, Nimtz M, Conradt HS.: A strategy for the mapping of N-glycans by high-ph anion-exchange chromatography with pulsed amperometric detection, Anal Biochem. Jun. 1992; 203(2):281-9.

Higuchi, Oheda, Kuboniwa, Tomonoh, Shimonaka, Ochi, 1992 ;Role of sugar chains in the expression of the biological activity of human erythropoietin, J. Biol. Chem., 267(11), 7703-9.

Hodges "Locations of Oligosaccharide Chains in Human βl-Protease Inhibitor and Oligosaccharide Structure at Each Site" Biochemistry 21 (1982) p. 2805.

Hodges "Structure of the Oligosaccharide Chains in Human βl-Protease Inhibitor" J. Biol. Chem. 254 (1979) p. 8208.

Hovgaard, D.; Mortensen, B. T.; Schifter, S.; Nissen, N. I. Clinical pharmacokinetic studies of a human haemopoietic growth factor, GM-CSF. Eur. J. Clin. Inv. 1992, 22, pp. 45-49.

Hovinen, J., "Ethyl[2-Deoxy-5-0-(4,4'-Dimethoxytrityl)-αaand β-D-Erythro-Pentofuranosyl] Acetates as Versatile Intermediates in Nucleic Acid Chemistry" Nucleosides Nucleotides 18 (1999) 1263-4.

Iakovenko, A., et al., ,,Semi-Synthetic Rab proteins as tools for studying intermolecular interactions FEBS Letters 468 (2000) 155-158.

Ingenito, R., et al., ,,Solid Phase Synthesis of Peptide C-Terminal Thioesters by Fmoc/t-Bu Chemistry J. Am. Chem Soc. 121 (1999) 11369.

Inoue, Wada, Takeuchi, 1994, an improved method for the purification of human erythropoietin with high in vivo activity from the urine of anemic patients, Biol Pharm Bull. 17(2), 180-4.

Iwamoto K. et al., "Polysaccharide-Coated Oil Droplets in Oil-in-Water Emulsions as Targetable Carriers for Lipophilic Drugs" Journal of of Pharmaceutical Sciences 1991, 80, No. 3, 219 ff.

Jaques L.W., Riesco B.F., Weltner W.: "NMR Spectroscopy and calcium binding of sialic acids: N-glycolylneuraminic acid and periodate-oxidized N-acetylneuraminic acid" Carbohydrate Research, vol. 83, 1980, pp. 21-32, XP002357104 The Netherlands.
Jia et al. "S-nitrosohaemoglobin: a dynamic actifity of blood involved in vascular control" (Nature, 380, (1996) 221-226.
Jones D S, et al; A convenient synthesis of N-(tert-butyloxycarbonyl)aminooxy ethers; Tetrahedron Letters, Elsevier Science Publishers, Amsterdam NL, vol. 41, No. 10, Mar. 4, 2000, pp. 1531-1533, XP004189789, ISSN: 0040-4039.
Jones David S, et al; Multivalent poly (ethylene glycol)-containing conjugates for in vivo antibody suppression Bioconjugate Chemistry, vol. 14, No. 6, Nov. 2003; pp. 1067-1076, XP002302390, ISSN: 1043-1802.
Jungheinrich et al. "Pharmacokinetics of Hydroxyethyl Starch" (Clin Pharmacokinet. 2006; 44(7): 681-699.
Kallin E.,"Coupling of Oligosaccharides to Proteins Using p-Trifluoroacetamidoaniline" Methods Enzymol. 1994, 247, 119-23.
Katsumi et al., "Development of Polyethylene Glycol-Conjugated Poly-S-Nitrosated Serum Albumin, as Novel S-Nitrosothiol for Prolonged Delivery of Nitric Oxide in the Blood Circulation in Vivo" 2005, The Journal of Pharmacology and Experimental Therapeutics vol. 314 No. 3, pp. 1117-1124.
Kaufman et al., ,,Synthesis, Processing, and Secretion of Recombnant Human Factor VIII Expressed in Mammalian Cells 1988, J. Biol. Chem., 263: 6352.
Kaushansky, K.; O'Hara, P. J.; Hart, C. E.; Forstran, J. W.; Hagen, F. S. Role of carbohydrate in the function of human Granulocyte-Macrophage Colony-Stimulating Factor. Biochemistry 1987, 26, pp. 4861-4867.
Keaney et al., "NO Forms an Adduct with Serum Albumin that Has Endothelium-derived Relaxing Factor-like Properties" J. Clin. Invest., 91., (1993) 1582-1589.
Keene J.L., Matzuk M.M., Otani T., Fauser B.C.J.M., Galway A.B., Hsueh A.J.W., Boime I.; "Expression of biologically active human follitropin in Chinese hamster ovary cells."; J. Biol. Chem. 264:4769-4775 (1989).
Keipert et al. ,,Functional properties of a new crosslinked hemoglobin designed for use as a red cell substitute (Transfusion, vol. 29 (1989), 767-773).
Kinstler et al. "Characterization and Stability of N-terminally PEGylated rhG-CSF", (1996) Pharm. Res. 13, 996-1002.
Kitamura et al, "Establishment and Characterization of a Unique Human Cell Line that Proliferates Dependently on GM-CSF, IL-3, or Erythropoietin" 1989, J. Cell Phys., 140, 323-334.
Kitamura et al., "Chemical Engineering of the Mono Antibody A7 by Polyethyylene Glycol for Targeting Cancer Chemotherapy" Cancer Res., vol. 51 (1991), pp. 4310-4315.
Kobayashi et al., "Reduced Immunogenicity of β-Lactoglobulin by Conjugation with Carboxymethyl Dextran Differing in Molecular Weight" J Agric Food Chem Feb. 2001; 49(2):823-31.
Kochendoerfer Gerd G et al; Design and chemical synthesis of a homogeneous polymer-modified erythropoiesis protein; Science; Feb. 1, 2003; vol. 299; No. 5608; pp. 884-887 (ISSN 1095-9203, XP002325217).
Kojima et al., "Mitomycin C-dextran conjugate: a novel high molecular weight pro-drug of mitomycin C" J. Pharm. Pharmakol., vol. 32 (1980), p. 30-34.
Komatsu, Y. et al. 1987, Cloning of granulocyte colony-stimulating factor cDNA from human macrophages and its expression in *Escherichia coli* Jpn J Cancer Res. 1987 78(11):1179-1181.
Kraehenbuhl J.P. et al, Preparation and Characterization of an Immuno Electron Microscope Tracer consisting of a Heme Octa Peptide coupled to FAB, Journal of Experimental Medicine, vol. 139, No. 1, 1974, pp. 208-223, XP002329912, ISSN: 0022-1007.
Krantz, Erythropoietin, 1991, Blood, 77(3):419-34 (Review).
Krystal, 1983, Physical and biological characterization of erythroblast enhancing factor (EEF), a late acting erythropoetic stimulator in serum distinct from erythropoietin, Exp. Hematol., 11(1), 18-31.
Krystal, 1984, "A Simple Microassay for Erythropoietin Based on 3H-Thymidine Incorporation into Spleen Cells from Phenylhydrazine Treated Mice" Exp. Heamatol., 11, 649-660.

Krystal, Pankratz, Farber, Smart, 1986, Purification of human erythropoietin to homogeneity by a rapid five-step procedure, Blood, 67(1), 71-9.
Kulicke et al., "Measurements of the Refractive Index Increment on Hydroxyethyl Starch as a Basis for Absolute Molecular Weight Determinations" *Starch*, vol. 43, Issue 10 (1991), 392-396.
Lahiri, "Antithrombin-Heparin Cofactor: An Inhibitor of Plasma Kallikrein" Arch. Biochem. Biophys. 175:737, 1976.
Laine et al. "Polyethylene glycol nephrotoxicity secondary to prolonged high-dose intravenous lorazepam" The Annals of Pharmacotherapy, Nov. 1995, vol. 29, No. 11, pp. 1110-1114 (abstract only).
Lapthorn, A J, Harris, D.C., Littlejohn, A, Lustbader, J W, Canfield, R E, Machin, K J, Morgan, F J, Isaacs, N W: Crystal structure of human chorionic gonadotropin. Nature, 369, 455-461, 1994.
Larionova N I et al: "Conjugation of the Bowman-Birk Soybean Proteinase Inhibitor with Hydroxyethylstarch", Applied Biochemistry and Biotechnology, Clifton, NJ, US, vol. 62, No. 2/3, 1997, pp. 175-182, XP001122297, ISSN: 0273-2289.
Lee Dong-Chan et al., "Functional Polymers for Layer-by-Layer Construction of Multilayers via Chemoselective Immobizization" Macromolecules, vol. 37, No. 5, 2004, 1849-1856.
Lee et al., "Conjugation of Trypsin by Termperature-Sensitive Polymers Containing a Carbohydrate Moiety: Thermal modulation of Enzyme Activity" Biotechnol Prog, 1998, 14; 508-516.
Lee V.H.L., Ed. Peptide and Protein Drug Delivery, Marcel Dekker, 1991, p. 65.
Leenders R G G et al: ,,beta-Glucuronyl Carbamate Based Promoieties Designed for Prodrugs in ADEPT, Tetrahedron Letters, Elsevier Science Publishers, Amsterdam, NL, vol. 36, No. 10, Mar. 6, 1995 pp. 1701-1704, XP004028569, ISSN: 0040-4039, p. 1702.
Lees A. et al., "Activation of soluble polysaccharides with 1-cyano-4-dimethylaminopyridinium tetraflouroborate for use in protein-polysaccharide conjugate vaccines and immunological reagents" Vaccine 1996, 14, 190-98.
Lesnefsky et al., High-Dose Iron-Chelator Therapy During Reperfusion with Deferoxamine-Hydroxyethyl Starch Conjugate Fails to Reduce Canine Infarct Size; Journal of Cardiovascular Pharmacology, vol. 16, No. 4, pp. 523-528 (1990).
Levy JH, Weisinger A, Ziomek CA, Echelard Y, Recombinant Antithrombin: Production and Role in Cardiovascular Disorder, Seminars in Thrombosis and Hemostasis 27, 4 (2001) 405-416.
Li et al. or cited in Goldstein and Gelb "An alternate preparation fo thioester resin linkers for solid-phase synthesis of peptide C-terminal thioacids" (2000) Tetrahedron Letters 41(16):2797-2800.
Li, X. et al., "Direct preparation of peptide thioesters using an Fmoc solid-phase method" (1998) Tetrahedron Letters 39(47):8669-8672.
Lieber, M. al., "A Continuous Tumor-Cell Line from a Human Lung Carcinoma with Properties of Type II Alveolar Epithelial Cells" Int. J. Cancer 17:62-70 (1976).
Lin C.E. et al. "L-Cysteine as a water-soluble cation scavenger in the removal of the 2,4,6- trimethoxybenzyl group from thiols" Tetrahedron Lett. 43 (2002) 4531-34.
Lin et al., "Cloning and expression of the human erythropoietin gene" 1985, PNAS 82, 7580-7584.
Lindsey J. S. at al., "Porphyrin Building Blocks for Modular Construction of Bioorganic Model Systems" Tetrahedron 50 (1994) pp. 8941-68, especially p. 8956.
Lipke et al., "Localized delivery of nitric oxide from hydrogels inhibits neointima formation in a rat carotid balloon injury model" 2005, Acta Biomaterialia 1, pp. 597-606.
Liu et al., "Characterization of the structural and functional changes of hemoglobin in dimethyl sulfoxide by spectroscopic techniques" Biochimica et Biophysica Acta, 1998, 138, p. 53-60.
Lomant A. J., G. "Chemical Probes of Extended Biological Structures: Synthesis and Properties of the Cleavable Protein Cross-linking Reagent{35S]Dithiobis(succinimidyl propionate)" Fairbanks, J. Mol., Biol. 1976, 104, 243-261.
Lönngren J., I.J. Goldstein, ,,Coupling of Aldobionic Acids to Proteins Using Water-Soluble Carbodiimide Methods Enzymol. 1994, 247, 116-118.
Lund et al., "Assessment of methods for covalent binding of nucleic acids to magnetic beads, Dynabeads, and the characteristics of the bound nucleic acids in hybridization reactions" Nucleic Acid Research, 1988, 16: 10861-10880.

Luo et al., "Contolled DNA delivery systems" (abstract) Pharm Res, 1999, 15: 1300-1308, Abstract.

Manger, Rademacher, Dwek, "1-N-Glycyl β-Oligosaccharide Derivatives as Stable Intermediates for the Formation of Glycoconjugate Probes" 1992, Biochemistry, 31, 10724-10732.

Manger, Wong, Rademacher, Dwek, "Synthesis of 1-N-Glycyl β-Oligosaccharide Derivatives. Reactivity of Lens culinaris Lectin with a Fluorescent Labeled Streptavidin Pseudoglycoprotein and Immobilized Neoglycolipid" 1992, Biochemistry, 31, 10733-10740.

Maout et al.; Hydroxyethylstarch Conjugated to Human Hemoglobin for use in Blood Transfusion: Comparison with Dextran Conjugates; Corbohydrates and Carbohydrate Polymers—Analysis, Biotechnology, Modification, Antiviral and other Applications, pp. 132-140 (1993).

March, J., Advanced Organic Chemistry, 4th edition, John Wiley and Sons, New York (1992) 409.

Masamune, S., et al., "A General, Selective Synthesis of Thiol Esters" Can. J. Chem. 53 (1975) 3693.

Masamune, S., et al., ,,Tylonolide Hemiacetal, the Aglycone of Tylosin, and Its Partial Synthesis J. Am. Chem. Soc. 98 (1976) 7874.

Masuda T., Shibuya S., Arai M., Yoshida S., Tomozawa T., Ohno A., Yamashita M., Honda T., "Synthesis and Anti-Influenza Evaluation of Orally Active Bicyclic Ether Derivatives Related to Zanamivir" Bioorganic & Medicinal Chemistry Letters, 13 (2003), 669-673.

McMahon et al., "Pharmacokinetics and Effects of Recombinant Human Erythropoietin After Intravenous and Subcutaneous Injections in Healthy Volunteers" 1990, Blood 76, 1718.

Mega, et al. "Studies on the Oligosaccharide Chains of Human α1-Protease Inhibitor" J. Biol. Chem. 255 (1980) p. 4053 + p. 4057.

Megson et al., "Inhibition of human platelet aggregation by a novel S-nitrosothiol is abolished by haemoglobin and red blood cells in vitro: implications for anti-thrombotic therapy" 2000, British Journal of Pharmacology 131, pp. 1391-1398.

Meinjohannes E. et al., "Novel sequential solid-phase synthesis of N-linked glycopeptides from natural sources" J. Chem. Soc., Perkin Trans. 1, 1998, 549-60.

Menache D, Grossman BJ, Jackson CM. Antithrombin III: physiology, deficiency and replacement therapy. Transfusion 32:580, 1992.

Menache, "Antithrombin III: introduction" Seminars in Hematology 28:1, 1991.

Merck Index 2006, Definition of Dimethyl Sulfoxide, Merck & Co., 14th Edition, accessed online: http//themerckindex.cambridgesoft. com/themerckindex/index.asp on Sep. 4, 2007.

Mikola H. et al; Introduction of aliphatic amino and hydroxy groups to keto steroids using O- substituted hydroxalamines Bioconjugate Chemistry; vol. 3, No. 2, Mar. 1992, pp. 182-186, XP000262175, ISSN: 1043-1802.

Minnema MC, Chang ACK, Jansen PM, Lubbers YTP, Pratt BM, Whittaker BG, Taylor FB, Hack CE, Friedman B, Recombinant human antithrombin III improves survival and attenuates inflammatory responses in baboons lethally challenged with Escherichia coli, Blood 95, 4 (2000) 1117-1123.

Miyake, Kung, Goldwasser, 1977, Purification of human erythropoietin., J Biol Chem., 252(15), 5558-64.

Moonen, P.; Mermod, J.J.; Ernst, J.F.; Hirschi, M.; DeLamarter, J.F. Increased biological activity of deglycosylated recombinant human granulocyte-macrophage colony-stimulating factor produced by yeast or animal cells. Proc. Natl. Acad. Sci. US. 1987, 84, pp. 4428-4431.

Mori K. et.al. "The Activation of Type 1 and Type 2 Plasminogen by Type I and Type II Tissue Plasminogen Activator" The Journal of Biological Chemistry 270 (1995) pp. 3261-3267.

Mosbech H, Djurup R, Dreborg S, Kaergaard Poulsen L, Stahl Skov P, Steringer I., "Hyposensitization in asthmatics with MPEG-modified and unmodified house dist mite extract" Allergy, 1990, vol. 45(2):130-141.

Mosmann, "Rapid Colorimetric Assay for Cellular Growth and Survival: Application to Proliferation and Cytotoxicity Assays" 1983, J.Immunol. Methods, 65, 55-63.

Mueller PP, Schlenke P, Nimtz M, Conradt HS, Hauser H.: Recombinant glycoprotein quality in proliferation-controlled BHK-21 cells, Biotechnol Bioeng. Dec. 5, 1999; 65(5):529-36.

Muir et al. "Expressed protein ligation: A general method for protein engineering" (1998) Proc. Natl. Acad. Sci. USA 95:6705-6710.

Mukaiyama, T., et al., "Peptide Synthesis via Oxidation-Reduction Condensation by the Use of Non-metallic Compound as a Mercaptan Scavenger" Bull. Chem. Soc. Jpn. 43 (1970) 1271.

Mumberg et al., "Regulatable promoters of Saccharomyces cerevisiaecomparison of transcriptional activity and their use for heterologous expression" (1994) Nucl. Acids Res., 22, 5767-5768.

Murano, et al. "Some Properties of Antithrombin-III and its Concentration in Human Plasma" Thromb. Res. 18:259, 1980.

N.J. Davies, S.L. Flitsch, "A novel method for the specific glycosylation of proteins" Tetrahedron Lett. 1991, 32, 6793-6796.

Nagata et al., The chromosomal gene structure and two mRNAs for human granulocyte colony-stimulating factor, EMBO J. 5: 575-581, 1986.

Nagata, S. et.al. 1986, Molecular cloning and expression of cDNA for human granulocyte colony-stimulating factor, Nature 319:415-418, 1986.

Nakane et al., "The Accumulation Mechanism of Cationic Mitomycin C-dextran Conjugates in the Liver: In-vivo Cellular Localization and In-vitro Interaction with Hepatocytes" J. Pharm. Pharmakol., vol. 40 (1988), p. 1-6.

Nathan et al. "Strategies for Covalent Attachment of Doxorubicin to Poly(PEG-Lys), a New Water-Soluble Poly(ether urethane)", Journal of Bioactive and Compatible Polymers, Lancaster, PA, US, vol. 9, No. 3, (1994), pp. 239-251.

Naunhof H. et al. "Characterization of two human mammary carcinomas, MT-1 and MT-3, suitable for invivo testing of ether lipids and their derivatives" Breast Cancer Res Treat. 87-95 (1992).

Nedospasov A.A. et al, Synthesis and some properties of aminooxyalkylcelluloses Bulletin of the Academy of Sciences of the USSR. Division of Chemical Science, Consultants Bureau, New York, US, vol. 25, 1976, pp. 1105-1110, XP 002025380.

Nimtz, M., Grabenhorst, E., Conradt, H.S., Sanz, L. & Calvete, J.J. (1999) Structural characterization of the oligosaccharide chains of native and crystallized boar seminal plasma spermadhesin PSP-I and PSP-II glycoforms. Eur, J. Biochem. 265, 703-718.

Nimtz, M., Martin, W., Wray, V., Klöppel, K.-D., Agustin, J. & Conradt, H.S. (1993) Structures of sialylated oligosaccharides of human erythropoietin expressed in recombinant BHK-21 cells. Eur J. Biochem. 213, 39-56.

Nimtz, M., Noll G., Päques, E. & Conradt, H.S. (1990) Carbohydrate structures of human tissue plasminogen activator variant expressed in recombinant Chinese hamster ovary cells. FEBS Lett. 271, 14-18.

Nohynek, G.J. et al.1997, Comparison of the potency of glycosylated and nonglycosylated recombinant human granulocyte colony-stimulating factors in neutropenic and nonneutropenic CD rats, Cancer Chemother Pharmacol (1997) 39;259-266.

Nomura T et al., Pharmacokinetic characteristics and therapeutic effects of mitomycn C-dextran conjugates after intratumoural injection, Journal of Controlled Release, vol. 52, No. 3, (1998), p. 239-252.

O'Shanessy D.J., M. Wilchek, "Immobilization of Glycoconjugates by Their Oligosaccharides: Use of Hydrazido-Derivatized Matrices" Anal. Biochem. 1990, 191, 1-8.

Ohta, Miyako; Kawasaki, Nana; Itoh, Satsuki and Hayakawa, Takao ; Usefulness of Glycopeptide Mapping by Liquid Chromatography/ Mass Spectrometry in Comparability Assessment of Glycoprotein Products, Biologicals vol. 30, Issue 3, Sep. 2002, pp. 235-244.

Okamoto A. et al., "A facile incorporation of the aldehyde function into DNA; 3-formylindole nucleoside as an aldehyde-containing universal nucleoside" Tetrahedron Lett. 2002, 43, 4581-4583.

Okamoto, M.; Nakai, M.; Nakayama, C.; Yanagi, H.; Matsui, H.; Noguchi, H.; Namiki, M.; Sakai, J.; Kadota, K.; Fukui, M.; Hara, H. Purification and characterization of three forms of differently glycosylated recombinant human Granulocyte-Macrophage Colony-Stimulating Factor. Arch. Biochem. Biophys. 1991, 286, pp. 562-568.

Olson, J. "Predominant Contribution of Surface Approximation to the Mechanism of Heparin Acceleration of the Antithrombin-Thrombin Reaction" Biol. Chem. 266:6353, 1991.

Olson, J. "Role of the Antithrombin-binding Pentasaccharide in Heparin Acceleration of Antithrombin-Proteinase Reactions" Biol. Chem. 267:12528,1992.

Opal, Steven M., et al. "Antithrombin, heparin, and heparan sulfate" Crit. Care Med. 2002, 30:325.

Organikum, Organisch-chemisches Grundpraktikum, 1984, Veb Deutscher Verlag der Wissenschaften, p. 472 (English Translation).

Pasut G et al.; "Antitumoral activity of PEG-gemcitabine prodrugs targeted by folic acid" Journal of controlled release, Elsevier, Amsterdam, NL, vol. 127, No. 3, May 8, 2008, pp. 239-248, XP022617739, ISSN: 0168-3659, DOI:10.1016/J. Jconrel. 2008.02. 002.

Pawlowski et al., Vaccine 17, (1999), 1474-1483, A new method of non-cross-linking conjugates of polysaccharides to protein via thioether bonds for the preparation of saccharide-protein conjugate vaccines.

Pedley et al., "The potential for enhanced tumour localization by poly(ethylene glycol) modification of anti-CEA antibody" Br. J. Cancer, vol. 79 (1994), pp. 1126-1130.

Peeters J.M. et al., "Comparison of four bifunctional reagents for coupling peptides to proteins and the effect of the three moieties on the immunogenicity of the conjugates" J. Immunol. Methods 1989, 120, 133-43.

Pelter, A., et al., "Synthesis of Thioesters by Reactions of Carboxylic Acids with Tris(ethylthio)borane" J. Chem Soc., Perkin trans I (1977) 1672.

Peluso, S., Imperiali, B. "Aspargine surrogates for the assembly of N-linked glycopeptides mimetics by chemoselective ligation" (2001), Tetrahedron Letters, vol. 42, p. 2085-2087.

Peri, F. et al, "Chemo- and Stereoselective Glycosylation of Hydroxylamino Derivatives: A Versatile Approach to Glycoconjugates", 1998, Tetrahedron 54, 12269-12278.

Peron et al., "Hydroxyethyl starch-induced renal insufficiency after plasma exchange in a patient whit polymyositis and liver cirrhosis" Clinical Nephrology, vol. 55 ( 2001), p. 408-411.

Peterson, The Physiological Inhibitions of Blood Coagulation and Fibrinolysis, Elsevier/ North-Holland Biomedical Press 1979, p. 43.

Pharma Business, Jul./Aug. 2000, "The World's Public Biotechnology Companies" pp. 45-60.

Quelle, Caslake, Burkert, Wojchowski, 1989, High-level expression and purification of a recombinant human erythropoietin produced using a baculovirus vector, Blood, 74(2), 652-7.

Rabiner, "Evaluation of a Stroma-Free Hemoglobin Solution for use as as Plasma Expander" J. Exp. Med. 126, (1967), 1127.

Radomsky J. and Temeriusz A.: "Thiazolidine-4(R)-carboxylic acids derived from sugars: part I, C-2-epimerisation in aqueous solutions" Carbohydrate Research, vol. 187, 1989, pp. 223-237, XP002357090 The Netherlands.

Ragnhammar, P.; Friesen, H-J.; Frödin, J-E.; Lefvert, A-K.; Hassan, M.; Österborg, A.; Mellstedt, H. Induction of anti-recombinant human Granulocyte-Macrophage Colony-Stimulating Factor (Escherichia coli-derived) antibodies and clinical effects in nonimmunocompromised patients. Blood 1994, 84, pp. 4078-4087.

Ragupathi G. et al., "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm" Glycoconj. J. 1998, 15, 217-21.

Ramos D. et al., "Enzymatic Synthesis of Neoglycopeptide Building Blocks" Angew. Chem. 2000, 112, 406-8.

Rapoport et al., "Protein Transport Across the Eukaryotic Endoplasmic Reticulum and Bacterial Inner Membranes" Annu Rev Biochem. 1996; 65:271-303.

Reddy K.R. et al. „Use of peginterferon alfa-2a (40 KD) (pagasys) for the treatment of Hepatits C Advanced Drug Delivery Reviews 54 (2002) 571-586.

Relihan, Michael, et al.. "Clearance Rate and Effect on Renal Function of Stroma-Free Hemoglobin Following Renal Ischemia" Ann. Surg. 176, (1972) 700.

Revoltella, R.; Laricchia-Robbio, L.; Moscato, S.; Genua, A.; Liberati, A Natural and therapy-induced anti-GM-CSF and anti-G-CSF antibodies in human serum. Leukemia and Lymphoma 1997, 26, pp. 29-34.

Reynolds et al., "S-nitrosohemoglobin deficiency: A Mechanism for loss of physiological activity in banked blood" 2007, PNAS vol. 104 No. 43, pp. 17058-17062.

Richter et al., Antibodies against Hydroxyethylstarch produced in Rabbits by Immunization with a Protein-Hydroxyethylstarch Conjugate; International Archives of Allergy and Applied Immunology, Vo. 52, No. 1-4, pp. 307-314 (1976).

Reidhaar-Olson, J.F. et al. 1996, Identification of residues critical to the activity of human granulocyte colony-stimulating factor, Biochemistry 35:9034-9041 1996.

Rodrigues et al., "Correlation of the acid-sensitivity of polyethylene glycol daunorubicin conjugates with their in vitro antiproliferative activity"Bioorganic Medicinal Chemistry 14 (2006) 4110-4117.

Roemisch, J. et al. "Antithrombin: a new look at the actions of a serine protease inhibitor" Blood Coagul Fibrinolysis. 2002, 13:657.

Rogers et al. "Effects of polymerization on the oxygen carrying and redox properties of diaspirin cross-linked hemoglobin" (Biochim. et Biophys. Acta, 1248 (1995), 135-142.

Rohrling J. et al; Synthesis and testing of a novel fluorescene label for carbonyls in carbohydrates and cellulosics Synlett 2001 Germany, No. 5., 2001, pp. 682-684, XP001203540; ISSN: 0936-5214.

Rose Keith; Facile synthesis of homogeneous artificial proteins; Journal of the American Chemical Society; vol. 116, No. 1; Jan. 12, 1994; pp. 30-33; XP002301786; ISSN: 0002-7863.

Rosenberg, Robert D. "Role of heparin and heparinlike molecules in thrombosis and atherosclerosis" Fed. Proc. 44:404,1985.

Rosenberg, Robert D., et al. "Antithrombin—III The Heaprin—Antithrombin System" Rev. Hematol. 2:351,1986.

Rotondaro, L., De Paolis, E., Ferrero, D., D'Alatri, L., Raucci, G., Fabbri, A., Gerwig, G. J., Kamerling, J. P., Mariani, M.F., Mele, A., De Santis, R. "Purificiation and Characterization of Two Recombinant Human Granulocyte Colony-Stimulating Factor Glycoforms" (1999) , Molecular Biotechnology, vol. 11, p. 117-128.

Rudolph et al., "Circulation persistence and biodistribution of lyophilized liposome-encapsulated hemoglobin: An oxygen-carrying resuscitative fluid" Crit. Care Med. 22, (1994) 142-150.

Rudolph, Alan S. "The Freeze-Dried Preservation of Liposome Encapsulated Hemoglobin: A Potential Blood Substitute" Cryobiology, 25, (1988) 1-8.

Rush, Derby, Smith, Merry, Rogers, Rohde, Katta, 1995, Microheterogeneity of erythropoietin carbohydrate structure, Anal Chem., 67(8), 1442-52.

Ruttmann T.G. et al; In vivo investigation into the effects of haemodilution with hydroxyethylstarch (200/0.5) and normal saline on coagulation, British Journal of Anaesthesia, vol. 80, No. 5, May 1998, pp. 612-616, XP002383610; ISSN: 0007-0912.

HYDROXYALKYL STARCH DERIVATIVES AND PROCESS FOR THEIR PREPARATION

CROSS-REFERENCE TO RELATED APPLICATIONS

This application is the National Stage of International Application No. PCT/EP2008/010660, filed on Dec. 15, 2008, which claims the priority of European Application No. 07024350.6. filed on Dec. 14, 2007, the contents of which are incorporated herein by reference in their entirety.

The invention relates to a method for the preparation of a hydroxyalkyl starch derivative which comprises reacting hydroxyalkyl starch (HAS) via the optionally oxidised reducing end of the HAS with the amino group M of a crosslinking compound which, apart from the amino group, comprises a specifically protected carbonyl group, namely an acetal group or a ketal group. The method may further comprise a reaction of the HAS derivative thus obtained with the amino group of a biologically active compound via alkylation, preferably via reductive amination. Moreover, the invention relates to the HAS derivatives obtainable or obtained by the inventive process and to specific HAS derivatives as such. The invention also relates to pharmaceutical compositions comprising the HAS derivatives containing the biologically active compound, these HAS derivates as therapeutic or prophylactic agent and the use of specific HAS derivatives for the preparation of medicaments.

Hydroxyalkyl starch (HAS), in particular hydroxyethyl starch (HES), is a substituted derivative of naturally occurring carbohydrate polymer amylopectin, which is present in corn starch at a concentration of up to 95% by weight, and is degraded by alpha-amylase in the body. HES, in particular, exhibits advantageous biological properties and is used as a blood volume replacement agent and in hemodilution therapy in the clinics (Sommermeyer et al., 1987, Krankenhauspharmazie, 8(8), 271-278; Weidler et al., 1991, Arzneimittel-forschung/Drug Res., 41, 494-498).

Some ways of producing a hydroxyethyl starch derivative are described in the art.

DE 26 16 086 discloses the conjugation of hemoglobin to hydroxyethyl starch wherein, in a first step, a cross-linking agent, e.g. bromocyane, is bound to hydroxyethyl starch and subsequently hemoglobin is linked to the intermediate product.

One important field in which HES is used is the stabilization of polypeptides which are applied, e.g., to the circulatory system in order to obtain a particular physiological effect. One specific example of these polypeptides is erythropoietin, an acid glycoprotein of approximately 34,000 kDa which is essential in regulating the level of red blood cells in the circulation.

A well-known problem with the application of polypeptides and enzymes is that these proteins often exhibit an unsatisfactory stability. Especially erythropoietin has a relatively short plasma half live (Spivak and Hogans, 1989, Blood 73, 90; McMahon et al., 1990, Blood 76, 1718). This means that therapeutic plasma levels are rapidly lost and repeated intravenous administrations must be carried out. Furthermore, in certain circumstances an immune response against the peptides is observed.

It is generally accepted that the stability of polypeptides can be improved and the immune response against these polypeptides is reduced when the polypeptides are coupled to polymeric molecules.

WO 94/28024 discloses that physiologically active polypeptides modified with polyethylene glycol (PEG) exhibit reduced immunogenicity and antigenicity and circulate in the bloodstream considerably longer than unconjugated proteins, i.e. have a longer clearance rate. However, PEG-drug conjugates exhibit several disadvantages, e.g. they do not exhibit a natural structure which can be recognized by elements of in vivo degradation pathways. Therefore, apart from PEG-conjugates, other conjugates and protein polymerates have been produced.

WO 02/080979 discloses compounds comprising a conjugate of an active agent and a hydroxyalkyl starch wherein active agent and hydroxyalkyl starch are either linked directly or via a linker compound. As far as the direct linkage is concerned, the reaction of active agent and hydroxyalkyl starch is carried out in an aqueous medium which comprises at least 10 wt.-% of water. No examples are given which are directed to a hydroxyalkyl starch linked to crosslinking compound via an amino group of said crosslinking compound wherein the crosslinking compound further contains a protected carbonyl group. Additionally, no examples are given showing a HAS derivative which is obtained by reacting said HAS derivative via said carbonyl group with an amino group of a biologically active agent.

WO 03/074087 discloses hydroxyalkyl starch protein conjugates in which the bonding between a hydroxyalkyl starch molecule and a protein is covalent and is the result of a coupling of a terminal aldehyde group of the hydroxyalkyl starch or a functional group which resulted from the reaction of said aldehyde group with a functional group of a protein.

WO 03/074088 discloses hydroxyalkyl starch conjugates with a low molecular weight compound in which the bonding between the hydroxyalkyl starch and the low molecular weight compound is covalent and is the result of a coupling of a terminal aldehyde group of the hydroxyalkyl starch or a functional group which resulted from the reaction of said aldehyde group with a functional group of a protein.

WO 2005/014024 discloses polymers functionalized by an aminooxy group or a derivative thereof, conjugates, wherein the functionalized polymers are covalently coupled with a protein by an oxime linking group, a process for preparing the functionalized polymers, a process for preparing the conjugates, functionalized polymers as obtainable by the process of the present invention, conjugates as obtainable by the process, and pharmaceutical compositions comprising at least one conjugate and the use of said conjugates and compositions for the prophylaxis or therapy of the human or animal body.

WO 2005/092390 discloses conjugates of hydroxyalkyl starch and a protein wherein these conjugates are formed by a covalent linkage between the hydroxyalkyl starch or a derivative of the hydroxyalkyl starch and the protein and a method of producing these conjugates and the use of these conjugates.

WO 2004/024777 discloses hydroxyalkyl starch derivates, particularly hydroxyalkyl starch derivatives obtainable by a process in which hydroxyalkyl starch is reacted with a primary or secondary amino group of a linker compound. According to an especially preferred embodiment, WO 2004/024777 discloses hydroxyalkyl starch derivatives obtainable by a process according to which hydroxyalkyl starch is reacted with a primary or secondary amino group of a linker compound and the resulting reaction product is reacted with a polypeptide, preferably with a glycoprotein and especially preferably with erythropoietin, via at least one other reactive group of the linker compound. A hydroxyalkyl starch which is especially preferred is hydroxyethyl starch. According to WO 2004/024777, the hydroxyalkyl starch and preferably the hydroxyl ethyl starch is reacted with the linker compound at its reducing end which is not oxidised prior to the reaction.

WO 2004/024776 discloses hydroxyalkyl starch derivates, particularly hydroxyalkyl starch derivatives obtainable by a process in which hydroxyalkyl starch is reacted with a primary or secondary amino group of a crosslinking compound or with two crosslinking compounds wherein the resulting hydroxyalkyl starch derivative has at least one functional group X which is capable of being reacted with a functional group Y of a further compound and wherein this group Y of the further compound is an aldehyde group, a keto group, a hemiacetal group, an acetal group, or a thio group. According to an especially preferred embodiment, WO 2004/024776 relates to hydroxyalkyl starch derivatives obtainable by a process according to which hydroxyalkyl starch is reacted with a primary or secondary amino group of a crosslinking compound, the resulting reaction product optionally being further reacted with a second crosslinking compound, wherein the resulting hydroxyalkyl starch derivative has at least one functional group X which is capable of being reacted with a functional group Y of a further compound and wherein this group Y is an aldehyde group, a keto group, a hemiacetal group, an acetal group, or a thio group, and the resulting reaction product is reacted with a polypeptide, preferably with a polypeptide such as AT III, IFN-beta or erythropoietin and especially preferably with erythropoietin, which comprises at least one of these functional groups Y. A hydroxyalkyl starch which is especially preferred is hydroxyethyl starch. According to WO 2004/024776 the hydroxyalkyl starch and preferably the hydroxyethyl starch is reacted with the linker compound at its reducing end which is optionally oxidised prior to the reaction.

WO 2005/092928 discloses conjugates of hydroxyalkyl starch, preferably hydroxyethyl starch, and a protein, wherein these conjugates are formed by a reductive amination reaction between at least one aldehyde group of the hydroxyalkyl starch or of a derivative of the hydroxyalkyl starch, and at least one amino group of the protein, so that the hydroxyalkyl starch or the derivative thereof is covalently linked to the protein via an azomethine linkage or an aminomethylene linkage. WO 2005/092928 also relates to a method of producing these conjugates and specific uses of the conjugates.

US 2006/0194940 A1 discloses water-soluble polymer alkanals. Among others, protected aldehyde reagents are disclosed which are reacted with a polymer. While poly(saccharides) are generically mentioned, especially preferred polymers are polyethylene glycols. Starches or, in particular, modified starches such as hydroxyalkyl starches are not disclosed in US 2006/0194940 A1. Consequently, US 2006/0194940 A1 contains no disclosures concerning specific ways of coupling a given linker compound to hydroxyalkyl starch. The same applies to U.S. Pat. No. 7,157,546 B2, EP 1 591 467 A1 and WO 2004/022630 A2.

U.S. Pat. No. 6,916,962 B2 discloses an aminoacetal crosslinking compound in unprotected and protected form. No disclosure is contained in this document relating to a possible coupling of this crosslinking compound with polymers other than polyethylene glycols. In particular, starches, let alone modified starches such as hydroxyalkyl starches are not disclosed in U.S. Pat. No. 6,916,962 B2. Consequently, U.S. Pat. No. 6,916,962 B2 contains no disclosures concerning specific ways of coupling a given linker compound to hydroxyalkyl starch. The same applies to U.S. Pat. No. 6,956,135 B2 and WO 03/049699 A2.

U.S. Pat. No. 5,990,237 discloses structures containing a protected aldehyde group. Compounds comprising these structures are preferably coupled to polyethylene glycol, and coupling is carried out via a halide as functional group comprised in the protected aldehyde group containing compounds, which halide group reacts with a hydroxy group of the polyethylene glycol.

It is an object of the present invention to provide a novel method to obtain hydroxyalkyl starch derivatives.

It is a further object of the present invention to provide novel HAS derivatives such as HAS derivatives obtained or obtainable by reacting HAS with specifically functionalized crosslinking compounds.

It is yet another object of the present invention to provide further novel HAS derivatives such as HAS derivatives obtained or obtainable by reacting the HAS derivatives—obtained or obtainable by reacting HAS with specifically functionalized crosslinking compounds—with a suitable functional group of biologically active compound.

Surprisingly, it was found that it is possible to use, for the preparation of specific HAS derivatives, a crosslinking compound which, on the one hand, can selectively be coupled to the optionally oxidized reducing end of a hydroxyalkyl starch via an amino group and, on the other hand, has—as a second functional group—a fully protected carbonyl group, namely an acetal group or a ketal group. Compared to embodiments where a crosslinking compound is employed having a free aldehyde or keto group or, e.g., a hemiacetal group as functional group, employing such a fully protected group drastically minimises the risk that, during reaction of HAS with the crosslinking compound, undesired oligomerisation or polymerisation between the crosslinking compound molecules takes places. Unexpectedly, it was found that deprotection of the acetal or ketal group comprised in the resulting HAS derivative is possible without at least partially destroying the specific chemical structure of the hydroxyalkyl starch, in particular the hydroxyethyl starch, being characterised by numerous functional groups such as acetal groups and ether groups. Therefore, the present invention allows for an extremely effective method of preparing a first HAS derivative by minimising the risk of oliogomerisation or polymerisation between the individual crosslinking compound molecules, combined with the possibility of deprotecting the functional groups of the resulting HAS derivatives without at least partial destruction of the HAS structure, in order to provide a HAS derivative allowing for an effective coupling with a biologically active compound.

Thus, the present invention relates to a method for the preparation of a hydroxyalkyl starch derivative, comprising (i) reacting hydroxyalkyl starch (HAS) of formula (I)

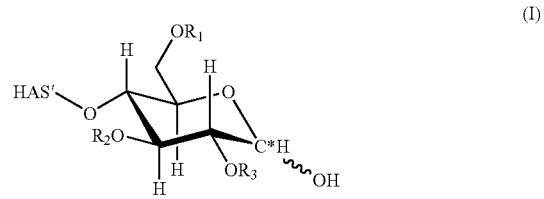

via carbon atom C* of the reducing end of the HAS with the amino group M of a crosslinking compound according to formula (II)

M-L-A wherein A is an acetal group or a ketal group; and L is a spacer bridging M and A, wherein C* is optionally oxidised prior to the reaction of HAS with M, obtaining a HAS derivative according to formula (III)

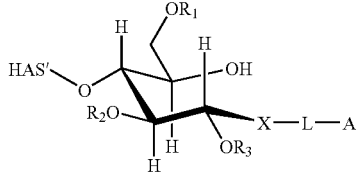
(III)

wherein X is the functional group resulting from the reaction of the amino group M with the HAS via carbon atom C* of the optionally oxidised reducing end of the HAS, and wherein HAS' is the remainder of the hydroxyalkyl starch molecule, and $R_1$, $R_2$ and $R_3$ are independently hydrogen or a linear or branched hydroxyalkyl group.

Further, the present invention relates to a hydroxyalkyl starch (HAS) derivative obtainable or obtained by this method.

Moreover, the present invention relates to a hydroxyalkyl starch (HAS) derivative of formula (III)

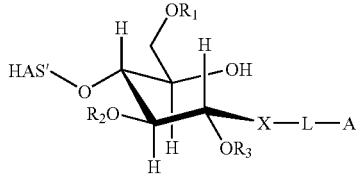
(III)

wherein A is an acetal or ketal group; L is a spacer bridging X and A;

wherein X is the functional group resulting from the reaction of an amino group M of a crosslinking compound of formula (II)

M-L-A with hydroxyalkyl starch (HAS) of formula (I)

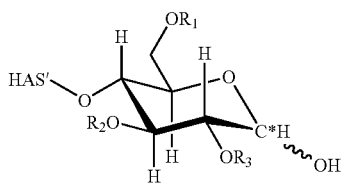
(I)

via carbon atom C* of the HAS, wherein C* is optionally oxidised prior to the reaction of HAS with M, wherein HAS' is the remainder of the hydroxyalkyl starch molecule and $R_1$, $R_2$ and $R_3$ are independently hydrogen or a linear or branched hydroxyalkyl group.

Hydroxyalkyl Starch

In the context of the present invention, the term "hydroxyalkyl starch" (HAS) refers to a starch derivative which has been substituted by at least one hydroxyalkyl group. A preferred hydroxyalkyl starch of the present invention has a constitution according to formula (I')

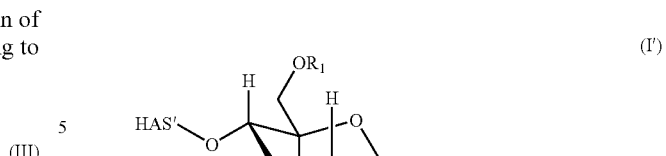
(I')

wherein HAS' is the remainder of the hydroxyalkyl starch molecule and $R_1$, $R_2$ and $R_3$ are independently hydrogen, a linear or branched hydroxyalkyl group or the group

—[(CR$^1$R$^2$)$_m$O]$_n$[CR$^3$R$^4$]$_o$—OH wherein $R^1$, $R^2$, $R^3$, and $R^4$ are independently selected from the group consisting of hydrogen, and alkyl group, preferably hydrogen and methyl group, m is 2 to 4, wherein the residues $R^1$ and $R^2$ may be the same or different in the m groups $CR^1R^2$;

n is 0 to 20, preferably 0 to 4;

o is 2 to 20, preferably 2 to 4, wherein the residues $R^3$ and $R^4$ may be the same or different in the o groups $CR^3R^4$.

Preferably, $R_1$, $R_2$ and $R_3$ are independently a group —(CH$_2$CH$_2$O)$_n$—H, wherein n is an integer, preferably 0, 1, 2, 3, 4, 5, or 6, and in particular, $R_1$, $R_2$ and $R_3$ are independently hydrogen or 2-hydroxyethyl.

In formula (I) and (I') the reducing end of the starch molecule is shown in the non-oxidised form and the terminal saccharide unit of HAS is shown in the hemiacetal form which, depending on e.g. the solvent, may be in equilibrium with the (free) aldehyde form. The abbreviation HAS' as used in the context of the present invention refers to the HAS molecule without the terminal saccharide unit at the reducing end of the HAS molecule. This is meant by the term "remainder of the hydroxyalkyl starch molecule" as used in the context of the present invention.

The term "hydroxyalkyl starch" as used in the present invention is not limited to compounds where the terminal carbohydrate moiety comprises hydroxyalkyl groups $R_1$, $R_2$ and/or $R_3$ as depicted, for the sake of brevity, in formulas (I) and (I'), but also refers to compounds in which at least one hydroxy group which is present anywhere, either in the terminal carbohydrate moiety and/or in the remainder of the hydroxyalkyl starch molecule, HAS', is substituted by a hydroxyalkyl group $R_1$, $R_2$ and/or $R_3$.

Hydroxyalkyl starch comprising two or more different hydroxyalkyl groups is also possible.

The at least one hydroxyalkyl group comprised in HAS may contain one or more, in particular two or more hydroxy groups. According to a preferred embodiment, the at least one hydroxyalkyl group comprised in HAS contains one hydroxy group.

The expression "hydroxyalkyl starch" also includes derivatives wherein the alkyl group is mono- or polysubstituted. In this context, it is preferred that the alkyl group is substituted with a halogen, especially fluorine, or with an aryl group. Furthermore, the hydroxy group of a hydroxyalkyl group may be esterified or etherified.

Furthermore, instead of alkyl, also linear or branched substituted or unsubstituted alkenyl groups may be used.

Hydroxyalkyl starch is an ether derivative of starch. Besides of said ether derivatives, also other starch derivatives can be used in the context of the present invention. For example, derivatives are useful which comprise esterified hydroxy groups. These derivatives may be e.g. derivatives of unsubstituted mono- or dicarboxylic acids with 2-12 carbon atoms or of substituted derivatives thereof. Especially useful are derivatives of unsubstituted monocarboxylic acids with 2-6 carbon atoms, especially derivatives of acetic acid. In this context, acetyl starch, butyryl starch and propionyl starch are preferred.

Furthermore, derivatives of unsubstituted dicarboxylic acids with 2-6 carbon atoms are preferred.

In the case of derivatives of dicarboxylic acids, it is useful that the second carboxy group of the dicarboxylic acid is also esterified. Furthermore, derivatives of monoalkyl esters of dicarboxylic acids are also suitable in the context of the present invention.

For the substituted mono- or dicarboxylic acids, the substitute groups may be preferably the same as mentioned above for substituted alkyl residues.

Techniques for the esterification of starch are known in the art (see e.g. Klemm D. et al, Comprehensive Cellulose Chemistry Vol. 2, 1998, Whiley-V C H, Weinheim, N.Y., especially chapter 4.4, Esterification of Cellulose (ISBN 3-527-29489-9).

According to a preferred embodiment of the present invention, hydroxyalkyl starch according to above-mentioned formula (I) is employed. The other saccharide ring structures comprised in HAS' may be the same as or different from the explicitly described saccharide ring, with the difference that they lack a reducing end.

As far as the residues $R_1$, $R_2$ and $R_3$ according to formula (I) are concerned there are no specific limitations. According to a preferred embodiment, $R_1$, $R_2$ and $R_3$ are independently hydrogen or a hydroxyalkyl group, a hydroxyaralkyl group or a hydroxyalkaryl group having of from 2 to 10 carbon atoms in the respective alkyl residue. Hydrogen and hydroxyalkyl groups having of from 2 to 10 carbon atoms are preferred. More preferably, the hydroxyalkyl group has from 2 to 6 carbon atoms, more preferably from 2 to 4 carbon atoms, and even more preferably from 2 to 3 carbon atoms. In a preferred embodiment, hydroxyalkyl starch is hydroxyethyl starch in which $R_1$, $R_2$ and $R_3$ are independently hydrogen or a group $(CH_2CH_2O)_n$—H, wherein n is an integer, preferably 0, 1, 2, 3, 4, 5, or 6.

"Hydroxyalkyl starch" therefore preferably comprises hydroxyethyl starch, hydroxypropyl starch and hydroxybutyl starch, wherein hydroxyethyl starch and hydroxypropyl starch are particularly preferred and hydroxyethyl starch is most preferred.

The alkyl, aralkyl and/or alkaryl group may be linear or branched and suitably substituted.

Therefore, the present invention also relates to a method and a HAS derivative as described above wherein $R_1$, $R_2$ and $R_3$ are independently hydrogen or a linear or branched hydroxyalkyl group with from 2 to 6 carbon atoms.

Thus, $R_1$, $R_2$ and $R_3$ preferably may be H, hydroxyhexyl, hydroxypentyl, hydroxybutyl, hydroxypropyl such as 2-hydroxypropyl, 3-hydroxypropyl, 1-hydroxyisopropyl, hydroxyethyl such as 2-hydroxyethyl, hydrogen and the 2-hydroxyethyl group being especially preferred.

Therefore, the present invention also relates to a method and a HAS derivative as described above wherein $R_1$, $R_2$ and $R_3$ are independently hydrogen or a 2-hydroxyethyl group, an embodiment wherein at least one residue $R_1$, $R_2$ and $R_3$ being 2-hydroxyethyl being especially preferred.

Hydroxyethyl starch (HES) is most preferred for all embodiments of the present invention.

Therefore, the present invention relates to the method and a HAS derivative as described above, wherein the polymer is hydroxyethyl starch and the derivative is a hydroxyethyl starch (HES) derivative.

HAS, in particular HES, is mainly characterized by the molecular weight distribution, the degree of substitution and the ratio of $C_2:C_6$ substitution. There are two possibilities of describing the substitution degree:

The degree of substitution (DS) of HAS is described relatively to the portion of substituted glucose monomers with respect to all glucose moieties.

The substitution pattern of HAS can also be described as the molar substitution (MS), wherein the number of hydroxyethyl groups per glucose moiety is counted.

In the context of the present invention, the substitution pattern of HAS, preferably HES, is referred to as MS, as described above (see also Sommermeyer et al., 1987, Krankenhauspharmazie, 8(8), 271-278, in particular p. 273).

MS is determined by Gas Chromatography after total hydrolysis of the HES molecule. MS values of respective HAS, in particular HES starting material are given. It is assumed that the MS value is not affected during the derivatization procedure in steps a) and b) of the process of the invention.

HAS and in particular HES solutions are present as polydisperse compositions, wherein each molecule differs from the other with respect to the polymerization degree, the number and pattern of branching sites, and the substitution pattern. HAS and in particular HES is therefore a mixture of compounds with different molecular weight. Consequently, a particular HAS and in particular HES solution is determined by average molecular weight with the help of statistical means. In this context, $M_n$ is calculated as the arithmetic mean depending on the number of molecules. Alternatively, $M_w$ (or MW), the weight average molecular weight, represents a unit which depends on the mass of the HAS, in particular HES.

In this context the number average molecular weight is defined by equation 1:

$$\overline{M}_n = \frac{\sum_i n_i \cdot M_i}{\sum_i n_i}$$

where $n_1$ is the number of molecules of species i of molar mass $M_i$.

$\overline{M}_n$ indicates that the value is an average, but the line is normally omitted by convention.

$M_w$ is the weight average molecular weight, defined by equation 2:

$$\overline{M}_w = \frac{\sum_i n_i \cdot M_i^2}{\sum_i n_i M_i}$$

where $n_1$ is the number of molecules of species i of molar mass $M_i$ $\overline{M}_w$ indicates that the value is an average, but the line is normally omitted by convention.

Preferably, the hydroxyalkyl starch, in particular the hydroxyethyl starch, used in the invention has a mean molecular weight (weight mean) of from 1 to about 1000 kDa, more preferably from about 1 to about 800 kDa, more preferably from about 1 to about 500 kDa. Hydroxyethyl starch can further exhibit a preferred molar substitution of from 0.1 to 3, preferably 0.1 to 2, more preferred 0.1 to 0.9 or 0.4 to 2, preferably 0.4 to 1.3, and a preferred ratio between $C_2:C_6$ substitution in the range of from 2 to 20 with respect to the hydroxyethyl groups.

The term "mean molecular weight" as used in the context of the present invention relates to the weight as determined according to the LALLS-(low angle laser light scattering)-GPC method as described in Sommermeyer et al., 1987, Krankenhauspharmazie, 8(8), 271-278; and Weidler et al., 1991, Arzneim.-Forschung/Drug Res., 41, 494-498. For mean molecular weights of 10 kDa and smaller, additionally, the calibration was carried out with a standard which had previously been qualified by LALLS-GPC.

According to a preferred embodiment of the present invention, the mean molecular weight of hydroxyethyl starch employed is from about 1 to about 1000 kDa, more preferably from about 1 to about 800 kDa, more preferably from about 1 to about 500 kDa, more preferably from about 2 to about 400 kDa, more preferably from about 5 to about 300 kDa, more preferably from about 10 to about 200 kDa, in particular from about 50 to about 150 kDa.

Further, the molar substitution of HAS and in particular HES is preferably from about 0.1 to about 3, preferably about 0.4 to about 1.3, such as 0.4, 0.5, 0.6, 0.7 0.8, 0.9, 1.0, 1.1, 1.2, or 1.3.

An example of HES having a mean molecular weight of about 5 to 300 kDa, preferably 50 to 150 kDa is a HES with a molar substitution of 0.1 to 3, preferably 0.4 to 1.3, such as 0.4, 0.5, 0.6, 0.7 0.8, 0.9, 1.0, 1.1, 1.2, or 1.3.

As far as the ratio of $C_2:C_6$ substitution is concerned, said substitution is preferably in the range of from 2 to 20, more preferably in the range of from 2 to 15 and even more preferably in the range of from 3 to 12.

Other Starches than Hydroxyalkyl Starches

In general, the methods of the present invention can also be carried out, and the derivatives of the present invention can also be prepared using other starches than hydroxyalkyl starches, in particular hydroxyethyl starch as described above, with the proviso that these starches also contain a reducing end being present in the hemiacetal form, optionally in equilibrium with the (free) aldehyde from, which reducing end may suitably be oxidised to give the respective oxidised form. In particular, a highly branched, unsubstituted or low-substituted starch product can be employed, i.e. a starch which has a significantly higher degree of branching than amylopectin and has the degree of alpha-1,6 branching of glycogen, or even exceeds this, and, if substituted, has a molar substitution MS of only up to 0.3, preferably of from 0.05 to 0.3. The term MS (molar substitution) as used in the context of this highly branched, unsubstituted or low-substituted starch product means the average number of hydroxyethyl or hydroxypropyl groups per anhydroglucose unit. The MS is normally measured by determining the content of hydroxyethyl or hydroxypropyl groups in a sample and computational allocation to the anhydroglucose units present therein. The MS can also be determined by gas chromatography. The degree of branching can be determined by a gas chromatographic methylation analysis as mol-% of the alpha-1,4,6-glycosidically linked anhydroglucoses in the polymer. The degree of branching is in every case an average because the highly branched, unsubstituted or low-substituted starch product of the invention is a polydisperse compound. The glucose units in said highly branched, unsubstituted or low-substituted starch product are linked via alpha-1,4- and alpha-1,6-linkages. The degree of branching means the proportion of alpha-1,4,6-linked glucose units in mol % of the totality of all anhydroglucoses. The $C_2/C_6$ ratio expresses the ratio or substitution at C-2 to that at C-6. The highly branched, unsubstituted or low-substituted starch product has a preferred degree of branching of from 6% to 50%, achievable by a transglucosidation step with the aid of branching enzymes. Even more preferably, the degree of branching is in the range of from 10 to 45, more preferably from 20 to 40 such as 20, 25, 30, 35, or 40. Also preferred are ranges of from more than 20 to 40, preferably from more than 20 to 30 such as from 21 to 40, preferably from 21 to 30. The starting material which can be used for this purpose is in principle any starch, but preferably waxy starches with a high proportion of amylopectin or the amylopectin fraction itself. The degree of branching which is necessary for the use according to the present invention of the starch products—as far as these "other starches" are concerned—is in the range from 8% to 20%, expressed as mol % of anhydroglucoses. This means that the starch products which can be used for the purposes of the invention have on average one alpha-1,6 linkage, and thus a branching point, every 12.5 to 5 glucose units. Preferred highly branched, unsubstituted or low-substituted starch products have a degree of branching of more than 10% and up to 20% and in particular from 11 to 18%. A higher degree of branching means a greater solubility of the starch products of the invention and a greater bioavailability of these dissolved starch products in the body. Particular preference is given to unmodified starch products with a degree of branching of more than 10%, in particular from 11% to 18%. The highly branched, unsubstituted or low-substituted starch product can be prepared by targeted enzymatic assembly using so-called branching or transfer enzymes, where appropriate followed by partial derivatisation of free hydroxyl groups with hydroxyethyl or hydroxypropyl groups. Instead of this it is possible to convert a hydroxyethylated or hydroxypropylated starch by enzymatic assembly using so-called branching or transfer enzymes into a highly branched, unsubstituted or low-substituted starch product. Obtaining branched starch products enzymatically from wheat starch with a degree of branching of up to 10% is known per se and described for example in WO 00/66633 A. Suitable branching or transfer enzymes and the obtaining thereof are disclosed in WO 00/18893 A, U.S. Pat. No. 4,454,161, EP 0 418 945 A, JP 2001294601 A or US 2002/065410 A. This latter publication describes unmodified starch products with degrees of branching of more than 4% and up to 10% or higher. The enzymatic transglycosilation can be carried out in a manner known per se, for example by incubating waxy corn starch, potato starch obtained from potatoes having a high amylopectin content, or starch obtained from rice, from manioc, from wheat, from wheat having a high amylopectin content, from corn, from corn having a high amolypectin content, or from corn having a high amylose content, with the appropriate enzymes under mild conditions at pH values between 6 and 8 and temperatures between 25 and 40° C. in aqueous solution. The molecular weight $M_w$ means, as used in the context of the highly branched, unsubstituted or low-substituted starch products, the weight average molecular weight. This can be determined in a manner known per se by various methods, i.e. by gel permeation chromatography (GPC) or high pressure liquid chromatography (HPLC) in conjunction with light scattering and RI detection. The $C_2/C_6$ ratio preferred for substituted starches is in the range from 5 to 9. The high degree of branching of the highly branched, unsubstituted or low-substituted starch products increases the solubility in water thereof to such an extent that hydroxyethyl or hydroxypropyl substitution can be wholly or substantially dispensed with in order to keep the starch product in solution. The average molecular weight of the highly branched, unsubstituted or low-substituted starch product can be increased in a suitable manner via the permeability limit of the peritoneum. The characteristic variable which can be used in this case is also the GPC value of the so-called bottom fraction BF90% (molecular weight at 90% of the peak area as a measure of the proportion of smaller molecule fractions). A greater ultrafiltration (UF) efficiency can be achieved by appropriate raising of the molecular weight with, at the same time, a drastically reduced absorption across the peritoneal membrane. At the same time, high molecular weight residual fragments which are produced by degradation by endogenous amylase, which can no longer be further degraded by amylase, and which are stored in organs or tissues, no longer occur or now occur to only a slight extent.

According to the present invention, hydroxyalkyl starch is reacted with a crosslinking compound M-L-A wherein M is an amino group and A is an acetal group or a ketal group, group M and group L being separated by a suitable spacer.

The Acetal or Ketal Group A

As far as the acetal group or ketal group A is concerned, no specific limitations exist. In the context of the present invention, the term "acetal group" also comprises sulphur acetals and nitrogen acetals, and the term "ketal group" also comprises sulphur ketals and nitrogen ketals. Additionally, as far as the term "acetal group" is concerned, hemiacetals are explicitly excluded, and as far as the term "ketal group" is concerned, hemiketals are explicitly excluded.

According to a preferred embodiment of the present invention, group A of the crosslinking compound M-L-A is a residue according to formula (IIa)

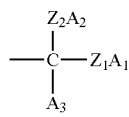

(IIa)

wherein $Z_1$ and $Z_2$ are each independently O or S or $NR_x$, preferably O, wherein $R_x$ is H or lower alkyl such as methyl, ethyl, or propyl such as n-propyl or i-propyl, or C(O)—$R_y$ wherein $R_y$ is preferably selected from the group consisting of $C_1$-$C_6$ alkyl and $C_6$-$C_{14}$ aryl, even more preferably selected from the group consisting of optionally substituted, preferably non-substituted methyl, ethyl, n-propyl, isopropyl, n-butyl, isobutyl, and tert-butyl; $R_x$ preferably being H;

$A_1$ and $A_2$ are each independently methyl, ethyl, n-propyl, isopropyl, n-butyl, tert-butyl, benzyl, 1,1,1-trichloroethyl, nitrobenzyl, methoxybenzyl, ethoxybenzyl, or are forming a ring according to formula (IIb)

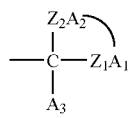

(IIb)

wherein $A_1$ and $A_2$, taken together, are —(CH$_2$)$_2$— or —(CH$_2$)$_3$— or —(CH$_2$CH(CH$_3$))—, and wherein $A_3$ is H or methyl, ethyl, n-propyl, isopropyl, n-butyl, isobutyl, pentyl, benzyl, or is forming a ring with the N atom of the amino group M or with a suitable atom comprised in L.

Preferably, at least one of $Z_1$ and $Z_2$ is O, more preferably both $Z_1$ and $Z_2$ are O.

As far as the residue $A_3$ is concerned, acetal groups are preferred according to the present invention, i.e. $A_3$ is preferably H.

If A is a ketal group, it is preferred that $A_3$ is methyl. Therefore, conceivable ketal groups A according to the present invention are, among others,

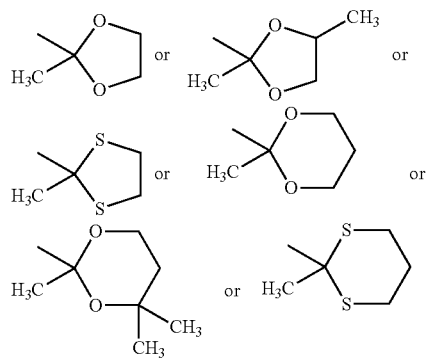

If $A_3$ is, e.g., forming a ring with either the N atom of the amino group M or with a suitable atom comprised in L, conceivable crosslinking compounds according to the present invention are, e.g.,

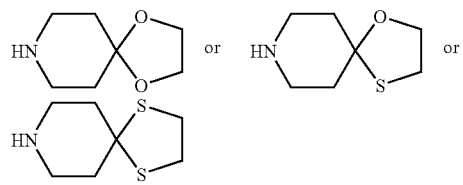

An especially preferred crosslinking compound according to the present invention is

i.e., the amino group M is a secondary amine, both $Z_1$ and $Z_2$ are O, and $A_1$ and $A_2$, taken together, are —(CH$_2$)$_2$—.

According to a preferred embodiment, $A_1$ and $A_2$ are each methyl or ethyl, even more preferably ethyl. Therefore, a particularly preferred acetal group A according to the present invention is —CH(OCH$_3$)$_2$ or CH(OC$_2$H$_5$)$_2$, in particular —CH(OC$_2$H$_5$)$_2$.

According to a further embodiment wherein $A_1$ and $A_2$ are forming a ring according to formula (IIb), $A_1$ and $A_2$, taken together, are preferably —(CH$_2$)$_2$—. As far as this embodiment is concerned, particularly preferred acetal groups A according to the present invention are

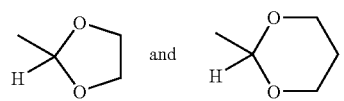

The Amino Group M

As far as the amino group M is concerned, no particular restrictions exist with the proviso that the amino group can be reacted with either the oxidised or non-oxidised reducing end, i.e. via carbon atom C* of the reducing terminal saccharide unit of HAS, preferably HES, in either the non-oxidised state, i.e. as hemiacetal or as free aldehyde group, or in the oxidised state, i.e. as lactone or as free carboxy group. The term "amino group" as used in this context of the present application also comprises suitable salts of the amino group, such as, e.g., protonated amino groups, with a pharmaceutically acceptable anion, such as, e.g., chloride, hydrogen sulfate, sulfate, carbonate, hydrogen carbonate, citrate, phosphate, or hydrogen phosphate.

Preferably, the amino group of the crosslinking compound M-L-A according to the present invention is a group according to formula (IIc)

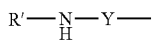

wherein Y is either absent or is a chemical moiety selected from the group consisting of

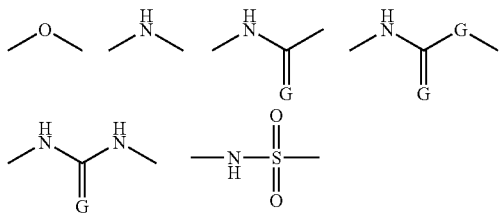

wherein G is O or S or NH, and, if present twice, each G is independently O or S or NH, G preferably being O, and wherein R' is H or a hydroxy group or an organic residue selected from the group consisting of alkyl, substituted alkyl, alkenyl, substituted alkenyl, alkynyl, substituted alkynyl, aryl, substituted aryl, arylalkyl, substituted arylalkyl, alkylaryl, and substituted alkylaryl. In this context, the term "alkyl" relates to non-branched alkyl residues, branched alkyl residues, and cycloalkyl residues. Preferably, each of these organic residues has from 1 to 10 carbon atoms. As conceivable substituents, halogens such as F, Cl or Br may be mentioned. Preferably, the organic residues are non-substituted hydrocarbons.

If R' is a hydroxy group, the preferred amino group of the present invention is HO—NH—, i.e. Y is absent.

Preferably, in case R' is an organic residue, R' is selected from the group consisting of alkyl and substituted alkyl, the alkyl residue being especially preferred. Even more preferably, the optionally substituted alkyl residue has from 1 to 10, more preferably from 1 to 6, more preferably from 1 to 4 such as 1, 2, 3, or 4 carbon atoms. Thus, preferred organic residues according to the present invention are methyl, ethyl, n-propyl, isopropyl, n-butyl, isobutyl, or t-butyl. According to an especially preferred embodiment, the organic residue R' is methyl or ethyl, in particular methyl.

Therefore, in case R' is an organic residue, preferred amino groups according to the present invention are, e.g., H$_3$C—CH$_2$—NH—, H$_3$C—NH—, H$_5$C$_6$—NH—, H$_3$C—CH$_2$—NH—O—, H$_3$C—NH—O—, H$_5$C$_6$—NH—O—, with H$_3$C—NH—, H$_5$C$_6$—NH—, and H$_3$C—NH—O— being particularly preferred.

According to the present invention, it is also possible that R' is not a separate residue but forms a ring structure with a suitable atom comprised in L or with residue A$_3$ of group A of the crosslinking compound. These structures are also comprised in above-mentioned definition of the term "alkyl" with respect to R'. By way of example, R' can form a ring structure with residue A$_3$ of group A of the crosslinking compound, A being a ketal group. Conceivable crosslinking compounds are, e.g.,

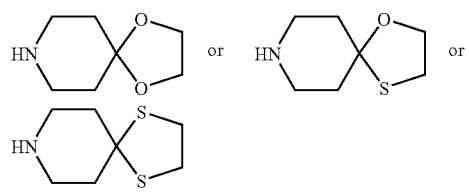

In this case, an especially preferred crosslinking compound according to the present invention is

i.e., the amino group M is a secondary amine, both Z$_1$ and Z$_2$ are O, and A$_1$ and A$_2$, taken together, are —(CH$_2$)$_2$—.

In a preferred embodiment of the present invention, R' is H. Thus, preferred amino groups M of the present are

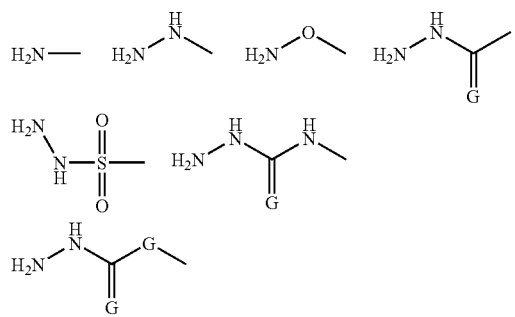

wherein G is O or S, and, if present twice, independently O or S, O being preferred.

Especially preferred amino groups M of the present invention, if R' is H, are H$_2$N—, H$_2$N—O—, and H$_2$N—NH—(C=O)—.

Hence, the present invention also relates to the method and the derivative mentioned above, wherein the amino group M is H$_2$N—, H$_2$N—O—, H$_2$N—NH—(C=O)—, H$_3$C—NH— or H$_3$C—NH—O—, preferably H$_2$N—, H$_2$N—O—, or H$_2$N—NH—(C=O)—.

The Spacer L

According to the present invention, functional groups M and A of the crosslinking compound are separated by a suitable spacer. The term "spacer" as used in this context of the present application relates to any suitable chemical moiety bridging M and A.

In general, there are no particular restrictions as to the chemical nature of the spacer L with the proviso that L has in particular chemical properties enabling carrying out the inventive method for the preparation of the novel derivatives and providing suitable chemical properties for the novel derivatives as far as their intended use is concerned.

According to a preferred embodiment of the present invention, L bridging M and A is a spacer comprising at least one structural unit according to formula (IId)

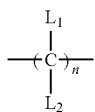
(IId)

wherein $L_1$ and $L_2$ are independently from each other H or an organic residue selected from the group consisting of alkyl, substituted alkyl, alkenyl, substituted alkenyl, alkynyl, substituted alkynyl, aryl, substituted aryl, arylalkyl, substituted arylalkyl, alkylaryl, substituted alkylaryl, and residues —O—R" wherein R" is selected from the group consisting of alkyl, substituted alkyl, alkenyl, substituted alkenyl, alkynyl, substituted alkynyl, aryl, substituted aryl, arylalkyl, substituted arylalkyl, alkylaryl, substituted alkylaryl.

In this context, the term "alkyl" relates to non-branched alkyl residues, branched alkyl residues, and cycloalkyl residues. As preferred substituents, halogens such as F, Cl or Br may be mentioned.

Preferably, $L_1$ and $L_2$ are independently from each other H or an organic residue selected from the group consisting of alkyl and substituted alkyl; more preferably, $L_1$ and $L_2$ are independently from each other H or alkyl; even more preferably, both $L_1$ and $L_2$ are H.

Preferably, if $L_1$ and $L_2$ are organic residues, each of $L_1$ and $L_2$ may independently contain 1 to 20, preferably 1 to 10, more preferably 1 to 8, more preferably 1 to 6, more preferably 1 to 4 carbon atoms. Especially preferred are residues $L_1$ and $L_2$ such as optionally substituted, preferably non-substituted methyl, ethyl, n-propyl, isopropyl, n-butyl, isobutyl, tert-butyl residues. According to the present invention, $L_1$ may be H and $L_2$ may be an organic residue as defined above.

As far as integer n is concerned, n is preferably from 1 to 20, preferably from 1 to 10, more preferably from 1 to 6, more preferably from 1 to 4, more preferably 2.

If integer n is greater than 1, the groups $(CL_1L_2)$ may be the same or different from each other. According to a preferred embodiment of the present invention, groups $(CL_1L_2)$ directly linked to each other have the same constitution.

According to a preferred embodiment of the present invention, the spacer L consists of a structural unit according to formula (IId) wherein $L_1$ and $L_2$ are as defined above. More preferably, integer n is from 1 to 20, more preferably from 1 to 10 such as 1, 2, 3, 4, 5, 6, 7, 8, 9 or 10. Even more preferably, each of the groups $(CL_1L_2)$ is $(CH_2)$ such that spacer L bridging M and A has the structure

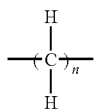

wherein n is an integer from 1 to 20, more preferably from 1 to 10 such as 1, 2, 3, 4, 5, 6, 7, 8, 9 or 10. Even more preferably, n is in the range of from 1 to 6, more preferably in the range of from 1 to 4, such as 1, 2, 3, or 4, and in particular 2.

Therefore, according to a particularly preferred embodiment of the present invention, spacer L is —$CH_2$—$CH_2$—.

According to further embodiments of the present invention, spacer L of the crosslinking compound comprises at least one structural unit according to formula (IId)

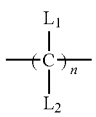
(IId)

wherein n, $L_1$ and $L_2$ are as defined above, preferably

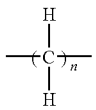

and wherein L further comprises at least one chemical moiety different from —$(CL_1L_2)$-.

In this context, embodiments may be mentioned wherein the spacer L consists of a structural unit —$(CL_1L_2)_n$- and a further chemical moiety T which separates —$(CL_1L_2)_n$- from group M or A. Also embodiments are conceivable wherein the spacer L consists of a structural unit —$(CL_1L_2)_n$- and two further chemical moieties $T_1$ and $T_2$ wherein $T_1$ separates —$(CL_1L_2)_n$- from group M and $T_2$ separates —$(CL_1L_2)_n$- from group A. Thus, the present invention also encompasses embodiments according to which the crosslinking compound has one of the following structures:

As to the chemical moieties T, $T_1$ or $T_2$, there are no particular restrictions as to their chemical nature with the proviso that L has in particular chemical properties enabling carrying out the inventive method for the preparation of the novel derivatives and providing suitable chemical properties for the novel derivatives as far as their intended use is concerned.

Therefore, T, $T_1$ and/or $T_2$ may comprise optionally substituted aryl residues, suitable heteroatoms, suitable functional groups, or the like. As far as functional groups are concerned, embodiments may be mentioned according to which these functional groups result from the preparation of the crosslinking compound wherein at least a first compound and at least a second compound are reacted with each other to give a compound M-L-A. By way of example, a first compound M-L'-$W_1$ and a second compound $W_2$-L"-A may be reacted to give crosslinking compound M-L-A wherein -L- is -L'-F-L"- and F represents the functional group resulting from the reaction of functional group $W_1$ with functional group $W_2$, and wherein at least one of L' and L" comprises the structure unit —$(CL_1L_2)_n$-. Such functional groups $W_1$ and $W_2$ may be suitably chosen. By way of example, one of groups $W_1$ and $W_2$, i.e. $W_1$ or $W_2$, may be chosen from the group consisting of the functional groups according to the following list while the other group, $W_2$ or $W_1$, is suitable selected and capable of forming a chemical linkage with $W_1$ or $W_2$, wherein $W_2$ or $W_1$ is also preferably selected from the above-mentioned group:

C—C-double bonds or C—C-triple bonds or aromatic C—C-bonds;
the thio group or the hydroxy group;
alkyl sulfonic acid hydrazides, aryl sulfonic acid hydrazides;
1,2-dioles;
1,2-amino-thioalcohols;
azides;
1,2-aminoalcohols;
the amino group —$NH_2$ or derivatives of the amino groups comprising the structure unit —NH— such as aminoalkyl groups, aminoaryl group, aminoaralkyl groups, or alkarylamino groups;
the hydroxylamino group —O—$NH_2$, or derivatives of the hydroxylamino group comprising the structure unit —O—NH—, such as hydroxylalkylamino groups, hydroxylarylamino groups, hydroxylaralkylamino groups, or hydroxylalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M', wherein G is O or S, and M' is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimid;
—NH—$NH_2$, or —NH—NH—;
—$NO_2$;
the nitril group;
carbonyl groups such as the aldehyde group or the keto group;
the carboxy group;
the —N=C=O group or the —N=C=S group;
vinyl halide groups such as the vinyl iodide or the vinyl bromide group or triflate;
—C≡C—H;
—(C=$NH_2$Cl)—OAlkyl
groups —(C=O)—$CH_2$-Hal wherein Hal is Cl, Br, or I;
—CH=CH—$SO_2$—;
a disulfide group comprising the structure —S—S—;
the group

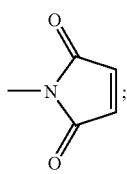

the group

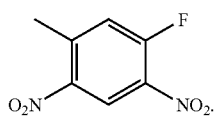

By way of example, $W_1$ or $W_2$ may be a carboxy group or an activated ester, and $W_2$ or $W_1$ may be an amino group or a hydroxy group such that F representing the functional group resulting from the reaction of functional group $W_1$ with functional group $W_2$, is an amid or an ester.

Therefore, by way of example, crosslinking compounds having a spacer L comprising, apart from structure unit —$(CL_1L_2)_n$-, a functional group, may have a constitution such as M-L'-(C=O)—NH—$(CL_1L_2)_n$-A or M-L'-(C=O)—O—$(CL_1L_2)_n$-A or M-L'-NH—(C=O)—$(CL_1L_2)_n$-A or M-L'-O—(C=O)—$(CL_1L_2)_n$-A or M-$(CL_1L_2)_n$-(C=O)—NH-L"-A or M-$(CL_1L_2)_n$-(C=O)—O-L"-A or M-$(CL_1L_2)_n$-NH—(C=O)-L"-A or M-$(CL_1L_2)_n$-O—(C=O)-L"-A wherein L' and L" may or may not comprise a structure unit —$(CL_1L_2)_n$-.

Among these structures, crosslinking compounds are preferred having constitutions M-L'-(C=O)—NH—$(CL_1L_2)_n$-A or M-$(CL_1L_2)_n$-(C=O)—NH-L"-A Also, among these structures, spacers are preferred wherein L' and L", if present, contain the structure unit —$(CL_1L_2)_n$-. In these cases, it is even more preferred that n is in the range of from 1 to 4, more preferably in the range of from 1 to 3, such as 1, 2, or 3. If a given spacer contains, for example, two structure units —$(CL_1L_2)_n$-, index n of each structure unit may be the same or different.

Therefore, the following crosslinking compounds are preferred having the following constitutions:

M-$(CL_1L_2)_n$-(C=O)—NH—$(CL_1L_2)_n$-A wherein each n is, independently from each other, preferably in the range of from 1 to 4, more preferably in the range of from 1 to 3, such as 1, 2, or 3. Accordingly, preferred spacers L have the constitution —$(CL_1L_2)_n$-(C=O)—NH—$(CL_1L_2)_n$-

Thus, particularly preferred crosslinking compounds containing —(C=O)—NH— are

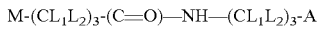

or

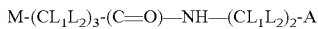

or

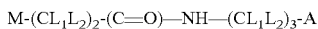

or

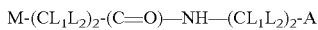

More preferred crosslinking compounds containing —(C=O)—NH— are

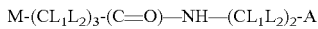

or

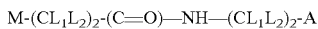

Even more preferably, $L_1$ and $L_2$ are both H. Thus, crosslinking compounds having the following constitutions

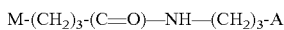

or

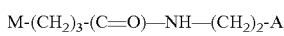

or

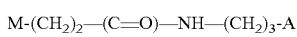

or

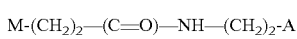

are especially preferred.

Crosslinking compounds having the following constitutions

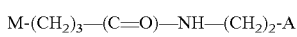

or

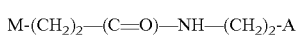

are most preferred.

By way of example, preferred crosslinking compounds of the present invention are

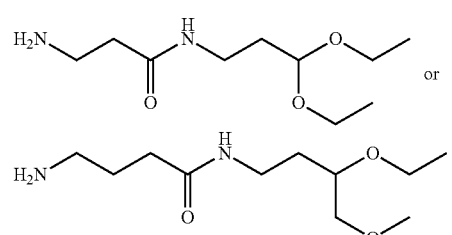

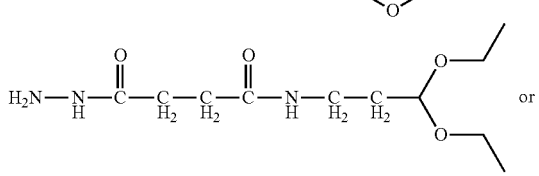

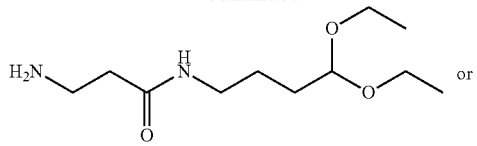

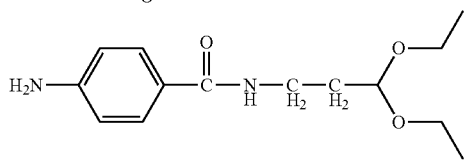

Again by way of example and in order to illustrate above-discussed structures, a crosslinking compound conceivable in the context of the present invention may be

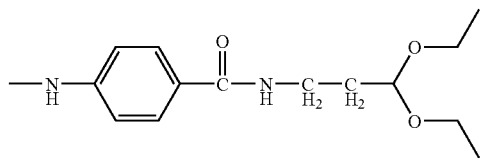 [SMILES: CCOC(CCNC(=O)c1ccc(NC)cc1)OCC]

According to a further embodiment of the present invention, spacer L may comprise more than one structure units —$(CL_1L_2)_n$- wherein these structure units may be same or different, i.e. the structure may differ in n and/or $L_1$ and/or $L_2$, wherein at least two such structure units may be separated by a heteroatom such as O or S. Preferably, according to this embodiment, the spacer L comprises at least one structure unit —$(CL_1L_2)_{n1}$-O—$(CL_1L_2)_{n2}$-, preferably —$(CH_2)_{n1}$-O—$(CH_2)_{n2}$ wherein n1 is equal to or different from n2, and wherein the spacer L is linked via —$(CL_1L_2)_{n1}$- to the amino group M of the crosslinking compound, i.e. the crosslinking compound comprising the following sub-structure

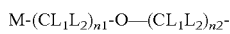

According to a preferred conceivable embodiment, spacer structures such as

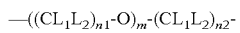

may be mentioned, with m being an integer from 1 to 20, preferably from 1 to 10, more preferably from 1 to 6 such as 1, 2, 3, 4, 5, or 6. Particularly preferably, m is 1, 2, or 3, more preferably 2 or 3. Preferably, n1 is from 2 to 4, and more preferably 2. Preferably, n2 is from 1 to 4, more preferably 1 or 2. Therefore, preferred structures are, by way of example,

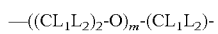

and more preferably

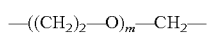

Again by way of example and in order to illustrate above-discussed structures, a crosslinking compound preferably used in the context of the present invention is

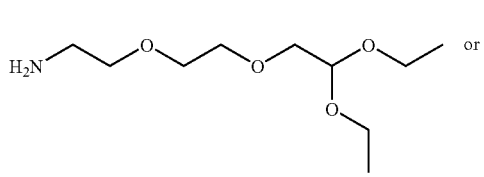

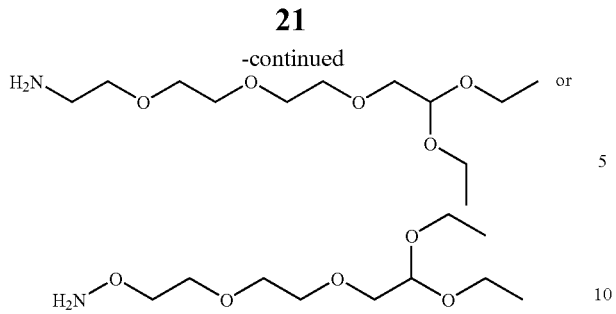

According to a further embodiment of the present invention, group M and group A may be separated by 2 suitable chemical moieties, at least one thereof comprising —($CL_1L_2$)n-, such that the N atom of group M and the C atom of ketal group A are forming a ring. A preferred embodiment was already presented above and has the structure

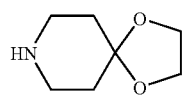

Especially preferred crosslinking compounds of the present invention are compounds having, as group M, the group $H_2N$— or the group $H_2N$—O— or the group $H_2N$—NH—(C=O)—, especially preferably the group $H_2N$—, and, as group A, an acetal group, preferably an acetal group having the structure

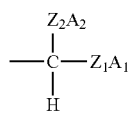

wherein, more preferably, $Z_1$ and $Z_2$ are O and, even more preferably, $A_1$ and $A_2$ are both ethyl. Even more preferably, the spacer L consists of structure unit —($CL_1L_2$)$_n$-, with $L_1$ and $L_2$ preferably being H, and integer n even more preferably being from 1 to 20, preferably from 1 to 10, more preferably from 1 to 6, more preferably from 1 to 4, more preferably 2.

Therefore, preferred crosslinking compounds according to the present invention are, by way of example,

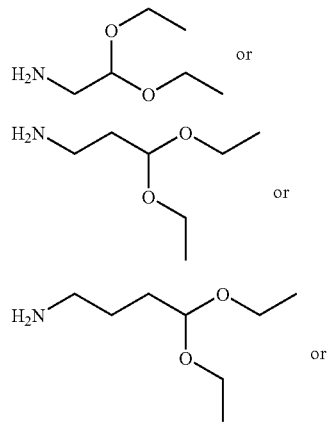

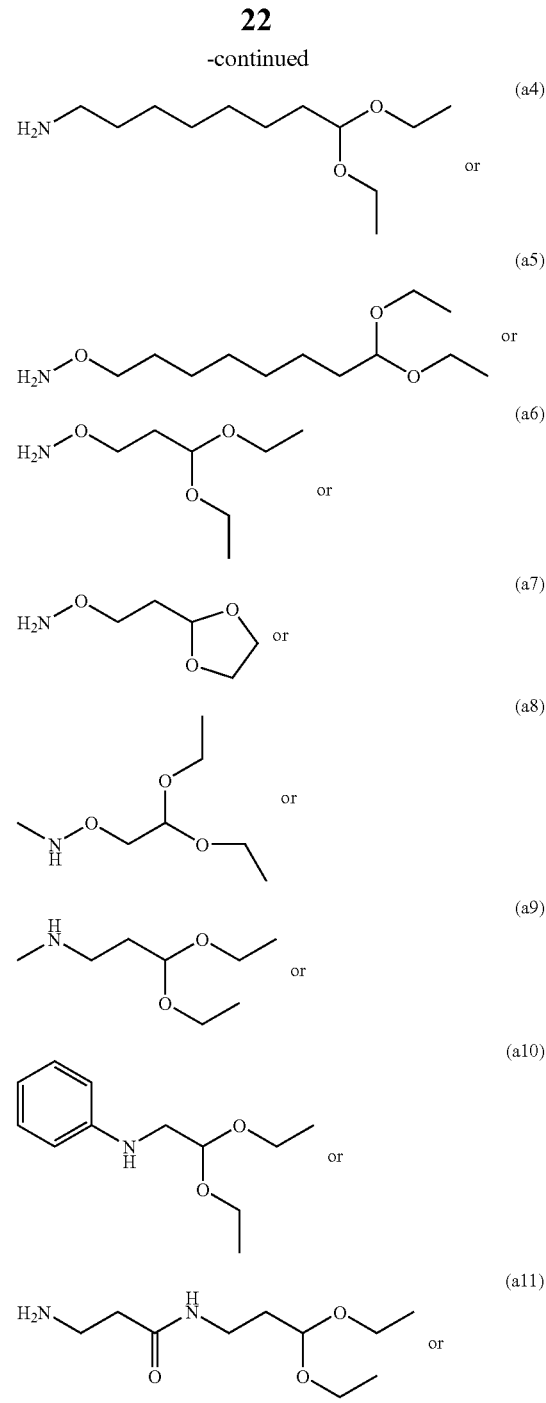

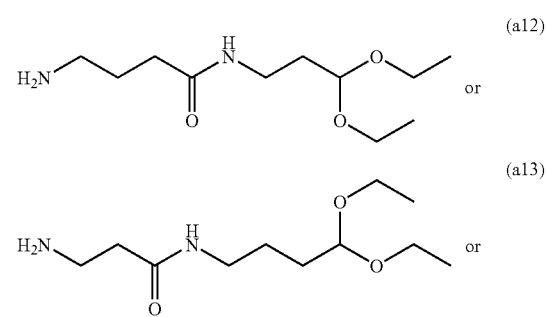

-continued (a14)
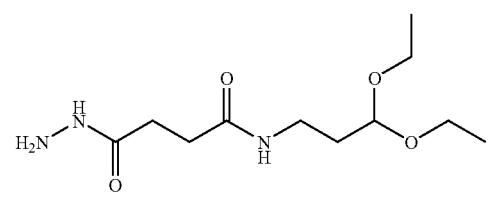

(a15)
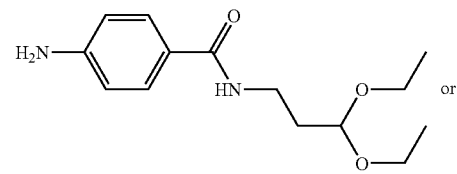

(a16)
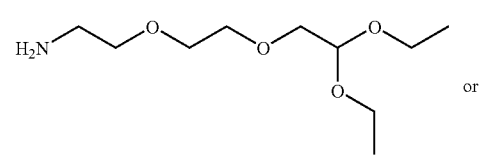

(a17)
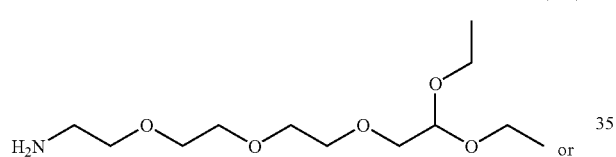

(a18)
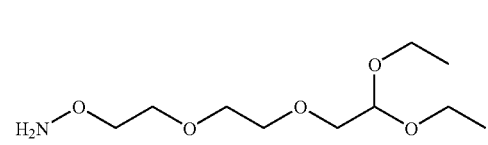

(a19)
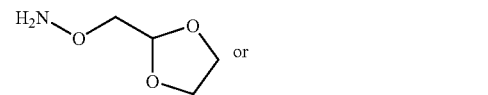

(a20)
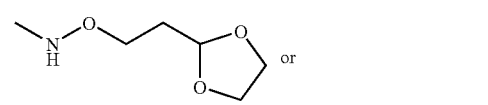

(a21)
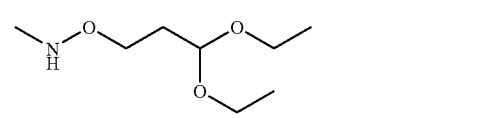

Even more preferably, the cross-linking compounds are selected from the group consisting of structures (a2), (a4), (a11), (a12), (a14), (a16), and (a18). More preferably, the cross-linking compounds are selected from the group consisting of structures (a2), (a11), (a12), (a14), (a16), and (a18). In particular, cross-linking compounds are selected from the group consisting of structures (a2), (a11), (a12), and (a16).

Particularly preferred as crosslinking compound M-L-A is 1-amino-3,3-diethoxypropane,

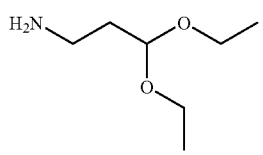

By way of example, conceivable amino-acetal crosslinking compounds according to the present invention are:

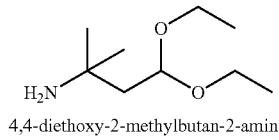
4,4-diethoxy-2-methylbutan-2-amine

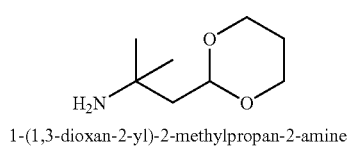
1-(1,3-dioxan-2-yl)-2-methylpropan-2-amine

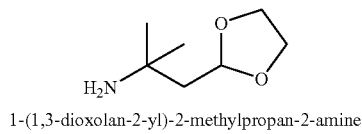
1-(1,3-dioxolan-2-yl)-2-methylpropan-2-amine

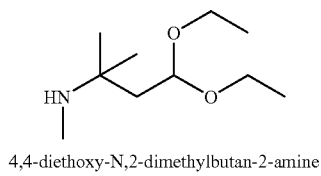
4,4-diethoxy-N,2-dimethylbutan-2-amine

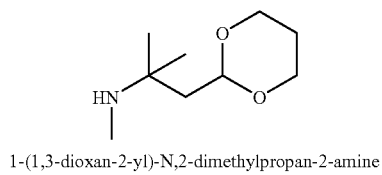
1-(1,3-dioxan-2-yl)-N,2-dimethylpropan-2-amine

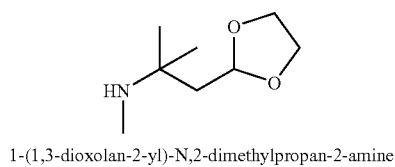
1-(1,3-dioxolan-2-yl)-N,2-dimethylpropan-2-amine

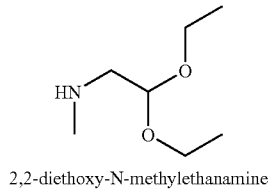
2,2-diethoxy-N-methylethanamine

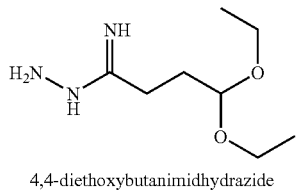
4,4-diethoxybutanimidhydrazide

-continued

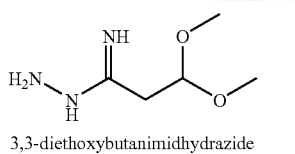

3,3-diethoxybutanimidhydrazide

By way of example, conceivable amino-ketal crosslinking compounds according to the present invention are:

1-oxa-4-thia-8-azaspiro[4·5]decane

1,4-dithia-8-azaspiro[4·5]decane

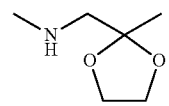

N-methyl-1-(2-methyl-1,3-dioxolan-2-yl)
methanamine

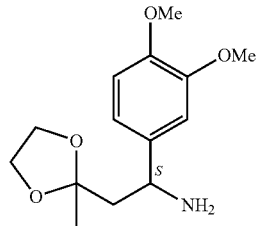

1-3,4-dimethoxyphenyl)-2-(2-methyl-
1,3-dioxolan-2-yl)ethanamine

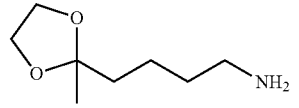

4-(2-methyl-1,3-dioxolan-2-yl)butan-1-amine

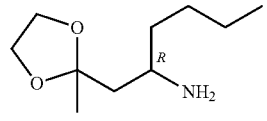

1-(2-methyl-1,3-dioxolan-2-yl)hexan-2-amine

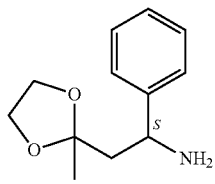

2-(2-methyl-1,3-dioxolan-2-yl)-1-
phenylethanamine

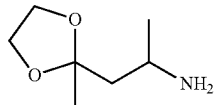

1-(2-methyl-1,3-dioxolan-2-yl)propan-2-amine

-continued

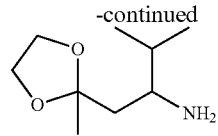

3-methyl-1-(2-methyl-1,3-dioxolan-2-yl)butan-2-amine

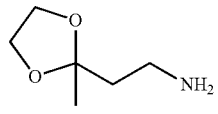

2-(2-(methyl-1,3-dioxolan-2-yl)ethanamine

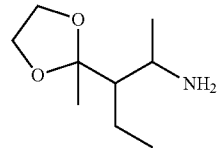

3-(2-methyl-1,3-dioxolan-2-yl)pentan-2-amine

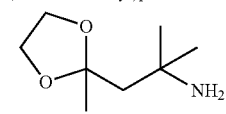

2-methyl-1-(2-methyl-1,3-dioxolan-2-yl)-propan-2-amine

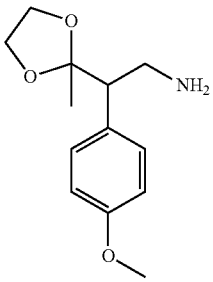

2-(4-methoxyphenyl)-2-(2-methyl-
1,3-dioxolan-2-yl)ethanamine

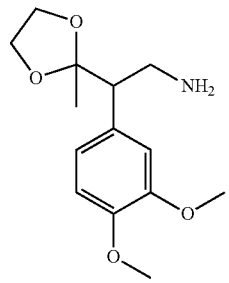

2-(3,4-dimethoxyphenyl)-2-(2-methyl-
1,3-dioxolan-2-yl)ethanamine

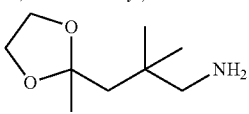

2,2-dimethyl-3-(2-methyl-1,3-dioxolan-
2-yl)propan-1-amine

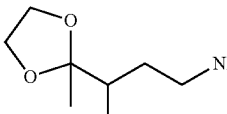

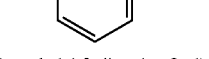

3-(2-methyl-1,3-dioxolan-2-yl)-3-
phenylpropan-1-amine

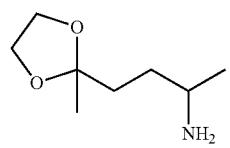

4-(2-methyl-1,3-dioxolan-
2-yl)butan-2-amine

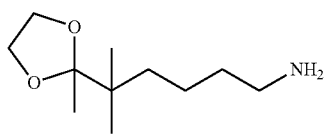

5-methyl-5-(2-methyl-1,3-dioxolan-
2-yl)hexan-1-amine

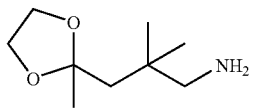

2,2-dimethyl-3-(2-methyl-1,3-dioxolan-
2-yl)propan-1-amine

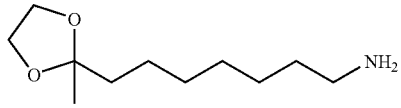

7-(2-methyl-1,3-dioxolan-2-yl)heptan-1-amine

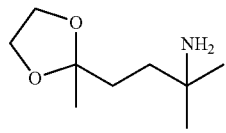

2-methyl-4-(2-methyl-1,3-dioxolan-2-yl)butan-2-amine

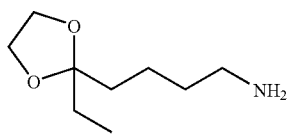

4-(2-methyl-1,3-dioxolan-2-yl)hexan-1-amine

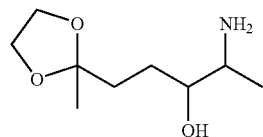

4-amino-1-(2-methyl-1,3-dioxolan-2-yl)pentan-3-ol

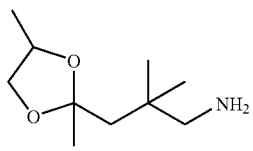

3-(2,4-dimethyl-1,3-dioxolan-2-yl)-2,2-dimethylpropan-1-amine

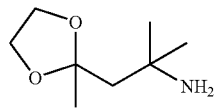

2-methyl-1-(2-methyl-1,3-dioxolan-2-yl)propan-2-amine

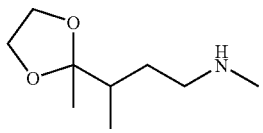

N-methyl-3-(2-methyl-1,3-dioxolan-2-yl)butan-1-amine

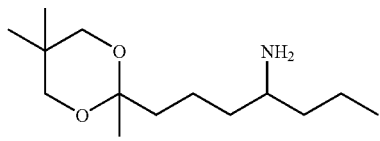

1-(2,5,5-trimethyl-1,3-dioxan-2-yl)heptan-4-amine

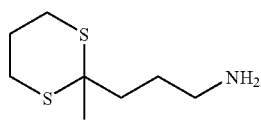

3-(2-methyl-1,3-dithian-2-yl)propan-1-amine

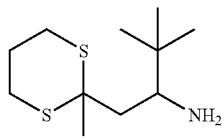

3,3-dimethyl-1-(2-methyl-1,3-dithian-2-yl)butan-2-amine

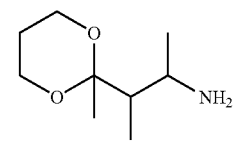

3-(2-methyl-1,3-dioxan-2-yl)butan-2-amine

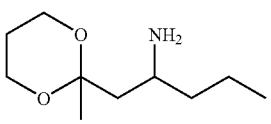

1-(2-methyl-1,3-dioxan-2-yl)pentan-2-amine

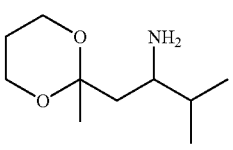

3-methyl-1-(2-methyl-1,3-dioxan-2-yl)butan-2-amine

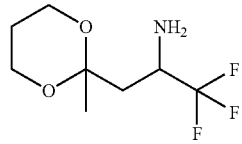

1,1,1-trifluoro-3-(2-methyl-1,3-dioxan-2-yl)propan-2-amine

Hydroxyalkyl Starch Derivative

Accordingly, the present invention relates to a hydroxyalkyl starch (HAS) derivative obtainable or obtained by the method as described above.

Moreover, the present invention relates to a HAS derivative of formula (III)

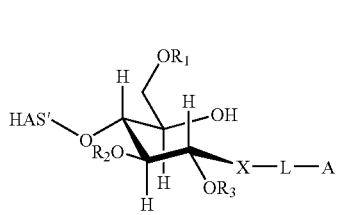

(III)

wherein A is an acetal or ketal group; L is a spacer bridging X and A;

wherein X is the functional group resulting from the reaction of an amino group M of a crosslinking compound of formula (II)

M-L-A with hydroxyalkyl starch (HAS) of formula (I)

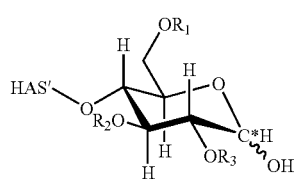

via carbon atom C* of the HAS, wherein C* is optionally oxidised prior to the reaction of HAS with M, wherein HAS' is the remainder of the hydroxyalkyl starch molecule and $R_1$, $R_2$ and $R_3$ are independently hydrogen or a linear or branched hydroxyalkyl group.

As far as preferred embodiments regarding HAS, preferably HES, L, A, $R_1$, $R_2$, and $R_3$ are concerned, specific reference is made to the embodiments as described hereinabove.

Further, the present invention relates to the HAS derivative as described above, wherein $R_1$, $R_2$ and $R_3$ are independently a group —(CH$_2$CH$_2$O)$_n$—H, wherein n is an integer, preferably 0, 1, 2, 3, 4, 5, or 6.

Further, the present invention relates to the HAS derivative as described above, wherein the hydroxyalkyl starch is hydroxyethyl starch (HES).

Further, the present invention relates to the HAS derivative as described above, wherein A is a residue according to formula (IIa)

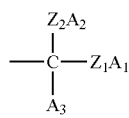

wherein
$Z_1$ and $Z_2$ are each independently O or S or NR$_x$, preferably O, wherein R$_x$ is H or lower alkyl such as methyl, ethyl, or propyl, preferably H;

$A_1$ and $A_2$ are each independently methyl, ethyl, n-propyl, isopropyl, n-butyl, tert-butyl, benzyl, 1,1,1-trichloroethyl, nitrobenzyl, methoxybenzyl, ethoxybenzyl, or are forming a ring according to formula (IIb)

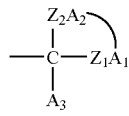

wherein $A_1$ and $A_2$, taken together, are —(CH$_2$)$_2$— or —(CH$_2$)$_3$— or —(CH$_2$CH(CH$_3$))—, and wherein $A_3$ is H or methyl, ethyl, n-propyl, isopropyl, n-butyl, isobutyl, pentyl, benzyl, or is forming a ring with the N atom of the amino group M or with a suitable atom comprised in L, $A_3$ preferably being H.

The precise chemical nature of group X of the HAS derivative according to the invention depends on the respective chemical nature of group M, on the oxidation state of the carbon atom C* of the reducing end of HAS, and on the reaction conditions such as solvent, temperature and so forth employed for the reaction. According to embodiments of the present invention wherein the carbon atom C* is employed in oxidised and non-oxidised state, specific and preferred examples are discussed in detail hereinunder.

Preferably, as far as X is concerned, the present invention relates to the HAS derivative as described above, wherein X is selected from the group consisting of —CH=N—, —CH$_2$—NH—, —CH=N—O—, —CH$_2$—NH—O—, —C(=O)—NH—, —C(=O)—NH—NH—, —CH=N—NH—(C=O)—, —CH$_2$—NH—NH—(C=O)—, preferably consisting of —CH$_2$—NH—, —CH=N—, —CH=N—O—, —CH$_2$—NH—O—, —CH=N—NH—(C=O)—, and —CH$_2$—NH—NH—(C=O)—, more preferably consisting of —CH$_2$—NH—, —CH=N—, —CH=N—O—, and —CH$_2$—NH—O—.

For certain embodiments of the group X, it is conceivable that the terminal saccharide unit of the HAS as present in the HAS derivative is present in a ring structure which may be in equilibrium with the open structure according to formula (III) above, the ring structure and the open structure having a certain equilibrium distribution. In these cases, and for the purpose of the present invention, formula (III) as given above comprises the open structure as well as the ring structure, and formula (III) does not restrict the HAS derivative to the open structure. For specific and preferred examples are discussed in detail hereinunder, the ring structure is shown in some cases.

Further, the present invention relates to the HAS derivative as described above, wherein L bridging M and A is a spacer comprising at least one structural unit according to formula (IId), preferably consisting of a structural unit according to formula (IId)

wherein $L_1$ and $L_2$ are independently from each other H or an organic residue selected from the group consisting of alkyl, substituted alkyl, alkenyl, substituted alkenyl, alkynyl, substituted alkynyl, aryl, substituted aryl, arylalkyl, substituted arylalkyl, alkylaryl, substituted alkylaryl, and residues —O—R" wherein R" is selected from the group consisting of alkyl, substituted alkyl, alkenyl, substituted alkenyl, alkynyl, substituted alkynyl, aryl, substituted aryl, arylalkyl, substituted arylalkyl, alkylaryl, substituted alkylaryl; preferably H or an organic residue selected from the group consisting of alkyl and substituted alkyl; more preferably H or alkyl; more preferably H, wherein n is an integer from 1 to 20, preferably from 1 to 10, more preferably from 1 to 6, more preferably from 1 to 4, more preferably 2.

The Optionally Oxidised Reducing End of HAS, Preferably HES

According to the present invention, HAS, preferably HES can be reacted via carbon atom C* of the terminal reducing end of the starch with amino group M of the crosslinking compound wherein C* is optionally oxidised prior to the reaction of HAS with M.

The term "the HAS is reacted via the reducing end" or "the HAS is reacted via carbon atom C* of the terminal reducing end" as used in the context of the present invention may relate to a process according to which the HAS is reacted predominantly via its (optionally selectively oxidised) reducing end.

This term "predominantly via its (optionally selectively oxidised) reducing end" relates to processes according to which statistically more than 50%, preferably at least 55%, more preferably at least 60%, more preferably at least 65%, more preferably at least 70%, more preferably at least 75%, more preferably at least 80%, more preferably at least 85%, more preferably at least 90%, and still more preferably at least 95% such as 95%, 96%, 97%, 98%, or 99% of the HAS molecules employed for a given reaction are reacted via at least one (optionally selectively oxidised) reducing end per HAS molecule, wherein a given HAS molecule which is reacted via at least one (optionally selectively oxidised) reducing end can be reacted in the same given reaction via at least one further suitable functional group which is comprised in said polymer molecule and which is not a reducing end. If one or more HAS molecule(s) is (are) reacted via at least one (optionally selectively oxidised) reducing end and simultaneously via at least one further suitable functional group which is comprised in this (these) HAS molecule(s) and which is not a (optionally selectively oxidised) reducing end, statistically preferably more than 50%, preferably at least 55%, more preferably at least 60%, more preferably at least 65%, more preferably at least 70%, more preferably at least 75%, more preferably at least 80%, more preferably at least 85%, more preferably at least 90%, and still more preferably at least 95% such as 95%, 96%, 97%, 98%, or 99% of all reacted functional groups of these HAS molecules, said functional groups including the (optionally selectively oxidised) reducing ends, are (selectively oxidised) reducing ends.

The term "reducing end" as used in the context of the present invention relates to the terminal aldehyde group of a HAS molecule which may be present as aldehyde group and/or as corresponding hemiacetal form and/or as acetal group, the acetal group having the following structure

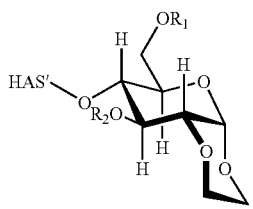

which can be present if residue —OR$_3$ according to formula (I) above is —O—CH$_2$—CH$_2$—OH.

In case the reducing end is oxidised, the oxidised reducing end is in the form of a carboxy group and/or of the corresponding lactone.

Oxidised Reducing End

Therefore, according to a first embodiment of the present invention, the crosslinking compound is reacted via the amino group with the oxidised C* atom of the terminal reducing end of HAS, preferably HES.

Although the oxidation may be carried out according to all suitable method or methods resulting in the oxidised reducing end of hydroxyalkyl starch, it is preferably carried out using an alkaline iodine solution as described, e.g., in Sommermeyer et al., U.S. Pat. No. 6,083,909, column 5, lines 63-67, and column 7, lines 25-39; column 8, line 53 to column 9, line 20, the respective content being incorporated into the present invention by reference.

Selectively oxidising the HAS, preferably the HES leads to HAS, preferably HES being a lactone

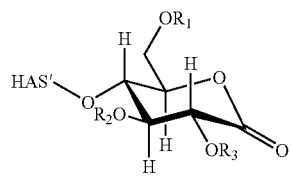

and/or a carboxylic acid

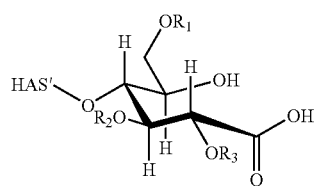

or a suitable salt of the carboxylic acid such as alkali metal salt, preferably as sodium and/or potassium salt, and HAS' preferably being HES'.

According to a first alternative of the present invention, this form of the HAS, preferably HES, is reacted as such with the amino group M of the crosslinking compound.

According to a second alternative of the present invention, the HAS, preferably HES, selectively oxidised at its reducing end, is first reacted with a suitable compound to give the HAS, preferably HES, comprising a reactive carboxy group.

Introducing the reactive carboxy group into the HAS which is selectively oxidised at its reducing end may be carried out by all conceivable methods and all suitable compounds.

According to a specific method of the present invention, the HAS which is selectively oxidised at its reducing end is reacted at the oxidised reducing end with at least one alcohol, preferably with at least one acidic alcohol such as acidic alcohols having a pK$_A$ value in the range of from 6 to 12 or of from 7 to 11 at 25° C. The molecular weight of the acidic alcohol may be in the range of from 80 to 500 g/mol, such as of from 90 to 300 g/mol or of from 100 to 200 g/mol.

Suitable acidic alcohols are all alcohols H—O—R$_A$ having an acidic proton and are capable of being reacted with the oxidised HAS to give the respective reactive HAS ester, preferably according to the formula

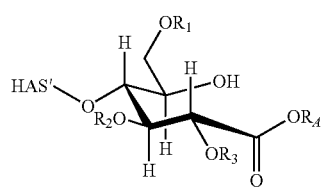

still more preferably according to formula

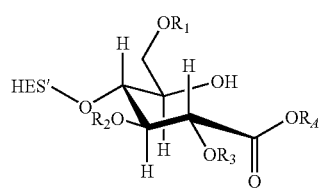

Preferred alcohols are N-hydroxy succinimides such as N-hydroxy succinimde or sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxysuccinimide and sulfo-N-hydroxysuccinimide being especially preferred. All alcohols may be employed alone or as suitable combination of two or more thereof. In the context of the present invention, it is also possible to employ a compound which releases the respective alcohol, e.g. by adding diesters of carbonic acid.

Therefore, the present invention also relates to a method as described above, wherein the HAS which is selectively oxidised at its reducing end is activated by reacting the oxidised HAS with an acidic alcohol, preferably with N-hydroxy succinimide and/or sulfo-N-hydroxy succinimide.

According to a preferred embodiment of the present invention, the HAS which is selectively oxidised at its reducing end is reacted at the oxidised reducing end with at least one carbonic diester $R_B$—O—(C=O)—O—$R_C$, wherein $R_B$ and $R_C$ may be the same or different. Preferably, this method gives reactive HAS according to the formula

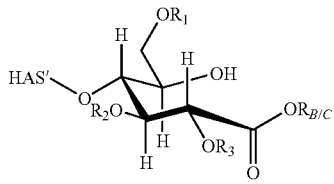

wherein HAS' is preferably HES'.

As suitable carbonic diester compounds, compounds may be employed whose alcohol components are independently N-hydroxy succinimides such as N-hydroxy succinimde or sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N,N'-disuccinimidyl carbonate and sulfo-N,N'-disuccinimidyl carbonate, with N,N'-disuccinimidyl carbonate being especially preferred.

Therefore, the present invention also relates a method as described above, wherein the HAS which is selectively oxidised at its reducing end is activated by reacting the oxidised HAS with N,N'-disuccinimidyl carbonate.

The acidic alcohol is reacted with the oxidised HAS or the salt of the oxidised HAS at a molar ratio of acidic alcohol:HAS preferably of from 5:1 to 50:1, more preferably of from 8:1 to 20:1, at a preferred reaction temperature of from 2 to 40° C., more preferably of from 10 to 30° C. and especially preferably of from 15 to 25° C. The reaction time is preferably in the range of from 1 to 10 h, more preferably of from 2 to 5 h, more preferably of from 2 to 4 h and particularly of from 2 to 3 h.

The carbonic diester compound is reacted with the oxidised HAS or the salt of the oxidised HAS at a molar ratio of diester compound:HAS generally of from 1:1 to 3:1, such as of from 1:1 to 1.5:1. The reaction time is generally in the range of from 0.1 to 12 h, like of from 0.2 to 6 h, or of from 0.5 to 2 h or of from 0.75 to 1.25 h.

According to a preferred embodiment of the present invention, reacting the oxidised HAS with acidic alcohol and/or carbonic diester is carried out in at least one aprotic solvent, such as in an anhydrous aprotic solvent having a water content of not more than 0.5 percent by weight, preferably of not more than 0.1 percent by weight. Suitable solvents are, among others, dimethyl sulfoxide (DMSO), N-methyl pyrrolidone, dimethyl acetamide (DMA), dimethyl formamide (DMF) and mixtures of two or more thereof. The reaction temperatures are preferably in the range of from 2 to 40° C., more preferably of from 10 to 30° C.

For reacting the oxidised HAS with the at least one acidic alcohol, at least one additional activating agent is employed.

Suitable activating agents are, among others, carbonyldiimidazole, carbodiimides such as diisopropyl carbodiimde (DIC), dicyclohexyl carbodiimides (DCC), 1-ethyl-3-(3-dimethylaminopropyl)carbodiimide (EDC), with dicyclohexyl carbodiimides (DCC) and 1-ethyl-3-(3-dimethylaminopropyl)carbodiimide (EDC) being especially preferred.

Therefore, the present invention also relates to the method as described above, where the HAS which is oxidised at its reducing end, is reacted with an acidic alcohol in the presence of an additional activating agent to give the reactive HAS ester.

According to one embodiment of the present invention, the reaction of the oxidised HAS with carbonic diester and/or acidic alcohol is carried out at a low base activity which may be determined by adding the reaction mixture to water with a volume ratio of water to reaction mixture of 10:1. Prior to the addition, the water which comprises essentially no buffer, has a pH value of 7 at 25° C. After the addition of the reaction mixture and by measuring the pH value, the base activity of the reaction mixture is obtained, having a value of preferably not more than 9.0, more preferably of not more than 8.0 and especially preferably of not more than 7.5.

According to another embodiment of the present invention, the oxidised HAS is reacted with N-hydroxy succinimide in dry DMA in the absence of water with EDC to selectively give the polymer N-hydroxy succinimide ester according to the formula

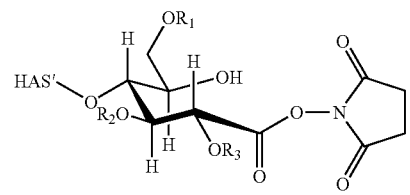

more preferably with HAS' being HES'.

This reaction does not give by-products resulting from reactions of EDC with OH groups of HES, and the rearrangement reaction of the O-acyl isourea formed by EDC and the oxidised HAS to the respective N-acyl urea is surprisingly suppressed.

According to another preferred embodiment of the present invention, the oxidised HAS is reacted with N,N'-disuccinimidyl carbonate in dry DMF in the absence of water and in the absence of an activating agent to selectively give the HAS-N-hydroxy succinimide ester according to the formula

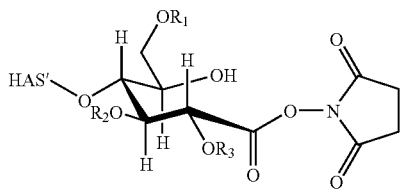

more preferably with HAS' being HES'.

According to another embodiment of the present invention, the HAS which is selectively oxidised at its reducing end is reacted at the oxidised reducing end with an azolide such as carbonyldiimidazole or carbonyl dibenzimidazole to give a polymer having a reactive carboxy group. In the case of carbonyldiimidazole, a reactive imidazolide HAS derivative according to formula

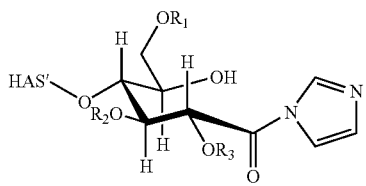

results, wherein HAS' is preferably HES'.

The reactive HAS derivative comprising at least one reactive carboxy group, preferably resulting from the reaction of the HAS with the acidic alcohol, the carbonate and/or the azolide, as described above, is then further reacted with the amino group M of the crosslinking compound M.

Reaction of the HAS via the oxidised reducing end, optionally further activated as described above, with amino group M can be carried out according to all suitable methods. Preferably, the amino group M is a primary amino group $H_2N-$ or a secondary amino group.

Generally, preferably polar aprotic solvents are used which may also contain a certain amount of water, such as up to 10 wt.-%. Preferred aprotic solvents are, among others, DMSO or DMF.

An example of a preferred reaction temperature range is from 0 to 80° C., more preferably from 0 to 70° C., more preferably from 0 to 60° C., more preferably from 0 to 50° C. and even more preferably from 0 to 40° C.

If crosslinking compounds are used for reaction with HAS having the reducing end in oxidised form which, according to a preferred embodiment, have $H_2N-$ as amino group M, a HAS derivative is obtained by step (i) of the present invention wherein the HAS and the crosslinking compound employed as starting materials are linked via an amid bond, wherein the obtained HAS derivative further contains the acetal or keto group A.

Therefore, the present invention also relates to the method as described above, wherein in (i), HAS is reacted via its oxidised reducing end with the amino group M of the crosslinking compound, M being $H_2N-$, and wherein the reaction is carried out at a temperature in the range of from 0 to 80° C., and wherein X is $-(C=O)-NH-$.

Accordingly, the present invention also relates to the HAS derivative, obtainable or obtained by the method as described above.

Moreover, the present invention also relates to the HAS derivative as such, having the following structure

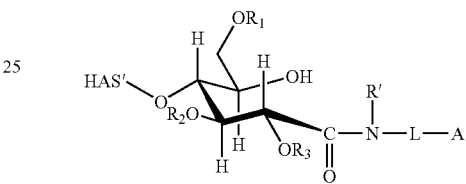

wherein R' is H if the amino group M of the crosslinking compound is a primary amino group, and wherein R' is a chemical moiety other than H if the amino group M of the crosslinking compound is a secondary amino group. The precise chemical nature of R' is dependent on the crosslinking compound, and thus, reference is made to the discussion of the generally possible and preferably employed crosslinking compounds hereinabove.

In accordance with above-described preferred crosslinking compounds employed for the present invention, the following HAS derivatives may be mentioned as preferred embodiments by way of example, wherein in each case, HAS is—according to preferred embodiments of the present invention— HES:

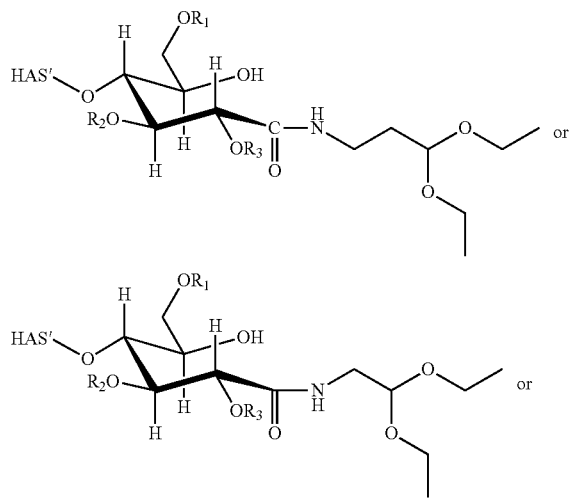

-continued
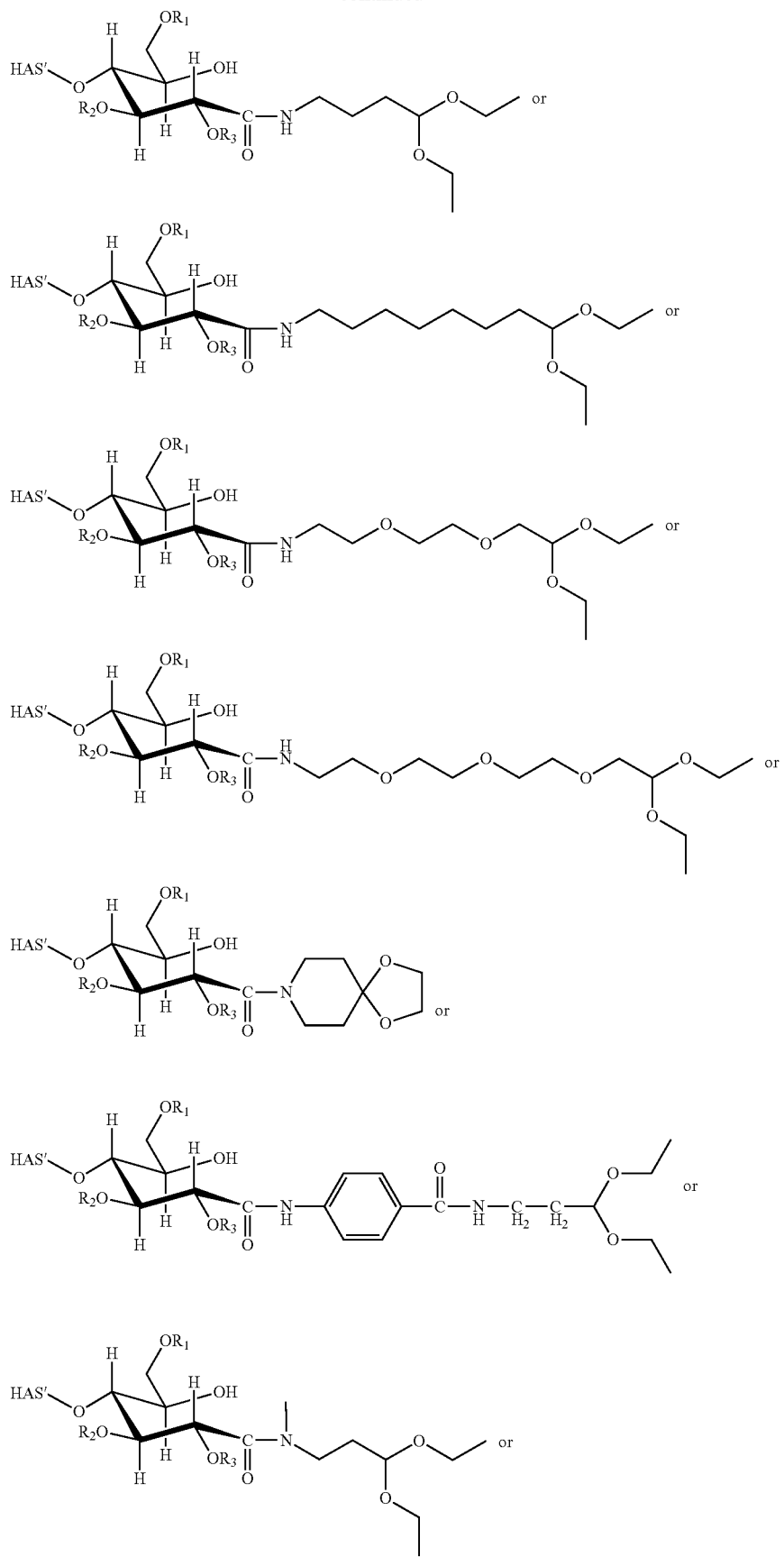

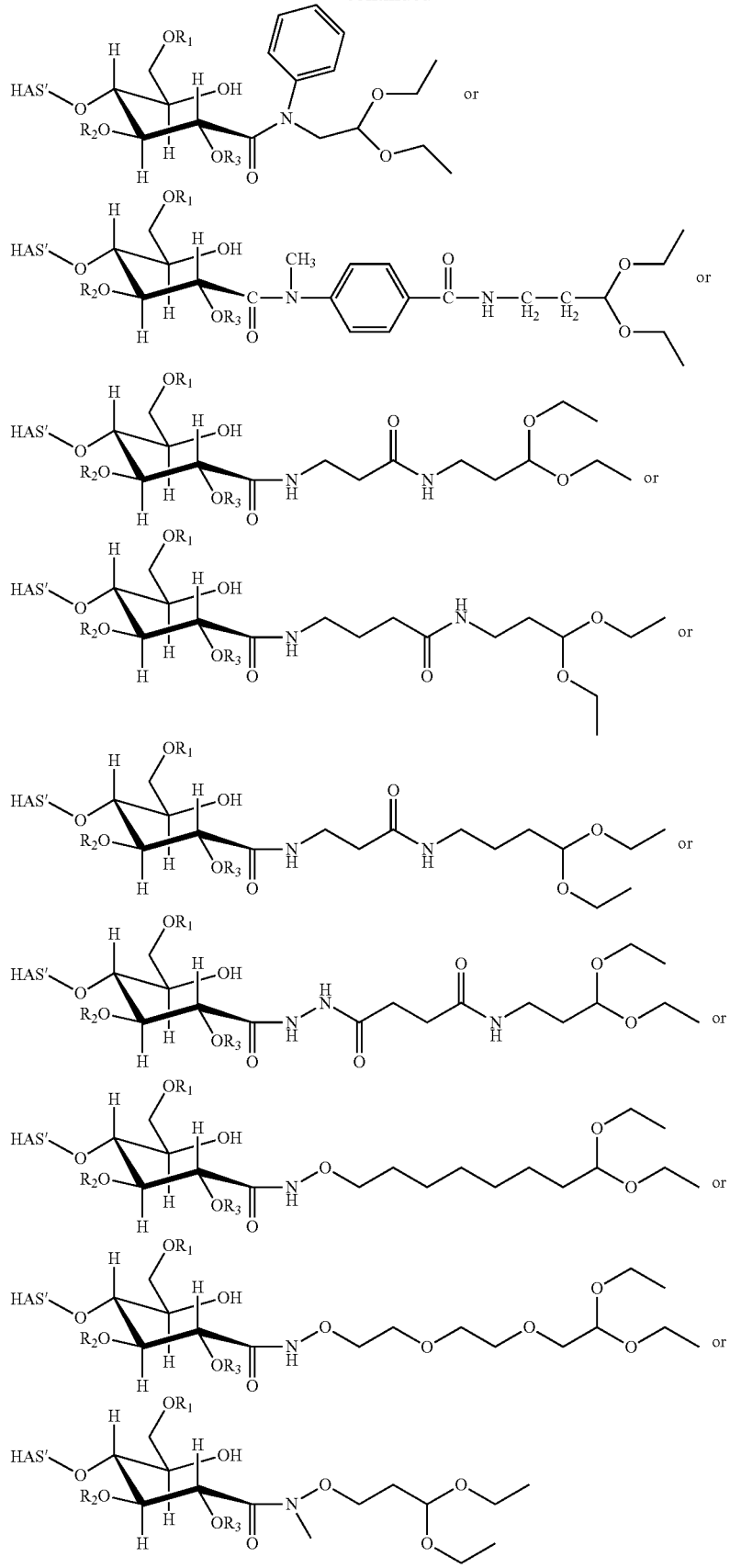

The HAS derivatives based on the cross-linking compounds selected from the group consisting of structures (a2), (a4), (a11), (a12), (a14), (a16), and (a18) are more preferred. Even more preferred are the HAS derivatives based on the cross-linking compounds selected from the group consisting of structures (a2), (a11), (a12), (a14), (a16), and (a18). Particularly preferred are the HAS derivatives based on the cross-linking compounds selected from the group consisting of structures (a2), (a11), (a12), and (a16).

According to an especially preferred embodiment, the present invention relates to a HES derivative having the following structure:

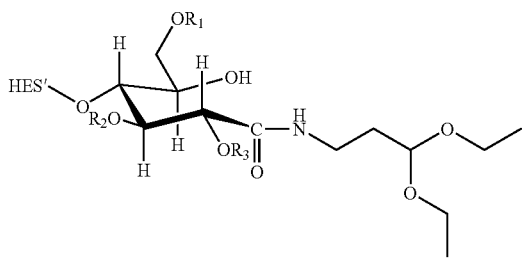

wherein, even more preferably, HES has a mean molecular weight from about 1 to about 1000 kDa, more preferably from about 1 to about 800 kDa, more preferably from about 1 to about 500 kDa, more preferably from about 2 to about 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7 0.8, 0.9, 1.0, 1.1, 1.2, or 1.3, and a ratio of $C_2:C_6$ substitution of preferably in the range of from 2 to 20, more preferably in the range of from 2 to 15 and even more preferably in the range of from 3 to 12.

Non-Oxidised Reducing End

According to a second and preferred embodiment of the present invention, the crosslinking compound is reacted via amino group with the non-oxidised C* atom of the terminal reducing end of HAS, preferably HES, i.e. the terminal aldehyde group of a HAS molecule may be present as aldehyde group and/or as corresponding hemiacetal form.

Reaction of the HAS via the non-oxidised reducing end, with amino group M can be carried out according to all suitable methods. Preferably, the amino group M is $H_2N$—, a suitable secondary amino group HNR'— such as, e.g., $H_3C$—NH—, $H_2N$—O—, or a suitable secondary hydroxyamino group HNR'—O— such as, e.g., $H_3C$—NH—O—, or $H_2N$—NH—(C=O)—.

Preferably, the amino group M is $H_2N$—, $H_2N$—O— or $H_2N$—NH—(C=O)—, even more preferably $H_2N$— or $H_2N$—O—, and in particular $H_2N$—.

According to a preferred embodiment of the present invention, this reaction is carried out in an aqueous system. The term "aqueous system" as used in this context of the present invention refers to a solvent or a mixture of solvents comprising water in the range of from at least 10% per weight, preferably at least 50% per weight, more preferably at least 80% per weight, even more preferably at least 90% per weight or up to 100% per weight, based on the weight of the solvents involved. As additional solvents, solvents such as DMSO, DMF, ethanol or methanol may be mentioned.

According to a preferred embodiment, if HAS is reacted with the crosslinking compound in an aqueous medium and the amino group M of the crosslinking compound is a hydroxylamine or a hydrazide, the temperature of the reaction is preferably in the range of from 5 to 45° C., more preferably in the range of from 10 to 30° C. and especially preferably in the range of from 15 to 25° C.

According to another preferred embodiment, if HAS is reacted with the crosslinking compound in an aqueous medium and the amino group M of the crosslinking compound is a group $H_2N$— or R'HN—, the reaction being a reductive amination, the temperature is preferably in the range of up to 100° C., more preferably in the range of from 10 to 90° C., more preferably in the range of from 20 to 80° C., more preferably in the range of from 30 to 70° C. and especially preferably in the range of from 40 to 60° C.

During the course of the reaction the temperature may be varied, preferably in the above-given ranges, or held essentially constant.

The reaction time for the reaction of HAS with crosslinking compound M may be adapted to the specific needs and is generally in the range of from 1 h to 7 d. In case, e.g., amino group M is a hydroxylamine or a hydrazide, the reaction time is preferably in the range of from 1 h to 3 d, more preferably of from 2 h to 48 h, and especially preferably of from 3 to 24 h.

In case, e.g., the reaction of HAS with the crosslinking compound is a reductive amination, the reaction time is preferably in the range of from 1 h to 7 d, more preferably in the range of from 4 h to 6 d, more preferably in the range of from 8 h to 5 d and even more preferably in the range of from 16 h to 3 d.

The pH value for the reaction of HAS with the crosslinking compound may be adapted to the specific needs such as the chemical nature of the reactants. In case, e.g., group M of the crosslinking compound is a hydroxylamine or a hydrazide, the pH value is preferably in the range of from 3 to 9, more preferably of from 4 to 8 and even more preferably of from 4.5 to 6.5.

In case, e.g., the reaction of HAS with the crosslinking compound is a reductive amination, the pH value is preferably in the range of from 3 to 9, more preferably in the range of from 3.5 to 8, and even more preferably in the range of from 4 to 6.

The suitable pH value of the reaction mixture may be adjusted, for each reaction step, by adding at least one suitable buffer. Among the preferred buffers, acetate buffers, preferably sodium acetate buffer, phosphate or borate buffers may be mentioned.

If crosslinking compounds are used for reaction with HAS having the reducing end in non-oxidised form which, according to a preferred embodiment, have $H_2N$— as amino group M, a HAS derivative is obtained by step (i) of the present invention wherein the HAS and the crosslinking compound employed as starting materials are linked via an imine bond, wherein the obtained HAS derivative further contains the acetal or keto group A. If the reaction is carried out under reductive amination conditions in the presence of a suitable reducing agent, a HAS derivative is obtained by step (i) of the present invention wherein the HAS and the crosslinking compound employed as starting materials are linked via an amine bond, wherein the obtained HAS derivative further contains the acetal or keto group A.

Therefore, the present invention also relates to the method as described above, wherein in (i), HAS is reacted, preferably in an aqueous system, via its non-oxidised reducing end with the amino group M of the crosslinking compound, M being $H_2N$—, and wherein the reaction is carried out at a temperature in the range of from 20 to 80° C. at a pH in the range of from 4 to 7, X being —CH=N—.

Further, the present invention also relates to the above-described method, wherein in (i), the reaction is carried out in the presence of a reducing agent, such as sodium borohydride, sodium cyanoborohydride, organic borane complex compounds such as a 4-(dimethylamine)pyridine borane complex, N-ethyldiisopropylamine borane complex, N-ethylmorpholine borane complex, N-methylmorpholine borane complex, N-phenylmorpholine borane complex, lutidine borane complex, triethylamine borane complex, or trimethylamine borane complex, preferably NaCNBH$_3$, to obtain a HAS derivative, X being —CH$_2$—NH—.

The concentration of these reducing agents used for the reductive amination of the present invention is preferably in the range of from 0.01 to 2.0 mol/l, more preferably in the range of from 0.05 to 1.5 mol/l, and more preferably in the range of from 0.1 to 1.0 mol/l, relating, in each case, to the volume of the reaction solution.

According to above-described preferred embodiment wherein M is H$_2$N— and reaction of the crosslinking compound with HAS is carried out under reductive amination conditions, the molar ratio of crosslinking compound:HAS is preferably in the range of from 1:1 to 100:1, more preferably from 2:1 to 80:1, more preferably from 3:1 to 70:1, more preferably from 4:1 to 60:1, and more preferably from 5:1 to 50:1.

According to above-described preferred embodiment wherein M is H$_2$N— and reaction of the crosslinking compound with HAS is carried out under reductive amination conditions, the concentration of HAS, preferably HES, in the aqueous system is preferably in the range of from 1 to 50 wt.-%, more preferably from 3 to 45 wt.-%, and more preferably from 5 to 40 wt.-%, relating, in each case, to the weight of the reaction solution.

If crosslinking compounds are used for reaction with HAS having the reducing end in non-oxidised form which, according to a preferred embodiment, have H$_2$N—O— or H$_2$N—NH—(C=O)— as amino group M, a HAS derivative is obtained by step (i) of the present invention wherein the HAS and the crosslinking compound employed as starting materials are linked via an —CH=N—O— bond or —CH=N—NH—(C=O)— bond, wherein the obtained HAS derivative further contains the acetal or keto group A. If the reaction is carried out under reducing conditions in the presence of a suitable reducing agent, a HAS derivative is obtained by step (i) of the present invention wherein the HAS and the crosslinking compound employed as starting materials are linked via a —CH$_2$—NH—O— bond or —CH$_2$—NH—NH—(C=O)— bond, wherein the obtained HAS derivative further contains the acetal or keto group A.

Therefore, the present invention also relates to the method as described above, wherein in (i), HAS is reacted, preferably in an aqueous system, via its non-oxidised reducing end with the amino group M of the crosslinking compound, M being H$_2$N—O— or H$_2$N—NH—(C=O)—, and wherein the reaction is carried out at a temperature in the range of from 5 to 80° C. at a pH in the range of from 4.5 to 6.5, X being —CH=N—O— or —CH=N—NH—(C=O)—.

Further, the present invention also relates to the above-described method, wherein in (i), the reaction is carried out in the presence of a reducing agent, such as sodium borohydride, sodium cyanoborohydride, organic borane complex compounds such as a 4-(dimethylamine)pyridine borane complex, N-ethyldiisopropylamine borane complex, N-ethylmorpholine borane complex, N-methylmorpholine borane complex, N-phenylmorpholine borane complex, lutidine borane complex, triethylamine borane complex, or trimethylamine borane complex, preferably NaCNBH$_3$, to obtain a HAS derivative, X being —CH$_2$—NH—O— or —CH$_2$—NH—NH—(C=O)—.

The concentration of these reducing agents used for this reaction of the present invention is preferably in the range of from 0.001 to 2.0 mol/l, more preferably in the range of from 0.01 to 1.0 mol/l, and more preferably in the range of from 0.1 to 0.8 mol/l, relating, in each case, to the volume of the reaction solution.

According to above-described preferred embodiment wherein M is H$_2$N—O— or H$_2$N—NH—(C=O)—, and the reaction of the crosslinking compound with HAS is carried out under reducing conditions, the molar ratio of crosslinking compound:HAS is preferably in the range of from 1:1 to 100:1, more preferably from 2:1 to 80:1, more preferably from 3:1 to 70:1, more preferably from 4:1 to 60:1, and more preferably from 5:1 to 50:1.

According to above-described preferred embodiment wherein M is H$_2$N— and reaction of the crosslinking compound with HAS is carried out under reductive amination conditions, the concentration of HAS, preferably HES, in the aqueous system is preferably in the range of from 1 to 50 wt.-%, more preferably from 3 to 45 wt.-%, and more preferably from 5 to 40 wt.-%, relating, in each case, to the weight of the reaction solution.

Accordingly, the present invention also relates to the HAS derivative, obtainable or obtained by the method(s) as described above.

Moreover, the present invention also relates to the HAS derivative as such, having the following structure

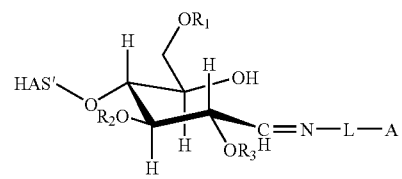

wherein, depending on the reaction conditions and/or the specific chemical nature of the crosslinking compound, the C=N double bond may be present in E or Z conformation where also a mixture of both forms may be present having a certain equilibrium distribution;

or, as far as the corresponding ring structure is concerned which for the purposes of the present invention shall be regarded as identical to the open structure above,

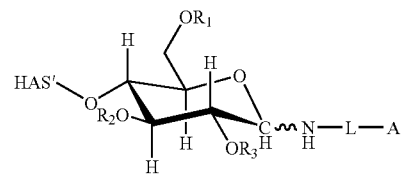

wherein depending on the reaction conditions and/or the specific chemical nature of crosslinking compound, these HAS derivatives may be present with the N atom in equatorial or axial position where also a mixture of both forms may be present having a certain equilibrium distribution;

or

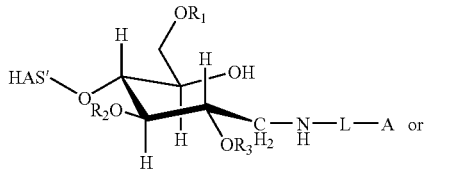

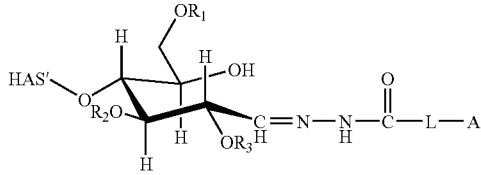

or the corresponding ring structure

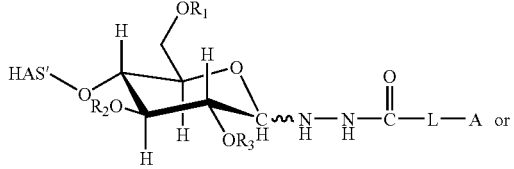

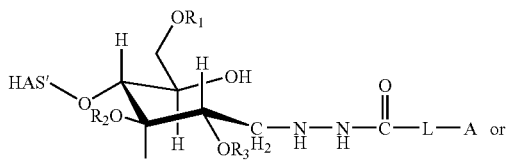

or the corresponding ring structure

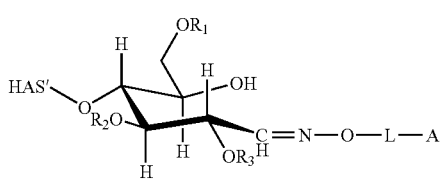

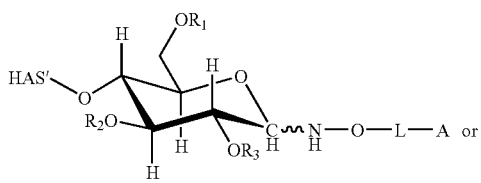

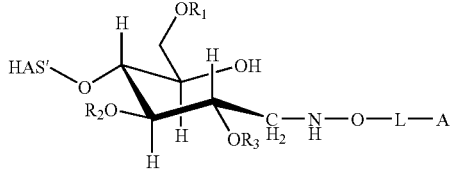

In accordance with above-described preferred crosslinking compounds, the following HAS derivatives may be mentioned as preferred embodiments by way of example, wherein in each case, HAS is—according to preferred embodiments of the present invention—HES:

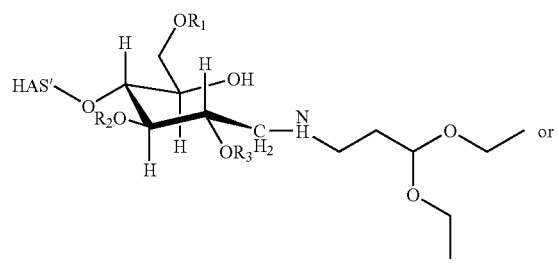

wherein the corresponding ring structure is included, or

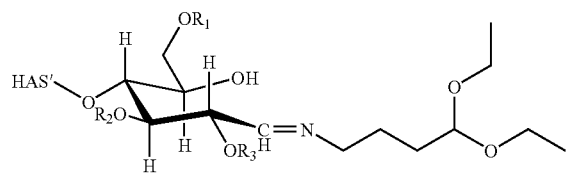

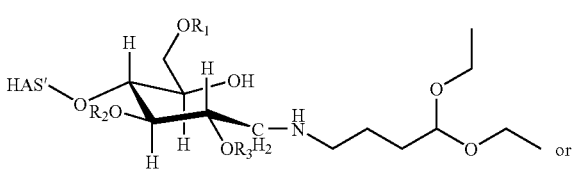

wherein the corresponding ring structure is included, or

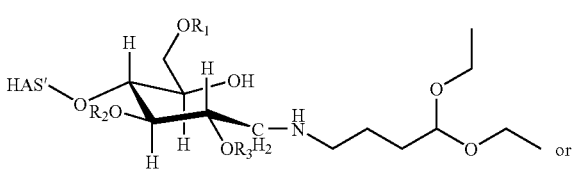

wherein the corresponding ring structure is included, or
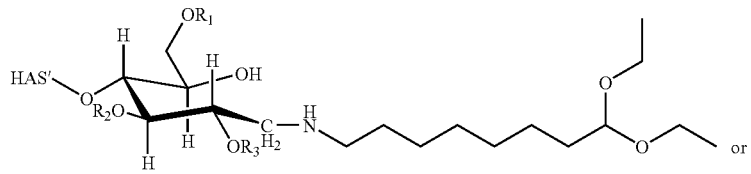
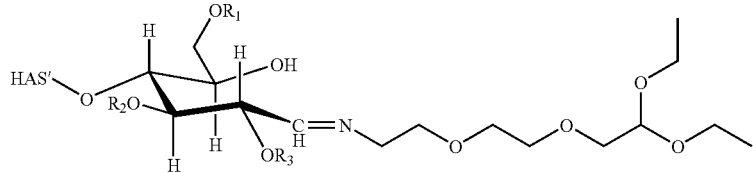
wherein the corresponding ring structure is included,
or
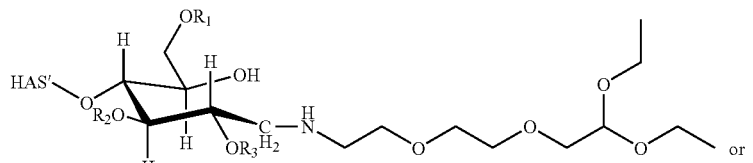
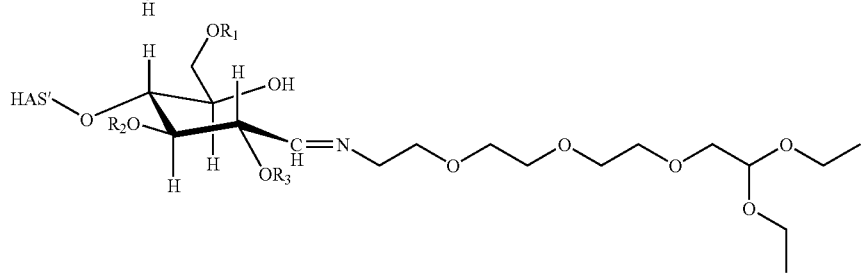
wherein the corresponding ring structure is included,
or
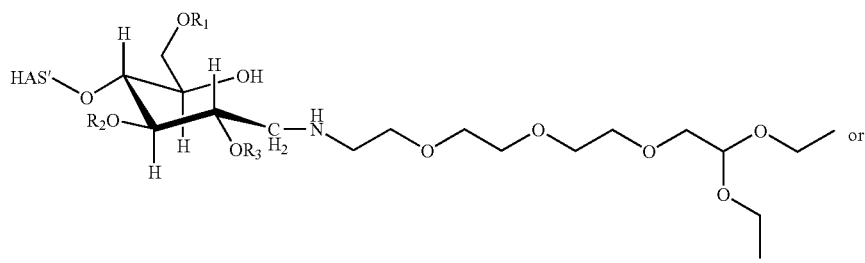
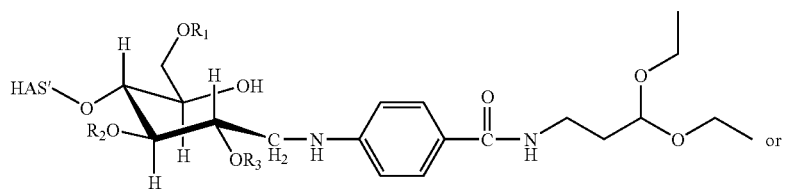

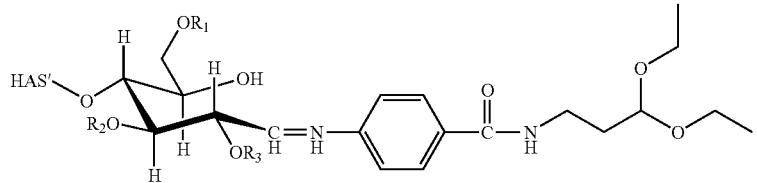
wherein the corresponding ring structure is included, or
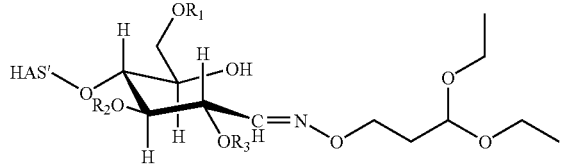
wherein the corresponding ring structure is included, or
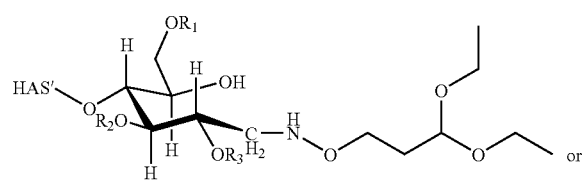
or
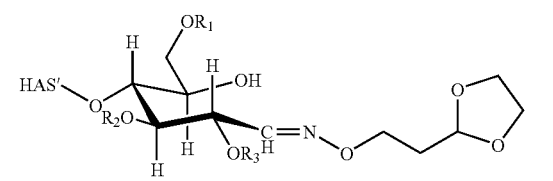
wherein the corresponding ring structure is included, or
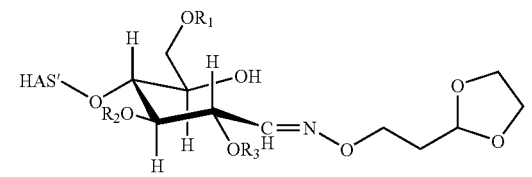
or
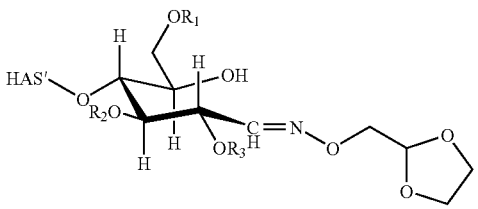
wherein the corresponding ring structure is included, or
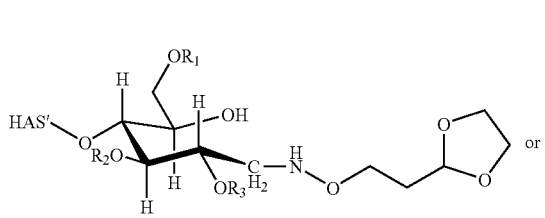
or
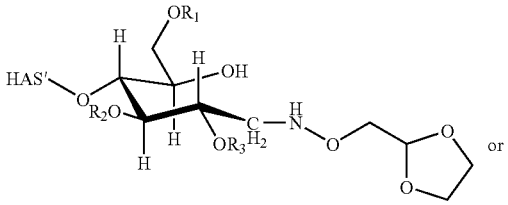
wherein the corresponding ring structure is included, or
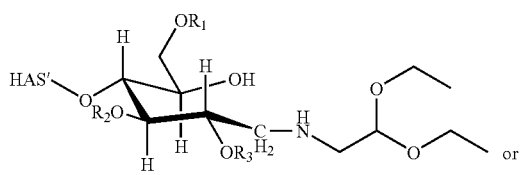
or

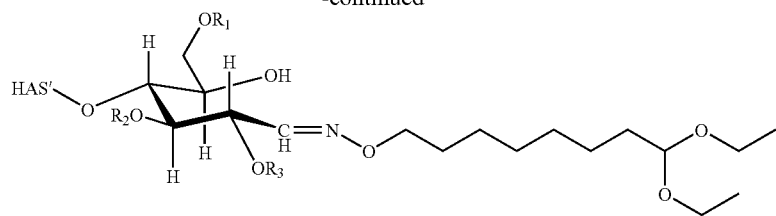
wherein the corresponding ring structure is included, or
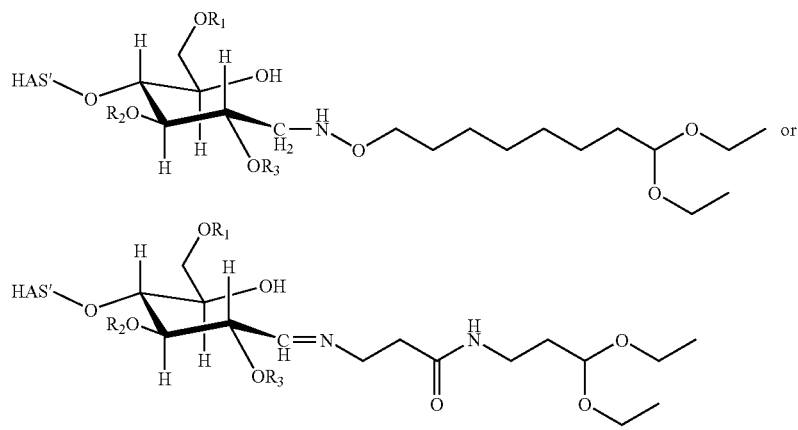
wherein the corresponding ring structure is included, or
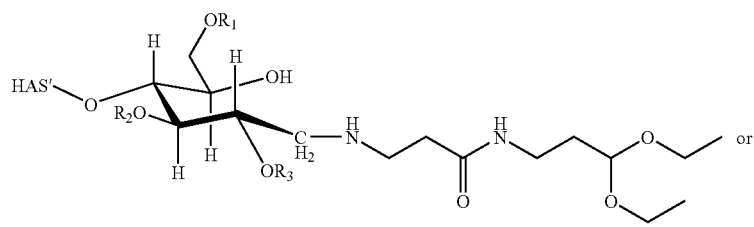
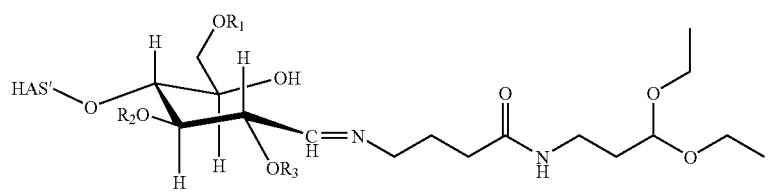
wherein the corresponding ring structure is included, or
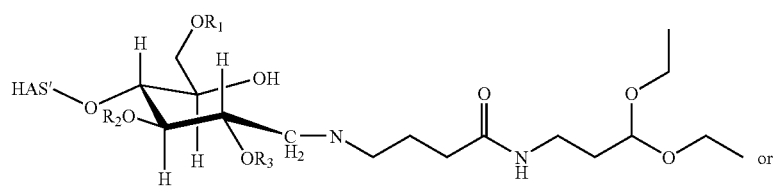

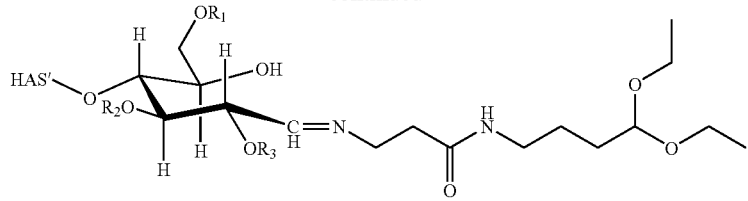
wherein the corresponding ring structure is included, or
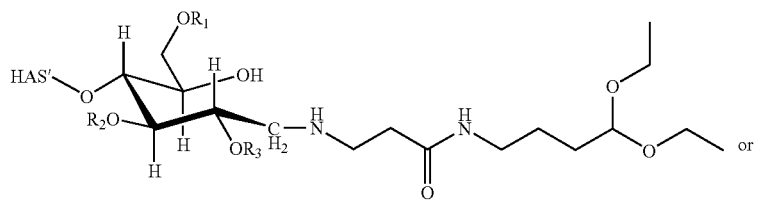
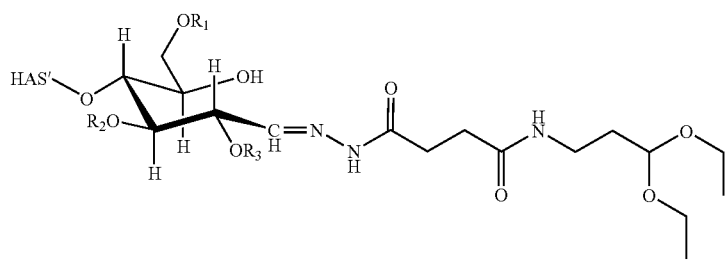
wherein the corresponding ring structure is included, or
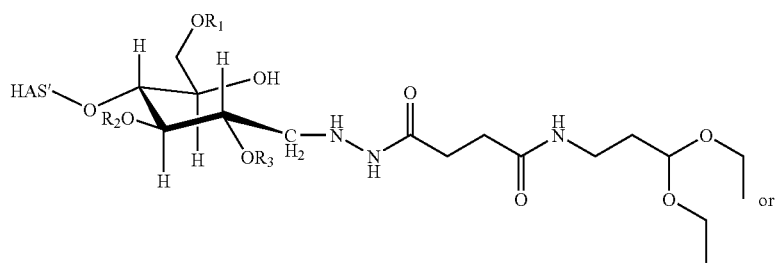
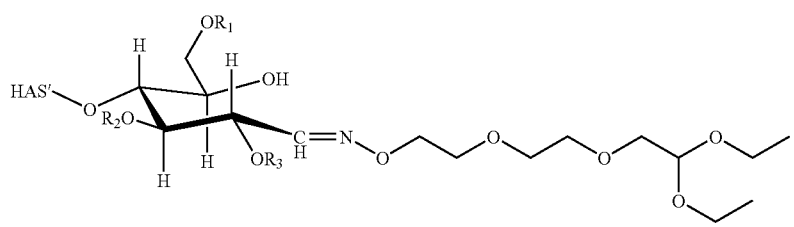
wherein the corresponding ring structure is included, or

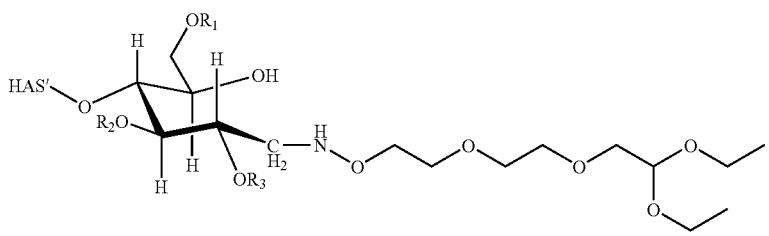

The HAS derivatives based on the cross-linking compounds selected from the group consisting of structures (a2), (a4), (a11), (a12), (a14), (a16), and (a18) are more preferred. Even more preferred are the HAS derivatives based on the cross-linking compounds selected from the group consisting of structures (a2), (a11), (a12), (a14), (a16), and (a18). Particularly preferred are the HAS derivatives based on the cross-linking compounds selected from the group consisting of structures (a2), (a11), (a12), and (a16).

According to an especially preferred embodiment, the present invention relates to a HES derivative having the following structure:

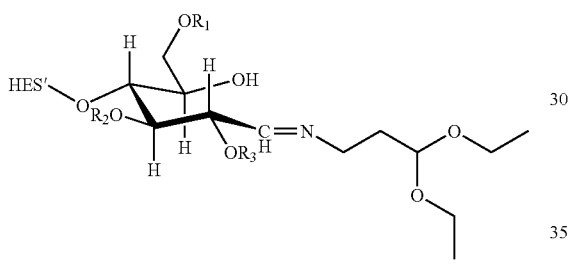

the corresponding ring structure

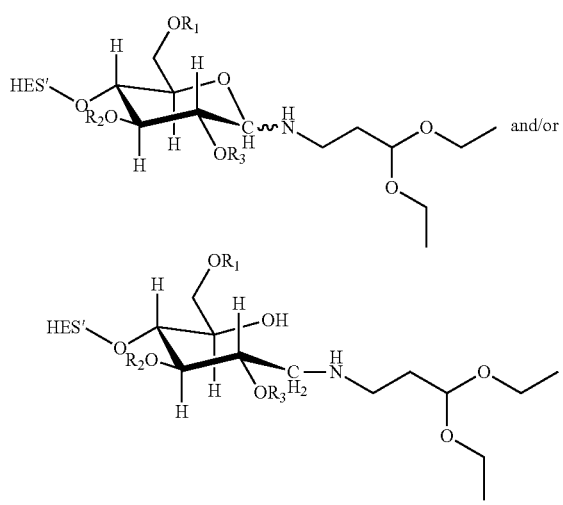

wherein, even more preferably, HES has a mean molecular weight from about 1 to about 1000 kDa, more preferably from about 1 to about 800 kDa, more preferably from about 1 to about 500 kDa, more preferably from about 2 to about 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7 0.8, 0.9, 1.0, 1.1, 1.2, or 1.3, and a ratio of $C_2$:$C_6$ substitution of preferably in the range of from 2 to 20, more preferably in the range of from 2 to 15 and even more preferably in the range of from 3 to 12.

Other Conceivable Embodiments with Regard to HAS

For the sake of completeness, it shall be mentioned that, while not preferred according to the present invention, it might be conceivable that HAS is oxidised prior to the reaction with the crosslinking compound such that at least two aldehyde groups would be introduced into HAS according to the following formula

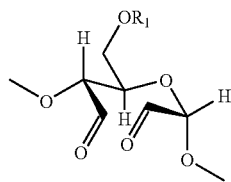

Generally, each oxidation agent or combination of oxidation agents might be employed capable of oxidising at least one saccharide ring of the polymer to give an opened saccharide ring having at least one, preferably at least two aldehyde groups. This reaction might be illustrated by the following reaction scheme showing a saccharide ring of HAS which is oxidised to give an opened ring having two aldehyde groups:

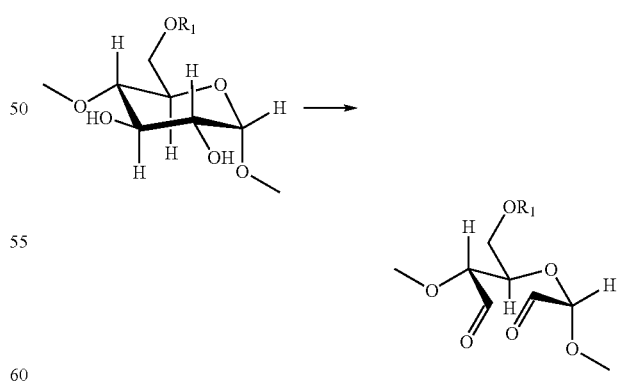

Suitable oxidising agents are, among others, periodates such as alkaline metal periodates or mixtures of two or more thereof, with sodium periodate and potassium periodate being preferred. It might be conceivable that these aldehyde groups could be reacted with the crosslinking compound M-L-A via amino group M.

Isolation and/or Purification

Generally, it is conceivable that the HAS derivative from step (i) of the present invention is subsequently reacted as described hereinunder. According to a preferred embodiment, the HAS derivative from step (i) is suitably purified after the reaction step (i).

For the purification of the HAS derivative from step (i), the following possibilities A) to C) can be mentioned by way of example, wherein possibility A) is preferred:

A) Ultrafiltration using water or an aqueous buffer solution having a concentration preferably of from 0.1 to 100 mmol/l, more preferably from 1 to 50 mmol/l and more preferably from 5 to 20 mmol/l such as about 10 mmol/ml, a pH in the range of preferably from 2 to 10, more preferably from 4 to 10, more preferably from 6 to 10 and more preferably from 8 to 10 such as about 9; the number of exchange cycles preferably is from 10 to 50, more preferably from 10 to 40 and even more preferably from 10 to 30 such as about 20.

B) Dialysis using water or aqueous buffer solution having a concentration preferably of from 0.1 to 100 mmol/l, more preferably from 1 to 50 mmol/l and more preferably from 5 to 20 mmol/l such as about 10 mmol/ml, a pH in the preferred range of from 2 to 10, more preferably from 4 to 10, more preferably from 6 to 10 and more preferably from 7 to 9; wherein a solution is employed containing the HAS derivative in a preferred concentration of from 5 to 20 wt.-%; and wherein buffer or water is used in particular in an excess of about 100:1 to the HES derivative solution.

C) Precipitation with ethanol or isopropanol, centrifugation and re-dissolving in water to obtain a solution having a preferred concentration of about 10 wt.-%, and subsequent ultrafiltration using water or an aqueous buffer solution having a concentration of preferably from 0.1 to 100 mmol/l, more preferably from 1 to 50 mmol/l and even more preferably from 5 to 20 mmol/l such as about 10 mmol/ml, a pH in the preferred range of from 2 to 10, more preferably from 4 to 10, more preferably from 6 to 10 and more preferably from 7 to 9; the number of exchange cycles is preferably from 10 to 40, more preferably from 10 to 30 and even more preferably from 10 to 20 such as 10.

After the preferred purification step, the HAS derivative is preferably obtained as a solid. According to further conceivable embodiments of the present invention, HAS derivative solutions or frozen HAS derivative solutions may be mentioned having preferred HAS derivative contents of from 2 to 40 wt.-%, wherein the pH of these solutions is preferably in a range of from 3 to 10 and the concentration of the buffer used is preferably in the range of from 0.1 to 1 mol/l.

Therefore, the present invention also relates to a method as described above, wherein, after (i), the HAS derivative obtained in (i) is purified using ultrafiltration using water or an aqueous buffer solution having a concentration of from 0.1 to 100 mmol/l, a pH in the range of from 2 to 10, the number of exchange cycles being from 10 to 50.

Reaction with Biologically Active Agent BA

According to a further preferred embodiment, the present invention relates to a method wherein above-described HES derivative

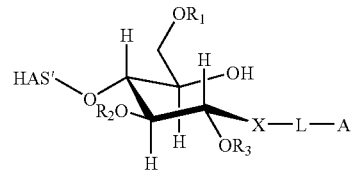

is further suitably reacted with a biologically active compound BA via acetal or ketal group A, which group A is preferably transformed to the corresponding aldehyde or keto group prior to the reaction with BA.

Most preferably, group A, preferably the corresponding aldehyde or keto group is reacted with an amino group, still more preferably with a primary amino group comprised in BA. For such cases and for the purposes of the present invention, BA is also represented as $H_2N$-BA' wherein BA' is the remainder of BA.

Therefore, the present invention also relates to the method as described above, further comprising
(ii) reacting the HAS derivative according to formula (III) via group A with an amino group of a biologically active agent $H_2N$-BA', via reductive amination, obtaining a HAS derivative according to formula (IV)

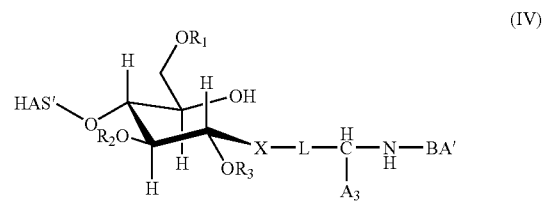

According to a first embodiment of the present invention, the HAS derivative obtained from (i) which has been preferably purified is suitably subjected to a transformation of group A to the corresponding aldehyde or keto group wherein the resulting HAS derivative is subjected to a suitable purification and/or isolation step prior to the reaction with BA. The transformation to the aldehyde or keto group is preferably performed by an acid-catalyzed hydrolysis reaction. The reaction is preferably carried out at a temperature of from 0 to 100° C., more preferably from 10 to 80° C. and more preferably from 20 to 60° C., at a pH which is preferably in the range of from 1 to 6, more preferably from 1 to 5, more preferably from 1 to 4, more preferably from 1 to 3 and even more preferably from 1 to less than 3. Purification and buffer-exchange of the hydrolysis reaction product can be achieved by methods well-known to those skilled in the art, e.g. by dialysis or ultrafiltration. The transformed material can be recovered from the solution as a solid e.g. by freeze-drying.

According to a second embodiment of the present invention, the HAS derivative obtained from (i) which has been preferably purified is suitably subjected to a transformation of group A to the corresponding aldehyde or keto group wherein the resulting HAS derivative is directly reacted with BA, i.e. without a separate suitable purification and/or isolation step of the HAS derivative comprising the aldehyde or keto group. The transformation to the aldehyde or keto group is preferably performed by an acid-catalyzed hydrolysis reaction. The reaction is preferably carried out at a temperature of from 0 to 100° C., more preferably from 10 to 80° C. and more preferably from 20 to 60° C., at a pH which is preferably in the range of from 1 to 6, more preferably from 1 to 5, more preferably from 1 to 4, more preferably from 1 to 3 and even more preferably from 1 to less than 3. The hydrolysis reaction product can be combined with the BA in a buffered solution either directly or after having adjusted the pH to a value compatible with the reaction with the BA.

Therefore, the present invention also relates to a method as described above wherein prior to (ii), group A of the HAS derivative according to formula (III) is transformed to the corresponding aldehyde or keto group.

According to a third conceivable embodiment of the present invention, the HAS derivative obtained from (i) which has been preferably purified is directly reacted with BA, i.e. reacted with BA under reaction conditions allowing for the in situ transformation of group A to the corresponding aldehyde or keto group without a separate suitable purification and/or isolation step and without a separate step for the transformation of group A to the corresponding aldehyde or keto group. The transformation to the aldehyde or keto group is preferably performed by an acid-catalyzed hydrolysis reaction. The reaction is preferably carried out at a temperature of from 0 to 100° C., more preferably from 10 to 80° C. and more preferably from 20 to 60° C., at a pH which is preferably in the range of from 1 to 6, more preferably from 1 to 5, more preferably from 1 to 4, more preferably from 1 to 3 and even more preferably from 1 to less than 3. The hydrolysis reaction product can be combined with the BA in a buffered solution either directly or after having adjusted the pH to a value compatible with the reaction with the BA.

Which method according to the above-mentioned three embodiments is carried out depends, for example, on the specific nature of the biologically active substance BA employed. If, e.g., a protein such as EPO, G-CSF or IFN alpha is employed as BA, above-identified first or second embodiment is generally suitable.

The reaction in step (ii) is preferably carried out in an aqueous system. The term "aqueous system" as used in this context of the present invention refers to a solvent or a mixture of solvents comprising water in the range of from at least 10% per weight, preferably at least 50% per weight, more preferably at least 80% per weight, even more preferably at least 90% per weight or up to 100% per weight, based on the weight of the solvents involved. As additional solvents, solvents such as DMSO, DMF, ethanol or methanol may be mentioned.

While it is conceivable to carry out the reaction in step (ii) under conditions to obtain the non-reduced form of the HAS derivative according to formula (IV), i.e.

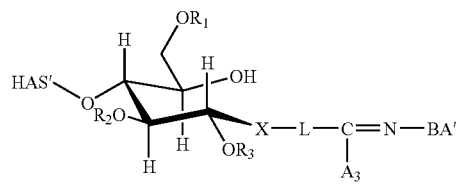

(IV)

it is particularly preferred to carry out the reaction according to step (ii) under reductive amination conditions in the presence of at least one suitable reducing agent. In particular, under these conditions the group —CH=N— obtained through the reaction of the aldehyde or keto group resulting from group A of the HAS derivative and the $H_2N$-group of BA is reduced to —$CH_2$—NH—.

By way of example, the following reducing agents may be employed: $NaBH(OAc)_3$, sodium borohydride, sodium cyanoborohydride, organic borane complex compounds such as a 4-(dimethylamine)pyridine borane complex, N-ethyldiisopropylamine borane complex, N-ethylmorpholine borane complex, N-methylmorpholine borane complex, N-phenylmorpholine borane complex, lutidine borane complex, triethylamine borane complex, or trimethylamine borane complex. $NaBH_4$ and $NaCNBH_3$ are preferred, and $NaCNBH_3$ is particularly preferred.

In one embodiment, the HAS derivative is added to an aqueous solution containing the biologically active agent. Preferably, subsequently the at least one reducing agent is added, in particular $NaCNBH_3$.

In an alternative embodiment, the HAS derivative may be optionally brought into an aqueous solution, and then BA is added. Preferably, subsequently the at least one reducing agent is added, in particular $NaCNBH_3$.

The reaction of the HAS derivative with the amino group of the biologically active compound BA in step (ii) is preferably carried out at a pH value of from 3 to 9, preferably of from 3 to 8, more preferably of from 3 to 7, more preferably from 3 to below 7, such as at a pH of 3 or 4 or 5 or 6. The suitable pH value of the reaction mixture may be adjusted by adding at least one suitable buffer. Among the preferred buffers, acetate buffers, preferably sodium acetate buffer, phosphate or borate buffers may be mentioned.

The reaction of the HAS derivative obtained in step b) with the amino group of the biologically active compound BA in step (ii) is preferably carried out at a temperature of from −10 to 100° C., preferably of from 0 to 50° C., more preferably of from 0 to 37° C., more preferably of from 0 to 25° C., such as 0, 5, 10, 15, 20, or 25° C.

The reaction time in step (ii) depends on the temperature, the ratio of HAS, in particular HES, derivative and compound BA and the absolute concentration of the HAS derivative and compound BA. Generally, reaction times from 5 min to 7 d, preferably from 1 h to 7 d are conceivable.

The molar ratio of HAS derivative obtained to compound BA in step (ii) is preferably from 0:1 to 200:1 equivalents, even more preferably from 1:1 to 100:1, based on the number average molecular weight ($M_n$) of the HAS derivative. Preferably, the molar ratio is from 1:1 to 50:1. Low molar ratios such as molar ratios of 50:1 or below, preferably from 1:1 to 20:1, more preferably from 1:1 to 10:1, and even more preferably from 2:1 to 9:1, more preferably from 3:1 to 8:1 and even more preferably from 4:1 to 7:1, are conceivable, for example, if BA is a protein, in particular IFN alpha.

In a particular preferred embodiment the concentration of the HAS derivative used in step (ii) is higher than about 10 wt.-%, in particular higher than about 15 wt.-%, in each case related to the weight of the reaction solution of (ii).

Therefore, the present invention also relates to the method as described above, wherein in (ii), the reaction is carried out, preferably in an aqueous system, in the presence of a reducing agent, preferably $NaCNBH_3$, at a temperature in the range of from 0 to 37° C., preferably 0 to 25° C. and a pH in the range of from 3 to 9, preferably 3 to below 7, and wherein in (ii), the molar ratio of the HAS derivative to biologically active agent BA is from 0.1:1 to 200:1 equivalents, preferably from 1:1 to 50:1 equivalents, based on the number average molecular weight ($M_n$) of the HAS derivative.

Preferred concentrations of BA, such as, e.g., preferred protein concentrations of the solution, preferably the aqueous solution, subjected to (ii) are in the range of from 0.1 to 10 g/l, more preferably from 1 to 9 g/l. The concentration of the HAS derivative in said solution, prior to (ii) and given in (w/v), is preferably in the range of from 0.1 to 50%, more preferably from 0.5 to 45% and more preferably from 1 to 40%.

According to a conceivable embodiment, the biologically active agent BA may be dissolved in an aqueous medium, preferably in an aqueous buffer solution, in particular in a sodium acetate buffer solution. The aqueous solution additionally may contain additives, such as detergents and/or dispersants, in particular selected from the group consisting of SDS, Chaps, Tween 20, Tween 80, Nonidet P-40, and Triton X 100. If a detergent and/or dispersant is used, it is preferably present in an amount of 0.005 to 3 wt.-%, preferably of 0.05 to 3 wt.-%, preferably about 0.5 wt.-%, based on the total weight of the aqueous solution.

If the at least one reducing agent is employed according to the present invention, and X, present in the HAS derivative employed for the reaction with BA, is, e.g., —CH═N—, —CH═N—O—, or —CH═N—NH—(C═O)— is preferably reduced to result in a functional group X, being $-CH_2-NH-$, $-CH_2-NH-O-$, or $-CH_2-NH-NH-(C{=}O)-$ under the reductive amination conditions used for the reaction in (ii).

The present invention thus also relates to the HAS derivative obtained or obtainable by the method as described above, in particular by a method as described above wherein in (ii), the reaction is carried out, preferably in an aqueous system, in the presence of a reducing agent, preferably $NaCNBH_3$, at a temperature in the range of from 0 to 37° C., preferably 0 to 25° C. and a pH in the range of from 3 to 9, more preferably from 3 to 7, more preferably from 3 to below 7, and wherein in (ii), the molar ratio of the HAS derivative to biologically active agent BA is from 0.1:1 to 200:1 equivalents, preferably from 1:1 to 10:1 equivalents, based on the number average molecular weight ($M_n$) of the HAS derivative employed in step (ii), in each case with the proviso that X is not an amid group. Particularly preferred molar ratios of the HAS derivative to biologically active agent BA are below 10, such from 1:1 to 9:1, more preferably from 1:1 to 8:1, more preferably from 1:1 to 7:1, more preferably from 1:1 to 6:1 and even more preferably from 1:1 to 5:1, such as about 1:1, about 2:1, about 3:1, about 4:1, or about 5:1. While such low molar ratios like molar ratios of 50:1 or below, more preferably of 10:1 or below are conceivable for several biologically active agents, they are preferred for e.g. proteins wherein IFN alpha is especially preferred. As far as, e.g., G-CSF and EPO are concerned, molar ratios of 50:1 or below such as, e.g., from 1:1 to 50:1, are preferred. In general, by way of example, molar ratios in the range of from 1:1 to 50:1 or from 2:1 to 40:1 or from 3:1 to 30:1 or from 4:1 to 20:1 or from 5:1 to 15:1 may be mentioned.

In case a protein is employed as biologically active agent BA according to the present invention, and especially at the preferred pH ranges given above, particularly at a pH below 7 and greater or equal 3, to react the HAS derivative predominantly with the amino group located at the N terminus of the protein. The term "predominantly" as used in the context of the present invention relates to an embodiment where at least 50%, preferably at least 60%, preferably at least 70%, preferably at least 80%, preferably at least 85% of the N-terminal amino groups available are reacted via reductive amination. It is also possible to react at least 90% or at least 95% or at least 96% or at least 97% or at least 98% or at least 99% of the N-terminal amino groups available. Although coupling to amino groups other than the N-terminal amino group could not be ruled out completely, it is believed that coupling via reductive amination according to the present invention at a pH of below 7, takes place essentially selectively at the N-terminal amino group. In particular, these reaction conditions are preferred for proteins which are stable at these conditions. Should a protein e.g. be acid labile, such as alpha1-antitrypsin (A1AT), then it is preferred to choose appropriate reaction conditions, in particular a pH from lower than 7.5 to greater than 5.

Therefore, the present invention also relates to a method for the preparation of a HAS derivative comprising BA', a HAS derivative obtainable or obtained by such method, and a HAS derivative according to formula (IV) as such, as described above, wherein the protein comprises the N-terminal amino group and at least one further amino group, said HAS derivative comprising the HAS being predominantly coupled to the N-terminal amino group.

Hence, the present invention also relates to a HAS derivative according to formula (IV)

(IV)

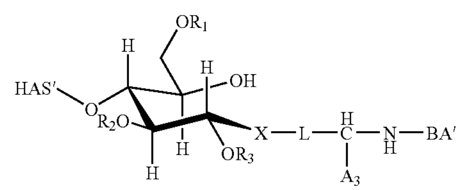

Moreover, the present invention also relates to a hydroxyalkyl starch derivative of formula (IV)

(IV)

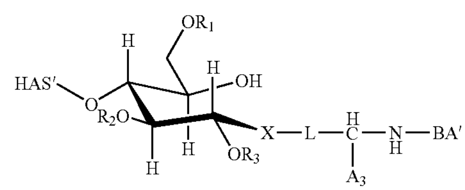

wherein X is a functional group resulting from the reaction of an amino group M of a crosslinking compound of formula (II)

M-L-A (II)

wherein X is not an amide group —C(═O)—NH—, with hydroxyalkyl starch (HAS) of formula (I)

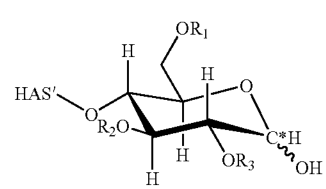

via carbon atom C* of the HAS, wherein C* is optionally oxidised, most preferably not oxidised prior to the reaction of HAS with M, wherein HAS' is the remainder of the hydroxyalkyl starch molecule and $R_1$, $R_2$ and $R_3$ are independently hydrogen or a linear or branched hydroxyalkyl group, wherein A is a residue according to formula (IIa)

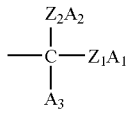

wherein $Z_1$ and $Z_2$ are each independently O or S or $NR_x$, preferably O, wherein $R_x$ is H or lower alkyl such as methyl, ethyl, or propyl such as n-propyl or i-propyl, or $C(O)$—$R_y$, wherein $R_y$ is preferably selected from the group consisting of $C_1$-$C_6$ alkyl and $C_6$-$C_{14}$ aryl, even more preferably selected from the group consisting of optionally substituted, preferably non-substituted methyl, ethyl, n-propyl, isopropyl, n-butyl, isobutyl, and tert-butyl; $R_x$ preferably being H;

$A_1$ and $A_2$ are each independently methyl, ethyl, n-propyl, isopropyl, n-butyl, tert-butyl, benzyl, 1,1,1-trichloroethyl, nitrobenzyl, methoxybenzyl, ethoxybenzyl, or are forming a ring according to formula (IIb)

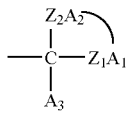

wherein $A_1$ and $A_2$, taken together, are —$(CH_2)_2$— or —$(CH_2)_3$— or —$(CH_2CH(CH_3))$—, and wherein $A_3$ is H or methyl, ethyl, n-propyl, isopropyl, n-butyl, isobutyl, pentyl, benzyl, or is forming a ring with the N atom of the amino group M or with a suitable atom comprised in L, $A_3$ preferably being H;

and wherein L is a spacer bridging M and A, wherein BA' is the remainder of a biologically active agent BA'-$NH_2$ remaining after the reaction of the amino group of BA via reductive amination with A or with the aldehyde group or keto group corresponding to A.

As to preferred embodiments with regard to HAS, preferably HES, and the crosslinking compound, reference is made to the respective disclosure above.

As far as the HAS derivative of formula (IV) is concerned, X is preferably selected from the group consisting of —$CH_2$—NH—, —CH=N—, —$CH_2$—NH—O—, and —CH=N—O—, more preferably —$CH_2$—NH— and —$CH_2$—NH—O—, most preferably —$CH_2$—NH—.

Moreover, as far as the HAS derivative of formula (IV) is concerned, L bridging M and A is preferably a spacer comprising at least one structural unit according to formula (IId), preferably consisting of a structural unit according to formula (IId)

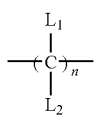

wherein $L_1$ and $L_2$ are independently from each other H or an organic residue selected from the group consisting of alkyl, substituted alkyl, alkenyl, substituted alkenyl, alkynyl, substituted alkynyl, aryl, substituted aryl, arylalkyl, substituted arylalkyl, alkylaryl, substituted alkylaryl, and residues —O—R" wherein R" is selected from the group consisting of alkyl, substituted alkyl, alkenyl, substituted alkenyl, alkynyl, substituted alkynyl, aryl, substituted aryl, arylalkyl, substituted arylalkyl, alkylaryl, substituted alkylaryl; preferably H or an organic residue selected from the group consisting of alkyl and substituted alkyl; more preferably H or alkyl; more preferably H, wherein n is an integer from 1 to 20, preferably from 1 to 10, more preferably from 1 to 6, more preferably from 1 to 4, more preferably 2.

The term "biologically active substance" (BA) as used in the context of the present invention relates to a substance which can affect any physical or biochemical property of a biological organism including, but not limited to, viruses, bacteria, fungi, plants, animals, and humans. In particular, the term "biologically active substance" as used in the context of the present invention relates to a substance intended for diagnosis, cure, mitigation, treatment, or prevention of disease in humans or animals, or to otherwise enhance physical or mental well-being of humans or animals. Examples of active substances include, but are not limited to, peptides, polypeptides, proteins, enzymes, small molecule drugs, dyes, lipids, nucleosides, nucleotides, oligonucleotides such as, e.g., oligonucleotides having a suitable spacer such as 5'-aminohexyl spacer, polynucleotides, nucleic acids, cells, viruses, liposomes, microparticles, and micelles. Preferably, a biologically active substance according to the present invention contains a native amino group.

Examples of proteins include, but are not limited to, erythropoietin (EPO), such as recombinant human EPO (rhEPO) or an EPO mimetic, colony-stimulating factors (CSF), such as G-CSF like recombinant human G-CSF (rhG-CSF), alpha-Interferon (IFN alpha), beta-Interferon (IFN beta) or gamma-Interferon (IFN gamma), such as IFN alpha and IFN beta like recombinant human IFN alpha or IFN beta (rhIFN alpha or rhIFN beta), interleukines, e.g. IL-1 to IL-34 such as IL-2 or IL-3 or IL-11 like recombinant human IL-2 or IL-3 (rhIL-2 or rhIL-3), serum proteins such as coagulation factors II-XIII like factor VIII, factor VII, factor IX, factor II, factor III, factor IV, factor V, factor VI, factor X, factor XI, factor XII, factor XIII, serine protease inhibitors such as alpha1-antitrypsin (A1AT), activated protein C (APC), plasminogen activators such as tissue-type plasminogen activator (tPA), such as human tissue plasminogen activator (hTPA), AT III such as recombinant human AT III (rhAT III), myoglobin, albumin such as bovine serum albumin (BSA), growth factors, such as epidermal growth factor (EGF), thrombocyte growth factor (PDGF), fibroblast growth factor (FGF), brain-derived growth factor (BDGF), nerve growth factor (NGF), B-cell growth factor (BCGF), brain-derived neurotrophic growth factor (BDNF), ciliary neurotrophic factor (CNTF), transforming growth factors such as TGF alpha or TGF beta, BMP (bone morphogenic proteins), growth hormones such as human growth hormone (hGH) like recombinant human growth hormone (rhGH), tumor necrosis factors such as TNF alpha or TNF beta, somatostatine, somatotropine, somatomedines, hemoglobin, hormones or prohormones such as insulin, gonadotropin, melanocyte-stimulating hormone (alpha-MSH), triptorelin, hypthalamic hormones such as antidiuretic hormones (ADH and oxytocin as well as releasing hormones and release-inhibiting hormones, parathyroid hormone, thyroid hormones such as thyroxine, thyrotropin, thyroliberin, calcitonin, glucagon, glucagon-like peptides (GLP-1, GLP-2 etc.), exendines such as exendin-4, leptin, such as recombinant human leptin (rhLeptin), Kemptide ($Trp^4$-Kemptide), vasopressin, gastrin, secretin, integrins, glycoprotein hormones (e.g. LH, FSH etc.), melanoside-stimulating hormones, lipoproteins and apolipoproteins such as apo-B, apo-E, apo-$L_a$, immunoglobulins such as IgG, IgE, IgM, IgA, IgD and fragments thereof, such as Fab fragment derived from human immunoglobuline G molecule (hFab), murin immunoglobuline G (mIgG), hirudin, tissue-pathway inhibitor, plant proteins such as lectin or ricin, bee-venom, snake-venom, immunotoxins, antigen E, alpha-proteinase inhibitor, ragweed allergen, melanin, oligolysine proteins, RGD proteins or optionally corresponding receptors for one of these proteins; prolactin or a mutant thereof, such as G129R, in which the wild type amino acid at position 129, glycine, is replaced by arginine (a tradename of this mutant is "LactoVert") and a functional derivative or fragment of any of these proteins or receptors.

The polypeptide is preferably selected from the group consisting of erythropoietin (EPO) such as recombinant human EPO (rhEPO), a colony-stimulating factor (CSF) such as G-CSF like recombinant human G-CSF (rhG-CSF), interferon (IFN) such as IFN alpha, IFN beta, IFN gamma like recombinant human IFN alpha (rhIFN alpha) or recombinant human IFN beta (rhIFN beta), factor VII such as recombinant human factor VIIa (rhFVIIa), factor IX such as recombinant human factor IX (rhFIX), growth hormone (GH such as recombinant human growth hormone (rhGH), Fab fragments such as Fab fragment derived from human immunoglobuline G molecule (hFab), immunoglobuline G such as murine immunoglobuline G (mIgG), glucagon-like peptide-1 (GLP-1), asparaginase such as recombinant asparaginase (rAsparaginase), leptin such as recombinant human leptin (rhLeptin), interleukin-2, interleukin-11, alpha-1-antitrypsin, an antibody, or an antibody fragment, and an alternative protein scaffold.

More preferably, the polypeptide is selected from the group consisting of erythropoietin (EPO) such as recombinant human EPO (rhEPO), a colony-stimulating factor (CSF) such as G-CSF like recombinant human G-CSF (rhG-CSF), interferon (IFN) such as IFN alpha, IFN beta, IFN gamma like recombinant human IFN alpha (rhIFN alpha) or recombinant human IFN beta (rhIFN beta), factor VII such as recombinant human factor VIIa (rhFVIIa), factor IX such as recombinant human factor IX (rhFIX), growth hormone (GH such as recombinant human growth hormone (rhGH), Fab fragments such as Fab fragment derived from human immunoglobuline G molecule (hFab), immunoglobuline G such as murine immunoglobuline G (mIgG), glucagon-like peptide-1 (GLP-1), asparaginase such as recombinant asparaginase (rAsparaginase), leptin such as recombinant human leptin (rhLeptin), interleukine-2, interleukine-11, and alpha-1-antitrypsin.

The active substance is preferably selected from the group composed of antibiotics, antidepressants, antidiabetics, antidiuretics, anticholinergics, antiarrhythmics, antiemetics, antitussives, antiepileptics, antihistamines, antimycotics, antisympathotonics, antithrombotics, androgens, antiandrogens, estrogens, antiestrogens, antiosteoporotics, antitumor agents, vasodilators, other antihypertensive agents, antipyretic agents, analgesics, antiinflammatory agents, beta blockers, immunosuppressants and vitamins.

Some additional, non-restrictive examples of active substances are alendronate, amikazin, atenolol, azathioprine, cimetidine, clonidine, cosyntropin, cycloserine, desmopressin, dihydroergotamine, dobutamine, dopamine, epsilon-aminocaproic acid, ergometrine, esmolol, famotidine, flecainide, folic acid, flucytosine, furosemide, ganciclovir, glucagon, hydrazaline, isoproterenol, ketamine, liothyronine, LHRH, merpatricin, methyldopa, metoprolol, neomicin, nimodipine, nystatin, oxytocin, phentolamine, phenylephrine, procainamide, procaine, propranolol, ritodrine, sotalol, terbutaline, thiamine, tiludronate, tolazoline, trimethoprim, tromethamine, vasopressin; amifostine, amiodarone, aminocaproic acid, aminohippurate sodium, aminoglutethimide, aminolevulinic acid, aminosalicylic acid, amsacrine, anagrelide, anastrozole, asparaginase (such as recombinant asparaginase, e.g. from E. coli (rAsparaginae)), anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicillinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforamide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Therefore, also chemical compounds known to the skilled person as "small molecules" are conceivable biologically active substances according to the present invention. The term "small molecule" as used in this context of the present invention relates to a biologically active chemical compound other than a protein and an oligonucleotide, including, however, peptides of up to 50 amino acids. Typical examples of such small molecules are listed in the foregoing paragraph.

Examples for an oligonucleotide are aptamers and siRNA. Also to be mentioned are peptide nucleic acids (PNA) as conceivable biologically active substances.

Therefore, the present invention also relates to a method as described above and a HAS derivative as described above, wherein the protein is erythropoietin (EPO) such as recombinant human EPO (rhEPO), a colony-stimulating factor (CSF) such as G-CSF like recombinant human G-CSF (rhG-CSF), interferon (IFN) such as IFN alpha, IFN beta, IFN gamma like recombinant human IFN alpha (rhIFN alpha) or recombinant human IFN beta (rhIFN beta), factor VII such as recombinant human factor VIIa (rhFVIIa), factor IX such as recombinant human factor IX (rhFIX), growth hormone (GH such as recombinant human growth hormone (rhGH), Fab fragments such as Fab fragment derived from human immunoglobuline G molecule (hFab), immunoglobuline G such as murine immunoglobuline G (mIgG), glucagon-like peptide-1 (GLP-1), asparaginase such as recombinant asparaginase (rAsparaginase), leptin such as recombinant human leptin (rhLeptin), interleukine-2, interleukine-11, alpha-1-antitrypsin, an antibody, or an antibody fragment, or an alternative protein scaffold.

The term "alternative protein scaffold" as used in the context of the present invention relates to a molecule having binding abilities similar to a given antibody wherein the molecule is based on an alternative non-antibody protein framework. In this context, the articles by A. Skerra, T. Hey et al., and H. K. Binz (see list of references below) may be mentioned.

As far as the biologically active substances (BA) of the present invention are concerned, these compounds may comprise one or more amino groups for coupling according to stage (ii) of the present invention. For cases where BA as such does not comprise an amino group suitable for this coupling, it is conceivable that at least one such amino group is introduced into BA by suitable functionalisation via methods known to the skilled person, prior to subjecting BA to (ii).

In accordance with above-described biologically active agents, in particular with above-described preferred biologically active agents, and in accordance with above-described preferred crosslinking compounds and the HAS derivatives obtained therefrom, the following HAS derivatives may be mentioned as preferred embodiments by way of example, wherein in each case, HAS is—according to preferred embodiments of the present invention—HES:

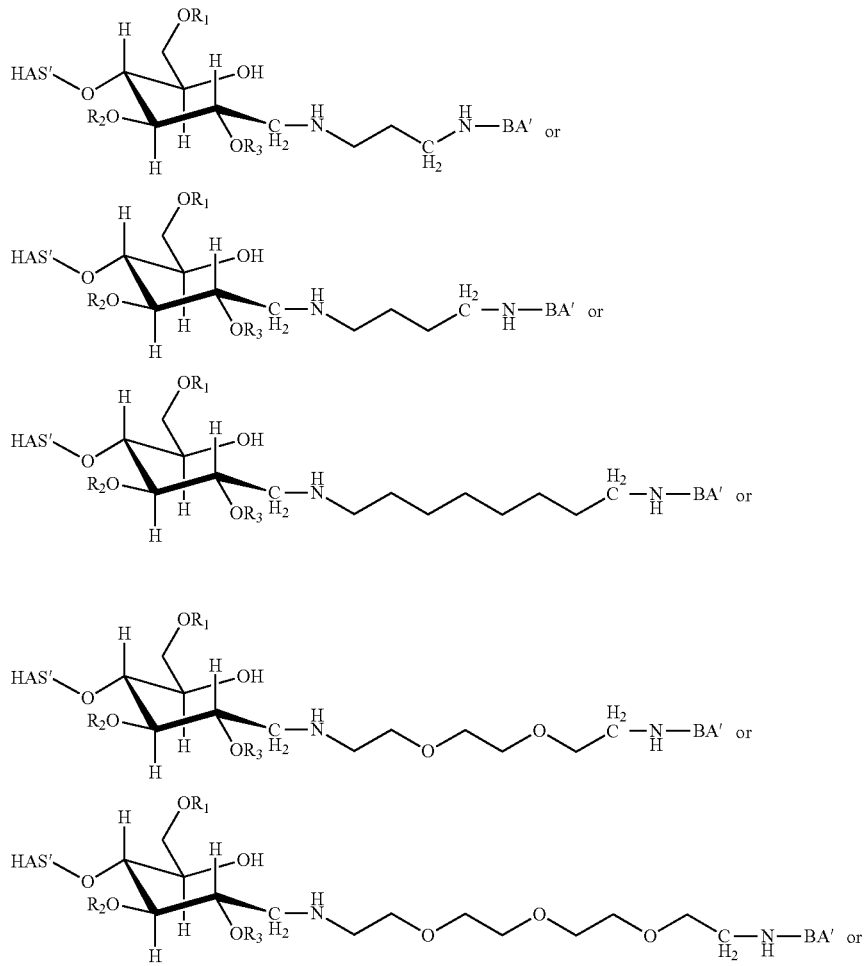

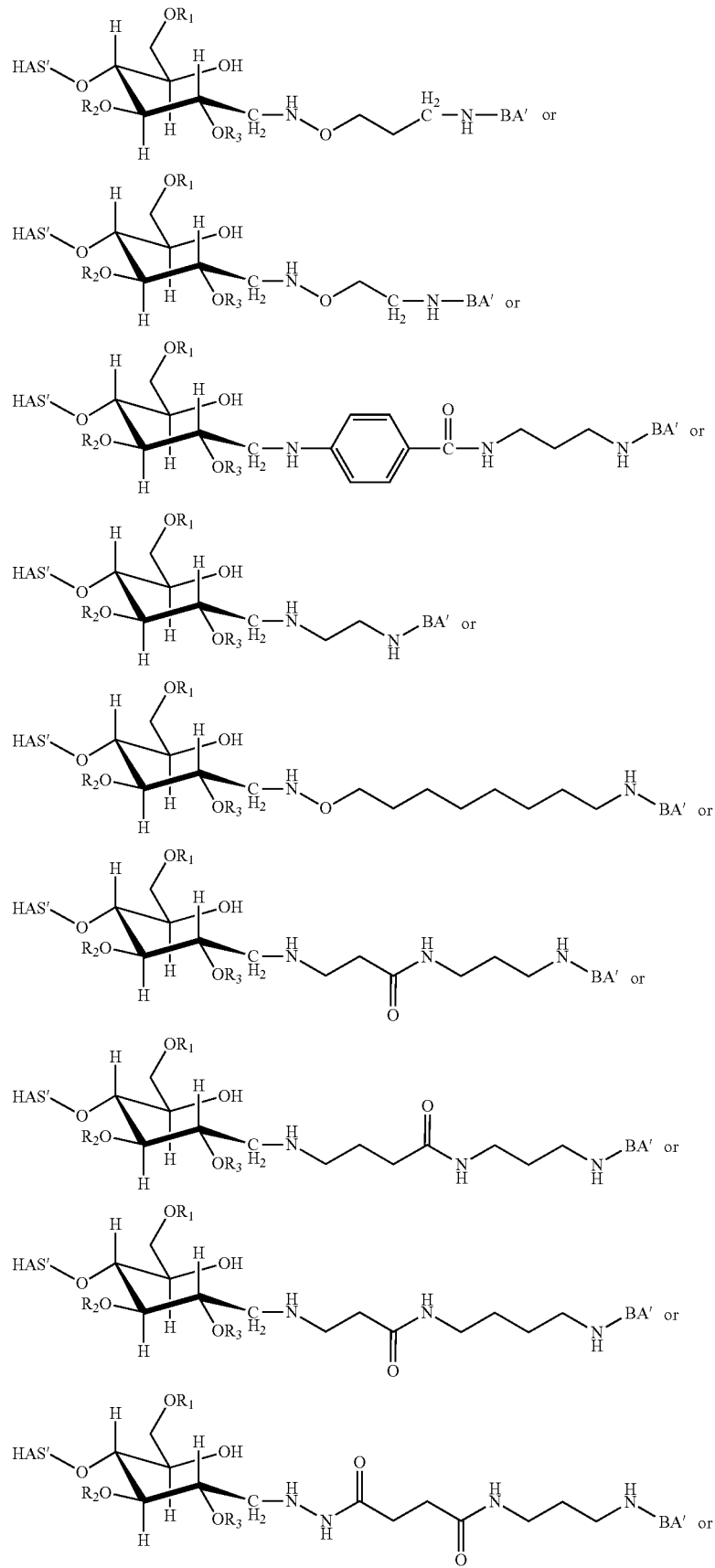

-continued

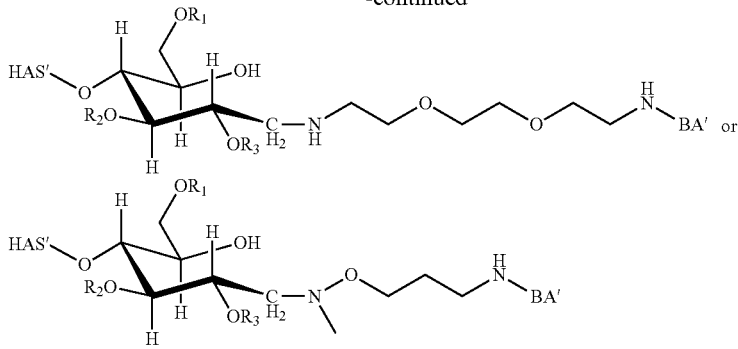

wherein BA' is a protein, more preferably, wherein the protein is erythropoietin (EPO) such as recombinant human EPO (rhEPO), a colony-stimulating factor (CSF) such as G-CSF like recombinant human G-CSF (rhG-CSF), interferon (IFN) such as IFN alpha, IFN beta, IFN gamma like recombinant human IFN alpha (rhIFN alpha) or recombinant human IFN beta (rhIFN beta), factor VII such as recombinant human factor VIIa (rhFVIIa), factor IX such as recombinant human factor IX (rhFIX), growth hormone (GH such as recombinant human growth hormone (rhGH), Fab fragments such as Fab fragment derived from human immunoglobuline G molecule (hFab), immunoglobuline G such as murine immunoglobulin G (mIgG), glucagon-like peptide-1 (GLP-1), asparaginase such as recombinant asparaginase (rAsparaginase), leptin such as recombinant human leptin (rhLeptin), interleukine-2, interleukine-11, alpha-1-antitrypsin, an antibody, or an antibody fragment, or an alternative protein scaffold, in particular wherein the protein is EPO, IFN alpha or G-CSF. Even more preferably, HAS' is HES', wherein, even more preferably, HES has a mean molecular weight of from about 1 to about 1000 kDa, more preferably from about 1 to about 800 kDa, more preferably from about 1 to 500 kDa, more preferably from about 2 to about 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7, 0.8, 0.9, 1.0, 1.1, 1.2, or 1.3, preferably of 0.7 to 1.3, such as 0.7, 0.8, 0.9, 1.0, 1.1, 1.2, or 1.3, most preferably about 1.0, 1.1, 1.2 or 1.3, and a ratio of $C_2:C_6$ substitution of preferably in the range of from 2 to 20, more preferably in the range of from 2 to 15 and even more preferably in the range of from 3 to 12.

According to especially preferred embodiments, the present invention relates to a HAS derivative according to formula

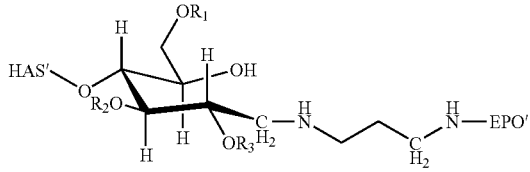

wherein HAS is preferably HES and wherein, even more preferably, HES has a mean molecular weight from about 1 to about 1000 kDa, more preferably from about 1 to about 800 kDa, more preferably from about 1 to about 500 kDa, more preferably from about 2 to about 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7, 0.8, 0.9, 1.0, 1.1, 1.2, or 1.3, and a ratio of $C_2:C_6$ substitution of preferably in the range of from 2 to 20, more preferably in the range of from 2 to 15 and even more preferably in the range of from 3 to 12.

According to further especially preferred embodiments, the present invention relates to a HAS derivative according to formula

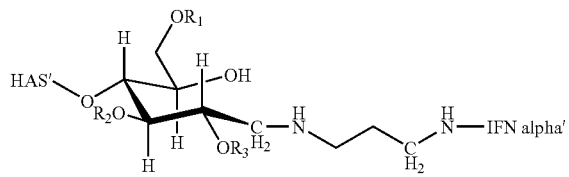

wherein HAS is preferably HES and wherein, even more preferably, HES has a mean molecular weight from about 1 to about 1000 kDa, more preferably from about 1 to about 800 kDa, more preferably from about 1 to about 500 kDa, more preferably from about 2 to 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7, 0.8, 0.9, 1.0, 1.1, 1.2, or 1.3, and a ratio of $C_2:C_6$ substitution of preferably in the range of from 2 to 20, more preferably in the range of from, 2 to 15 and even more preferably in the range of from 3 to 12.

According to further especially preferred embodiments, the present invention relates to a HAS derivative according to formula

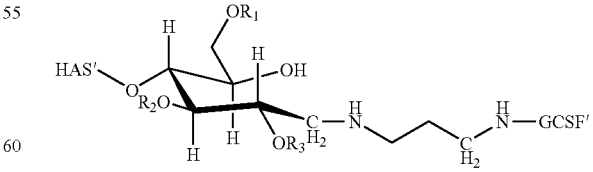

wherein HAS is preferably HES and wherein, even more preferably, HES has a mean molecular weight from about 1 to about 1000 kDa, more preferably from about 1 to about 800 kDa, more preferably from about 1 to about 500 kDa, more preferably from about 2 to about 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7, 0.8, 0.9, 1.0, 1.1, 1.2, or 1.3, and a ratio of $C_2$:$C_6$ substitution of preferably in the range of from 2 to 20, more preferably in the range of from 2 to 15 and even more preferably in the range of from 3 to 12.

According to further especially preferred embodiments, the present invention relates to a HAS derivative according to formula

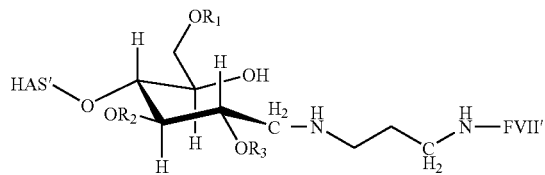

wherein HAS is preferably HES and wherein, even more preferably, HES has a mean molecular weight from about 1 to about 1000 kDa, more preferably from about 1 to about 800 kDa, more preferably from about 1 to about 500 kDa, more preferably from about 2 to about 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7, 0.8, 0.9, 1.0, 1.1, 1.2, or 1.3, and a ratio of $C_2$:$C_6$ substitution of preferably in the range of from 2 to 20, more preferably in the range of from 2 to 15 and even more preferably in the range of from 3 to 12.

According to further especially preferred embodiments, the present invention relates to a HAS derivative according to formula

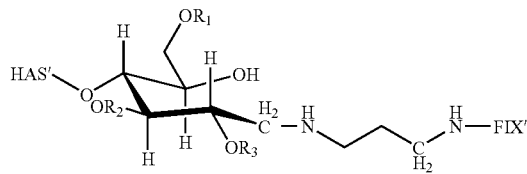

wherein HAS is preferably HES and wherein, even more preferably, HES has a mean molecular weight from about 1 to about 1000 kDa, more preferably from about 1 to about 800 kDa, more preferably from about 1 to about 500 kDa, more preferably from about 2 to about 400 kDa, more preferably from about 5 to about 300 kDa, more preferably from about 10 to about 200 kDa, in particular from about 50 to about 150 kDa, a molar substitution of 0.1 to 3, preferably 0.4 to 1.3, such as 0.4, 0.5, 0.6, 0.7, 0.8, 0.9, 1.0, 1.1, 1.2, or 1.3, and a ratio of $C_2$:$C_6$ substitution of preferably in the range of from 2 to 20, more preferably in the range of from 2 to 15 and even more preferably in the range of from 3 to 12.

According to a further aspect, the present invention relates to a HAS derivative comprising BA' as described above, or a HAS derivative comprising BA' as described above, obtained or obtainable by a method as described above, for use in a method for the treatment of the human or animal body.

Moreover, the present invention relates to a HAS derivative comprising BA' as described above, or a HAS derivative comprising BA' as described above, obtained or obtainable by a method as described above, as a therapeutic or prophylactic agent.

Furthermore, the present invention relates to a pharmaceutical composition comprising in a therapeutically effective amount a HAS derivative comprising BA' as described above, or a HAS derivative comprising BA' as described above, obtained or obtainable by a method as described above.

The HAS derivatives of the present invention, comprising BA', may be administered by suitable methods such as e.g. enteral, parenteral or pulmonary methods preferably administered by i.v., s.c. or i.m. routes. The specific route chosen will depend upon the condition being treated. Preferably, the derivatives may be administered together with a suitable carrier, such as known in the art (e.g. as used in the first generation/unmodified biopharmaceutical, albumin-free or with albumin as an excipient), a suitable diluent, such as sterile solutions for i.v., i.m., or s.c. application. The required dosage will depend on the severity of the condition being treated, the patient's individual response, the method of administration used, and the like. The skilled person is able to establish a correct dosage based on his general knowledge.

As far as the pharmaceutical compositions according to the present invention comprising the HAS derivative comprising BA', as described above, are concerned, the HAS derivatives may be used in combination with a pharmaceutical excipient. Generally, the HAS derivative will be in a solid form which can be combined with a suitable pharmaceutical excipient that can be in either solid or liquid form. As excipients, carbohydrates, inorganic salts, antimicrobial agents, antioxidants, surfactants, buffers, acids, bases, and combinations thereof may be mentioned. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient may also include an inorganic salt or buffer such as citric acid, sodium chloride, potassium chloride, sodium sulfate, potassium nitrate, sodium phosphate monobasic, sodium phosphate dibasic, and combinations thereof. The pharmaceutical composition according to the present invention may also comprise an antimicrobial agent for preventing or deterring microbial growth, such as, e.g., benzalkonium chloride, benzethonium chloride, benzyl alcohol, cetylpyridinium chloride, chlorobutanol, phenol, phenylethyl alcohol, phenylmercuric nitrate, thimersol, and combinations thereof. The pharmaceutical composition according to the present invention may also comprise an antioxidant, such as, e.g., ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof. The pharmaceutical composition according to the present invention may also comprise a surfactant, such as, e.g., polysorbates, or pluronics sorbitan esters; lipids, such as phospholipids such as lecithin and other phosphatidylcholines, phosphatidylethanolamines acids and fatty esters; steroids, such as cholesterol; and chelating agents, such as EDTA or zinc. The pharmaceutical composition according to the present invention may also comprise acids or bases such as, e.g., hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof, and/or sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof. Generally, the excipient will be present in pharmaceutical composition according to the present invention in an amount of 0.001 to 99.999 wt.-%, preferably from 0.01 to 99.99 wt.-%, more preferably from 0.1 to 99.9 wt.-%, in each case based on the total weight of the pharmaceutical composition.

According to another aspect, the present invention also relates to the use of a HAS derivative, preferably a HES derivative as described above, wherein BA is EPO, for the preparation of a medicament for the treatment of anemic disorders or hematopoietic dysfunction disorders or diseases related hereto.

According to another aspect, the present invention also relates to the use of a HAS derivative, preferably a HES derivative as described above, wherein BA is G-CSF, for the preparation of a medicament for the treatment of haemophilia A for the treatment of a disorder characterized by a reduced hematopoietic or immune function. According to a preferred embodiment, the disorder characterized by a reduced hematopoietic or immune function, is a result of chemotherapy, radiation therapy, infectious disease, severe chronic neutropenia, or leukemia.

According to another aspect, the present invention also relates to the use of a HAS derivative, preferably a HES derivative as described above, wherein BA is IFN alpha, for the preparation of a medicament for the treatment of leukaemia e.g. hairy cell leukaemia, chronic myelogeneous leukaemia, multiple myeloma, follicular lymphoma, cancer, e.g. carcinoid tumour, malignant melanoma and hepatitis, e.g. chronic hepatitis B and chronic hepatitis C.

According to another aspect, the present invention also relates to the use of a HAS derivative, preferably a HES derivative as described above, wherein BA is IFN gamma, for the preparation of a medicament for the treatment of osteoporosis and/or chronic malignant disease.

According to another aspect, the present invention also relates to the use of a HAS derivative, preferably a HES derivative as described above, wherein BA is IL-2, for the preparation of a medicament for the treatment of osteoporosis and/or chronic malignant disease.

According to another aspect, the present invention also relates to the use of a HAS derivative, preferably a HES derivative as described above, wherein BA is IL-11, for the preparation of a medicament for the treatment of platelet transfusions following myelosuppressive chemotherapy.

According to another aspect, the present invention also relates to the use of a HAS derivative, preferably a HES derivative as described above, wherein BA is A1AT, for the preparation of a medicament for the treatment of emphysema, cystic fibrosis, atopic dermatitis, and/or bronchitis.

According to another aspect, the present invention also relates to the use of a HAS derivative, preferably a HES derivative as described above, wherein BA is IFN beta, for the preparation of a medicament for the treatment of multiple sclerosis, preferably relapsing forms of multiple sclerosis.

According to another aspect, the present invention also relates to the use of a HAS derivative, preferably a HES derivative as described above, wherein BA is factor VII for the preparation of a medicament for the treatment of episodes in hemophilia A or B patients with inhibitors to Factor VIII or Factor IX.

According to another aspect, the present invention also relates to the use of a HAS derivative, preferably a HES derivative as described above, wherein BA is factor IX for the preparation of a medicament for the control and prevention of hemorrhagic episodes in patients with hemophilia B, e.g. congenital factor IX deficiency or Christmas disease, including control and prevention of bleeding in surgical settings.

LIST OF REFERENCES

Sommermeyer et al., 1987, Krankenhauspharmazie, 8(8), 271-278
Weidler et al., 1991, Arzneimittelforschung/Drug Res., 41, 494-498
DE 26 16 086
Spivak and Hogans, 1989, Blood 73, 90
McMahon et al., 1990, Blood 76, 1718
WO 94/28024
WO 02/080979
WO 03/074087
WO 03/074088
WO 2005/014024
WO 2005/092390
WO 2004/024777
WO 2004/024776
WO 2005/092928
US 2006/0194940 A1
U.S. Pat. No. 7,157,546 B2
EP 1 591 467 A1
WO 2004/022630 A2
U.S. Pat. No. 6,916,962 B2
U.S. Pat. No. 6,956,135 B2
WO 03/049699 A2
U.S. Pat. No. 5,990,237
Klemm D. et al, Comprehensive Cellulose Chemistry Vol. 2, 1998, Whiley-VCH, Weinheim, N.Y., especially chapter 4.4, Esterification of Cellulose (ISBN 3-527-29489-9
WO 00/66633 A
WO 00/18893 A
U.S. Pat. No. 4,454,161
EP 0 418 945 A
JP 2001294601 A
US 2002/065410 A
U.S. Pat. No. 6,083,909
A. Skerra, Curr Opin Mol Ther. 9(4), 2007, pp. 336-344
T. Hey et al., Trends Biotechnol. 23 (10), 2005, pp. 514-522
H. K. Binz et al., Nat Biotechnol. 23 (10), 2005, pp. 1257-1268
WO2005/083103 A1
K. R. Reddy et al. Advanced Drug Delivery Reviews 54 (2002) pp. 571-586

DESCRIPTION OF THE FIGURES

FIG. 1 shows the SDS-PAGE analysis of an oxHES-IFNa coupling reactions according to example 2. The separation was performed under reducing conditions using the NuPAGE system (Invitrogen) with 4-12% Bis-Tris gels (1.0 mm) and a MOPS running buffer according to the manufacturers instructions.

Load: 10 μg protein as reaction mix.
M: Marker, Mark12 (Invitrogen).
Lanes 1-4: reaction mixtures according to example 2.
Successful HESylation of the target protein (19 kDa) becomes visible as a smeary band with a broad mass distribution ranging from 30 to >200 kDa.

Figure 2:
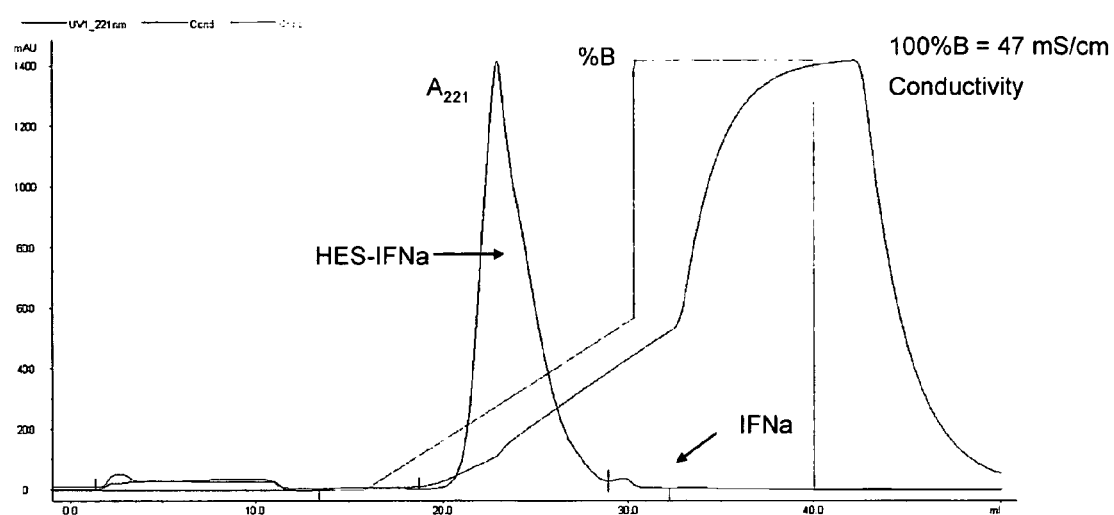

FIG. 2: Anion exchange chromatography of an oxHES55/0.7-IFNa coupling reaction FIG. 2 shows the chromatographic separation monitored by UV-Vis spectroscopy at 221 nm on an ion exchange column of an oxHES55/0.7-IFNa coupling reaction according to example 2. Chromatography conditions were as follows:

Chromatography system: Äkta Explorer 100 (GE Healthcare).
Column: Hi Trap Q HP 1 ml (GE Healthcare)
Eluent A: 10 mM Tris.Cl, pH 8.0.
Eluent B: 10 mM Tris.Cl, 0.5 M NaCl, pH 8.0.
Operating conditions: flow rate 1 ml/min, 21° C.

| Run parameters: | | |
| --- | --- | --- |
| equilibration sample load | 10 CV | 0% B |
| wash | 2 CV | 0% B |
| elution | 16 CV | 0-50% B |
| regeneration | 10 CV | 100% B |
| reequilibration | 8 CV | 0% B |

Load: 2 mg protein/ml resin as reaction mix according to example 2, 20 fold diluted in Eluent A and adjusted to pH 8.0.

Non-reacted, excessive HES is found in the flowthrough. The HESylation weakens the interaction of the protein with the column resulting in decreased elution times for the conjugate as compared to the unmodified protein.

Figure 3:
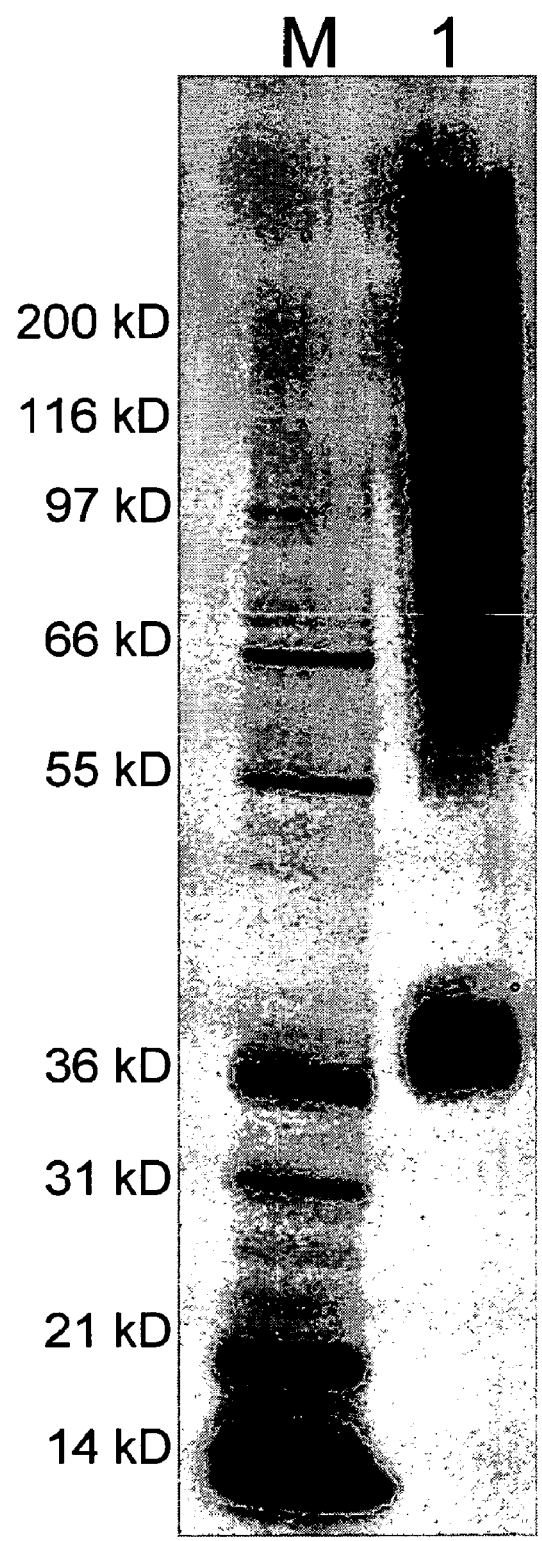

FIG. 3: SDS-PAGE analysis of an oxHES55/0.7-EPO coupling reaction

FIG. 3 shows the SDS-PAGE analysis of an oxHES55/0.7-EPO coupling reaction according to example 3. The separation was performed under reducing conditions using the NuPAGE system (Invitrogen) with 4-12% Bis-Tris gels (1.0 mm) and a MOPS running buffer according to the manufacturers instructions. Load: 10 μg protein as reaction mixture.

M: Marker, Mark12 (Invitrogen).
Lane 1: reaction mixture according to example 3.
Lane 2: EPO starting material prior to conjugation.

Successful HESylation of the target protein (~35-40 kDa) becomes visible as a smeary band with a broad mass distribution ranging from 55 to >200 kDa.

Figure 4:
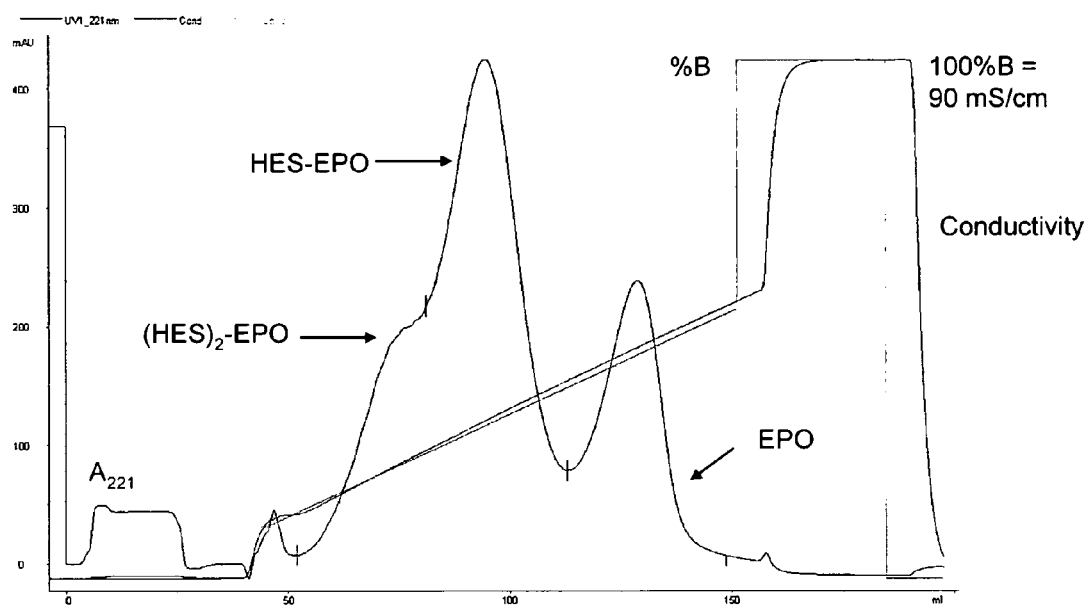

FIG. 4: Cation exchange chromatography of an oxHES55/0.7-EPO coupling reaction FIG. 4 shows the chromatographic separation monitored by UV-Vis spectroscopy at 221 nm on an ion exchange column of an oxHES55/0.7-EPO coupling reaction according to example 3. Chromatography conditions were as follows:

Chromatography system: Äkta Explorer 100 (GE Healthcare).
Column: HiTrap SP HP (GE Healthcare).
Eluent A: 20 mM sodium acetate, pH 4.0.
Eluent B: 20 mM sodium acetate, 1M NaCl, pH 4.0.
Operating conditions: flow rate 5 ml/min, 21° C.

| Run parameters: | | |
| --- | --- | --- |
| equilibration sample load | 10 CV | 0% B |
| wash1 | 2 CV | 0% B |
| wash2 | 2 CV | 10% B |
| elution | 21 CV | 10-52% B |
| regeneration | 8 CV | 100% B |
| reequilibration | 5 CV | 0% B |

Load: 2 mg protein/ml resin as reaction mix according to example 3, 10 fold diluted in Eluent A Non-reacted, excessive HES is found in the flowthrough. The HESylation weakens the interaction of the protein with the column resulting in decreased elution times for the conjugate as compared to the unmodified protein.

Figure 5:
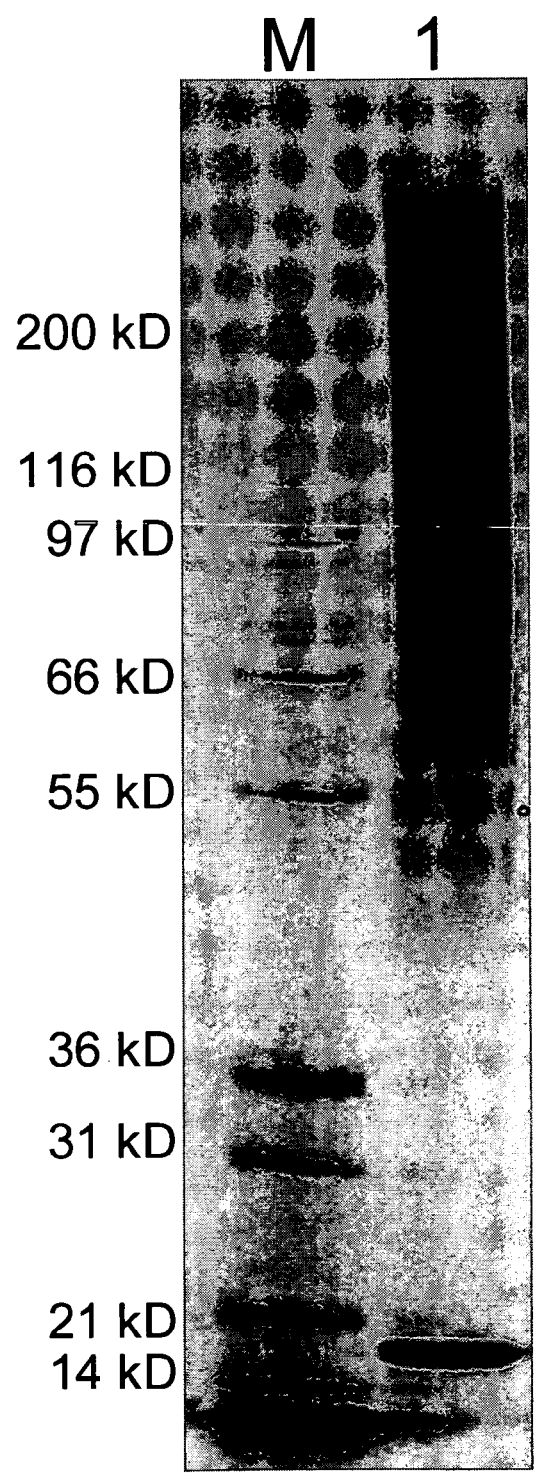

FIG. 5: SDS-PAGE analysis of an oxHES100/1.0-IFNa coupling reaction

FIG. 5 shows the SDS-PAGE analysis of an oxHES-IFNa coupling reaction according to example 5. The separation was performed under reducing conditions using the NuPAGE system (Invitrogen) with 4-12% Bis-Tris gels (1.0 mm) and a MOPS running buffer according to the manufacturers instructions.

Load: 10 μg protein as reaction mix.
M: Marker, Mark12 (Invitrogen).
lane 1: reaction mixture according to example 5.

Successful HESylation of the target protein (19 kDa) becomes visible as a smeary band with a broad mass distribution ranging from 50 to >200 kDa.

Figure 6:
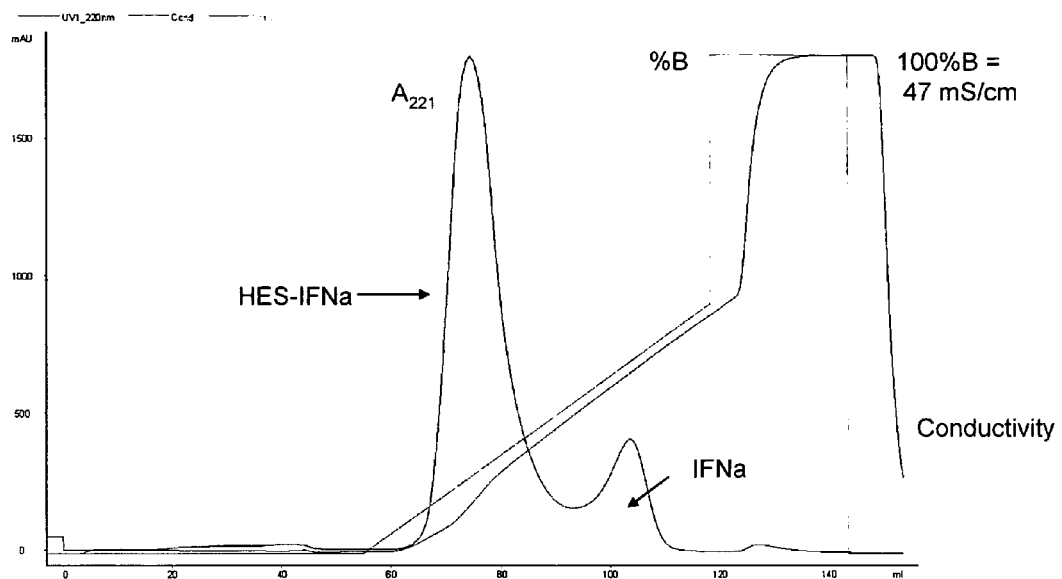

FIG. 6: Anion exchange chromatography of an oxHES100/1.0-IFNa coupling reaction FIG. 6 shows the chromatographic separation monitored by UV-Vis spectroscopy at 221 nm on an ion exchange column of an oxHES100/1.0-IFNa coupling reaction according to example 5. Chromatography conditions were as follows:

Chromatography system: Äkta Explorer 100 (GE Healthcare).
Column: Hi Trap Q HP 5 ml (GE Healthcare).
Eluent A: 10 mM Tris.Cl, pH 8.0.
Eluent B: 10 mM Tris.Cl, 0.5 M NaCl, pH 8.0.
Operating conditions: flow rate 1 ml/min, 21° C.

| Run parameters: | | |
| --- | --- | --- |
| equilibration sample load | 10 CV | 0% B |
| wash | 2 CV | 0% B |
| elution | 12.5 CV | 0-50% B |
| regeneration | 5 CV | 100% B |
| reequilibration | 5 CV | 0% B |

Load: 2 mg protein/ml resin as reaction mix according to example 5, 20 fold diluted in Eluent A and adjusted to pH 8.0

Non-reacted, excessive HES is found in the flowthrough. The HESylation weakens the interaction of the protein with the column resulting in decreased elution times for the conjugate as compared to the unmodified protein.

Figure 7:
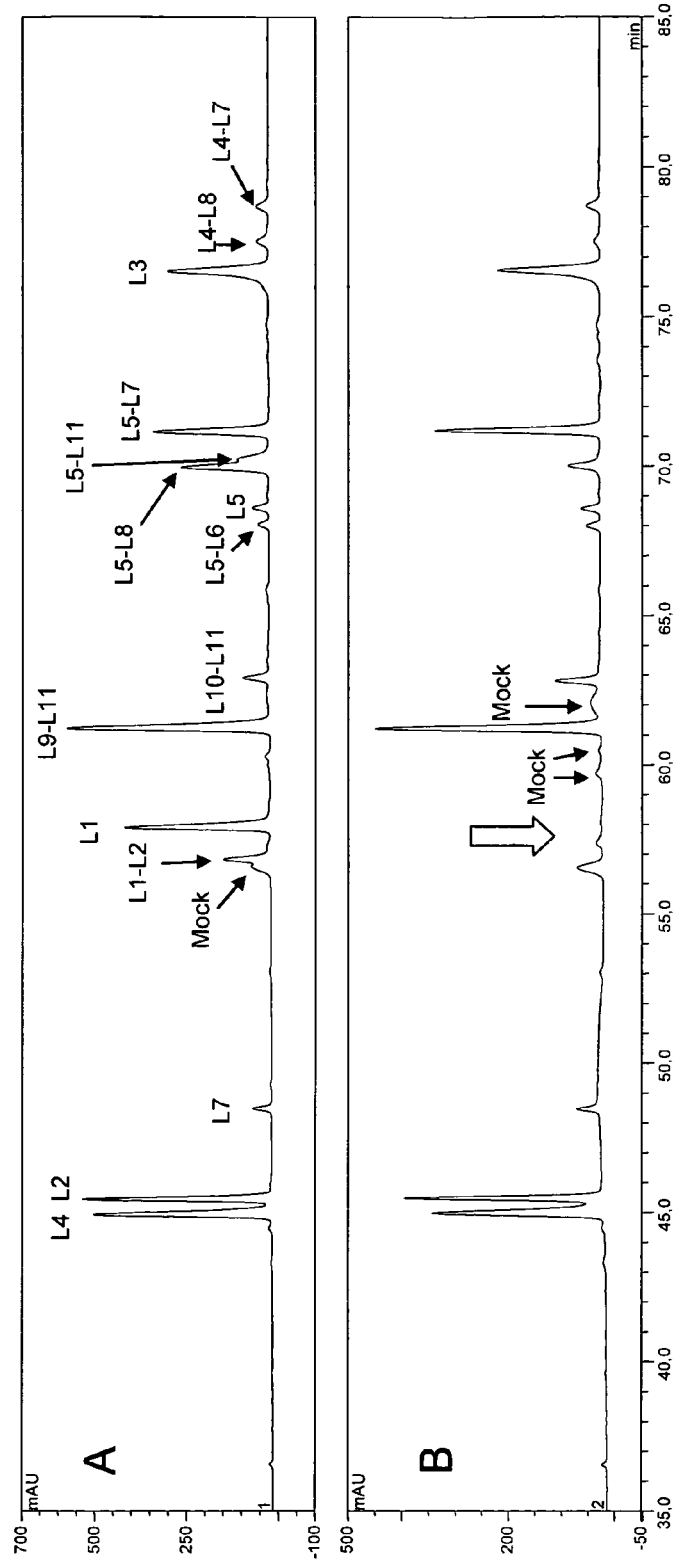

FIG. 7: Peptide Mapping of an oxHES100/1.0-IFNa conjugate

FIG. 7 shows the chromatographic separation of an IEX-purified oxHES-IFNa conjugate according to example 5 treated with Endo-LysC.

The proteolysis was performed using 7.5% Endo-LysC in 50 mM Tris-Cl, pH 8.6, 0.01% SDS at 37° C. o/n. Samples were denatured with DTT and guanidinium chloride and analyzed by RP-HPLC on a 4.6×250 mm Jupiter C4 column (Phenomenex) run with a water/acetonitrile gradient with TFA. The chromatograms shown were monitored at 214 nm.

The arrow indicates the region of the chromatogram where strong differences between the chromatograms for the protein (A) and the conjugate (B) are visible. The peaks for L1 and L1/L2 (the N-terminal peptide resulting from the Endo-Lys C treatment) is strongly reduced for the conjugate sample while the other fragments remain virtually unaffected. These data suggest a preferential coupling of the HES to the N-terminus of IFNa.

Figure 8:
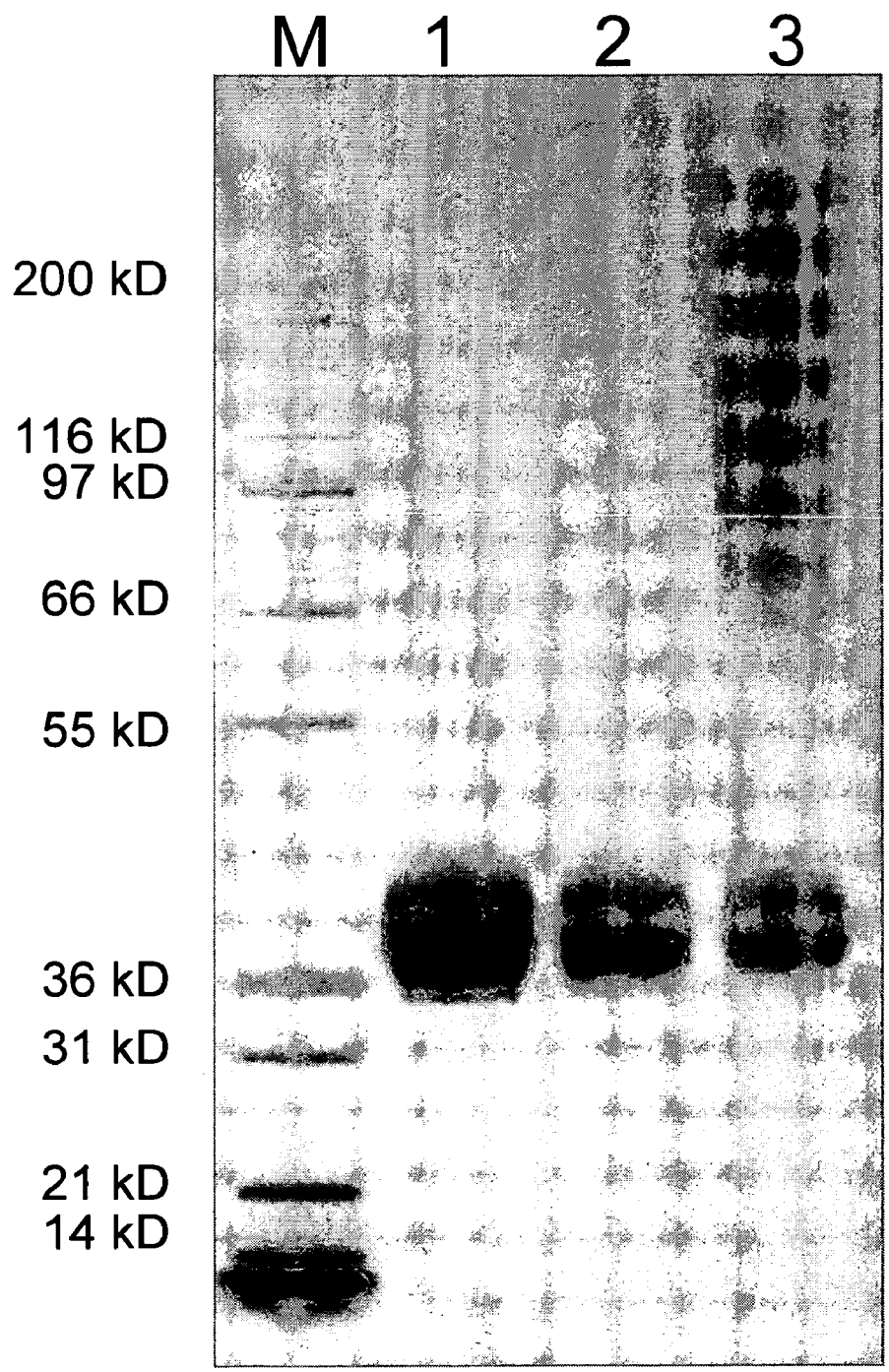

FIG. 8: SDS-PAGE analysis of an oxHES100/1.0-EPO coupling reaction

FIG. 8 shows the SD S-PAGE analysis of an oxHES100/1.0-EPO coupling reaction according to example 6. The separation was performed under reducing conditions using the NuPAGE system (Invitrogen) with 4-12% Bis-Tris gels (1.0 mm) and a MOPS running buffer according to the manufacturers instructions.

Load: 10 µg protein as reaction mixture.
M: Marker, Mark12 (Invitrogen).
Lane 1: 10 µg EPO starting material prior to conjugation.
Lane 2: 5 µg EPO starting material prior to conjugation.
Lane 3: reaction mixture according to example 6.

Successful HESylation of the target protein (~35-40 kDa) becomes visible as a smeary band with a broad mass distribution ranging from 70 to >200 kDa.

Figure 9:
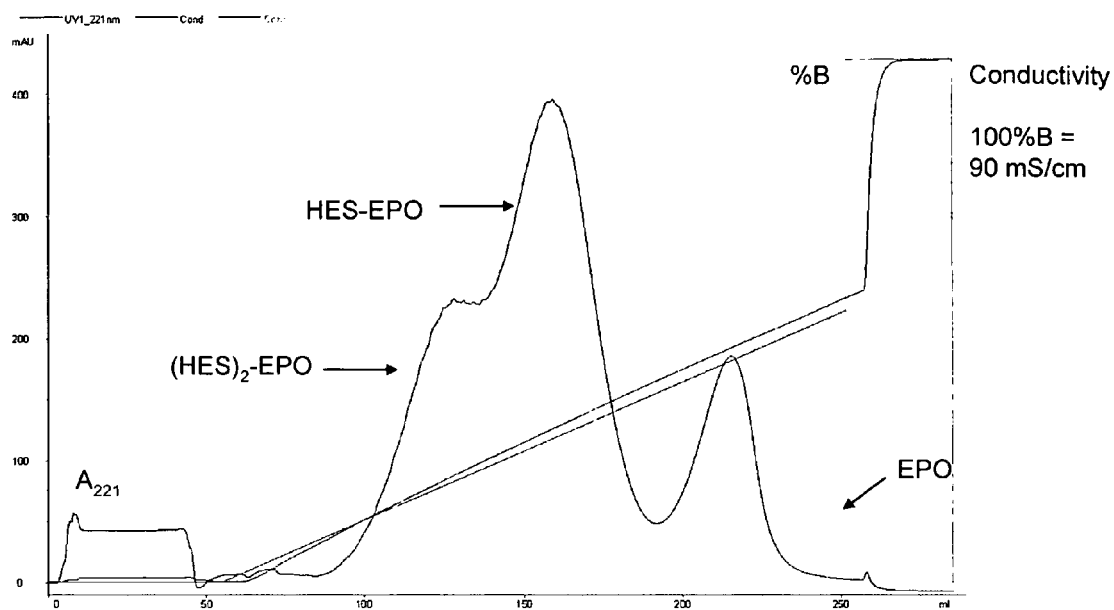
Figure 14:
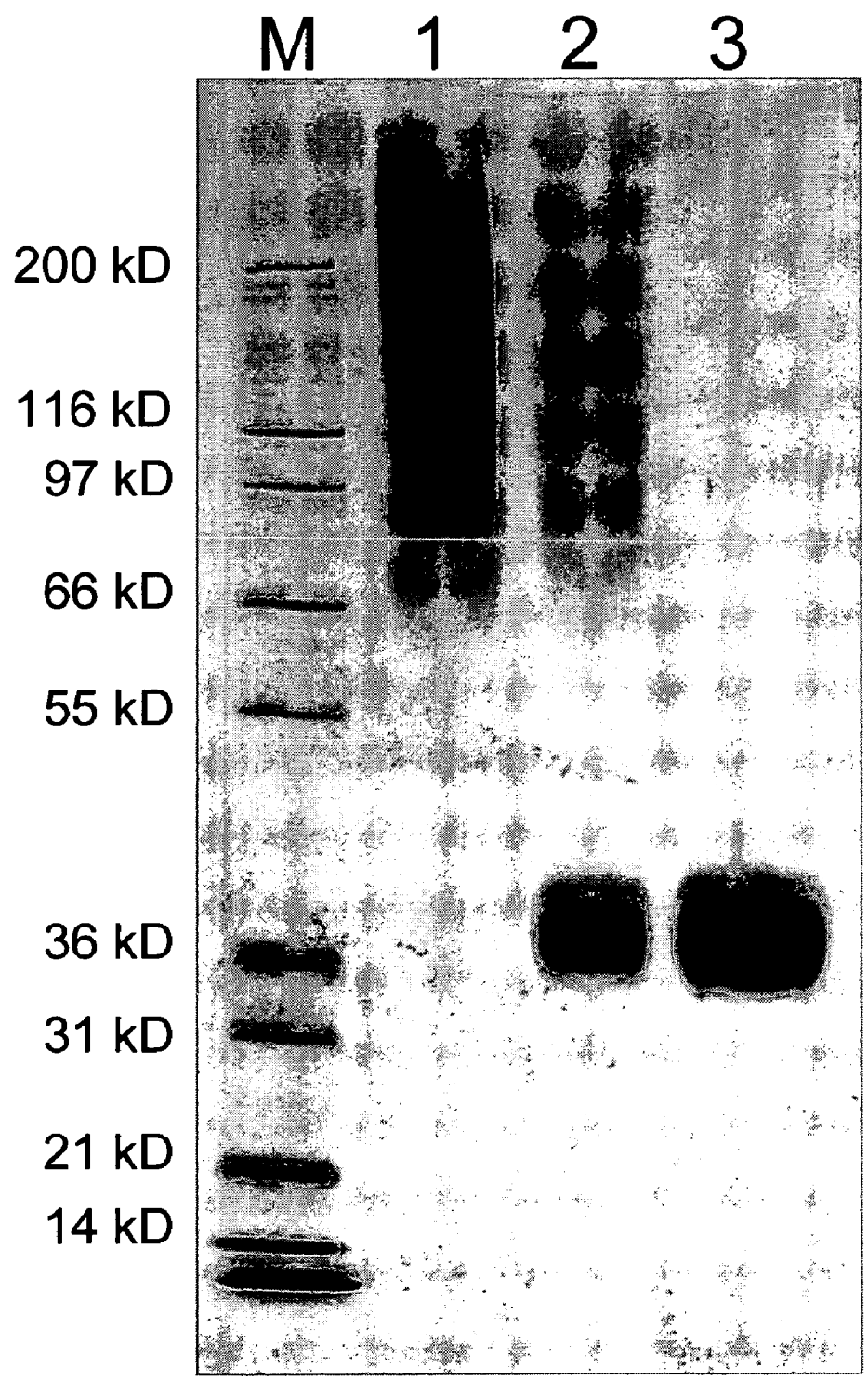

FIG. 9: Cation exchange chromatography of an oxHES100/1.0-EPO coupling reaction FIG. 14 shows the chromatographic separation monitored by UV-Vis spectroscopy at 221 nm on an ion exchange column of an oxHES100/1.0-EPO coupling reaction according to example 6. Chromatography conditions were as follows:

Chromatography system: Äkta Explorer 100 (GE Healthcare).
Column: 2×5 ml HiTrap SP HP (GE Healthcare).
Eluent A: 20 mM sodium acetate, pH 4.0.
Eluent B: 20 mM sodium acetate, 1M NaCl, pH 4.0.
Operating conditions: flow rate 5 ml/min, 21° C.

| Run parameters: | | |
|---|---|---|
| equilibration sample load | 10 CV | 0% B |
| wash1 | 2 CV | 0% B |
| wash2 | 2 CV | 10% B |
| elution | 21 CV | 10-52% B |
| regeneration | 2.5 CV | 100% B |
| reequilibration | 5 CV | 0% B |

Load: 2 mg protein/ml resin as reaction mix according to example 6, 10 fold diluted in Eluent A Non-reacted, excessive HES is found in the flowthrough. The HESylation weakens the interaction of the protein with the column resulting in decreased elution times for the conjugate as compared to the unmodified protein.

Figure 10:
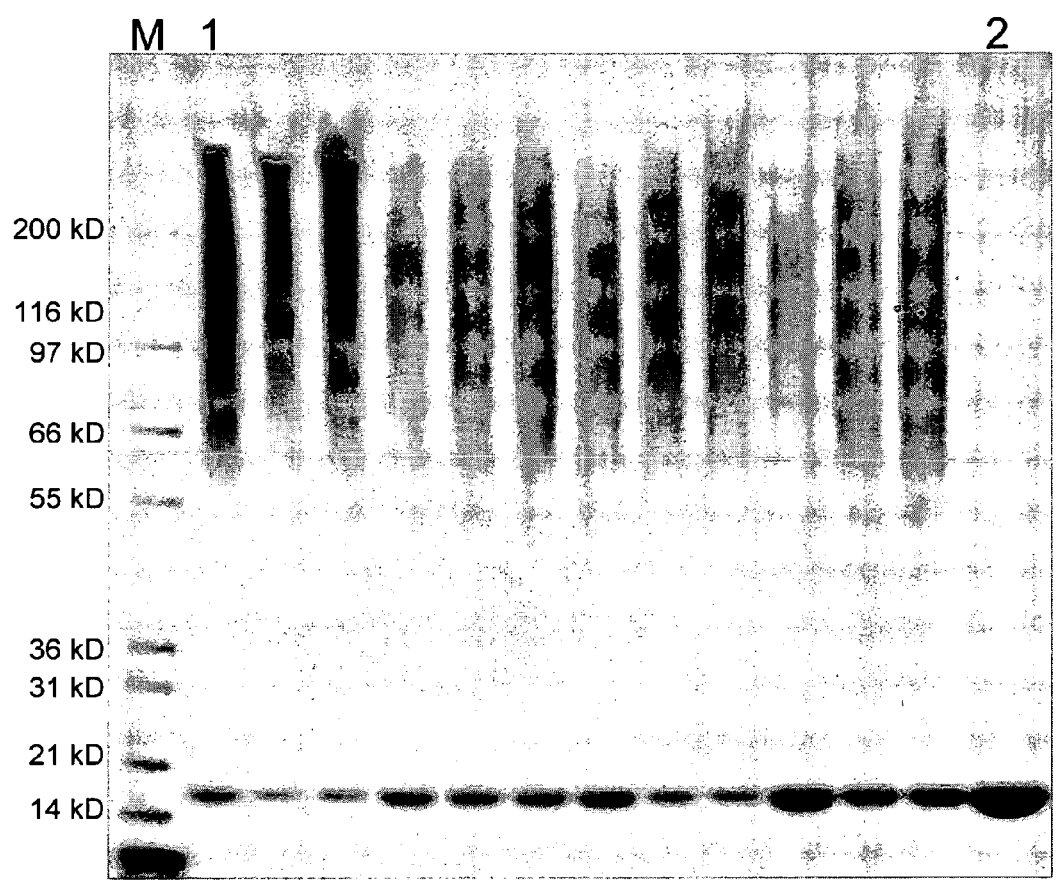

FIG. 10: SDS-PAGE analysis of an oxHES100/1.0-G-CSF coupling reaction

FIG. 10 shows the SDS-PAGE analysis of an oxHES100/1.0-G-CSF coupling reaction according to example 7. The separation was performed under reducing conditions using the NuPAGE system (Invitrogen) with 4-12% Bis-Tris gels (1.0 mm) and a MOPS running buffer according to the manufacturers instructions.

Load: 10 µg protein as reaction mixture.
M: Marker, Mark12 (Invitrogen).
Lane 1: reaction mixture according to example 7.
Lane 2: G-CSF starting material prior to conjugation.

Successful HESylation of the target protein (~18 kDa) becomes visible as a smeary band with a broad mass distribution ranging from 50 to >200 kDa.

Figure 11:
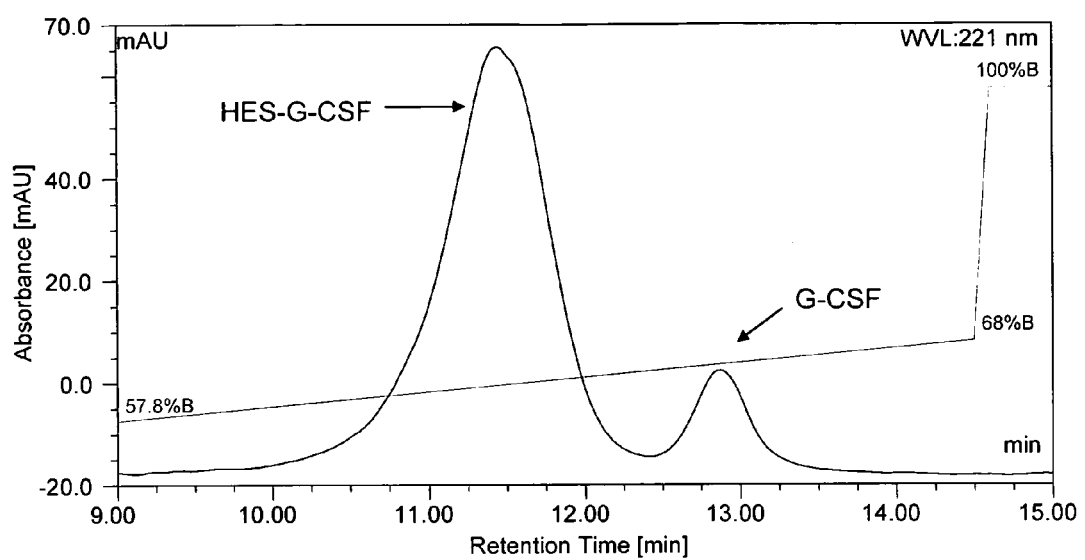

FIG. 11: RP-HPLC analysis of an oxHES100/1.0-G-CSF coupling reaction

FIG. 11 shows a section of the RP-HPLC analysis of an oxHES100/1.0-G-CSF coupling reaction according to example 7 monitored by UV-Vis spectroscopy at 221 nm. Chromatography conditions were as follows:

Chromatography system: Summit, P580 (HPG) (Dionex).
Column: Jupiter C18, 300 A, 5 µm, 4.6×150 mm (Phenomenex).
Eluent A: 0.1% trifluoroacetic acid in water.
Eluent B: 0.1% trifluoroacetic acid in acetonitrile.
Operating conditions: flow rate 1 ml/min, 20° C.
Gradient: 0-5 min, 5-55% B; 5-12 min, 55-68% B; 12-17 min, 100% B; 17-22 min, 5% B; gradient delay 2.5 min.

Load: 10 µs protein as reaction mix, diluted in water to a protein concentration of 0.1 mg/ml.

The main peak at 11.5 min is the HES protein conjugate separated from free G-CSF eluting at ~13 min.

Figure 12:
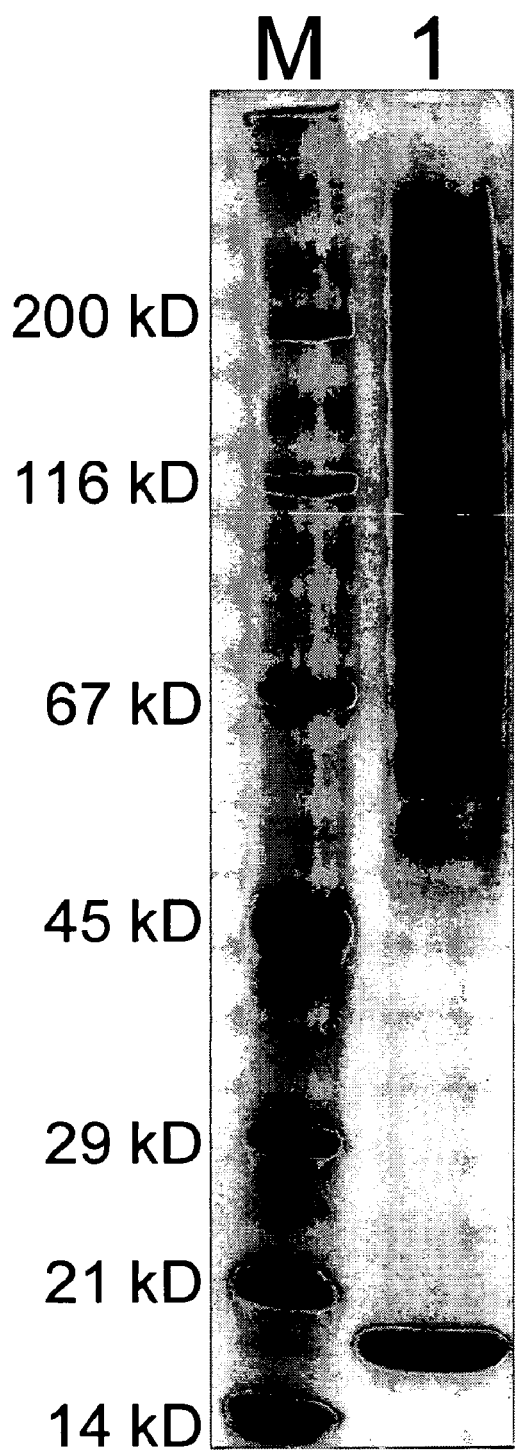

FIG. 12: SDS-PAGE analysis of an HES100/1.0-IFNa coupling reaction

FIG. 12 shows the SDS-PAGE analysis of a HES-IFNa coupling reaction according to example 10. The separation was performed under reducing conditions using the NuPAGE system (Invitrogen) with 4-12% Bis-Tris gels (1.0 mm) and a MOPS running buffer according to the manufacturers instructions.

Load: 10 µg protein as reaction mixture.
M: Marker, unstained protein marker 5-200 kDa (Serva).
Lane 1: reaction mixture according to example 9.

Successful HESylation of the target protein (19 kDa) becomes visible as a smeary band with a broad mass distribution ranging from 50 to >200 kDa.

Figure 13:
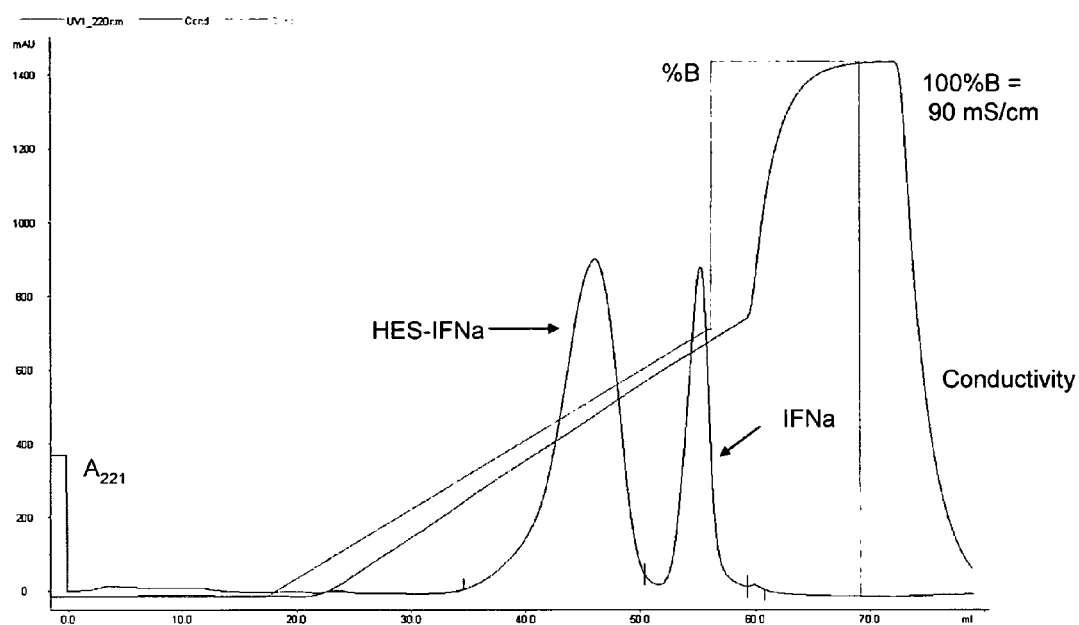

FIG. 13: Anion exchange chromatography of an HES100/1.0-IFNa coupling reaction FIG. 13 shows the chromatographic separation monitored by UV-Vis spectroscopy at 221 nm on an ion exchange column of an HES100/1.0-IFNa coupling reaction according to example 10. Chromatography conditions were as follows:

Chromatography system: Äkta Explorer 100 (GE Healthcare).
Column: 5 ml HiTrap SP HP (GE Healthcare).
Eluent A: 20 mM sodium acetate, pH 4.0.
Eluent B: 20 mM sodium acetate, 1M NaCl, pH 4.0.
Operating conditions: flow rate 5 ml/min, 21° C.

| Run parameters: | | |
|---|---|---|
| equilibration sample load | 10 CV | 0% B |
| wash1 | 2 CV | 0% B |
| elution | 20 CV | 0-50% B |
| regeneration | 10 CV | 100% B |
| reequilibration | 5 CV | 0% B |

Load: 3 mg protein/ml resin as reaction mix according to example 9, 10 fold diluted in Eluent A Non-reacted, excessive HES is found in the flowthrough. The HESylation weakens the interaction of the protein with the column resulting in decreased elution times for the conjugate as compared to the unmodified protein.

FIG. 14: SDS-PAGE analysis of an HES100/1.0-EPO coupling reaction

FIG. 14 shows the SDS-PAGE analysis of an HES100/1.0-EPO coupling reaction according to example 11. The separation was performed under reducing conditions using the NuPAGE system (Invitrogen) with 4-12% Bis-Tris gels (1.0 mm) and a MOPS running buffer according to the manufacturers instructions.

Load: 10 μg protein as reaction mixture.
M: Marker, Mark12 (Invitrogen).
Lane 1: IEX purified HES EPO conjugate.
Lane 2: reaction mixture according to example 11.
Lane 3: 5 μg EPO starting material prior to conjugation.

Successful HESylation of the target protein (~35-40 kDa) becomes visible as a smeary band with a broad mass distribution ranging from 70 to >200 kDa.

Figure 15:
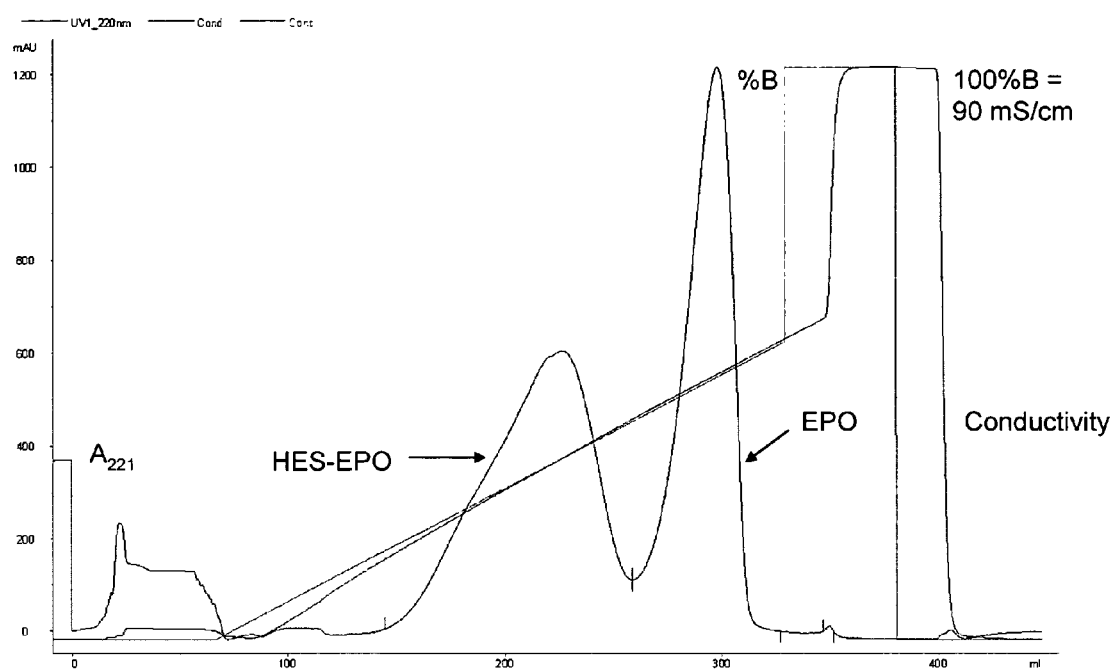

FIG. 15: Cation exchange chromatography of an HES100/1.0-EPO coupling reaction

FIG. 15 shows the chromatographic separation monitored by UV-Vis spectroscopy at 221 nm on an ion exchange column of an HES100/1.0-EPO coupling reaction according to example 11. Chromatography conditions were as follows:

Chromatography system: Äkta Explorer 100 (GE Healthcare).
Column: 4×5 ml HiTrap SP HP (GE Healthcare).
Eluent A: 20 mM sodium acetate, pH 4.0.
Eluent B: 20 mM sodium acetate, 1M NaCl, pH 4.0.
Operating conditions: flow rate 5 ml/min, 21° C.

| Run parameters: | | |
| --- | --- | --- |
| equilibration sample load | 5 CV | 0% B |
| wash1 | 2 CV | 0% B |
| elution | 13 CV | 0-52% B |
| regeneration | 2.5 CV | 100% B |
| reequilibration | 2.5 CV | 0% B |

Load: 3 mg protein/ml resin as reaction mix according to example 11, 2 fold diluted in Eluent A.

Non-reacted, excessive HES is found in the flowthrough. The HESylation weakens the interaction of the protein with the column resulting in decreased elution times for the conjugate as compared to the unmodified protein.

Figure 16:
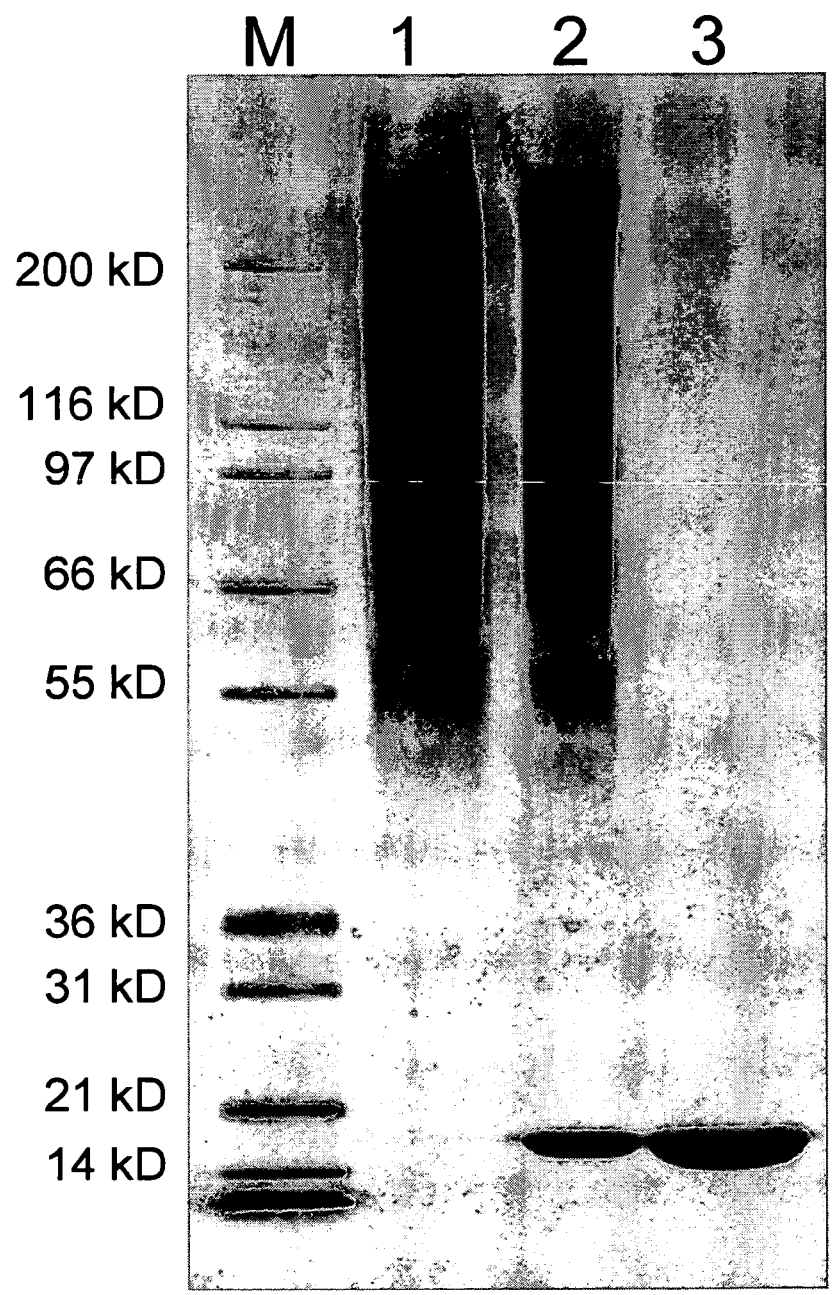

FIG. 16: SDS-PAGE analysis of an HES100/1.0-G-CSF coupling reaction

FIG. 16 shows the SDS-PAGE analysis of an HES100/1.0-G-CSF coupling reaction according to example 12. The separation was performed under reducing conditions using the NuPAGE system (Invitrogen) with 4-12% Bis-Tris gels (1.0 mm) and a MOPS running buffer according to the manufacturers instructions.

Load: 10 μg protein as reaction mixture.
M: Marker, Mark12 (Invitrogen).
Lane 1: IEX purified HES G-CSF conjugate.
Lane 2: reaction mixture according to example 12.
Lane 3: 5 μg G-CSF starting material prior to conjugation.

Successful HESylation of the target protein (~18 kDa) becomes visible as a smeary band with a broad mass distribution ranging from 50 to >200 kDa.

Figure 17:
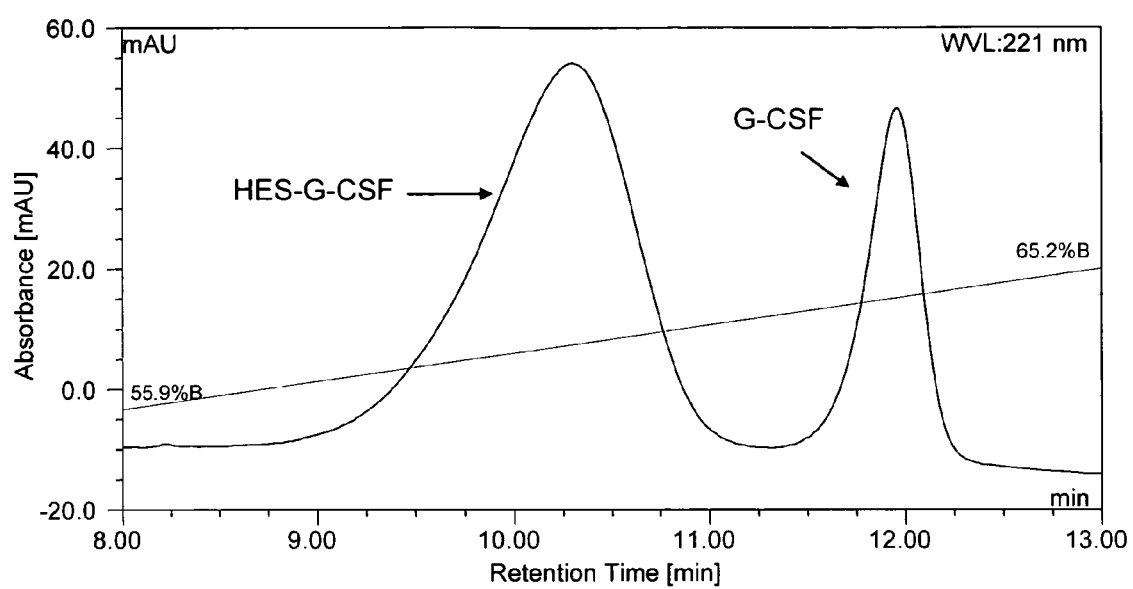

FIG. 17: RP-HPLC analysis of an HES100/1.0-G-CSF coupling reaction

FIG. 17 shows a section of the RP-HPLC analysis of an HES100/1.0-G-CSF coupling reaction according to example 12 monitored by UV-Vis spectroscopy at 221 nm. Chromatography conditions were as follows:

Chromatography system: Summit, P580 (LPG) (Dionex).
Column: Jupiter C18, 300 A, 5 μm, 4.6×150 mm (Phenomenex).
Eluent A: 0.1% trifluoroacetic acid in water.
Eluent B: 0.1% trifluoroacetic acid in acetonitrile.
Operating conditions: flow rate 1 ml/min, 20° C.
Gradient: 0-5 min, 5-55% B; 5-12 min, 55-68% B; 12-17 min, 100% B; 17-22 min, 5% B; gradient delay 2.5 min.

Load: 10 μg protein as reaction mixture, diluted in water to a protein concentration of 0.1 mg/ml.

The main peak at 10-10.5 min is the HES protein conjugate separated from free G-CSF eluting at ~12 min.

Figure 18:
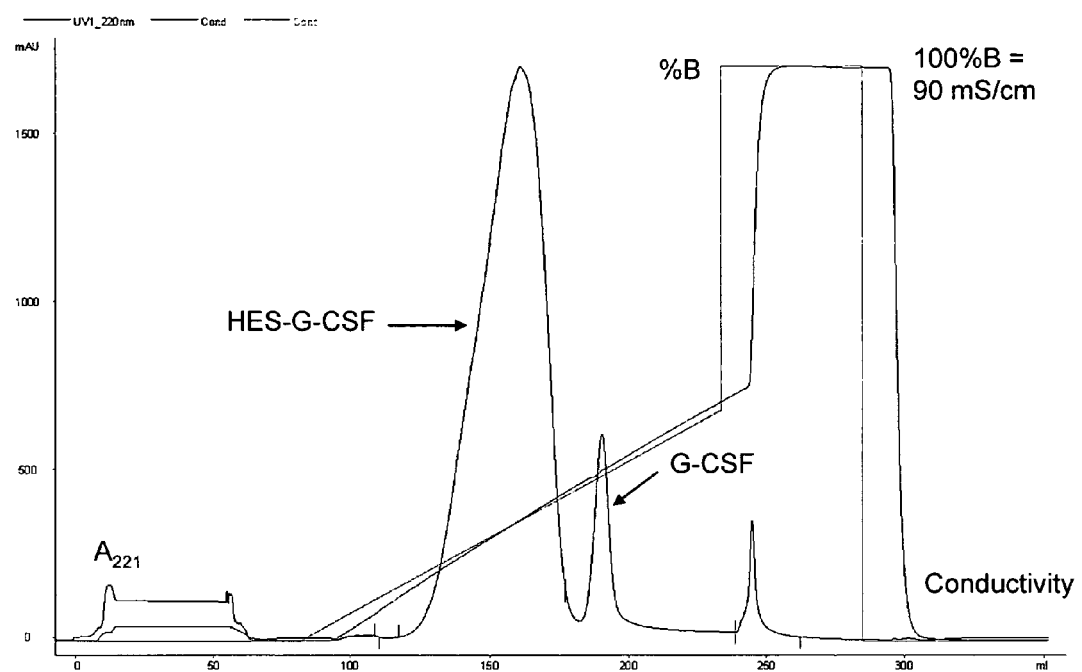
Figure 19:
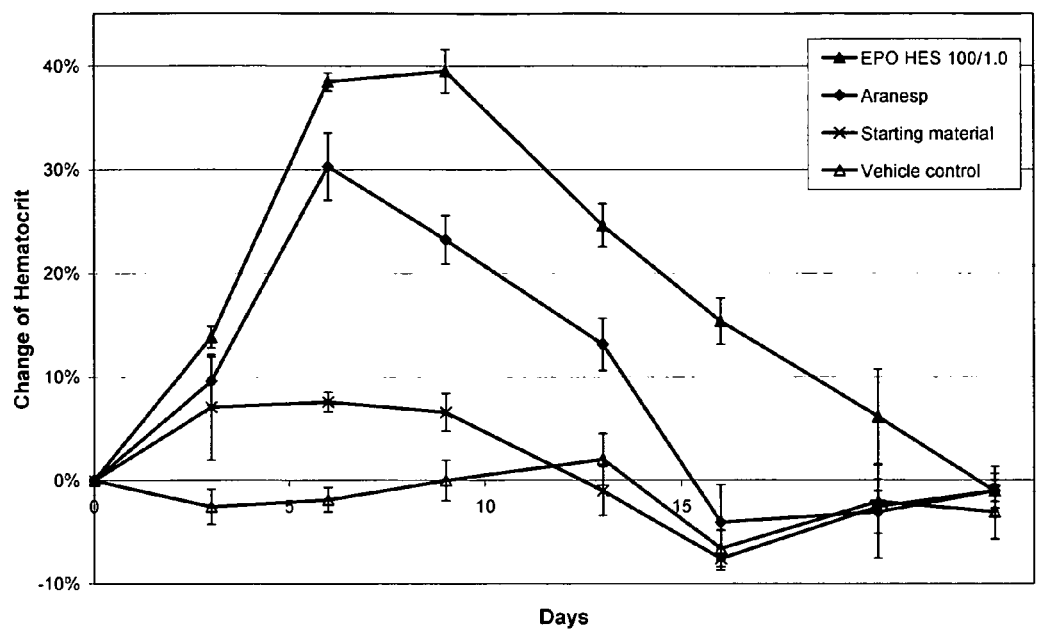
Figure 20:
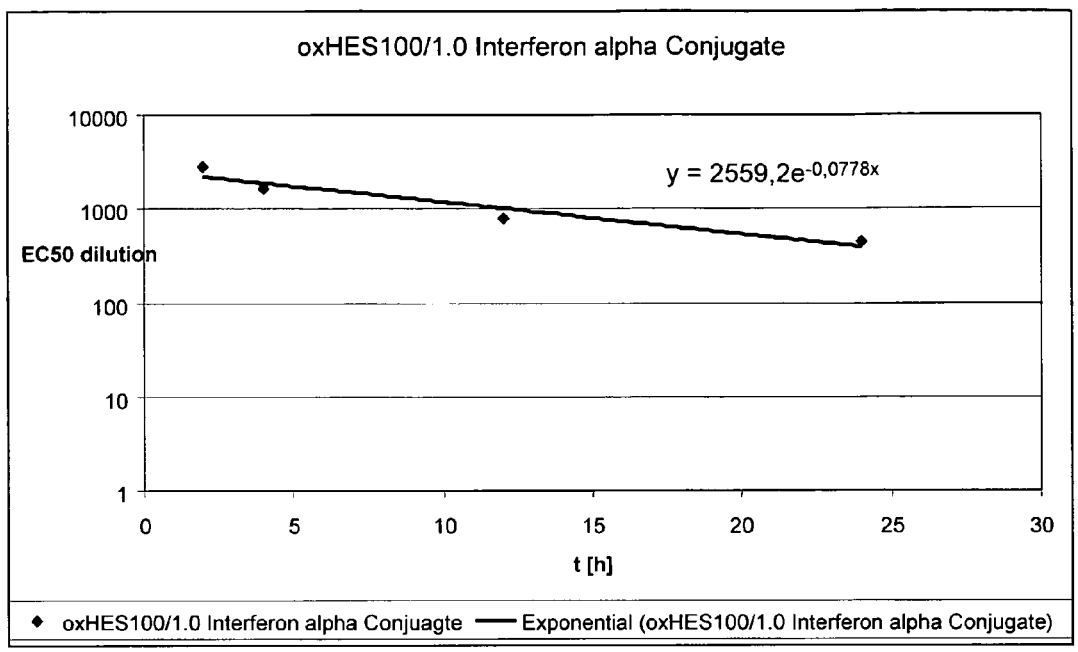

FIG. 18: Cation exchange chromatography of an HES100/1.0-G-CSF coupling reaction FIG. 18 shows the chromatographic separation monitored by UV-Vis spectroscopy at 221 nm on an ion exchange column of an HES100/1.0-G-CSF coupling reaction according to example 12. Chromatography conditions were as follows:

Chromatography system: Äkta Explorer 100 (GE Healthcare).
Column: 2×5 ml HiTrap SP HP (GE Healthcare).
Eluent A: 20 mM sodium acetate, pH 4.0.
Eluent B: 20 mM sodium acetate, 1M NaCl, pH 4.0.
Operating conditions: flow rate 5 ml/min, 21° C.

| Run parameters: | | |
| --- | --- | --- |
| equilibration sample load | 5 CV | 0% B |
| wash | 2 CV | 0% B |
| elution | 15 CV | 0-40% B |
| regeneration | 5 CV | 100% B |
| reequilibration | 5 CV | 0% B |

Load: 3 mg protein/ml resin as reaction mix according to example 12, 2 fold diluted in Eluent A.

Non-reacted, excessive HES is found in the flowthrough. The HESylation weakens the interaction of the protein with the column resulting in decreased elution times for the conjugate as compared to the unmodified protein.

FIGS. 19-23 are referred to in the context of the respective examples.

FIG. 24

Figure 24:
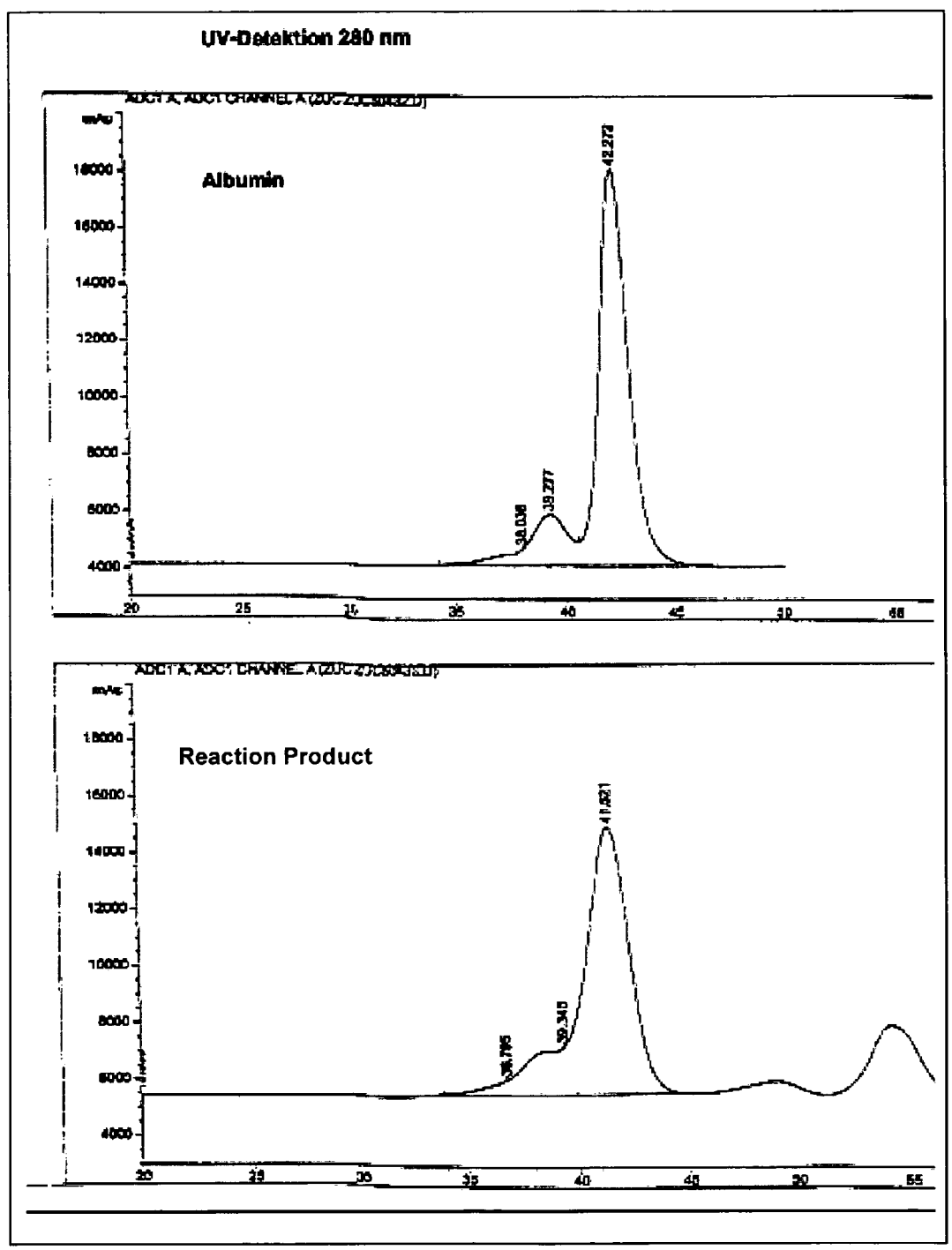

FIG. 24 shows a section of the HPGPC analysis of an oxHBS-BSA coupling reaction according to "additional data (A.2)" monitored by UV-Vis spectroscopy at 280 nm. Chromatography conditions were as follows:

Chromatography system: Shimadsu LC 10 AD/UV-Detektor: TSP UV 2000
Column: Superose 6 10/300 GL (Pharmacia).
Eluent: Phosphate buffer: (3.887 g $Na_2HPO_4 \times 2\ H_2O$, 1.967 g $NaH_2PO_4 \times 2\ H_2O$, 11.688 g NaCl, 0.05 g $NaN_3$ were dissolved in water for chromatography (Reagent Pharmakopoea Europaea) up to a total volume of 1.0 l. The solution was filtered utilizing a 0.45 μm filter)
Operating conditions: flow rate 0.4 ml/min, 20° C.
Load: 0.9 mg protein as reaction mixture, dissolved in 100 μl to a protein concentration of 9 mg/ml.

The upper part shows the BSA starting material prior to the coupling reaction. From left to right, the peaks are at 38.038, 39.277, and 42.272.

The lower part shows the HBS-BSA conjugate. From left to right, the peaks are at 36.795, 39.345, and 41.521.

Figure 25:
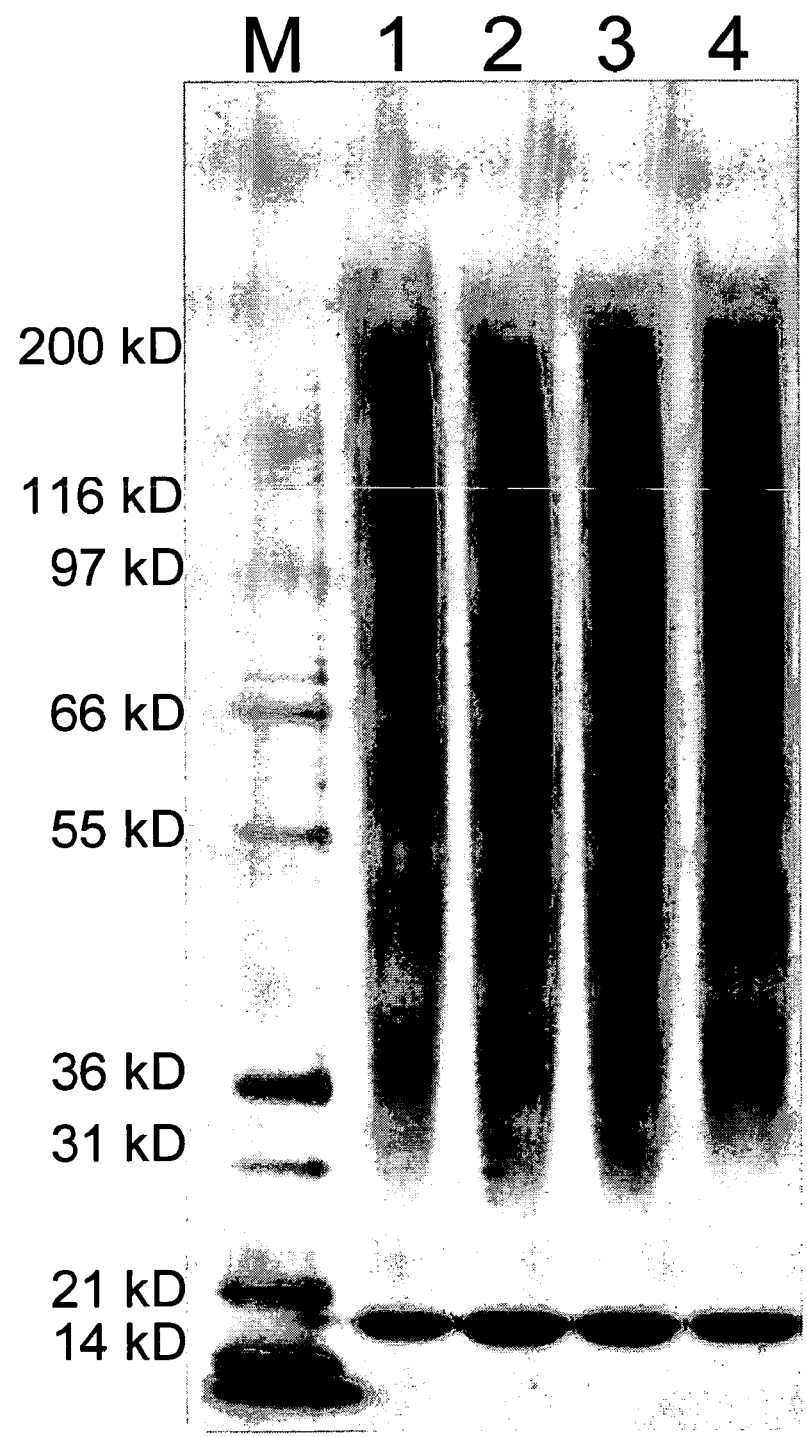

FIG. 25: SDS-PAGE analysis of an oxHBS-IFNa coupling reaction

FIG. 25 shows the SDS-PAGE analysis of an oxHBS-IFNa coupling reaction according to "additional data (A.3)". The separation was performed under reducing conditions using the NuPAGE system (Invitrogen) with 4-12% Bis-Tris gels (1.0 mm) and a MOPS running buffer according to the manufacturers instructions.

Load: 10 μg protein as reaction mixture.
M: Marker, Mark12 (Invitrogen).

Lanes 1-4: reaction mixtures according to "additional data (A.3)".

Successful HBSylation of the target protein (19 kDa) becomes visible as a smeary band with a broad mass distribution ranging from 30 to >200 kDa.

Figure 26:
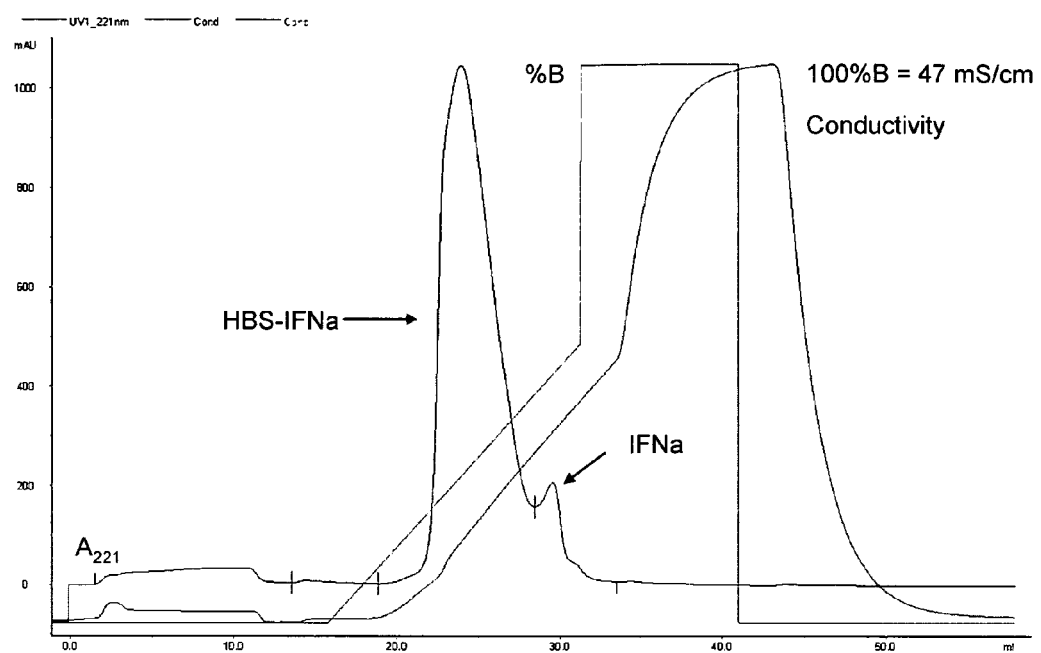

FIG. 26: Anion exchange chromatography of an oxHBS-IFNa coupling reaction

FIG. 26 shows the chromatographic separation monitored by UV-Vis spectroscopy at 221 nm of an oxHBS-IFNa coupling reaction according to additional data (A.3) using an ion exchange column. Chromatography conditions were as follows:

Chromatography system: Äkta Explorer 100 (GE Healthcare).
Column: Hi Trap Q HP 1 ml (GE Healthcare).
Eluent A: 10 mM Tris·Cl, pH 8.0.
Eluent B: 10 mM Tris·Cl, 0.5 M NaCl, pH 8.0.
Operating conditions: flow rate 1 ml/min, 20° C.

| Run parameters: | | |
| --- | --- | --- |
| equilibration | 10 CV | 0% B |
| sample load | | |
| wash | 2 CV | 0% B |
| elution | 16 CV | 0-50% B |
| regeneration | 10 CV | 100% B |
| reequilibration | 8 CV | 0% B |

Load: reaction mixture according to example 3, 20 fold diluted in Eluent A and adjusted to pH 8.0.

Non-reacted, excessive HBS is found in the flowthrough. The HBSylation weakens the interaction of the protein with the column resulting in decreased elution times for the conjugate as compared to the unmodified protein.

Figure 27:
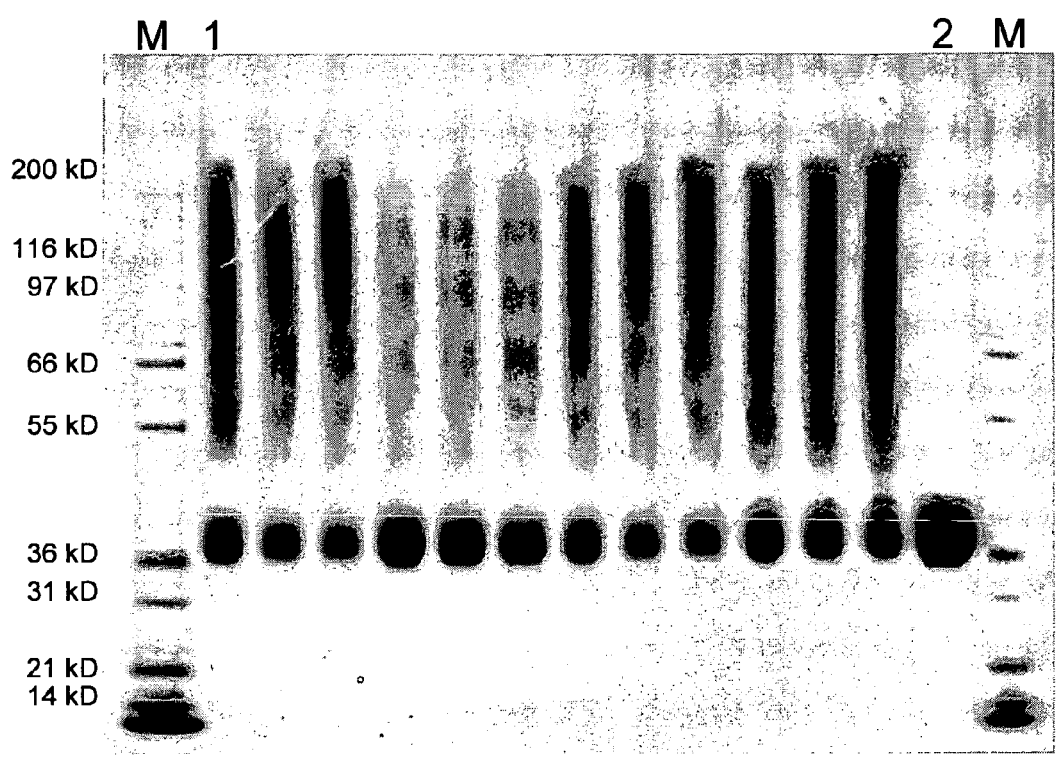

FIG. 27: SDS-PAGE analysis of an oxHBS-EPO coupling reaction

FIG. 27 shows the SDS-PAGE analysis of an oxHBS-EPO coupling reaction according to "additional data (A.4)". The separation was performed under reducing conditions using the NuPAGE system (Invitrogen) with 4-12% Bis-Tris gels (1.0 mm) and a MOPS running buffer according to the manufacturers instructions.

Load: 10 µg protein as reaction mixture.
M: Marker, Mark12 (Invitrogen).
Lane 1: reaction mixture according to "additional data (A.4)".
Lane 2: EPO starting material prior to conjugation.

Successfull HBSylation of the target protein (~35-40 kDa) becomes visible as a smeary band with a broad mass distribution ranging from 45 to >200 kDa.

Figure 28:
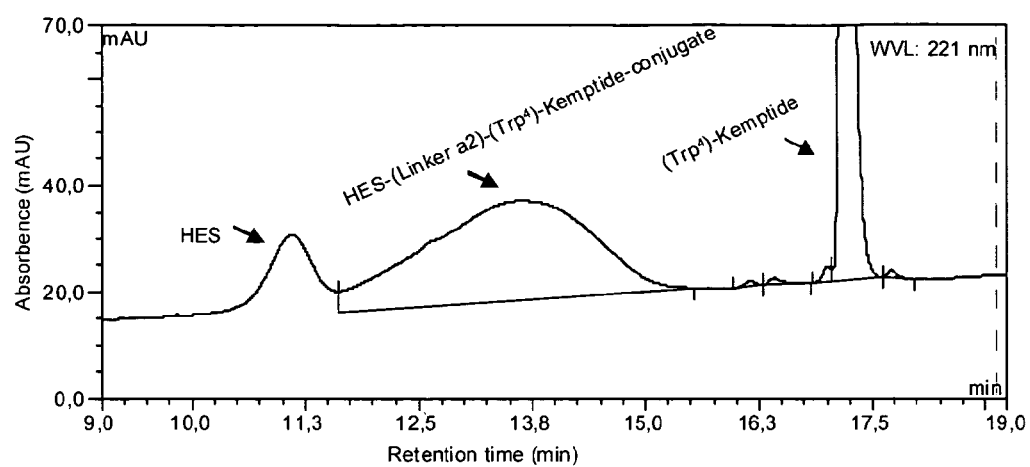

FIG. 28: RP-HPLC analysis of a coupling reaction using HES100/1.0, linker (a2) and (Trp$^4$)-Kemptide FIG. 28 shows a section of the RP-HPLC analysis of a coupling reaction using HES100/1.0, linker (a2) and (Trp$^4$)-Kemptide according to example 18, Table 3 monitored by UV-Vis spectroscopy at 221 nm. Chromatography conditions were as follows:

Chromatography system: Shimadzu LC 20 Prominence, LC 20AT (LPG) (Shimadzu).
Column: Jupiter C18, 300 A, 5 µm, 4.6×150 mm (Phenomenex).
Eluent A: 0.1% trifluoroacetic acid in water.
Eluent B: 0.1% trifluoroacetic acid in acetonitrile.
Operating conditions: flow rate 1 ml/min, 20° C.
Gradient: 0-15 min, 2-30% B; 15-20 min, 30-98% B; 20-27 min, 2% B.

Load: 5 µg protein as reaction mixture, diluted in water to a protein concentration of 0.05 mg/ml.

The main peak at 11.5-15 min is the HES Peptide conjugate separated from free (Trp$^4$)-Kemptide eluting at ~17 min.

Figure 29:
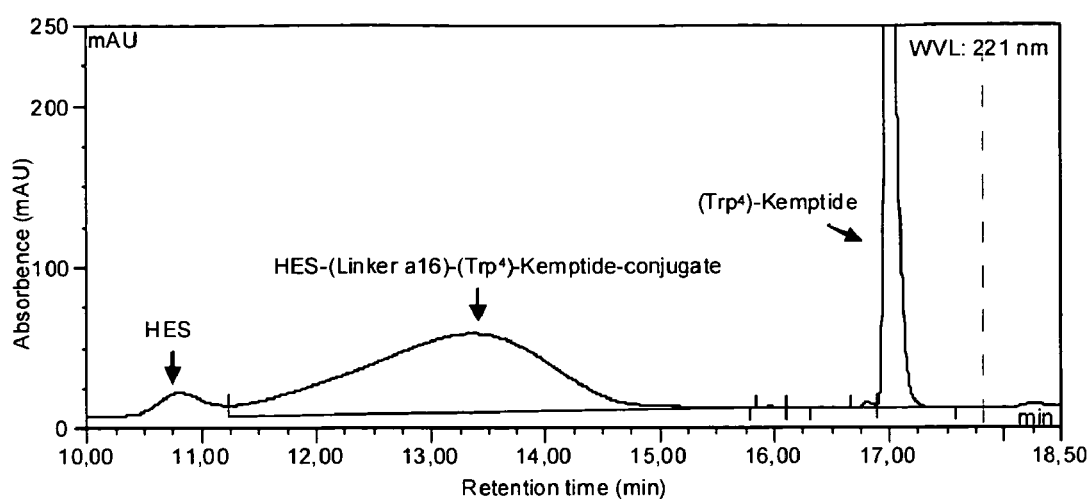

FIG. 29: RP-HPLC analysis of a coupling reaction using HES100/1.0, linker (a16) and (Trp$^4$)-Kemptide FIG. 29 shows a section of the RP-HPLC analysis of a coupling reaction using HES100/1.0, linker (a16) and (Trp$^4$)-Kemptide according to example 18, Table 5, line 13 monitored by UV-Vis spectroscopy at 221 nm Chromatography conditions were as follows:

Chromatography system: Shimadzu LC 20 Prominence, LC 20AT (LPG) (Shimadzu).
Column: Jupiter C18, 300 A, 5 µm, 4.6×150 mm (Phenomenex).
Eluent A: 0.1% trifluoroacetic acid in water.
Eluent B: 0.1% trifluoroacetic acid in acetonitrile.
Operating conditions: flow rate 1 ml/min, 20° C.
Gradient: 0-15 min, 2-30% B; 15-20 min, 30-98% B; 20-27 min, 2% B.

Load: 5 µg protein as reaction mixture, diluted in water to a protein concentration of 0.05 mg/ml.

The main peak at 11.5-15 min is the HES Peptide conjugate separated from free (Trp$^4$)-Kemptide eluting at ~17 min.

Figure 30:
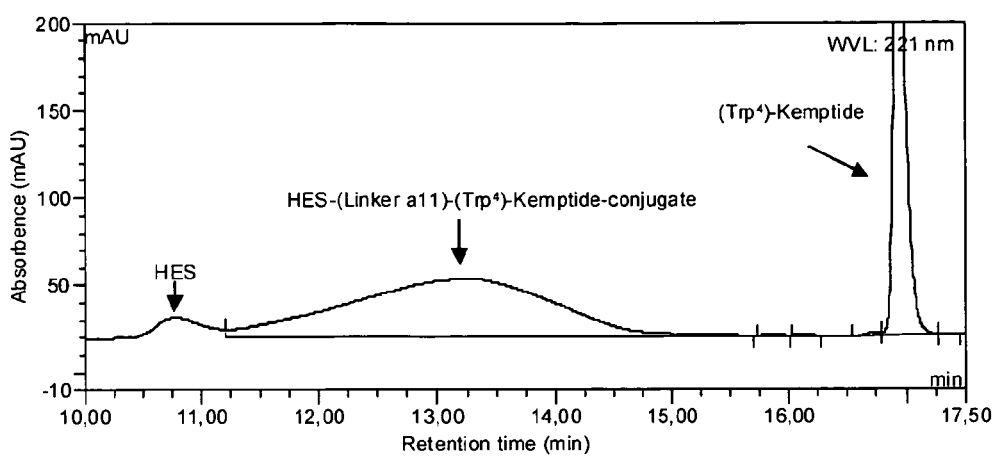

FIG. 30: RP-HPLC analysis of a coupling reaction using HES100/1.0, linker (a11) and (Trp$^4$)-Kemptide FIG. 30 shows a section of the RP-HPLC analysis of a coupling reaction using HES100/1.0, linker (a11) and (Trp$^4$)-Kemptide according to example 18, Table 5, line 24 monitored by UV-Vis spectroscopy at 221 nm. Chromatography conditions were as follows:

Chromatography system: Shimadzu LC 20 Prominence, LC 20AT (LPG) (Shimadzu).
Column: Jupiter C18, 300 A, 5 µm, 4.6×150 mm (Phenomenex).
Eluent A: 0.1% trifluoroacetic acid in water.
Eluent B: 0.1% trifluoroacetic acid in acetonitrile.
Operating conditions: flow rate 1 ml/min, 20° C.
Gradient: 0-15 min, 2-30% B; 15-20 min, 30-98% B; 20-27 min, 2% B.

Load: 5 µg protein as reaction mixture, diluted in water to a protein concentration of 0.05 mg/ml.

The main peak at 11.5-15 min is the HES Peptide conjugate separated from free (Trp$^4$)-Kemptide eluting at ~17 min.

Figure 31:
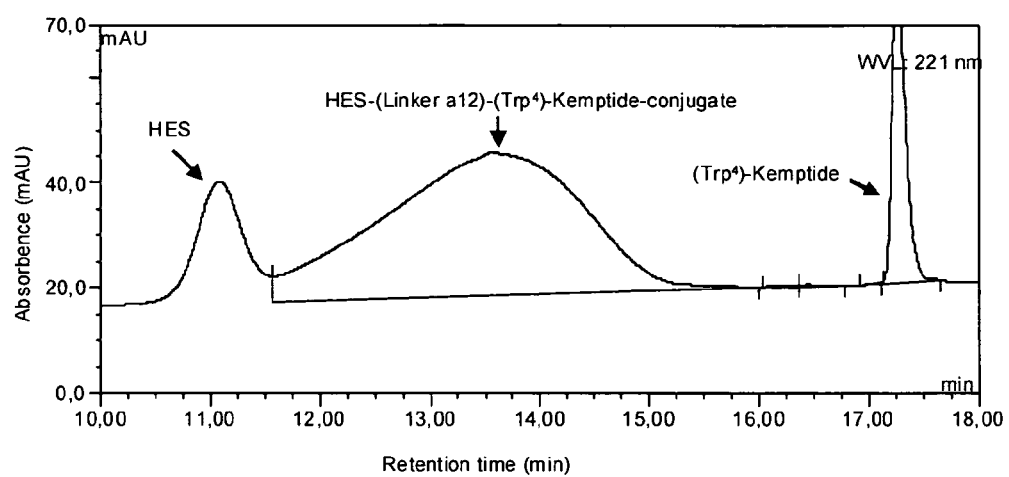

FIG. 31: RP-HPLC analysis of a coupling reaction using HES100/1.0, linker (a12) and (Trp$^4$)-Kemptide FIG. 31 shows a section of the RP-HPLC analysis of a coupling reaction using HES100/1.0, linker (a12) and (Trp$^4$)-Kemptide according to example 18, Table 5, line 30 monitored by UV-Vis spectroscopy at 221 nm. Chromatography conditions were as follows:

Chromatography system: Shimadzu LC 20 Prominence, LC 20AT, (LPG) (Shimadzu).
Column: Jupiter C18, 300 A, 5 µm, 4.6×150 mm (Phenomenex).
Eluent A: 0.1% trifluoroacetic acid in water.
Eluent B: 0.1% trifluoroacetic acid in acetonitrile.
Operating conditions: flow rate 1 ml/min, 20° C.
Gradient: 0-15 min, 2-30% B; 15-20 min, 30-98% B; 20-27 min, 2% B.

Load: 5 µg protein as reaction mixture, diluted in water to a protein concentration of 0.05 mg/ml.

The main peak at 11.5-15 min is the HES Peptide conjugate separated from free (Trp$^4$)-Kemptide eluting at ~17 min.

Figure 32:
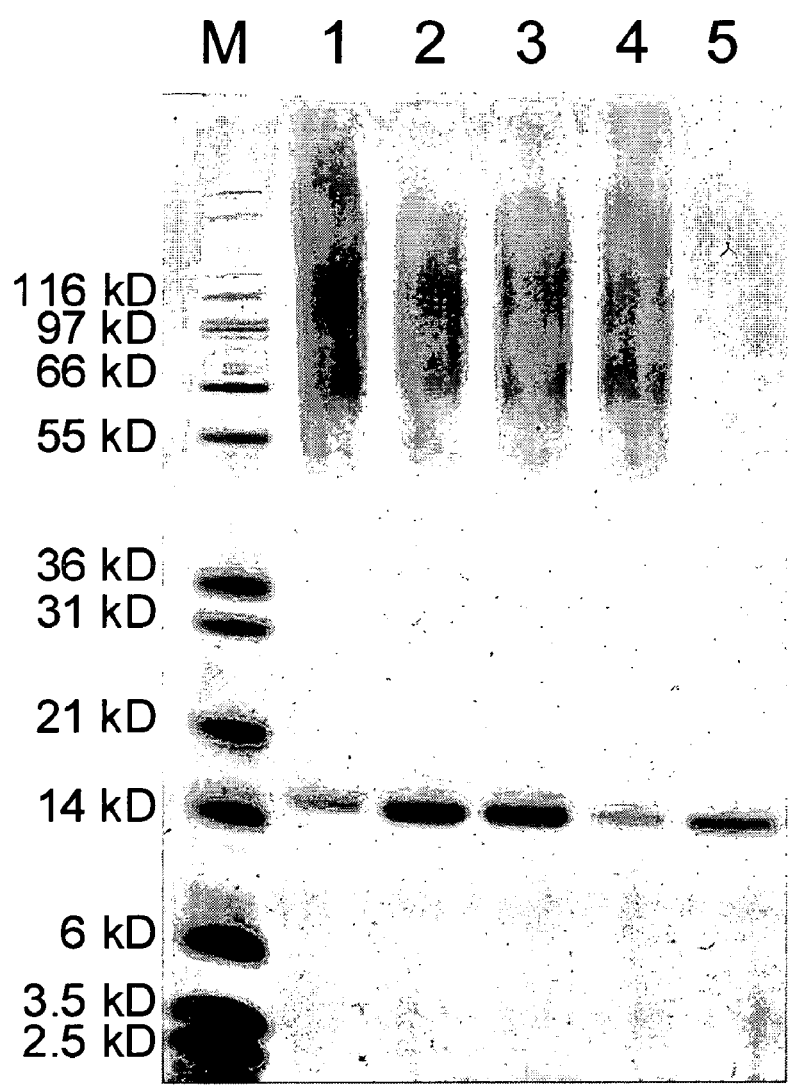

FIG. 32: SDS-PAGE analysis of HES100/1.0-G-CSF coupling reactions

FIG. 32 shows the SDS-PAGE analysis of HES100/1.0-G-CSF coupling reactions according to example 18. The separation was performed under reducing conditions using the NuPAGE system (Invitrogen) with 4-12% Bis-Tris gels (1.0 mm) and a MES running buffer according to the manufacturers instructions.

M: Marker, Mark12 (Invitrogen).

Lane 1: reaction mixture according to Table 5, line 7 (10 µg protein loaded).

Lane 2: reaction mixture according to Table 5, line 16 (10 µg protein loaded).

Lane 3: reaction mixture according to Table 5, line 27 (10 µg protein loaded).

Lane 4: reaction mixture according to Table 5, line 33 (10 µg protein loaded).

Lane 5: 0.5 µg rhG-CSF starting material prior to conjugation.

Successful HESylation of the target protein (~18 kDa) becomes visible as a smeary band with a broad mass distribution ranging from 50 to >200 kDa.

Figure 33:
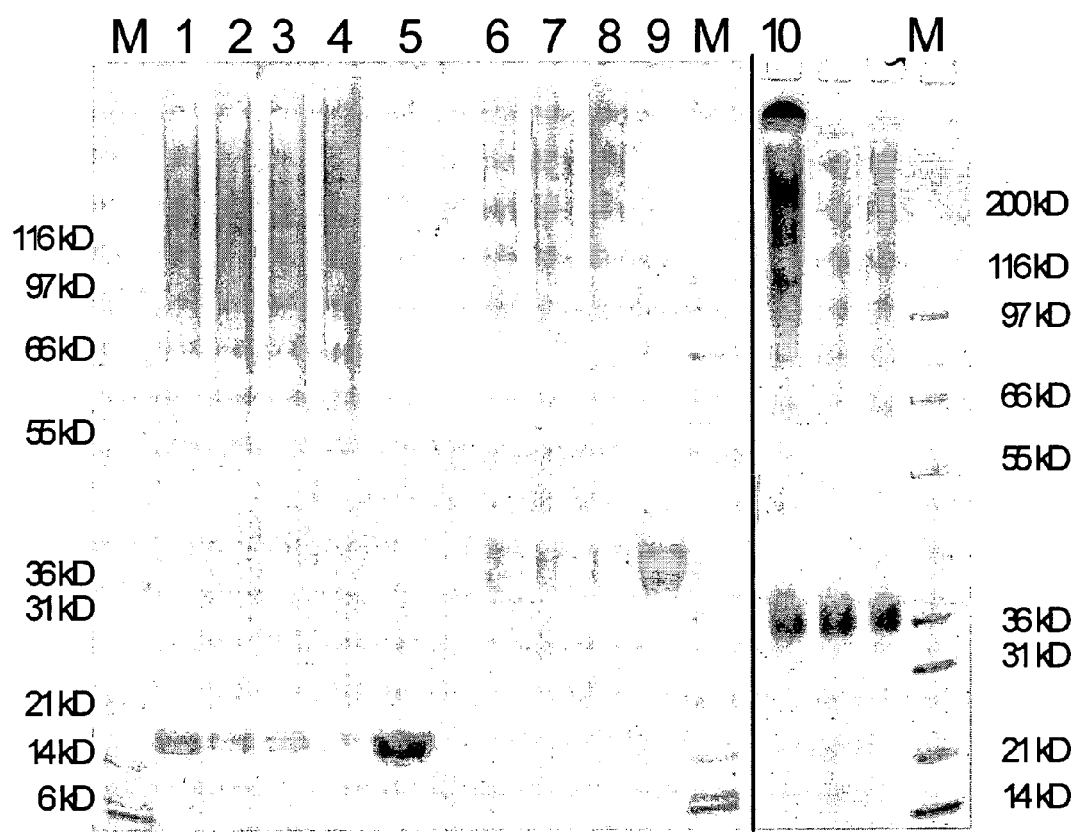

FIG. 33: SDS-PAGE analysis of HES100/1.0-IFNa and HES100/1.0-EPO coupling reactions FIG. 33 shows the SDS-PAGE analysis of coupling reactions between HES100/1.0 and rhIFNα or rhEPO according to example 18. The separation was performed under reducing conditions using the NuPAGE system (Invitrogen) with 4-12% Bis-Tris gels (1.0 mm) and MOPS running buffer according to the manufacturers instructions. For the electrophoretic separation shown on the right MES buffer was used instead of MOPS.

Typical load: 10 µg protein either starting material or as reaction mixture.

M: Marker, Mark12 (Invitrogen).

Lane 1: reaction mixture according to Table 5, line 4.
Lane 2: reaction mixture according to Table 5, line 14.
Lane 3: reaction mixture according to Table 5, line 25.
Lane 4: reaction mixture according to Table 5, line 31.
Lane 5: rhIFNα starting material prior to conjugation.

Successful HESylation of the target protein (~19 kDa) becomes visible as a smeary band with a broad mass distribution ranging from 50 to >200 kDa.

Lane 6: reaction mixture according to Table 5, line 15.
Lane 7: reaction mixture according to Table 5, line 5.
Lane 8: reaction mixture according to Table 5, line 32.
Lane 9: rhEPO starting material prior to conjugation.
Lane 10: reaction mixture according to Table 5, line 26.

Successful HESylation of the target protein (~35-40 kDa) becomes visible as a smeary band with a broad mass distribution ranging from 60 to >200 kDa.

EXAMPLES

Example 1

Preparation of oxHES55/0.7-N-(3-Propioaldehydediethylacetal)

HES aldonic acid (oxHES) was synthesized as described in example 9 of WO 2005/083103 A (in said document, the preparation is described for a hyperbranched starch, HBS) starting from HES with a molecular weight of 55 kDa and a molar substitution of 0.7 (HES55/0.7).

30 g oxHES 55/0.7, dried for 2 d at 80° C., were dissolved in 60 ml dry dimethylformamide (DMF) and the solution was heated to 70° C. 25 g 1-amino-3,3-diethoxypropane in 50 ml dry DMF were added and the reaction mixture was heated at 70° C. for 48 h. DMF and excess 1-amino-3,3-diethoxypropane were removed at 60-80° C. in vacuo utilizing a rotary evaporator. The remaining crude solid was washed with acetone until no colour was detectable in the washing solution. The product was dissolved in 500 ml water and purified by ultrafiltration utilizing a membrane with a cut-off of 10000 Dalton. When the pH of the retentate had reached a value of 6-7, it was readjusted to 9 utilizing 0.1 M sodium hydroxide solution. This procedure was repeated four times. Finally the product was lyophilised.

Example 2

Preparation of oxHES 55/0.7 Interferon Alpha 2b (IFNa) Conjugate

To 400 mg of acetal prepared in example 1 an appropriate amount of 10 mM HCl was added to yield a solution with a concentration of 40% (w/v). The solution was incubated under stirring at 21° C. for 24 h to deprotect the aldehyde function. The pH-value was adjusted to the value used in the conjugation buffer by addition of 0.1 M NaOH. Interferon-alpha (recombinant human interferon alpha-2b manufactured by recombinant DNA technology using *Escherichia coli* (*E. coli*), the interferon alpha-2b being composed of 165 amino acids and presenting an amino acid sequence which is identical to natural human interferon alpha-2b (hIFN-alpha-2b)) was concentrated up to 16 mg/ml and transferred into a suitable conjugation buffer (0.1 M sodium acetate buffer, pH 4.0) using ultrafiltration devices.

A 10 fold molar excess of oxHES aldehyde (based on $M_w$) was used with a protein concentration in the reaction mixture of 6 mg/ml; the oxHES aldehyde concentration was 20% (w/v). The deprotected oxHES aldehyde was combined with the protein solution and the reductive amination reaction was started by addition of a freshly prepared $NaCNBH_3$ solution (0.5 M in conjugation buffer) to yield a final concentration of reducing agent of 20 mM. After thorough mixing, the reaction was incubated o/n at 10° C.

Figure 1:
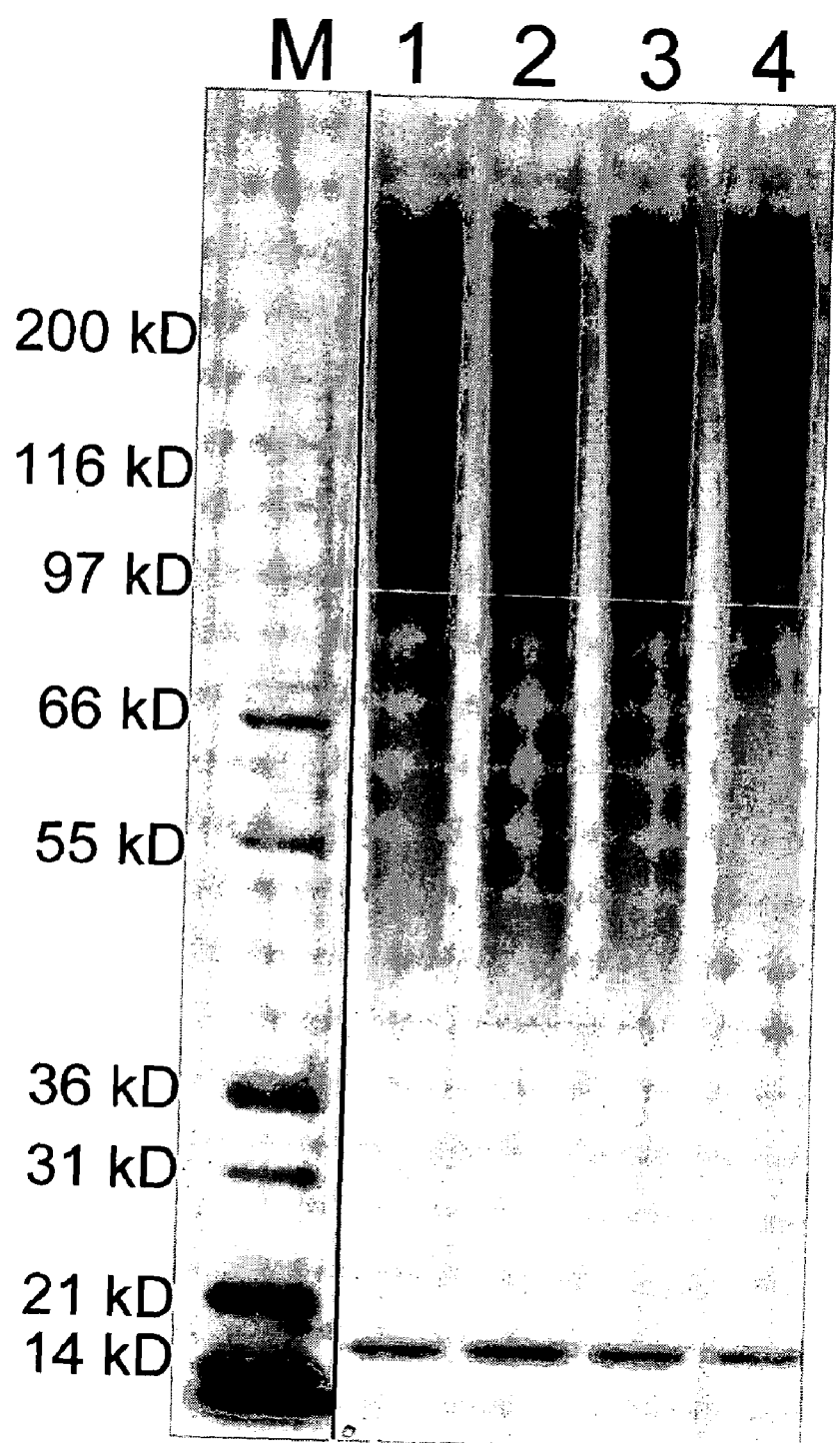
FIG. 1: SDS-PAGE analysis of an oxHES55/0.7-IFNa coupling reaction

Reaction mixtures were analyzed by SDS-PAGE (FIG. 1) and reversed phase chromatography on a C18 column (Phenomenex, Jupiter) to prove successful coupling and for determination of the conjugation yield. Elution was carried out using an acidic water/acetonitrile gradient with 0.1% TFA.

The HESylated interferon-alpha was separated from non-reacted compounds by anion-exchange chromatography using a Q HP column on an Äkta system (GE Healthcare). Eluent A was 10 mM Tris·Cl, pH 8.0, Eluent B was 10 mM Tris·Cl, 0.5 M NaCl, pH 8.0. The gradient for separation of conjugate and non-modified protein was 0% B=>50% B in 16 CV (FIG. 2).

Example 3

Preparation of oxHES 55/0.7 Erythropoietin (EPO) Conjugates

To 400 mg of acetal prepared in example 1 an appropriate amount of 10 mM HCl was added to yield a solution with a concentration of 40% (w/v). The solution was incubated under stirring at 21° C. for 24 h to deprotect the aldehyde function. The pH value was adjusted to the value used in the conjugation buffer by addition of 0.1 M NaOH. The deprotected oxHES aldehyde was combined with an EPO (recombinant human EPO having the amino acid sequence of human EPO and essentially the same characteristics as the commercially available Erypo® (Ortho Biotech, Jansen-Cilag) or NeoRecormon® (Roche)) solution (10 mg/ml in the reaction buffer 0.1 M sodium acetate buffer, pH 5). OxHES aldehyde was added at a 10 fold molar excess (based on $M_w$) compared to the EPO concentration. The resulting EPO concentration in the reaction mixture was 5 mg/ml, the oxHES aldehyde concentration was 10% (w/v). The reductive amination reaction was started by addition of a 0.5 M NaCNBH$_3$ solution made up in reaction buffer to yield a final concentration of reducing agent of 20 mM. After thorough mixing, the reaction was incubated o/n at 0° C.

Reaction mixtures were analyzed by SDS-PAGE (FIG. 3) and reversed phase chromatography on a C18 column (Phenomenex, Jupiter) to prove successful coupling and for determination of the conjugation yield. Elution of the RP-HPLC was carried out using an acidic water/acetonitrile gradient with 0.1% TFA.

The HESylated EPO was separated from non-reacted compounds by cation-exchange chromatography using an SP HP column on an Äkta system (GE Healthcare). Eluent A was 20 mM sodium acetate, pH 4.0, Eluent B was 20 mM sodium acetate, 1 M NaCl, pH 4.0. The gradient for separation of conjugate and non-modified protein was 10% B, 2 CV; 10% B=>52% B in 21 CV (FIG. 4).

HES coupling sites in the target protein were identified by peptide mapping of the IEX-purified HES-protein conjugate. The conjugates were digested using a suitable protease (2% Endoproteinase Lys-C, pH 8.6, 37° C., o/n) and the resulting fragments were separated by reversed phase chromatography on a C4 column (Phenomenex, Jupiter) using an acidic water/acetonitrile gradient with TFA. HESylation sites in the protein could be identified indirectly by reduction or disappearance of the respective peptides in the chromatogram as compared to control digests of the target protein alone.

Example 4

Preparation of oxHES100/1.0-N-(3-Propioaldehydediethylacetal)

HES aldonic acid (oxHES) was synthesized as described in example 9 of WO 2005/083103 A (in said document, the preparation is described for a hyperbranched starch, HBS) starting from HES with a molecular weight of 100 kDa and a molar substitution of 1.0 (HES100/1.0).

30 g oxHES 100/1.0, dried for 2 d at 80° C., were dissolved in 150 ml dry dimethylformamide (DMF) and the solution was heated to 70° C. 25 g 1-amino-3,3-diethoxypropane in 60 ml dry DMF were added and the reaction mixture was heated at 70° C. for 48 h.

DMF and excess 1-amino-3,3-diethoxypropane were removed at 60-80° C. in vacuo utilizing a rotary evaporator. The remaining crude solid was washed with acetone until no colour was detectable in the washing solution. The product was dissolved in 500 ml water and purified by ultrafiltration utilizing a membrane with a cut-off of 10,000 Dalton. When the pH of the retentate had reached a value of 6-7, it was readjusted to 9 utilizing 0.1 M sodium hydroxide solution. This procedure was repeated four times. Finally the product was lyophilised.

Example 5

Preparation of HES 100/1.0 Interferon Alpha (IFNa) Conjugate from Oxidized HES

To 400 mg of acetal prepared in example 4 an appropriate amount of 10 mM HCl was added to yield a solution with a concentration of 40% (w/v). The solution was incubated under stirring at 21° C. o/n to deprotect the aldehyde function. The pH-value was adjusted to the value used in the conjugation buffer by addition of 0.1 M NaOH.

Interferon-alpha (recombinant human interferon alpha-2b manufactured by recombinant DNA technology using *Escherichia coli* (*E. coli*), the interferon alpha-2b being composed of 165 amino acids and presenting an amino acid sequence which is identical to natural human interferon alpha-2b (hIFN-alpha-2b)) was concentrated up to 16 mg/ml and transferred into a suitable conjugation buffer (0.1 M sodium acetate buffer, pH 4.0) using ultrafiltration devices.

A 6 fold molar excess of oxHES aldehyde (based on $M_n$) was used with a final protein concentration in the reaction mixture of 8 mg/ml; the oxHES aldehyde concentration was 20% (w/v). The deprotected oxHES aldehyde was combined with the protein solution and the reductive amination reaction was started by addition of a freshly prepared NaCNBH$_3$ solution (0.5 M in conjugation buffer) to yield a final concentration of reducing agent of 20 mM. After thorough mixing, the reaction was incubated o/n at 5° C. Reaction mixtures were analyzed by SDS-PAGE (FIG. 5) and reversed phase chromatography on a C18 column (Phenomenex, Jupiter) to prove successful coupling and for determination of the conjugation yield. Elution was carried out using an acidic water/acetonitrile gradient with 0.1% TFA.

The HESylated Interferon-alpha was separated from non-reacted compounds by anion-exchange chromatography using a Q HP column on an Äkta system (GE Healthcare). Eluent A was 10 mM Tris·Cl, pH 8.0, Eluent B was 10 mM Tris·Cl, 0.5 M NaCl, pH 8.0. The gradient for separation of conjugate and non-modified protein was 0% B=>50% B in 12.5 CV (FIG. 6).

HES coupling sites in the target protein were identified by peptide mapping of the IEX-purified HES-protein conjugate. The conjugates were digested using a suitable protease (2% Endoproteinase Lys-C, pH 8.6, 37° C., o/n) and the resulting fragments were separated by reversed phase chromatography on a C4 column (Phenomenex, Jupiter) using an acidic water/acetonitrile gradient with TFA. HESylation sites in the protein could be identified indirectly by reduction or disappearance of the respective peptides in the chromatogram as compared to control digests of the target protein alone (FIG. 7).

Example 6

Preparation of an HES 100/1.0 Erythropoietin (EPO) Conjugate from Oxidized HES

To 400 mg of acetal prepared in example 4 an appropriate amount of 10 mM HCl was added to yield a solution with a concentration of 40% (w/v). The solution was incubated at 21° C. for 24 h to deprotect the aldehyde function. The pH-value was adjusted to the value used in the conjugation buffer by addition of 0.1 M NaOH.

The deprotected oxHES aldehyde was combined with an EPO (recombinant human EPO having the amino acid sequence of human EPO and essentially the same characteristics as the commercially available Erypo® (Ortho Biotech, Jansen-Cilag) or NeoRecormon® (Roche)) solution (10 mg/ml in the reaction buffer 0.1 M sodium acetate buffer, pH 5). OxHES aldehyde was added at a 15 fold molar excess (based on $M_n$) compared to the EPO concentration. The resulting EPO concentration in the reaction mixture was 3.7 mg/ml, the oxHES aldehyde concentration was 15% (w/v). The reductive amination reaction was started by addition of a 0.5 M NaCNBH$_3$ solution made up in reaction buffer to yield a final concentration of reducing agent of 20 mM. After thorough mixing, the reaction was incubated o/n at 10° C.

Reaction mixtures were analyzed by SDS-PAGE (FIG. 8) and reversed phase chromatography on a C18 column (Phenomenex, Jupiter) to prove successful coupling and for determination of the conjugation yield. Elution was carried out using an acidic water/acetonitrile gradient with 0.1% TFA.

The HESylated EPO was separated from non-reacted compounds by cation-exchange chromatography using an SP HP column on an Äkta system (GE Healthcare). Eluent A was 20 mM sodium acetate, pH 4.0, Eluent B was 20 mM sodium acetate, 1 M NaCl, pH 4.0. The gradient for separation of conjugate and non-modified protein was 10% B, 2 CV; 10% B=>52% B in 21 CV (FIG. 9).

HES coupling sites in the target protein were identified by peptide mapping of the IEX-purified HES-protein conjugate. The conjugates were digested using a suitable protease (2% Endoproteinase Lys-C, pH 8.6, 37° C., o/n) and the resulting fragments were separated by reversed phase chromatography on a C4 column (Phenomenex, Jupiter) using an acidic water/acetonitrile gradient with TFA. HESylation sites in the protein could be identified indirectly by reduction or disappearance of the respective peptides in the chromatogram as compared to control digests of the target protein alone.

Example 7

Preparation of an HES 100/1.0 Granulocyte Colony Stimulating Factor (G-CSF) Conjugate from Oxidized HES To 400 mg of acetal prepared in example 4 an appropriate amount of 10 mM HCl was added to yield a solution with a concentration of 40% (w/v). The solution was incubated at 21° C. o/n to deprotect the aldehyde function. The pH-value was adjusted to the value used in the conjugation buffer by addition of 0.1 M NaOH.

The deprotected oxHES aldehyde was combined with a rh-Met-G-CSF solution (5 mg/ml in the reaction buffer 0.1 M sodium acetate buffer, pH 5; G-CSF expressed by $E.$ $coli$ having the same amino acid sequence and essentially the same characteristics as the commercially available Neupogen® from Amgen, München, D). OxHES aldehyde was added at a 30 fold molar excess (based on $M_n$) compared to the G-CSF concentration. The resulting G-CSF concentration in the reaction mixture was 1.9 mg/ml, the oxHES aldehyde concentration was 20% (w/v). The reductive amination reaction was started by addition of a 0.5 M NaCNBH$_3$ solution made up in reaction buffer to yield a final concentration of reducing agent of 20 mM. After thorough mixing, the reaction was incubated o/n at 0° C. Reaction mixtures were analyzed by SDS-PAGE (FIG. 10) and reversed phase chromatography (FIG. 11) on a C18 column (Phenomenex, Jupiter) to prove successful coupling and for determination of the conjugation yield. Elution was carried out using an acidic water/acetonitrile gradient with 0.1% TFA.

Example 8

Preparation of HES100/1.0-N-(3-Propioaldehydediethylacetal)

15 g HES 100/1.0 were dissolved in 35 g sodium acetate buffer (pH=5 and c=1 mol) and 2.07 ml of 1-amino-3,3-diethoxypropane as well as 1.885 g of sodium cyano borohydride were added. The reaction mixture was stirred at 60° C. for 16-24 h, diluted to with 100 ml water, neutralized with diluted sodium hydroxide solution and worked up by ultrafiltration using a membrane with a cut-off of 10,000 Da against ammonium hydrogen carbonate buffer (pH=9, c=10 mmol/l, 45 cycles) as well as water for the last 5 exchange cycles. The purified and concentrated HES derivative solution (approximately 20 wt-%) was dialyzed against sodium hydroxide solution (pH=12) at 60° C. using a membrane with a cut off of 10,000 Da. Thereafter the product was isolated by lyophilisation.

Example 9

Preparation of HES100/1.0-N-(3-Propioaldehyde)

10 g of HES-N-(3-Propioaldehydediethylacetal) from example 8 were dissolved in 100 ml of aqueous HCl, pH=2 (c=10 mmol/l) and stirred at 40° C. for 16-24 h. The reaction mixture was purified by ultrafiltration using a membrane with a cut off of 10,000 Da against aqueous HCl, pH=2 (10 cycles) as well as water for the last 5 exchange cycles. The isolation of the product was carried out by lyophilisation.

Example 10

Preparation of an HES 100/1.0 Interferon alpha (IFNa) Conjugate from HES

To 400 mg of acetal prepared in example 8 an appropriate amount of 10 mM HCl was added to yield a solution with a concentration of 40% (w/v). The solution was incubated under stirring at 21° C. o/n to deprotect the aldehyde function. The pH-value was adjusted to the value used in the conjugation buffer by addition of 0.1 M NaOH.

Interferon-alpha (recombinant human interferon alpha-2b manufactured by recombinant DNA technology using $Escherichia$ $coli$ ($E.$ $coli$), the interferon alpha-2b being composed of 165 amino acids and presenting an amino acid sequence which is identical to natural human interferon alpha-2b (hIFN-alpha-2b)) was concentrated up to 16 mg/ml and transferred into a suitable conjugation buffer (0.1 M sodium acetate buffer, pH 4.0) using ultrafiltration devices.

A 5 fold molar excess of HES aldehyde (based on $M_w$) was used with a final protein concentration in the reaction mixture of 7 mg/ml; the HES aldehyde concentration was 18% (w/v). The deprotected HES aldehyde was combined with the protein solution and the reductive amination reaction was started by addition of a freshly prepared NaCNBH$_3$ solution (0.5 M in conjugation buffer) to yield a final concentration of reducing agent of 20 mM. After thorough mixing, the reaction was incubated o/n at 5° C.

Reaction mixtures were analyzed by SDS-PAGE (FIG. 12) and reversed phase chromatography on a C18 column (Phenomenex, Jupiter) to prove successful coupling and for determination of the conjugation yield. Elution was carried out using an acidic water/acetonitrile gradient with 0.1% TFA.

The HESylated IFNalpha was separated from non-reacted compounds by cation-exchange chromatography using an SP HP column on an Äkta system (GE Healthcare). Eluent A was 20 mM sodium acetate, pH 4.0, Eluent B was 20 mM sodium acetate, 1 M NaCl, pH 4.0. The gradient for separation of conjugate and non-modified protein was 0% B=>50% B in 20 CV (FIG. 13).

HES coupling sites in the target protein were identified by peptide mapping of the IEX-purified HES-protein conjugate. The conjugates were digested using a suitable protease (2% Endoproteinase Lys-C, pH 8.6, 37° C., o/n) and the resulting fragments were separated by reversed phase chromatography on a C4 column (Phenomenex, Jupiter) using an acidic water/acetonitrile gradient with TFA. HESylation sites in the protein could be identified indirectly by reduction or disappearance of the respective peptides in the chromatogram as compared to control digests of the target protein alone.

Example 11

Preparation of an HES 100/1.0 Erythropoietin (EPO) Conjugate from HES

The deprotected HES aldehyde from example 9 was combined with an EPO (recombinant human EPO having the amino acid sequence of human EPO and essentially the same characteristics as the commercially available Erypo® (Ortho Biotech, Jansen-Cilag) or NeoRecormon® (Roche)) solution (10 mg/ml in the reaction buffer 0.1 M sodium acetate buffer, pH 5). HES aldehyde was added at a 40 fold molar excess (based on $M_n$) compared to the EPO concentration. The resulting EPO concentration in the reaction mix was 3.2 mg/ml, the HES aldehyde concentration was 30% (w/v). The reductive amination reaction was started by addition of a 0.5 M $NaCNBH_3$ solution made up in reaction buffer to yield a final concentration of reducing agent of 20 mM. After thorough mixing, the reaction was incubated o/n at 5° C.

Reaction mixtures were analyzed by SDS-PAGE (FIG. 14) and reversed phase chromatography on a C18 column (Phenomenex, Jupiter) to prove successful coupling and for determination of the conjugation yield. Elution was carried out using an acidic water/acetonitrile gradient with 0.1% TFA.

The HESylated EPO was separated from non-reacted compounds by cation-exchange chromatography using an SP HP column on an Äkta system (GE Healthcare). Eluent A was 20 mM sodium acetate, pH 4.0, Eluent B was 20 mM sodium acetate, 1 M NaCl, pH 4.0. The gradient for separation of conjugate and non-modified protein was 0% B=>52% B in 13 CV (FIG. 15).

Example 12

Preparation of an HES 100/1.0 Granulocyte Colony Stimulating Factor (G-CSF) Conjugate from HES The deprotected HES aldehyde from example 9 was combined with a rh-Met-G-CSF solution (5 mg/ml in the reaction buffer 0.1 M sodium acetate buffer, pH 5; G-CSF expressed by E. coli having the same amino acid sequence and essentially the same characteristics as the commercially available Neupogen® from Amgen, München, D). HES aldehyde was added at a 40 fold molar excess (based on $M_n$) compared to the G-CSF concentration. The resulting G-CSF concentration in the reaction mix was 1.3 mg/ml, the HES aldehyde concentration was 20% (w/v). The reductive amination reaction was started by addition of a 0.5 M $NaCNBH_3$ solution made up in reaction buffer to yield a final concentration of reducing agent of 20 mM. After thorough mixing, the reaction was incubated o/n at 10° C.

Reaction mixtures were analyzed by SDS-PAGE and reversed phase chromatography on a C18 column (Phenomenex, Jupiter) to determine the conjugation yield. Elution of the RP-HPLC was carried out using an acidic water/acetonitrile gradient with 0.1% TFA.

Reaction mixtures were analyzed by SDS-PAGE (FIG. 16) and reversed phase chromatography (FIG. 17) on a C18 column (Phenomenex, Jupiter) to prove successful coupling and for determination of the conjugation yield. Elution of the RP-HPLC was carried out using an acidic water/acetonitrile gradient with 0.1% TFA.

The HESylated G-CSF was separated from non-reacted compounds by cation-exchange chromatography using an SP HP column on an Äkta system (GE Healthcare). Eluent A was 20 mM sodium acetate, pH 4.0, Eluent B was 20 mM sodium acetate, 1 M NaCl, pH 4.0. The gradient for separation of conjugate and non-modified protein was 0% B=>40% B in 15 CV (FIG. 18).

Example 13

Pharmacodynamic in-vivo Bioassay in Mice (HES-EPO Conjugate According to Example 11)

Balb C mice obtained from Harlan Winkelmann GmbH (Borchen, Germany) weighing approximately 18-20 grams were group housed (max. 10 per cage) in Euro Standard Typ III (LxBxH 425×266×185 mm) cages at a room temperature of 21° C. and a relative humidity of 55%. "Tapvei Einstreu" 4×4×1 mm (wood of Aspen) was used as bedding material for the cages. Additionally wood wool was offered. The cages were changed and cleaned once a week. Drinking water (pH 3.8-4; sulfuric acid) was offered ad libitum. The animal cages were numbered. Within a cage the animals were ear marked and additionally colour coded.

On the day of allocation approx. and one week before commencement of treatment, an initial health check has been performed. Only healthy animals were used.

The HES EPO conjugate as obtained in example 11, the unmodified starting material (rHuEPO) and Aranesp® from Amgen were tested as a single bolus, subcutaneous dose in 4 mice per group at a dosage of 100 µg/kg body weight, based on the protein content of the samples. The same volume of PBS as vehicle control was included.

At several time points (day 0, 3, 6, 9, 13, 16, 20, and 23) samples of approximately 30-60 µl whole blood were taken from the tail vein or the retrobulbar venous plexus using "Hämatokrit-Kapillaren" containing Na-heparin (Hirschmann Laborgeräte, Germany) and the whole blood was centrifuged for 6 minutes at 10.000 rpm in a Hettich Hämatocrit 210 centrifuge (Tuttlingen, Germany) to determine the hematocrit of each whole blood sample. The erythropoietic response and duration were monitored as a function change of hematocrit [%] as a function of time (see FIG. 19)

These data show that all samples containing EPO, Aranesp® or EPO conjugate were capable in raising the hematocrit. Aranesp® was capable to increase the potency compared to starting material 3-4 fold and as well the HES EPO conjugate was capable to increase the potency of 1.5-2 fold compared to Aranesp®.

Example 14

Pharmacodynamic in-vivo Bioassay in Mice (HES-IFN Alpha onjugate According to Example 5)

One oxHES100/1.0 Interferon alpha Conjugate, prepared according to Example 5 was tested in the in vivo assay according to example 13. The EC50 dilution of the serum samples was half-logarithmically plotted against the time after iv.-injection. Half-life was calculated from the slope of the exponential fit-curve. The half life of the sample was 8.9 hours (see FIG. 20).

Figure 21:
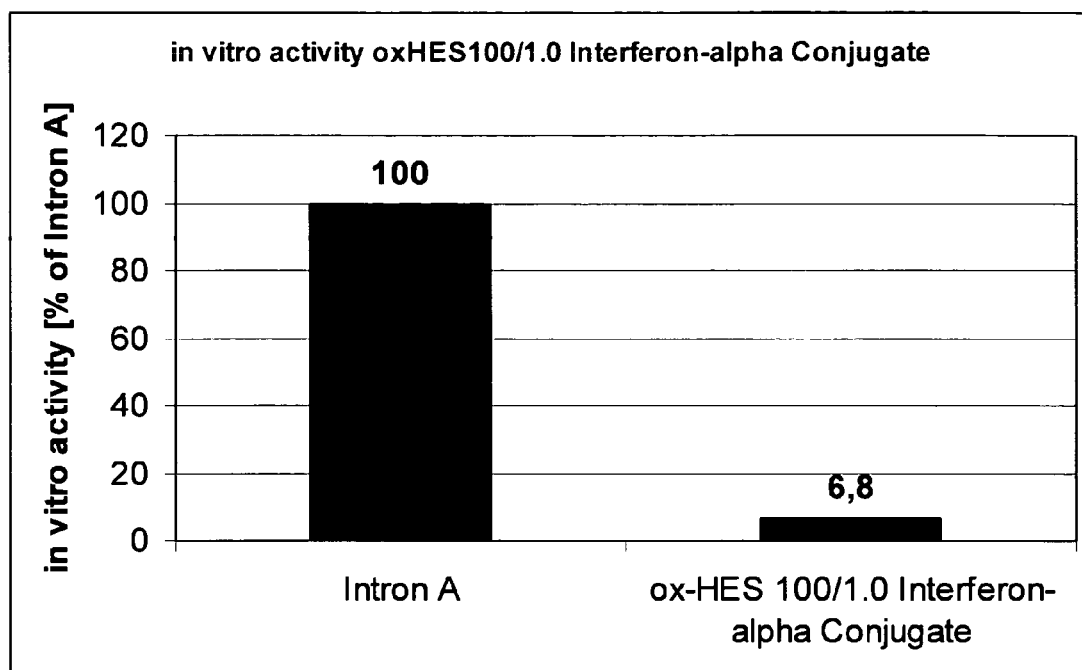

The relative in vitro activity of an oxHES100/1.0 Interferon alpha conjugate, prepared according to Example 5 compared to Intron A is shown in FIG. 21 (as to the determination of the in vitro activity, see example 16 below).

Example 15

Pharmacodynamic in-vivo Bioassay in Mice (HES-IFN Alpha Conjugate According to Example 10)

Figure 22:
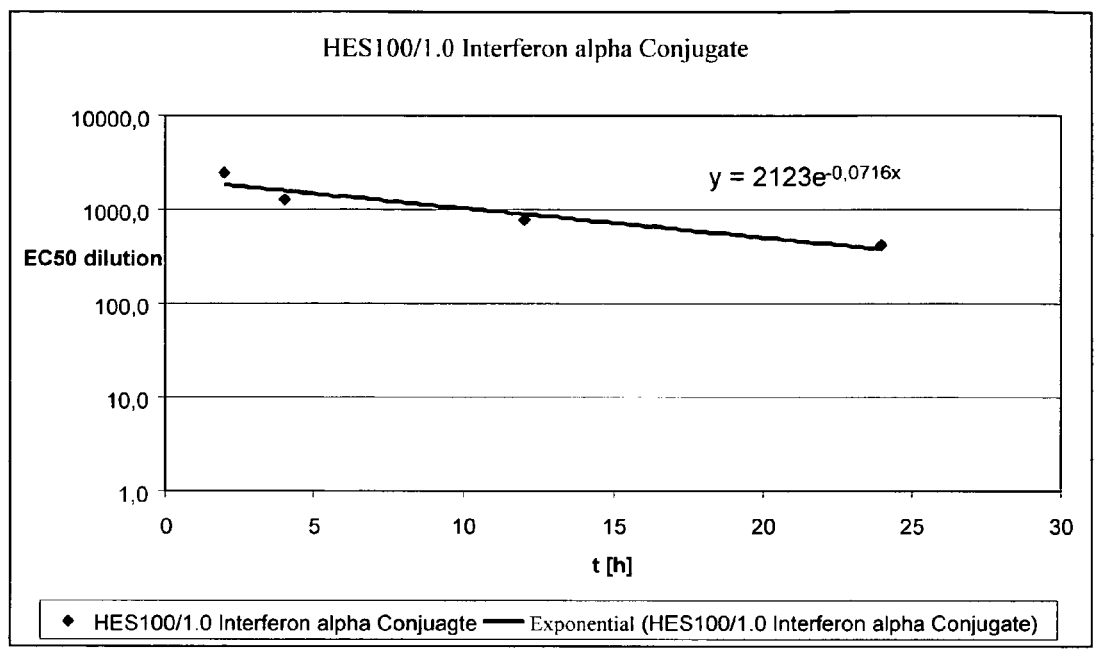

Three HES100/1.0 Interferon alpha Conjugates, prepared according to Example 10 were tested in the in vivo assay according to example 13. The medium of the EC50 dilution of the serum samples was half-logarithmically plotted against the time after iv.-injection. Half-life was calculated from the slope of the exponential fit-curve. The average half life of the samples was 9.7 hours (FIG. 22).

For unmodified IFN-alpha, the antiviral activity of serum was too low to calculate a serum half-life. In K. R. Reddy et al. Advaced Drug Delivery Reviews 54 (2002) pp. 571-586 a serum half-life of IFN-alpha in rats (i.v.) of 2 h was determined.

Figure 23:
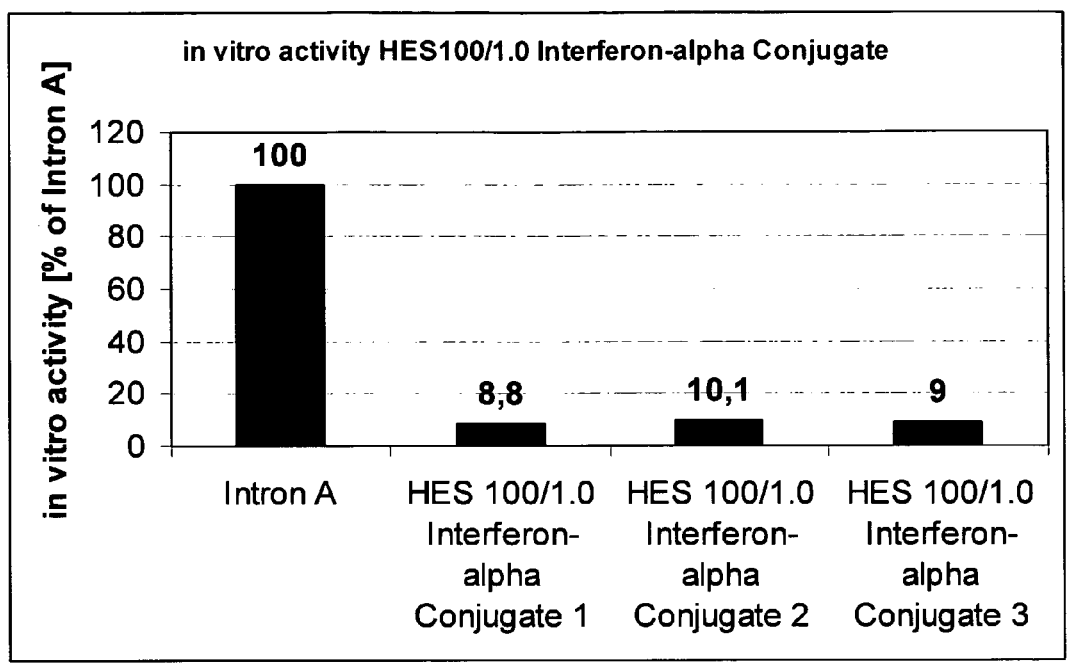

The relative in vitro activity of three HES100/1.0 Interferon alpha Conjugates, prepared according to Example 10 compared to Intron A is shown in FIG. 23 (as to the determination of the in vitro activity, see example 16 below).

Example 16

Description of the Test Procedure: Antiviral Activity of Interferon-Alpha (Examples 14 and 15)

After pre-diluting the Test Items in cell culture medium, serial two-fold dilutions were prepared. In 96 well microtiter plates, diluted Interferon was added—in four-fold replicate per dilution- to freshly trypsinized MDBK cells (40.000 cells per well). The assays were incubated for 24 hours at 37° C. (total volume per well: 175 µl.

Subsequently, 50 µL diluted VSV stock solution were added to each well (except for the positive control wells) resulting in a multiplicity of infection of 0.1. The following controls were included in each assay: 12 wells that received virus plus cell culture medium instead of Interferon (negative control) and 12 wells that received cell culture medium instead of Interferon and virus (positive control).

The assays were incubated for 42 hours at 37° C.

At the end of the incubation period the cell culture supernatant of each well was replaced with 50 µL of a solution of MTT (at least 2 mg/mL in cell culture medium). The cells were incubated for three hours. The purple formazan dye formed by the proliferating cells was solubilized by adding 100 µL solution of isopropanol/HCl (isopropanol with 40 mM HCl) to each well. Subsequently, the absorbance values of the solutions were measured at 570/630 nm in a microtiter plate reader.

The proliferative activity of MDBK cells grown in the presence of Interferon and VSV was calculated for each dilution of Interferon as follows:

$$\frac{((\text{Mean absorbance of four Interferon treated wells}) - (\text{Mean absorbance of negative control})) * 100}{(\text{Mean absorbance of positive control}) - (\text{Mean absorbance of negative control})}$$

The antiviral activity of Interferon-alpha was determined in four separate assays for each of the Test Items.

In the assay system described above, the respective conjugates HES 100/1.0 Interferon alpha Conjugate (example 15 and 10, respectively) and oxHES100/1.0-Interferon alpha Conjugate (example 14 and 5, respectively) were tested compared to unmodified IFN-alpha starting material, namely Intron A. The CPE50 concentration of the materials was calculated.

Example 17

Preparation of HES-Linker Derivatives According to the Invention

In example 17, inventive HES-linker derivatives were produced. On the one hand, for a given linker structure, HES was varied with respect to the mean molecular weight, and with respect to its molar substitution. On the other hand, the chemical nature of the linker was varied, for a given HES starting material.

The amounts of HES indicated in the following Tables 1 and 2 were dissolved in the appropriate volume ("buffer V") of sodium acetate buffer (1 mol/l, pH=5) by vigorous stirring and moderate heating (up to 40° C.). To the clear solution, the indicated amount of linker (40 equivalents referred to $M_n$ of the HES species) was added. In some cases, the amount of linker was added as a "DMF-linker" solution. Therefore the required amount of linker was dissolved in a small amount of DMF and the resulting clear DMF-linker solution, indicated in Table 2 as "DMF-linker solution V" was added to the reaction mixture. Finally, solid NaCNBH$_3$, indicated as NaCNBH$_3$ amount was dissolved in the stirred solution to give a final concentration of typically 0.6 M, and the reaction mixture was heated and stirred at 60° C. for 18-24 h.

To work up the reaction, the mixture was diluted by ultrapure water to give a final concentration of about 100 mg/ml (10% mN) HES derivative and purified either by ultrafiltration (UF) or by dialysis (D) using a membrane with a cut-off of 10 kDa and ultrapure water as solvent. In case of linker (a2) and (a3), 10 mM NH$_4$HCO$_3$-buffer, pH=9 following by ultrapure water was used for the ultrafiltration.

For the subsequent deprotection, the purified HES-derivative solution (10%, 100 mg/ml) was acidified by concentrate HCl solution to give the "c (HCl)" with the appropriate "pH level". The mixture was stirred and heated at 40° C. for the reaction time "t" and afterwards neutralized (dil. NaOH), worked up by ultrafiltration (membrane cut-off 10 kDa) using the appropriate "work up solvent" and finally lyophilized to give a white to yellowish powder.

The derivatization was verified by successfully coupling to a target molecule (Kemptide, see the following example 18, Tables 3, 4, and 5). For the HES-derivatives, prepared using linker (a15) and (a10), the successful derivatization was checked by spectral properties. All HES-derivatives, prepared as described above were used for the conjugation to the targets, listed in example 18 in Tables 3, 4, and 5.

Abbreviations used in Tables 1 and 2:

| | |
|---|---|
| D | dialysis |
| DMF | dimethylformamide |
| HES | Hydroxyethylstarch |
| HCl | hydrochloric acid |
| NaCNBH$_3$ | sodium cyano borohydride |
| NaOH | sodium hydroxide |
| UF | ultrafiltration |

-continued

| Abbreviations used in Tables 1 and 2: | |
|---|---|
| V | Volume |
| Water | ultrapure water (milliQ) |

The HES-Derivative of HES 100/1.0 and linker structure (a2) was prepared according to Examples 8 and 9 of this invention. Linker structure (a2) relates to the structure (a2) as defined hereinabove, i.e. to 1-amino-3,3-diethoxypropane,

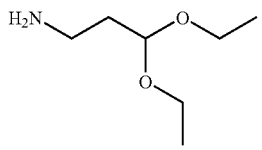

TABLE 1

Variation of HES moiety (example 17)

| | Starting material | | Derivatization | | | |
|---|---|---|---|---|---|---|
| linker | HES species | HES amount [g] | Linker amount [ml] | NaCNBH$_3$ amount [g] | buffer V [ml] | Kind of work up* |
| (a2) | 100/1.0 | 15 | 2.07 | 1.885 | 35 | UF |
| (a2) | 30/0.4 | 5 | 1.7 | 0.628 | 11.7 | UF |
| (a2) | 30/1.0 | 10 | 2.94 | 1.256 | 23.3 | UF |
| (a2) | 60/0.7 C2/C6 = 6 | 5 | 0.69 | 0.628 | 11.67 | UF |
| (a2) | 60/0.7 C2/C6 = 8.5 | 5 | 0.82 | 0.628 | 11.67 | UF |
| (a2) | 60/1.0 C2/C6 = 6 | 15 | 2.25 | 1.884 | 35 | UF |
| (a2) | 60/1.0 C2/C6 = 8.5 | 5 | 0.8 | 0.628 | 11.67 | UF |
| (a2) | 100/0.4 | 5 | 0.42 | 0.628 | 11.67 | UF |
| (a2) | 100/0.7 | 5 | 0.52 | 0.628 | 11.67 | UF |
| (a2) | 100/1.3 | 5 | 0.43 | 0.628 | 11.67 | UF |
| (a2) | 150/0.4 | 5 | 0.32 | 0.628 | 11.67 | UF |
| (a2) | 150/1.0 | 15 | 0.95 | 1.885 | 11.67 | UF |
| (a2) | 300/1.0 | 5 | 0.16 | 0.628 | 11.67 | UF |

| | Starting material | | Deprotection | | | |
|---|---|---|---|---|---|---|
| linker | HES species | c (HCl) [mM] | pH level | t [h] | Work up solvent | |
| (a2) | 100/1.0 | 10 | 2 | 18-24 | 10 mM HCl/water | |
| (a2) | 30/0.4 | 10 | 2 | 18-24 | 10 mM HCl/water | |
| (a2) | 30/1.0 | 10 | 2 | 18-24 | 10 mM HCl/water | |
| (a2) | 60/0.7 C2/C6 = 6 | 10 | 2 | 18-24 | 10 mM HCl/water | |
| (a2) | 60/0.7 C2/C6 = 8.5 | 10 | 2 | 18-24 | 10 mM HCl/water | |
| (a2) | 60/1.0 C2/C6 = 6 | 10 | 2 | 18-24 | 10 mM HCl/water | |
| (a2) | 60/1.0 C2/C6 = 8.5 | 10 | 2 | 18-24 | 10 mM HCl/water | |
| (a2) | 100/0.4 | 10 | 2 | 18-24 | 10 mM HCl/water | |
| (a2) | 100/0.7 | 10 | 2 | 18-24 | 10 mM HCl/water | |
| (a2) | 100/1.3 | 10 | 2 | 18-24 | 10 mM HCl/water | |
| (a2) | 150/0.4 | 10 | 2 | 18-24 | 10 mM HCl/water | |
| (a2) | 150/1.0 | 10 | 2 | 18-24 | 10 mM HCl/water | |
| (a2) | 300/1.0 | 10 | 2 | 18-24 | 10 mM HCl/water | |

*NH$_4$HCO$_3$-buffer (10 mM, pH = 9) followed by ultrapure water was used for the ultrafiltration.

TABLE 2

Variation of the linker structure (example 17)

| | Starting material | | Derivatization | | | | | |
|---|---|---|---|---|---|---|---|---|
| linker | HES species | HES amount [g] | linker amount [mg] | NaCNBH$_3$ amount [g] | buffer V [ml] | DMF linker solution V [ml] | rxn V | Kind of work up |
| (a1)# | 100/1.0 | 5 | 366 | 628.3 | 11.67 | — | — | D |
| (a3)# | 100/1.0 | 15 | 1058 | 1883 | 35 | — | — | UF |
| (a4)# | 100/1.0 | 1 | 135.5 | 125.6 | 2 | 0.33 | 2.33 | D |
| (a16)# | 100/1.0 | 1 | 138 | 125.6 | 2 | 0.33 | 2.33 | D |
| (a17)# | 100/1.0 | 10 | 1654 | 1256 | 23.3 | — | — | UF |
| (a11)# | 100/1.0 | 1 | 136 | 125.6 | 2 | 0.33 | 2.33 | D |
| (a12)# | 100/1.0 | 1 | 144.6 | 125.6 | 2 | 0.33 | 2.33 | D |
| (a13)# | 100/1.0 | 0.5 | 72.4 | 62.83 | 1 | 0.16 | 1.67 | D |
| (a18)# | 100/1.0 | 10 | 1479 | 1256 | 23.3 | — | — | UF |
| (a5)# | 100/1.0 | 0.5 | 72.72 | 94.25 | *1.95 + 0.05 (HOAc) | — | — | UF** |
| (a14)# | 100/1.0 | 0.5 | 85.81 | 62.8 | 1.17 | — | — | D |
| (a15)# | 100/1.0 | 0.5 | 83 | 62.83 | *1.0 + 0.08 (HOAc) | — | — | UF** |
| (a10)# | 60/1.0 | 0.2 | 20& | 6.5 + 43 μl DMSO | 1.6 + 0.1 (HOAc) | — | — | D |
| (a21)# | 100/1.0 | 1 | 55.3 | — | 3.34 | — | — | D |

TABLE 2-continued

Variation of the linker structure (example 17)

| Starting material | | Deprotection | | | |
|---|---|---|---|---|---|
| linker | HES species | c (HCl) [mM] | pH level | t [h] | Work up solvent |
| (a1)# | 100/1.0 | 10 | 2 | 18-24 | water |
| (a3)# | 100/1.0 | 10 | 2 | 18-24 | 10 mM HCl/water |
| (a4)# | 100/1.0 | 10 | 2 | 18-24 | water |
| (a16)# | 100/1.0 | 100 | 1 | 2 | water |
| (a17)# | 100/1.0 | 100 | 1 | 2 | water |
| (a11)# | 100/1.0 | 10 | 2 | 18-24 | water |
| (a12)# | 100/1.0 | 10 | 2 | 18-24 | water |
| (a13)# | 100/1.0 | 10 | 2 | 18-24 | water |
| (a18)# | 100/1.0 | 100 | 1 | 2 | water |
| (a5)# | 100/1.0 | 10 | 2 | 18-24 | water |
| (a14)# | 100/1.0 | 10 | 2 | 18-24 | water |
| (a15)# | 100/1.0 | 10 | 2 | 18-24 | water |
| (a10)# | 60/1.0 | — | — | — | — |
| (a21)# | 100/1.0 | 10 | 2 | 18-24 | water | as defined in the context of the present invention
*DMSO instead of sodium acetate buffer
**centrifugation of diluted and neutralized reaction mixture before ultrafiltration
&20 equivalents instead of 40 (referred to $M_n$ of HES) were used.

Example 18

Preparation of HES-Linker-Biologically Active Agent Derivatives According to the Invention The amount of the target molecule as indicated in the following Tables 3, 4, and 5 was transferred into the appropriate reaction buffer. The indicated amount of the HES-linker derivative (defined by the linker and the HES species) was dissolved in reaction buffer and mixed with the target substance solution. NaCNBH$_3$—typically as a freshly prepared 0.5 M stock solution in reaction buffer—was added to a final concentration of typically 20 mM. The reaction mixture was incubated under temperature control at the temperature "rxn T" for the reaction time "rxn t".

The final reaction volume ("rxn V") and the resulting concentrations and ratios of the reactants are given in Tables 3, 4, and 5.

The success of the conjugation reaction was shown by chromatographic analysis (RP-HPLC, SE-HPLC) or SDS-PAGE (see FIGS. 28 to 33 for selected derivatives). In all coupling reactions described herein a target-HES conjugate was detectable. The reaction conditions for the various target molecules were not optimized.

Abbreviations used:

| | |
|---|---|
| rhIFNα: | recombinant human interferon-alpha 2b |
| rhEPO: | recombinant human erythropoietin |
| rhG-CSF: | recombinant human granulocyte colony stimulating factor with an additional N-terminal methionine |
| rhFIX | recombinant human clotting factor IX |
| rhFVIIa: | recombinant human clotting factor VIIa |
| rhGH | recombinant human growth hormone |
| hFab | Fab fragment derived from a human immunoglobuline G molecule |
| mIgG | murine immunoglobuline G |
| GLP-1 | Glucagon-like peptide-1; Amino acids 1-37 |
| rAsparaginase | recombinant asparaginase from E. coli |
| NH$_2$-DNA | Oligonucleotide with 5'-Aminohexylspacer having the sequence GGC TAC GTC CAG GAG CCA CCT |
| rhLeptin | recombinant human leptin |
| AmphoB | Amphotericin B, CAS No. 1397-89-3 |
| Kemptide | Trp$^4$-Kemptide (Leu-Arg-Arg-Trp-Ser-Leu-Gly), CAS No. 80224-16-4 |
| NaOAc | sodium acetate containing buffer |
| HEPES | 4-(2-Hydroxyethyl)-1-piperazineethanesulfonic acid, CAS No. 7365-45-9 |

TABLE 3

Variation of target substances (example 18)

| linker | HES species | target molecule | buffer system | target amount | HES amount [mg] | HES:target | HES % (w/v) |
|---|---|---|---|---|---|---|---|
| (a2) | 100/1.0 | rhIFNα | 0.1 M NaOAc, pH 4 | 3 mg | 76 | 5:1 ($M_w$) | 18 |
| (a2) | 100/1.0 | rhFIX | 0.1 M HEPES, pH 7 | 3.5 mg | 133 | 29:1 | 25 |
| (a2) | 100/1.0 | rhFVIIa | 0.1 M NaOAc, pH 5 | 40 µg | 2.6 | 50:1 | 16 |
| (a2) | 100/1.0 | rhGH | 0.1 M Citrate, pH 6 | 0.1 mg | 16 | 60:1 | 40 |
| (a2) | 100/1.0 | mIgG | 0.1 M NaOAc, pH 5 | 0.1 mg | 3 | 80:1 | 3 |
| (a2) | 100/1.0 | hFab | 0.1 M NaOAc, pH 5 | 50 µg | 3.8 | 60:1 | 20 |
| (a2) | 100/1.0 | GLP-1 | 0.1 M NaOAc, pH 5 | 30 µg | 26 | 60:1 | 20 |
| (a2) | 100/1.0 | rAsparaginase | 0.1 M NaOAc, pH 5 | 30 µg | 4 | 80:1 | 26 |
| (a2) | 100/1.0 | NH$_2$-DNA | 0.05 M HEPES, pH 7 10 mM Mg$^{2+}$ | 10 µg | 5.5 | 60:1 | 20 |

TABLE 3-continued

Variation of target substances (example 18)

| | | | | | | | |
|---|---|---|---|---|---|---|---|
| (a2) | 100/1.0 | rhLeptin | 0.1 M NaOAc, pH 5 | 0.1 mg | 22.5 | 60:1 | 25 |
| (a2) | 100/1.0 | AmphoB | 0.1 M NaOAc, pH 5; 80% DMSO | 20 µg | 78 | 60:1 | 40 |
| (a2) | 100/1.0 | Kemptide | 0.1 M NaOAc, pH 5 | 30 µg | 12.1 | 5.6:1 | 20 |

| linker structure | HES species | target molecule | target conc. [g/l] | NaCNBH$_3$ [mg] | rxn V [µl] | rxn T [° C.] | rxn t [h] |
|---|---|---|---|---|---|---|---|
| (a2) | 100/1.0 | rhIFNα | 7 | 20 | 425 | 5 | 18 |
| (a2) | 100/1.0 | rhFIX | 6.7 | 20 | 531 | 10 | 18 |
| (a2) | 100/1.0 | rhFVIIa | 2.5 | 20 | 16 | 10 | 18 |
| (a2) | 100/1.0 | rhGH | 2.5 | 20 | 41 | 5 | 18 |
| (a2) | 100/1.0 | mIgG | 0.9 | 20 | 107 | 5 | 48 |
| (a2) | 100/1.0 | hFab | 2.7 | 20 | 19 | 5 | 18 |
| (a2) | 100/1.0 | GLP-1 | 0.2 | 20 | 83 | 21 | 18 |
| (a2) | 100/1.0 | rAsparaginase | 2 | 20 | 15 | 5 | 18 |
| (a2) | 100/1.0 | NH$_2$-DNA | 0.4 | 20 | 16 | 30 | 18 |
| (a2) | 100/1.0 | rhLeptin | 1.1 | 20 | 90 | 10 | 18 |
| (a2) | 100/1.0 | AmphoB | 0.1 | 20 | 195 | 21 | 18 |
| (a2) | 100/1.0 | Kemptide | 0.5 | 20 | 61 | 5 | 18 |

TABLE 4

Variation of the HES moiety (example 18)

| linker | HES species | target | buffer system | target [mg] | HES [mg] | HES:target | HES % |
|---|---|---|---|---|---|---|---|
| (a2) | 30/0.4 | rhIFNα | 0.1 M NaOAc pH 4 | 5 | 40 | 8:1 | 6.5 |
| (a2) | 30/1.0 | rhIFNα | 0.1 M NaOAc pH 4 | 5 | 52 | 8:1 | 8.3 |
| (a2) | 60/0.7 C2/C6 = 6 | rhIFNα | 0.1 M NaOAc pH 4 | 5 | 97 | 8:1 | 16 |
| (a2) | 60/0.7 C2/C6 = 8.5 | rhIFNα | 0.1 M NaOAc pH 4 | 5 | 82 | 8:1 | 13 |
| (a2) | 60/1.0 C2/C6 = 6 | rhIFNα | 0.1 M NaOAc pH 4 | 5 | 94 | 8:1 | 15 |
| (a2) | 60/1.0 C2/C6 = 8.5 | rhIFNα | 0.1 M NaOAc pH 4 | 5 | 85 | 8:1 | 14 |
| (a2) | 100/0.4 | rhIFNα | 0.1 M NaOAc pH 4 | 10 | 314 | 8:1 | 25 |
| (a2) | 100/0.7 | rhIFNα | 0.1 M NaOAc pH 4 | 5 | 130 | 8:1 | 21 |
| (a2) | 100/1.0 | rhIFNα | 0.1 M NaOAc pH 4 | 5 | 125 | 8:1 | 20 |
| (a2) | 100/1.3 | rhIFNα | 0.1 M NaOAc pH 4 | 5 | 154 | 8:1 | 15 |
| (a2) | 150/0.4 | rhIFNα | 0.1 M NaOAc pH 4 | 10 | 415 | 8:1 | 33 |
| (a2) | 150/1.0 | rhIFNα | 0.1 M NaOAc pH 4 | 5 | 187 | 8:1 | 30 |
| (a2) | 300/1.0 | rhIFNα | 0.1 M NaOAc pH 4 | 10 | 2437 | 24:1 | 40 |
| (a2) | 30/1.0 | rhEPO | 0.1 M NaOAc pH 5 | 4.5 | 173 | 50:1 | 23 |
| (a2) | 60/1.0 | rhEPO | 0.1 M NaOAc pH 5 | 4.5 | 313 | 40:1 | 30 |
| (a2) | 100/1.0 | rhEPO | 0.1 M NaOAc pH 5 | 60 | 5683 | 40:1 | 30 |
| (a2) | 150/1.0 | rhEPO | 0.1 M NaOAc pH 5 | 4.5 | 885 | 50:1 | 35 |

| linker | HES species | target | target conc. [g/l] | NaCNBH$_3$ [mM] | rxn V | rxn T [° C.] | rxn t [h] |
|---|---|---|---|---|---|---|---|
| (a2) | 30/0.4 | rhIFNα | 8 | 20 | 626 µl | 5 | 18 |
| (a2) | 30/1.0 | rhIFNα | 8 | 20 | 625 µl | 5 | 18 |
| (a2) | 60/0.7 C2/C6 = 6 | rhIFNα | 8 | 20 | 625 µl | 5 | 18 |
| (a2) | 60/0.7 C2/C6 = 8.5 | rhIFNα | 8 | 20 | 625 µl | 5 | 18 |
| (a2) | 60/1.0 C2/C6 = 6 | rhIFNα | 8 | 20 | 628 µl | 5 | 18 |
| (a2) | 60/1.0 C2/C6 = 8.5 | rhIFNα | 8 | 20 | 625 µl | 5 | 18 |
| (a2) | 100/0.4 | rhIFNα | 8 | 20 | 1257 µl | 5 | 18 |
| (a2) | 100/0.7 | rhIFNα | 8 | 20 | 624 µl | 5 | 18 |
| (a2) | 100/1.0 | rhIFNα | 8 | 20 | 625 µl | 5 | 18 |
| (a2) | 100/1.3 | rhIFNα | 8 | 20 | 627 µl | 5 | 18 |
| (a2) | 150/0.4 | rhIFNα | 8 | 20 | 1257 µl | 5 | 18 |
| (a2) | 150/1.0 | rhIFNα | 8 | 20 | 623 µl | 5 | 18 |
| (a2) | 300/1.0 | rhIFNα | 1.6 | 20 | 6093 µl | 5 | 18 |
| (a2) | 30/1.0 | rhEPO | 6 | 20 | 750 µl | 10 | 18 |
| (a2) | 60/1.0 | rhEPO | 4.3 | 20 | 1043 µl | 10 | 18 |
| (a2) | 100/1.0 | rhEPO | 3.2 | 20 | 18.9 ml | 10 | 18 |
| (a2) | 150/1.0 | rhEPO | 1.8 | 20 | 2528 µl | 10 | 18 |

TABLE 5

Variation of the linker structure (example 18)

| | linker | HES species | target | buffer system | target | HES [mg] | HES:target |
|---|---|---|---|---|---|---|---|
| 1 | (a1) | 100/1.0 | Kemptide | 0.1 M NaOAc pH 5 | 30 µg | 12.3 | 5.6:1 |
| 2 | (a3) | 100/1.0 | rhEPO | 0.1 M NaOAc pH 5 | 0.1 mg | 10.4 | 40:1 |
| 3 | (a4) | 100/1.0 | Kemptide | 0.1 M NaOAc pH 5 | 30 µg | 12.1 | 5.6:1 |
| 4 | (a4) | 100/1.0 | rhIFNα | 0.1 M NaOAc pH 4 | 0.1 mg | 2.7 | 8:1 |
| 5 | (a4) | 100/1.0 | rhEPO | 0.1 M NaOAc pH 5 | 100 µg | 4.3 | 20:1 |
| 6 | (a4) | 100/1.0 | rhG-CSF | 0.1 M NaOAc pH 5 | 53 µg | 5.2 | 30:1 |
| 7 | (a4) | 100/1.0 | rhLeptin | 0.1 M NaOAc, pH 5 | 0.1 mg | 22.5 | 60:1 |
| 8 | (a4) | 100/1.0 | $NH_2$-DNA | 0.05 M HEPES, pH 7 | 10 µg | 5.5 | 60:1 |
| 9 | (a4) | 100/1.0 | rhFVIIa | 0.1 M NaOAc pH 5 | 40 µg | 2.6 | 50:1 |
| 10 | (a4) | 100/1.0 | hFab | 0.1 M NaOAc, pH 5 | 50 µg | 3.8 | 60:1 |
| 11 | (a4) | 100/1.0 | rhGH | 0.1 M Citrate, pH 6 | 0.1 mg | 17 | 60:1 |
| 12 | (a4) | 100/1.0 | AmphoB | 0.1 M NaOAc, pH 5; 80% DMSO | 20 µg | 83 | 60:1 |
| 13 | (a16) | 100/1.0 | Kemptide | 0.1 M NaOAc pH 5 | 30 µg | 12.1 | 5.6:1 |
| 14 | (a16) | 100/1.0 | rhIFNα | 0.1 M NaOAc pH 4 | 0.1 mg | 2.7 | 8:1 |
| 15 | (a16) | 100/1.0 | rhEPO | 0.1 M NaOAc pH 5 | 100 µg | 8.6 | 40:1 |
| 16 | (a16) | 100/1.0 | rhG-CSF | 0.1 M NaOAc pH 5 | 44 µg | 4.3 | 30:1 |
| 17 | (a16) | 100/1.0 | rhLeptin | 0.1 M NaOAc, pH 5 | 0.1 mg | 22.5 | 60:1 |
| 18 | (a16) | 100/1.0 | hFab | 0.1 M NaOAc, pH 5 | 50 µg | 3.8 | 60:1 |
| 19 | (a16) | 100/1.0 | rhGH | 0.1 M Citrate, pH 6 | 0.1 mg | 18 | 60:1 |
| 20 | (a17) | 100/1.0 | Kemptide | 0.1 M NaOAc pH 5 | 30 µg | 12.1 | 5.6:1 |
| 21 | (a17) | 100/1.0 | rhEPO | 0.1 M NaOAc pH 5 | 4 mg | 513 | 60:1 |
| 22 | (a17) | 100/1.0 | rhFVIIa | 0.1 M NaOAc pH 5 | 40 µg | 2.6 | 50:1 |
| 23 | (a17) | 100/1.0 | rhLeptin | 0.1 M NaOAc, pH 5 | 0.1 mg | 22.5 | 60:1 |
| 24 | (a11) | 100/1.0 | Kemptide | 0.1 M NaOAc pH 5 | 30 µg | 12.1 | 5.6:1 |
| 25 | (a11) | 100/1.0 | rhIFNα | 0.1 M NaOAc pH 4 | 0.1 mg | 2.7 | 8:1 |
| 26 | (a11) | 100/1.0 | rhEPO | 0.1 M NaOAc pH 5 | 2 mg | 173 | 40:1 |
| 27 | (a11) | 100/1.0 | rhG-CSF | 0.1 M NaOAc pH 5 | 55 µg | 5.4 | 30:1 |
| 28 | (a11) | 100/1.0 | rhGH | 0.1 M Citrate, pH 6 | 0.1 mg | 18 | 60:1 |
| 29 | (a11) | 100/1.0 | hFab | 0.1 M NaOAc, pH 5 | 50 µg | 3.8 | 60:1 |
| 30 | (a12) | 100/1.0 | Kemptide | 0.1 M NaOAc pH 5 | 30 µg | 12.1 | 5.6:1 |
| 31 | (a12) | 100/1.0 | rhIFNα | 0.1 M NaOAc pH 4 | 0.1 mg | 2.7 | 8:1 |
| 32 | (a12) | 100/1.0 | rhEPO | 0.1 M NaOAc pH 5 | 11 mg | 478 | 20:1 |
| 33 | (a12) | 100/1.0 | rhG-CSF | 0.1 M NaOAc pH 5 | 47 µg | 4.6 | 30:1 |
| 34 | (a13) | 100/1.0 | Kemptide | 0.1 M NaOAc pH 5 | 30 µg | 12.1 | 5.6:1 |
| 35 | (a18) | 100/1.0 | Kemptide | 0.1 M NaOAc pH 5 | 30 µg | 12.1 | 5.6:1 |
| 36 | (a18) | 100/1.0 | rhEPO | 0.1 M NaOAc pH 5 | 4 mg | 342 | 40:1 |
| 37 | (a5) | 100/1.0 | Kemptide | 0.1 M NaOAc pH 5 | 30 µg | 12.1 | 5.6:1 |
| 38 | (a14) | 100/1.0 | Kemptide | 0.1 M NaOAc pH 5 | 30 µg | 54.3 | 25:1 |
| 39 | (a21) | 100/1.0 | Kemptide | 0.1 M NaOAc pH 5 | 30 µg | 54.3 | 25:1 |

| | linker | HES species | target | HES % | target conc. [g/l] | NaCNBH$_3$ [mM] | rxn V [µl] | rxn T [° C.] | rxn t [h] |
|---|---|---|---|---|---|---|---|---|---|
| 1 | (a1) | 100/1.0 | Kemptide | 20 | 0.49 | 20 | 61 | 5 | 18 |
| 2 | (a3) | 100/1.0 | rhEPO | 30 | 2.9 | 20 | 35 | 10 | 18 |
| 3 | (a4) | 100/1.0 | Kemptide | 20 | 0.5 | 20 | 61 | 5 | 18 |
| 4 | (a4) | 100/1.0 | rhIFNα | 20 | 7.5 | 20 | 13 | 5 | 18 |
| 5 | (a4) | 100/1.0 | rhEPO | 20 | 4.7 | 20 | 21 | 5 | 18 |
| 6 | (a4) | 100/1.0 | rhG-CSF | 15 | 1.5 | 20 | 35 | 10 | 18 |
| 7 | (a4) | 100/1.0 | rhLeptin | 25 | 1.1 | 20 | 90 | 5 | 18 |
| 8 | (a4) | 100/1.0 | $NH_2$-DNA | 20 | 0.4 | 20 | 16 | 30 | 18 |
| 9 | (a4) | 100/1.0 | rhFVIIa | 7 | 1.1 | 20 | 39 | 10 | 18 |
| 10 | (a4) | 100/1.0 | hFab | 20 | 2.7 | 20 | 19 | 5 | 18 |
| 11 | (a4) | 100/1.0 | rhGH | 40 | 2.3 | 20 | 44 | 5 | 18 |
| 12 | (a4) | 100/1.0 | AmphoB | 40 | 0.1 | 20 | 208 | 21 | 18 |
| 13 | (a16) | 100/1.0 | Kemptide | 20 | 0.5 | 20 | 61 | 5 | 18 |
| 14 | (a16) | 100/1.0 | rhIFNα | 20 | 7.5 | 20 | 13 | 5 | 18 |
| 15 | (a16) | 100/1.0 | rhEPO | 30 | 3.5 | 20 | 29 | 5 | 18 |
| 16 | (a16) | 100/1.0 | rhG-CSF | 15 | 1.5 | 20 | 29 | 10 | 18 |
| 17 | (a16) | 100/1.0 | rhLeptin | 25 | 1.1 | 20 | 90 | 5 | 18 |
| 18 | (a16) | 100/1.0 | hFab | 20 | 2.7 | 20 | 19 | 5 | 18 |
| 19 | (a16) | 100/1.0 | rhGH | 40 | 2.3 | 20 | 44 | 5 | 18 |
| 20 | (a17) | 100/1.0 | Kemptide | 20 | 0.5 | 20 | 61 | 5 | 18 |
| 21 | (a17) | 100/1.0 | rhEPO | 40 | 3.1 | 20 | 1284 | 5 | 18 |
| 22 | (a17) | 100/1.0 | rhFVIIa | 6 | 0.9 | 20 | 43 | 10 | 18 |
| 23 | (a17) | 100/1.0 | rhLeptin | 25 | 1.1 | 20 | 90 | 10 | 18 |
| 24 | (a11) | 100/1.0 | Kemptide | 20 | 0.5 | 20 | 61 | 5 | 18 |
| 25 | (a11) | 100/1.0 | rhIFNα | 20 | 7.5 | 20 | 13 | 5 | 18 |
| 26 | (a11) | 100/1.0 | rhEPO | 30 | 3.5 | 20 | 579 | 5 | 18 |
| 27 | (a11) | 100/1.0 | rhG-CSF | 15 | 1.5 | 20 | 36 | 10 | 18 |
| 28 | (a11) | 100/1.0 | rhGH | 40 | 2.3 | 20 | 44 | 5 | 18 |
| 29 | (a11) | 100/1.0 | hFab | 20 | 2.7 | 20 | 19 | 5 | 18 |
| 30 | (a12) | 100/1.0 | Kemptide | 20 | 0.5 | 20 | 61 | 5 | 18 |
| 31 | (a12) | 100/1.0 | rhIFNα | 20 | 7.5 | 20 | 13 | 5 | 18 |

TABLE 5-continued

Variation of the linker structure (example 18)

| 32 | (a12) | 100/1.0 | rhEPO    | 20 | 4.6 | 20 | 2389 | 5  | 18 |
| 33 | (a12) | 100/1.0 | rhG-CSF  | 15 | 1.5 | 20 | 31   | 10 | 18 |
| 34 | (a13) | 100/1.0 | Kemptide | 20 | 0.5 | 20 | 61   | 5  | 18 |
| 35 | (a18) | 100/1.0 | Kemptide | 20 | 0.5 | 20 | 61   | 5  | 18 |
| 36 | (a18) | 100/1.0 | EPO      | 30 | 3.5 | 20 | 1141 | 5  | 18 |
| 37 | (a5)  | 100/1.0 | Kemptide | 20 | 0.5 | 20 | 61   | 5  | 18 |
| 38 | (a14) | 100/1.0 | Kemptide | 20 | 0.1 | 20 | 271  | 5  | 18 |
| 39 | (a21) | 100/1.0 | Kemptide | 20 | 0.1 | 20 | 271  | 25 | 18 |

Additional Data (A.1) Preparation of oxHBS-N-(3-Propioaldehydediethylacetal) from HBS 7 kDa Hyper branched starch (HBS) aldonic acid was synthesized according to example 9 of WO2005/083103 A1 starting from a hyperbranched starch ($M_w$=7000 Dalton (7 kDa), average degree of branching: 15 mol %). The aldonic acid obtained was transferred into the corresponding lactone by drying for 24 h at 80° C. (the abbreviation "oxHBS" refers to the HBS aldonic acid as well as to the corresponding lactone).

5 g of the lactone were dissolved in 15 ml 1-amino-3,3-diethoxypropane and 10 ml of dry DMF and stirred at 70° C. for 48 h. Excess 1-amino-3,3-diethoxypropane and DMF (dimethylformamide) were evaporated under vacuum and the resulting pale yellow solid was washed with acetone until the yellow colour disappeared. The product was dissolved in water and purified by ultrafiltration utilizing a membrane with a cut-off of 1000 Dalton until the pH of the filtrate reached a value of >6.

The retentate was treated with 2 g of an acidic cation exchange resign (Amberlite® 120) for 2 h, the resign was filtered off and the remaining solution lyophilized. The $^1$H-NMR Spectrum of the compound showed a triplett at 1.7 and a multiplett at 1.2 ppm representing the methyl- and the methylene groups in alpha-position to the nitrogen atom of the residue of the linker compound (1-amino-3,3-diethoxypropane).

(A.2) Preparation of oxHBS 7 kDa—Bovine Serum Albumin (BSA) Conjugate

750 µg of acetal prepared in (A.1) were dissolved in 5 ml 0.01 N HCl. The pH was adjusted to 2.0 with 1 N HCl, and the reaction mixture was stirred at 21° C. for 18 h. 2 ml of a 1% BSA solution in acetate buffer (pH=7.0) were added to 200 µl of the mixture prepared before. 140 mg sodium cyanoborohydride were dissolved in 5 ml 0.1 N acetate buffer (pH=7.0), and an aliquot of 50 ml was added to the reaction mixture immediately. The reaction mixture was stored at 4° C. for 15 h. Analysis of the reaction mixture by size-exclusion chromatography revealed a reaction yield of 90% HBS-BSA conjugate. (FIG. 24)

(A.3) Preparation of oxHBS 65 kDa—Interferon-Alpha Conjugate

To 400 mg of a 65 kDa HBS-N-(3-propioaldehydediethylacetal) prepared analogously to (A.1) an appropriate amount of 10 mM HCl was added to yield a solution with a concentration of 40% (w/v) and a pH value of 2. The solution was incubated under stirring at 21° C. o/n (overnight) to deprotect the aldehyde function. The pH-value was adjusted to the value used in the conjugation buffer by addition of 0.1 M NaOH prior to coupling.

Interferon-alpha (recombinant human interferon alpha-2b manufactured by recombinant DNA technology using *Escherichia coli* (*E. coli*), the interferon alpha-2b being composed of 165 amino acids and presenting an amino acid sequence which is identical to natural human interferon alpha-2b (hIFN-alpha-2b)) was concentrated up to 16 mg/ml and transferred into a suitable conjugation buffer (0.1 M sodium acetate buffer, pH 4.0) using ultrafiltration devices.

A 10 fold molar excess of oxHBS aldehyde (based on $M_w$) was used with a final protein concentration in the reaction mixture of 6 mg/ml; the oxHBS aldehyde concentration was 20% (w/v). The deprotected oxHBS aldehyde was combined with the protein solution and the reductive amination reaction was started by addition of a freshly prepared NaCNBH$_3$ solution (0.5 M in conjugation buffer) to yield a final concentration of reducing agent of 20 mM. After thorough mixing, the reaction was incubated o/n at 10° C.

The reaction mixtures were analyzed by SDS-PAGE (FIG. 25) and reversed phase chromatography on a C18 column (Phenomenex, Jupiter) to prove successful coupling and for determination of the conjugation yield. Elution was carried out using an acidic water/acetonitrile gradient with 0.1% TFA.

The HBS-Interferon-alpha was separated from non-reacted compounds by anion-exchange chromatography using a Q HP column on an Äkta system (GE Healthcare). Eluent A was 10 mM Tris·Cl, pH 8.0, Eluent B was 10 mM Tris·Cl, 0.5 M NaCl, pH 8.0. The gradient for separation of conjugate and non-modified protein was 0% B=>50% B in 16 CV (FIG. 26).

(A.4) Preparation of oxHBS 65 Erythropoietin (EPO) Conjugate

To 400 mg of a 65 kDa HBS-N-(3-propioaldehydediethylacetal) prepared analogously to (A.1) an appropriate amount of 10 mM HCl was added to yield a solution with a concentration of 40% (w/v). The solution was incubated under stirring at 21° C. o/n to deprotect the aldehyde function. The pH-value was adjusted to the value used in the conjugation buffer by addition of 0.1 M NaOH.

The deprotected oxHBS aldehyde was combined with an EPO (recombinant human EPO having the amino acid sequence of human EPO and essentially the same characteristics as the commercially available Erypo® (Ortho Biotech, Jansen-Cilag) or NeoRecormon® (Roche)) solution (10 mg/ml in the reaction buffer 0.1 M sodium acetate buffer, pH 5). OxHBS aldehyde was added at a 20 fold molar excess (based on $M_w$) compared to the EPO concentration. The resulting EPO concentration in the reaction mix was 4.6 mg/ml, the oxHBS aldehyde concentration was 20% (w/v). The reductive amination reaction was started by addition of a 0.5 M NaCNBH$_3$ solution made up in reaction buffer to yield a final concentration of reducing agent of 20 mM. After thorough mixing, the reaction was incubated o/n at 10° C.

The reaction mixtures were analyzed by SDS-PAGE (FIG. 27) and reversed phase chromatography (FIG. A.4-1) on a C18 column (Phenomenex, Jupiter) to prove successful coupling and for determination of the conjugation yield. Elution was carried out using an acidic water/acetonitrile gradient with 0.1% TFA.

The invention claimed is:

1. A hydroxyalkyl starch derivative, having the structure

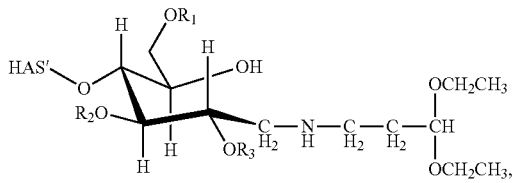

wherein HAS' is the remainder of the hydroxyalkyl starch molecule and $R_1$, $R_2$, and $R_3$ are each independently hydrogen or a linear or branched hydroxyalkyl group.

2. A hydroxyalkyl starch derivative, having the structure

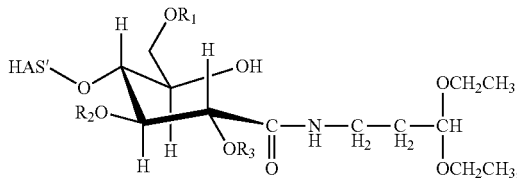

wherein HAS' is the remainder of the hydroxyalkyl starch molecule and $R_1$, $R_2$, and $R_3$ are each independently hydrogen or a linear or branched hydroxyalkyl group.

3. A hydroxyalkyl starch (HAS) derivative according to the following formula

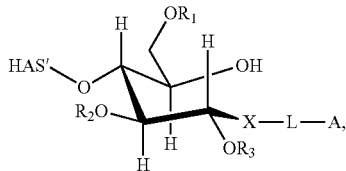

wherein HAS' is the remainder of the hydroxyalkyl starch molecule; $R_1$, $R_2$, and $R_3$ are each independently hydrogen or a linear or branched hydroxyalkyl group; A is an acetal or ketal group; X is selected from the group consisting of —CH=N—, —CH$_2$—NH—, —CH=N—O—, —CH$_2$—NH—O—, —C(=O)—NH—, and —C(=O)—NH—NH—; and L is a spacer bridging X and A.

4. The HAS derivative of claim 3, wherein $R_1$, $R_2$, and $R_3$ are each independently a group —(CH$_2$CH$_2$O)$_n$—H; and n is an integer.

5. The HAS derivative of claim 3, wherein the hydroxyalkyl starch is hydroxyethyl starch (HES).

6. The HAS derivative of claim 3, wherein A is a residue according to the formula

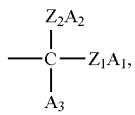

$Z_1$ and $Z_2$ are each independently O or S or $NR_x$; $R_x$ is H, methyl, ethyl, n-propyl, i-propyl, or C(O)—$R_y$; $R_y$ is either a $C_1$-$C_6$ alkyl or a $C_6$-$C_{14}$ aryl; $A_1$ and $A_2$ are each independently methyl, ethyl, n-propyl, isopropyl, n-butyl, tert-butyl, benzyl, 1,1,1-trichloroethyl, nitrobenzyl, methoxybenzyl, ethoxybenzyl, or form a ring according to the formula

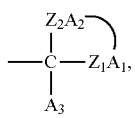

$A_3$ is H, methyl, ethyl, n-propyl, isopropyl, n-butyl, isobutyl, pentyl, benzyl, or forms a ring with the N atom of X or with a suitable atom in L.

7. The HAS derivative of claim 3, wherein L comprises at least one structural unit according to the formula

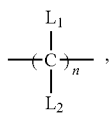

$L_1$ and $L_2$ are each independently H or an organic residue selected from the group consisting of alkyl, substituted alkyl, alkenyl, substituted alkenyl, alkynyl, substituted alkynyl, aryl, substituted aryl, arylalkyl, substituted arylalkyl, alkylaryl, substituted alkylaryl, and residues —O—R"; R" is selected from the group consisting of alkyl, substituted alkyl, alkenyl, substituted alkenyl, alkynyl, substituted alkynyl, aryl, substituted aryl, arylalkyl, substituted arylalkyl, alkylaryl, and substituted alkylaryl; and n is an integer from 1 to 20.

8. The HAS derivative of claim 7, wherein L comprises at least one structural unit —(CL$_1$L$_2$)$_{n_1}$-O-(CL$_1$L$_2$)$_{n_2}$-, $n_1$ is equal to or different from $n_2$, $n_1$ is an integer from 2 to 4, and $n_2$ is an integer from 1 to 4.

9. The HAS derivative of claim 7, wherein L is -((CL$_1$L$_2$)$_2$-O)$_m$—(CL$_1$L$_2$)-, and m is 1, 2, or 3.

10. The HAS derivative of claim 7, wherein L is -(CL$_1$L$_2$)$_{n_3}$-(C=O)—NH-(CL$_1$L$_2$)$_{n_4}$-, and $n_3$ and $n_4$ are each independently in the range of from 1 to 4.

11. The HAS derivative of claim 7, wherein L is selected from the group consisting of —(CH$_2$)$_3$—(C=O)—NH—(CH$_2$)$_3$—, —(CH$_2$)$_3$—(C=O)—NH—(CH$_2$)$_2$—, —(CH$_2$)$_2$—(C=O)—NH—(CH$_2$)$_3$—, and —(CH$_2$)$_2$—(C=O)—NH—(CH$_2$)$_2$—.

* * * * *